(12) United States Patent
Hsieh

(10) Patent No.: US 8,455,219 B2
(45) Date of Patent: Jun. 4, 2013

(54) MAMMALIAN EXPRESSION VECTORS AND USES THEREOF

(75) Inventor: Chung-Ming Hsieh, Newton, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/368,618

(22) Filed: Feb. 8, 2012

(65) Prior Publication Data

US 2012/0237976 A1 Sep. 20, 2012

Related U.S. Application Data

(62) Division of application No. 12/354,568, filed on Jan. 15, 2009, now Pat. No. 8,187,836.

(60) Provisional application No. 61/021,282, filed on Jan. 15, 2008, provisional application No. 61/104,546, filed on Oct. 10, 2008.

(51) Int. Cl.
*C07K 16/324* (2006.01)
*C07K 2316/52* (2006.01)
*C07K 2316/96* (2006.01)
*C07K 2317/21* (2006.01)

(52) U.S. Cl.
USPC .......... 435/69.1; 435/252.3; 435/320.1; 435/455; 536/23.5

(58) Field of Classification Search
None
See application file for complete search history.

(56) References Cited

U.S. PATENT DOCUMENTS

| 6,461,606 | B1 | 10/2002 | Flotte et al. | |
|---|---|---|---|---|
| 7,371,542 | B2 * | 5/2008 | Ivanova et al. | 435/69.1 |
| 8,187,836 | B2 * | 5/2012 | Hsieh | 435/69.1 |
| 2005/0064467 | A1 | 3/2005 | Ivanova et al. | |
| 2006/0177896 | A1 | 8/2006 | Mach et al. | |
| 2007/0065912 | A1 | 3/2007 | Carson et al. | |

FOREIGN PATENT DOCUMENTS

WO WO2007014162 A2 2/2007

OTHER PUBLICATIONS

European Search Report issued in corresponding EP Application No. 09703045.6, dated May 19, 2011.
M. J. Evans et al: "Rapid expression of an anti-human C5 chimeric Fab utilizing a vector that replicates in COS and 293 cells" Journal of Immunological Methods, Elsevier Science Publishers B.V., Amsterdam, NL, vol. 184: No. 1, Jul. 17, 1995.
A. Stary et al: "Simian Virus 40 (SV40) Large T Antigen-Dependent Amplification of an Epstein-Barr Virus-SV40 Hybrid Shuttle Vector Integrated into the Human Hela Cell Genone", Journal of General Virology, Society for General Microbiology, Spencers Wood, GB, vol. 73: No. Part 07, Jul. 1, 1992.
DuBridge, Robert B. et al., "Analysis of Mutation in Human Cells by Using an Epstein-Barr Virus Shuttle System," Molecular and Cellular Biology, vol. 7(1):379-387 (1987).
International Search Report and Written Opinion for Application No. PCT/US09/31136, dated Jul. 20, 2009.
Office Action from European Patent Application No. 09703045.6, dated Mar. 5, 2012.

* cited by examiner

*Primary Examiner* — Michail Belyavskyi
(74) *Attorney, Agent, or Firm* — Lathrop & Gage LLP; James H. Velema

(57) ABSTRACT

The present invention features nucleic acids for recombinant protein expression in mammalian cell culture. The episomal vectors of the invention promote high protein production in mammalian cells expressing the SV40 T Ag or Epstein-Barr virus nuclear antigen (e.g., COS7 or HEK293-6E cells). The methods and systems are useful, for example, in pharmaceutical drug development and cloning, especially for the production of antibodies.

31 Claims, 25 Drawing Sheets

MAMMALIAN EXPRESSION VECTORS AND USES THEREOF

RELATED APPLICATIONS

This application is a divisional application of U.S. patent application Ser. No. 12/354,568, filed on Jan. 15, 2009 (now U.S. Pat. No. 8,187,836), which claims priority to U.S. provisional application Ser. No. 61/021,282, filed on Jan. 15, 2008, and to U.S. provisional application Ser. No. 61/104,546, filed on Oct. 10, 2008, the contents of each of which are hereby incorporated by reference in their entirety.

BACKGROUND OF THE INVENTION

Stable production of proteins, including biologics, can be accomplished by transfecting host cells with vectors containing DNA that encodes the protein. Maintenance of the vector in the cell line can be achieved through a variety of means, including extrachromosomal replication through episomal origins of replication. Episomal vectors contain an origin of replication that promotes replication of the vector when the sequence is bound by a replication initiation factor. Episomal vectors have several advantages over vectors that require insertion into the host genome. For example, episomal vectors decrease phenotypic changes in the cell that may result from integration of a vector into the host genome. Episomal vectors may also be isolated from the transfected cells using standard DNA extraction protocols.

With the evolving importance of therapeutic proteins, i.e., biologics, efforts must be made to optimize protein production, while improving efficiency of the overall production process. Thus, improvements in efficiency must be weighed against the protein production capacity of the vector. There is a need for better expression systems that provide efficient cloning options, as well as high levels of the desired protein product. It would be advantageous to decrease the number of cloning steps involved in the production of biologics, especially antibodies, to improve time requirements and minimize cost. It would also be advantageous to provide vectors that provide adequate protein production for both small and large scale cell cultures. The present invention overcomes the limitations of conventional vectors, by providing additional advantages that will be apparent from the detailed description below.

SUMMARY OF THE INVENTION

Recombinant proteins may be produced by mammalian cell transient transfection, especially during the pharmaceutical drug discovery process. A variety of host cells may be used to express proteins, including mammalian cells such as COS and human embryonic kidney (HEK) cells. Episomal vectors rely on both an origin of replication and a trans-acting replication initiation factor that binds the origin. Replication initiation factors, such as Epstein-Barr virus nuclear antigen (EBNA) that binds the OriP of the Epstein-Barr virus, may be cloned into the episomal vector, or, alternatively, may be expressed by the host cell into which the vector is transfected. Thus, episomal vectors may be specific to certain cell lines that express the trans-acting factor required to activate replication through the origin of replication.

The present invention eliminates the need for different episomal vector backbones for recombinant protein expression. The present invention provides episomal vectors comprising at least two different episomal origins of replication, which allow the same vector to be used in different cell types for protein expression. Different origins of replication allow the vector to be used in different types of mammalian cells that provide the necessary trans-acting replication factors and allow the vector to replicate. By eliminating the need to re-clone the gene of interest for protein production, the instant invention improves efficiency and reduces costs associated with multiple vectors, while at the same time maintaining protein production levels. A surprising aspect of the invention is that the addition of nucleotides to the vector, i.e., a second origin of replication, does not negatively impact the vector's ability to produce protein at the desired levels.

In a preferred embodiment, the vectors of the invention comprise antibody heavy or light chain constant regions. Thus, an antibody light or heavy chain variable region may be cloned into the vector upstream of the light or heavy chain constant region, respectively, further improving the efficiency of the expression system. The episomal vectors promote high protein production in mammalian cells expressing the SV40 T Ag or Epstein-Barr virus nuclear antigen (e.g., COS7 or HEK293-6E cells).

The present invention provides an optimal combination of elements for protein yield, production efficiency, and reduced cost, which are all important elements for protein production, especially in the pharmaceutical industry and the production of biologic proteins, such as antibodies. Other features and advantages of the invention are described in the detailed description and claims below.

In one aspect, the invention provides an expression vector comprising: a) an OriP origin of replication derived from Epstein-Barr virus (EBV); (b) an SV40 origin of replication; (c) an insertion site for inserting a gene of interest; and (d) a nucleic acid sequence encoding an antibody heavy or light chain constant region, operably linked to the insertion site. In an embodiment, the gene of interest is an antibody heavy or light chain variable region, for example, a murine, a humanized, a chimeric or a human antibody heavy or light chain variable region. In a particular embodiment, the antibody heavy chain variable region is the heavy chain variable region of an antibody selected from the group consisting of adalimumab, ABT-325, and ABT-874. In another particular embodiment, the antibody light chain variable region is the light chain variable region of an antibody selected from the group consisting of adalimumab, ABT-325, and ABT-874. The antibody heavy chain constant region is murine, humanized, chimeric or human, for example, and may be an antibody heavy constant region is selected from the group consisting of gamma 1, z, a; gamma 1, z, non-a; gamma 2, n+; gamma 2, n−; and gamma 4. The gamma 1, z, non-a antibody heavy chain constant region may further comprise an alanine mutation at position 234 of the heavy chain constant region. In another embodiment, the gamma 1, z, non-a antibody heavy chain constant region may further comprise an alanine mutation at either position 235 or 237 of the antibody heavy chain constant region.

In an embodiment, the antibody light chain constant region is a human kappa isotype or a human lambda isotype. In an embodiment, the antibody heavy chain constant region is a murine gamma 1 isotype or a murine gamma 2a isotype. In another embodiment, the antibody light chain constant region is a murine kappa isotype. In an embodiment, the antibody heavy chain constant region is an Fc domain. In an embodiment, the heavy or light chain antibody variable region is 5' to the insertion site.

In an embodiment, the expression vector further comprises a promoter operably linked to the insertion site, wherein the promoter is either an EF-1α promoter or a cytomegalovirus (CMV) promoter.

In an embodiment, the expression vector further comprises a selectable marker, such as an ampicillin resistance gene.

In an embodiment, the CMV promoter comprises a nucleic acid sequence that is at least 80%, at least 85%, at least 90%, at least 95%, at least 96%, at least 97%, at least 98% or at least 99% identical to nucleotides 1 to 608 of SEQ ID NO: 1. In a particular embodiment, the CMV promoter comprises nucleotides 1 to 608 of SEQ ID NO: 1.

In an embodiment the EF-1α promoter is human. In an embodiment, the EF-1α promoter comprises a nucleic acid sequence that is at least 80%, at least 85%, at least 90%, at least 95%, at least 96%, at least 97%, at least 98% or at least 99% identical to nucleotides 76 to 1267 of SEQ ID NO: 2. In a particular embodiment, the EF-1α promoter comprises nucleotides 76 to 1267 of SEQ ID NO: 2.

In an embodiment, the OriP origin of replication comprises a nucleic acid sequence that is at least 80%, at least 85%, at least 90%, at least 95%, at least 96%, at least 97%, at least 98% or at least 99% identical to nucleotides 1795 to 3545 of SEQ ID NO: 1.

In an embodiment, the SV40 origin of replication comprises a nucleic acid sequence that is at least 80%, at least 85%, at least 90%, at least 95%, at least 96%, at least 97%, at least 98% or at least 99% identical to nucleotides 5834 to 6140 of SEQ ID NO: 1. In a particular embodiment, the SV40 origin of replication comprises nucleotides 5834 to 6140 of SEQ ID NO: 1.

Exemplary expression vector of the invention comprise a nucleic acid sequence that is at least 80%, at least 85%, at least 90%, at least 95%, at least 96%, at least 97%, at least 98% or at least 99% identical to a sequence selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 and 32. In particular embodiments, the expression vector comprises a nucleic acid sequence selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 and 32.

Expression vectors of the invention are also provided in FIGS. 1, 2, and 14-25. Additional vectors of the invention are described in FIGS. 8-13.

In another aspect, the invention provides a mammalian host cell comprising the vector of the invention. The mammalian host may be a COS cell, such as a COS 7 cell, or a human embryonic kidney (HEK) cell, such as a HEK-293 cell.

In another aspect, the invention provides a kit comprising a vector of the invention.

In another aspect, the invention provides a method of producing a recombinant protein comprising introducing an expression vector of the invention into a mammalian host cell, culturing the mammalian host cell under suitable conditions so as to express the protein, and recovering the protein.

In another aspect, the invention provides an expression vector comprising a nucleic acid sequence encoding a signal peptide. In one embodiment, the gene of interest is operably linked to a nucleic acid encoding a signal peptide.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which.

DETAILED DESCRIPTION OF THE INVENTION

I. Definitions

Figure 1:
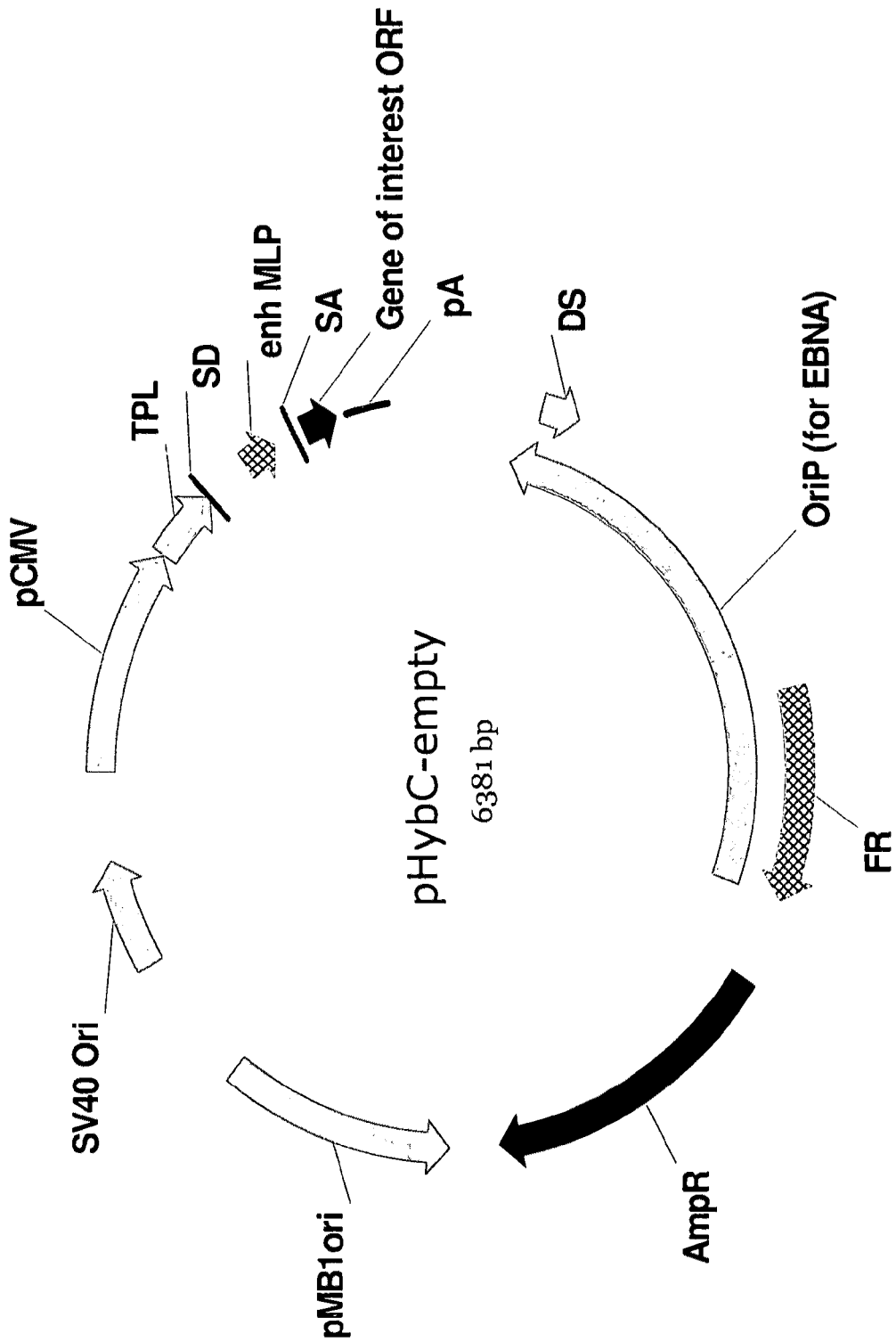
FIG. 1 shows a map of the empty pHyb-C vector. Features include a SV40 eukaryotic origin of replication, a cytomegalovirus eukaryotic expression promoter (pCMV), Tripartite leader sequence (TPL), a splice donor site (SD), an Adenovirus major late enhancer element (enh MLP), a splice acceptor site (SA), an open reading frame (ORF) region for a gene of interest followed by a poly A signal (pA), a dyad symmetry element (DS), an Epstein Barr virus-derived eukaryotic origin of replication (OriP), a repeat region (FR), an ampicillin resistance marker (AmpR) and a bacterial origin of replication (pMB1ori).

In order that the present invention may be more readily understood, certain terms are first defined herein.

The term "nucleic acid" or "nucleic acid molecule," as used herein, is intended to include DNA, RNA, mRNA, cDNA, genomic DNA, and analogs thereof. A nucleic acid molecule may be single-stranded or double-stranded, but preferably is double-stranded DNA. A nucleic acid may be isolated, or integrated into another nucleic acid molecule, e.g., an expression vector or the chromosome of an eukaryotic host cell.

An "isolated" nucleic acid molecule is one that is separated from other nucleic acid molecules that are present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The terms "recombinant vector" or "vector", used interchangeably herein, refers to a nucleic acid molecule capable of transporting another nucleic acid to which it has been linked. One type of vector is a "plasmid", which refers to a circular double stranded DNA loop into which additional DNA segments may be ligated. Alternatively, a vector can be linear. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. In a preferred embodiment, the vectors of the invention are episomal mammalian vectors. The term "construct", as used herein, also refers to a vector.

Certain vectors are capable of directing the expression of genes to which they are operatively linked. An "expression vector" or "recombinant expression vector" is a nucleic acid molecule encoding a gene that is expressed in a host cell, and, furthermore, contains the necessary elements to control expression of the gene. Typically, an expression vector comprises a transcription promoter, a gene of interest, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. In one embodiment, the expression vector of the invention comprises more that one origin of replication, thus not limiting the vector to one cell type.

As used herein, the term "episomally replicating vector" or "episomal vector" refers to a vector that is typically and very preferably not integrated into the genome of the host cell, but exists in parallel. An episomally replicating vector, as used herein, is replicated during the cell cycle and in the course of this replication the vector copies are distributed statistically in the resulting cells depending on the number of the copies present before and after cell division. Preferably, the episomally replicating vector may take place in the nucleus of the host cell, and preferably replicates during S-phase of the cell cycle. Moreover, the episomally replicating vector is replicated at least once, i.e., one or multiple times, in the nucleus of the host cell during S-phase of the cell cycle. In a very preferred embodiment, the episomally replicating vector is replicated once in the nucleus of the host cell during S-phase of the cell cycle.

As used herein, the terms "origin of replication sequences" or "origin of replication," used interchangeably herein, refer to sequences which, when present in a vector, initiate replication. An origin of replication may be recognized by a replication initiation factor or, alternatively, by a DNA helicase.

As used herein, "recombination" refers to a process by which nucleic acid material, e.g., DNA, is exchanged between two nucleic acid molecules, for example, in a microorganism. As used herein, "homologous recombination" refers to a process by which nucleic acid material is exchanged between two nucleic acid molecules through regions or segments of sequence homology, or preferably, sequence identity (e.g., a high degree of sequence identity). In exemplary embodiments, the nucleic acid material is located on a chromosome or an episome of the microorganism. In another exemplary embodiments, the nucleic acid material is located extrachromasomally, for example, on a plasmid. Recombination can occur between linear and/or circular DNA molecules.

As used herein, the term "gene of interest" refers to an exogenous DNA sequence that is added to the vector of the invention. The gene of interest, for example, may comprise a coding sequence that can be either spaced by introns or that is a cDNA encoding the open reading frame. The "gene of interest" as used herein, refers to the DNA sequence that is added to the vector of the invention for eventual protein expression. The region of the vector to which the gene of interest is cloned is referred to herein as an "insertion site." Preferably, the gene of interest comprises a portion of the antibody or fusion protein that is expressed using a vector of the invention. For example, the heavy chain variable region of the antibody adalimumab, i.e., the gene of interest, is cloned into the vector of the invention that comprises a heavy chain constant region.

In one embodiment of the invention, the vector comprises an antibody light or heavy chain constant region that is 3' to the insertion site for the gene of interest and is operably linked thereto. Thus, in one embodiment, the gene of interest is a variable region of a light or heavy chain of an antibody that is operably linked to the antibody light or heavy chain constant region encoded in the vector of the invention.

A nucleotide sequence is "operably linked" when placed into a functional relationship with another nucleotide sequence. For example, DNA encoding a signal peptide is operably linked to DNA encoding a protein or polypeptide if, when expressed, the sequences encode the signal peptide in frame with the protein or polypeptide. Likewise, a promoter or enhancer is operably linked to a nucleotide sequence encoding a protein or polypeptide if expression of the protein or polypeptide is promoted or enhanced. In one embodiment, nucleotide sequences that are operably linked are contiguous (e.g., in the case of a signal sequences). Alternatively, nucleotide sequences that are operably linked can be non-contiguous (e.g., in the case of enhancers). In one embodiment, the nucleic acid sequence encoding an antibody light or heavy chain constant region is operably linked to the gene of interest, e.g., a heavy or light chain variable region.

The term "promoter" includes any nucleic acid sequence sufficient to direct transcription in a eukaryotic cell, including inducible promoters, repressible promoters and constitutive promoters. Typically, a promoter includes elements that are sufficient to render promoter-dependent gene expression controllable in a cell type-specific, tissue-specific or temporal-specific manner, or inducible by external signals or agents. Such elements can be located in the 5' or 3' or intron sequence regions of a particular gene. Ordinarily, gene expression will be constitutive, although regulatable promoters can be employed in the present invention if desired. Gene expression can also be controlled by transcription-regulation using heat, light, or metals, such as by the use of metallothionine genes or heat shock genes.

"Upstream" and "downstream" are terms used to describe the relative orientation between two elements present in a nucleotide sequence or vector. An element that is "upstream" of another is located in a position closer to the 5' end of the sequence (i.e., closer to the end of the molecule that has a phosphate group attached to the 5' carbon of the ribose or deoxyribose backbone if the molecule is linear) than the other element. An element is said to be "downstream" when it is located in a position closer to the 3' end of the sequence (i.e., the end of the molecule that has an hydroxyl group attached to the 3' carbon of the ribose or deoxyribose backbone in the linear molecule) when compared to the other element.

As used herein, the term "stuffer sequence" refers to a nucleic acid sequence, preferably in a vector, which is flanked by restriction enzyme sites at both the 5' and 3' ends. The stuffer sequence is located in a vector at the insertion site for the nucleic acid encoding the gene of interest. During the cloning process, the stuffer sequence is digested away from the vector using the appropriate restriction enzymes, and the nucleic acid encoding the gene of interest is ligated or homologously recombined into the vector at the former position of the stuffer sequence. Preferably, the stuffer sequence is large enough to provide sufficient distance between the 5' and 3' restriction enzyme sites so that the restriction enzyme can efficiently cut the vector. In addition, it is preferred that the length of the stuffer sequence is different than the size of the nucleic acid encoding the gene of interest, e.g., a stuffer sequence of about 300 base pairs or less or about 400 base pairs or more may be used for a nucleic acid encoding the gene of interest that is about 350 base pairs. In another embodiment, the stuffer sequence is about 1 kb in size.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The six CDRs of a $V_H$ and $V_L$ combination form an antigen binding site. In the case of an antibody composed of two H chains and two L chains, the antibody may contain two identical antigen binding sites, two different antigen binding sites that bind the same antigen, or two antigen binding sites that bind different antigens. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., IL-1α, IL-1β). The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al, (1989) Nature 341:544-546), which consists of a $V_H$ or $V_L$ domain; and (vi) an isolated complementarity determining region (CDR). Furthermore, although the two domains of the Fv fragment, VL and $V_H$, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. In one embodiment if the invention, the antibody fragment is selected from the group consisting of a Fab, an Fd, an Fd', a single chain Fv (scFv), an scFv$_a$, and a domain antibody (dAb).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) *Human Antibodies and Hybridomas* 6:93-101) and use of a cysteine residue, a marker peptide and a C-terminal polyhistidine tag to make bivalent and biotinylated scFv molecules (Kipriyanov et al. (1994) *Mol. Immunol.* 31:1047-1058). Antibody portions, such as Fc, Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

The term "domain" refers to a folded protein structure that retains its tertiary structure independently of the rest of the protein. Generally, domains are responsible for discrete functional properties of proteins, and in many cases may be added, removed or transferred to other proteins without loss of function of the remainder of the protein and/or of the domain. By single antibody variable domain is meant a folded polypeptide domain comprising sequences characteristic of antibody variable domains. It therefore includes complete antibody variable domains and modified variable domains, for example, in which one or more loops have been replaced by sequences that are not characteristic of antibody variable domains, or antibody variable domains that have been truncated or comprise N- or C-terminal extensions, as well as folded fragments of variable domains that retain at least in part the binding activity and specificity of the full-length domain.

Variable domains of the invention may be combined to form a group of domains; for example, complementary domains may be combined, such as VL domains being combined with VH domains. Non-complementary domains may also be combined, e.g., VH domain and a second VH domain. Domains may be combined in a number of ways, involving linkage of the domains by covalent or non-covalent means.

A "dAb" or "domain antibody" refers to a single antibody variable domain ($V_H$ or $V_L$) polypeptide that specifically binds antigen. In one embodiment, the vector of the invention is used to express a dAb.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes (see, e.g., Taylor et al. (1992) *Nucl. Acids Res.* 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include chimeric, CDR-grafted and humanized antibodies.

The term "human antibody" refers to antibodies having variable and constant regions corresponding to, or derived from, human germline immunoglobulin sequences as described by, for example, Kabat et al. (See Kabat, et al. (1991) *Sequences of Proteins of Immunological Interest*, Fifth Edition, U.S. Department of Health and Human Services, NIH Publication No. 91-3242). The human antibodies of the invention, however, may include amino acid residues not encoded by human germline immunoglobulin sequences (e.g., mutations introduced by random or site-specific mutagenesis in vitro or by somatic mutation in vivo), for example in the CDRs and in particular CDR3.

Recombinant human antibodies of the invention have variable regions, and may also include constant regions, derived from human germline immunoglobulin sequences (See Kabat et al. (1991) *Sequences of Proteins of Immunological Interest*, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis or backmutation or both.

The term "backmutation" refers to a process in which some or all of the somatically mutated amino acids of a human antibody are replaced with the corresponding germline residues from a homologous germline antibody sequence. The heavy and light chain sequences of a human antibody of the invention are aligned separately with the germline sequences in the VBASE database to identify the sequences with the highest homology. Differences in the human antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the human antibody should not be included in the final human antibody. To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. Backmutation may occur at any stage of antibody optimization.

The term "chimeric antibody" refers to antibodies that comprise heavy and light chain variable region sequences from one species and constant region sequences from another species, such as antibodies having murine heavy and light chain variable regions linked to human constant regions.

The term "CDR-grafted antibody" refers to antibodies that comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies that comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

As used herein, the terms "linked," "fused" or "fusion" are used interchangeably. These terms refer to the joining together of two more elements or components, by whatever means including chemical conjugation or recombinant means. An "in-frame fusion" or "operably linked" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, an in-frame linker sequence.

As used herein, the term "Fc region" includes amino acid sequences derived from the constant region of an antibody heavy chain. In some embodiments, an Fc region includes a polypeptide comprising the constant region of an antibody excluding the first constant region immunoglobulin domain.

An Fc region may be a functionally equivalent analog of an Fc region. A functionally equivalent analog of an Fc region may be a variant Fc region, comprising one or more amino acid modifications to a wild-type or naturally existing Fc region. In some embodiments, variant Fc regions possess at least 50% homology with a naturally existing Fc region, with about 80% to 99% being preferred, including at least about 85% homology, at least about 90% homology, at least about 95% homology, at least about 96% homology, at least about 97% homology, at least 98% homology, or at least about 99% homology. Functionally equivalent analogs of an Fc region may comprise one or more amino acid residues added to or deleted from the N- or C-termini of the protein, preferably no more than 30, most preferably no more than 10. Functionally equivalent analogs of an Fc region include Fc regions operably linked to a fusion partner.

The terms "Fc fusion" or "Fc fusion protein", as used herein, include a protein wherein one or more proteins, polypeptides or small molecules is operably linked to an Fc region or derivative thereof. The term "Fc fusion" as used herein is intended to be synonymous with terms such as "Ig fusion", "Ig chimera", and "receptor globulin" (sometimes with dashes) as used in the prior art (Chamow et al., 1996, *Trends Biotechnol* 14:52-60; Ashkenazi et al., 1997, *Curr Opin Immunol* 9:195-200). An Fc fusion combines one or more Fc regions, or variant(s) thereof, of an immunoglobulin with a fusion partner, which in general can be any protein, polypeptide, peptide, or small molecule. In some embodiments, the role of the non-Fc part of an Fc fusion, i.e., the fusion partner, may be to mediate target binding, and thus it can be functionally analogous to the variable regions of an antibody.

A variety of linkers may be used in the present invention to covalently link Fc polypeptides to a fusion or conjugate partner or to generate an Fc fusion. As used herein, the terms "linker", "linker sequence", "spacer", "tethering sequence" or equivalents thereof refer to a molecule or group of molecules (such as a monomer or polymer) that connects two molecules and can serve to place the two molecules in a preferred configuration. A number of strategies may be used to covalently link molecules together. These include, but are not limited to, polypeptide linkages between N- and C-termini of proteins or protein domains, linkage via disulfide bonds, and linkage via chemical cross-linking reagents.

II. Vectors of the Invention

Figure 2:
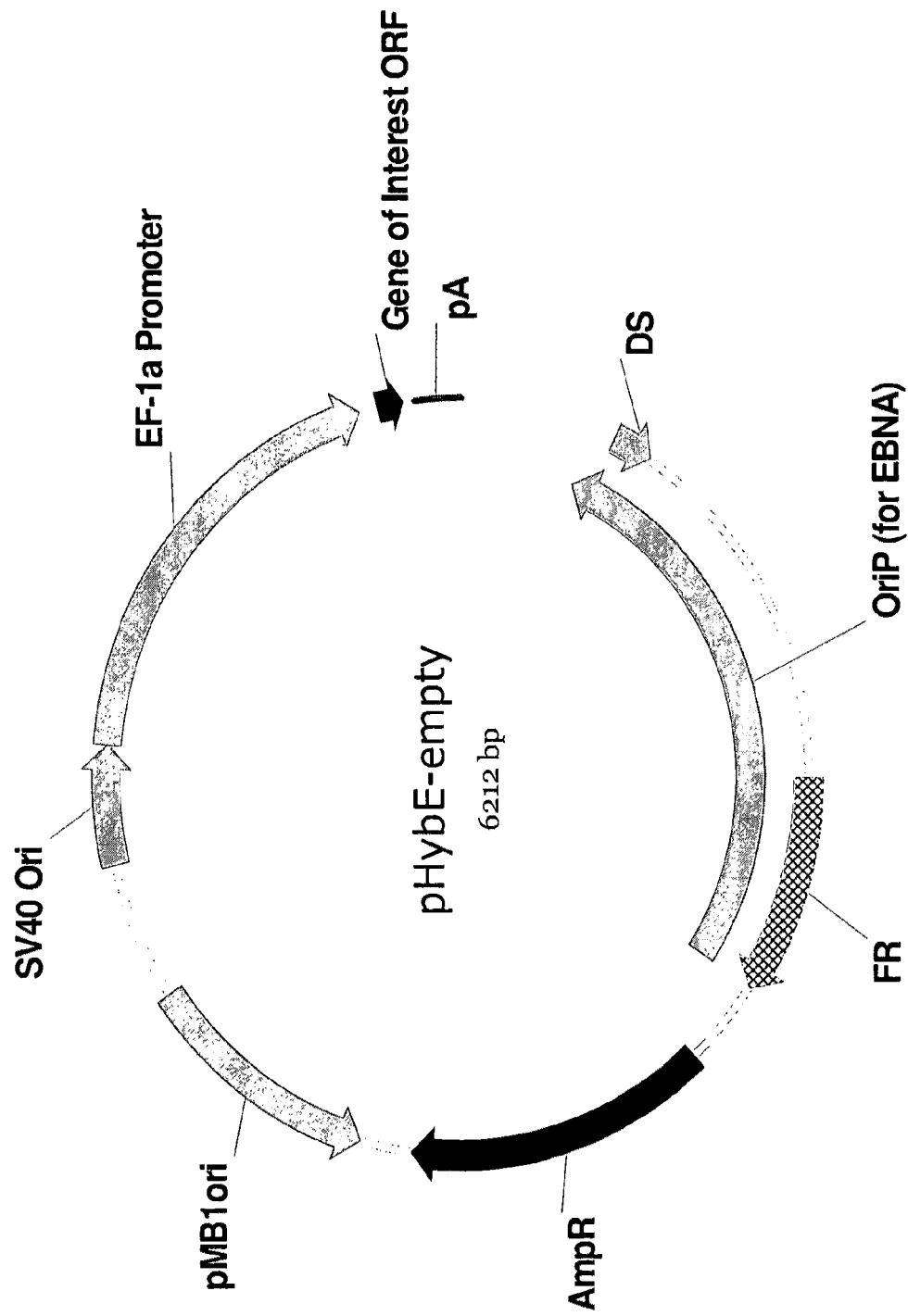
FIG. 2 shows a map of the empty pHyb-E vector. Features include a SV-40 eukaryotic origin of replication, an EF-1α eukaryotic promoter, an open reading frame (ORF) region for a gene of interest followed by a poly A signal (pA), a dyad symmetry element (DS), an Epstein Barr virus-derived eukaryotic origin of replication (OriP), a repeat region (FR), an ampicillin resistance marker (AmpR) and a bacterial origin of replication (pMB1ori).

The invention provides episomal vectors for expressing proteins in mammalian host cells. The vectors of the invention are based on the inclusion of two episomal origins of replication that allow the vector to be used in any cell line containing trans-acting replication initiation factors to either of the origins of replication. While the vector may also contain the replication initiation factor that binds the origin of replication, in a preferred embodiment the trans-acting replication factor is provided by the host cell. In addition, in one embodiment, the vectors of the invention provide efficient and effective means for production of antibodies and Fc fusion proteins, as the vectors contain heavy or light chain constant regions operably linked to a gene of interest. Examples of vectors of the invention are described in FIGS. 1, 2, and 8 to 25. In addition, sequences of exemplary vectors are provided in SEQ ID NOs: 1 to 32. FIGS. 1 and 2 (and corresponding SEQ ID NOs: 1 and 2) describe the "open" vector, i.e., the vector of the invention that does not contain antibody heavy or light chain constant regions and a gene of interest. FIGS. 8-25 provides maps of vectors of the invention which also comprise various murine or human constant regions, with sites for cloning a gene of interest.

The vector of the invention comprises at least two distinct origins of replication, e.g., OriP origin of replication derived from Epstein-Barr virus (EBV) and an SV40 origin of replication. The origin of replication may be derived from a DNA virus, more preferably from a DNA virus that allows for episomal replication, including origins of replication derived from, for example, Epstein-Barr virus, Herpes simplex virus, Herpesvirus Saimiri, Murine Gammaherpesvirus 68, Human Cytomegalovirus, Mouse Cytomegalovirus, Pseudorabiesvirus, Simian Virus 40, Polyoma virus, human BK virus, Bovine Papilloma virus, and Adeno-associated virus.

In one embodiment, the origin of replication is from Epstein-Barr virus, e.g., oriP, or functional parts thereof (examples of Epstein-Barr functional origins are described in Aiyar et al. (1998) *EMBO* Journal, 17:6394). The Epstein-Barr virus origin of replication (OriP) is composed of 2 main elements and multiple cis-acting elements that facilitate DNA synthesis by the cell and a viral maintenance element. The first of the two main elements contains a family of repeats (FR), which comprise the EBNA binding sites (shown in FIGS. 1 and 2). EBNA is the replication initiation factor that initiates replication of the vector via OriP (see Genbank accession number V01555 (gi:94734074) for EBNA sequence). The second element contained in OriP contains a so called dyad symmetry (DS) and its function is to serve as an origin recognition element. Generally, the DS and FR elements are spaced by several base pairs, typically 1000 bp. The relative orientation of OriP, and in particular of DS and FR, can be altered without affecting OriP function. The orientation of OriP, and in particular of DS and FR, relative to the other elements positioned on the expression vectors of the invention, can be altered without affecting OriP function. In a preferred embodiment of the invention, wherein the origin of replication is an Epstein-Barr virus origin of replication (OriP), and wherein the OriP comprises a family of repeats (FR) and a dyad symmetry (DS), the consecutive order is such that the DS element is between the gene of interest and the FR element. In one embodiment, the vector of the invention comprises an OriP (Epstein-Barr virus) origin of replication comprising nucleotides 1795 to 3545 of SEQ ID NO: 1, or sequences 80%, 85%, 90%, 95%, 96%, 97%, 98%, or 99% identical thereto.

In another embodiment, the vector comprises an SV40 origin of replication. The SV40 (Simian Virus 40) origin of replication (described, for examp-1e, in FIGS. 1 and 2 as "SV40 Ori") requires a single viral protein, the large T-antigen, for initiation of replication of the vector via this origin. The SV40 origin of replication may be used in episomal vectors to replicate and maintain said vector (see Calos (1996) *Trends Genetics* 12: 462; Harrison et al. (1994) *J Virol* 68:1913; Cooper et al. (1997) *PNAS* 94:6450; and Ascenzi-ono et al. (1997) *Cancer Lett* 118:135). In one embodiment, the vector of the invention comprises an SV40 origin of replication comprising nucleotides 5834 to 6140 of SEQ ID NO: 1, or sequences 80%, 85%, 90%, 95%, 96%, 97%, 98%, or 99% identical thereto.

Functional variants of origins of replication describe herein are also encompassed in the meaning of origin of replication according to the present application.

In addition to the episomal origins of replication, the vector of the invention may also have an origin of replication for replicating the vector in bacteria. An example, as shown in FIGS. 1 and 2 and not meant to be limiting, is the pMB 1 ori, which functions in *E. coli*.

The vector of the invention may also include a selectable marker. The selection marker may facilitate the cloning and amplification of the vector sequences in prokaryotic and eukaryotic organisms. In certain embodiments, the selection marker will confer resistance to a compound or class of compounds, such as an antibiotic. An exemplary selection marker that can be used with the nucleic acid molecules and expression systems of the present invention is one that confers resistance to puromycin. Alternatively, selection markers may be used that confer resistance to hygromycin, gpt, neomycin, zeocin, ouabain, blasticidin, kanamycin, geneticin, gentamicin, ampicillin, tetracycline, streptomycin, spectinomycin, nalidixic acid, rifampicin, chloramphenicol, zeocin or bleomycin, or markers such as DHRF, hisD, trpB, or glutamine synthetase.

Also included in the vector of the invention are regulatory elements that are necessary for transcription and translation of the gene of interest (as well as the selectable marker), into proteins. The transcriptional regulatory elements normally comprise a promoter 5' of the gene sequence to be expressed, transcriptional initiation and termination sites, and polyadenylation signal sequence. The term "transcriptional initiation site" refers to the nucleic acid in the construct corresponding to the first nucleic acid incorporated into the primary transcript, i.e., the mRNA precursor; the transcriptional initiation site may overlap with the promoter sequences. The term "transcriptional termination site" refers to a nucleotide sequence normally represented at the 3' end of a gene of interest or the stretch of sequences to be transcribed, that causes RNA polymerase to terminate transcription. The polyadenylation signal sequence, or poly-A addition signal provides the signal for the cleavage at a specific site at the 3' end of eukaryotic mRNA and the post-transcriptional addition in the nucleus of a sequence of about 100-200 adenine nucleotides (polyA tail) to the cleaved 3' end. The polyadenylation signal sequence includes the sequence AATAAA located at about 10-30 nucleotides upstream from the site of cleavage, plus a downstream sequence.

A regulatory element that may be included in the vector of the invention is a promoter. The promoter can be constitutive or inducible. An enhancer (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include the enhancer sequences as well (e.g., CMV IE P/E; SV40 P/E; MPSV P/E). Splice signals may be included where necessary to obtain spliced transcripts. To produce a secreted polypeptide, the selected sequence will generally include a signal sequence encoding a leader peptide that directs the newly synthesized polypeptide to and through the ER membrane where the polypeptide can be routed for secretion. The leader peptide is often but not universally at the amino terminus of a secreted protein and is cleaved off by signal peptidases after the protein crosses the ER membrane. The selected sequence will generally, but not necessarily, include its own signal sequence. Where the native signal sequence is absent, a heterologous signal sequence can be fused to the selected sequence. Numerous signal sequences are known in the art and available from sequence databases such as GenBank and EMBL. Translational regulatory elements include a translational initiation site (AUG), stop codon and poly A signal for each individual polypeptide to be expressed. An internal ribosome entry site (IRES) is included in some constructs.

Promoters for use in the present invention include viral, mammalian and yeast promoters, e.g., murine beta globin promoter, ubiquitin promoter, polyoma promoter, mammalian cytomegalovirus (CMV) promoter, yeast alcohol oxidase, phosphoglycerokinase promoter, lactose inducible promoters, galactosidase promoter, adeno-associated viral promoter, poxvirus promoter, retroviral promoters, rous sarcoma virus promoter, adenovirus promoters, SV40 promoter, hydroxymethylglutaryl coenzyme A promoter, thymidine kinase promoter, H5R poxvirus promoters, adenovirus type 2MPC late promoter, alpha-antrypsin promoter, fox IX promoter, immunoglobulin promoter, CFTR surfactant promoter, albumin promoter and transferrin promoter. A promoter selected for use with nucleic acids and expression vectors of the invention can provide for (1) high levels of expression, e.g., in driving expression of the gene of interest, or (2) decreased levels of expression (after weakening by modification), e.g., in driving expression of the selectable marker gene. Preferably, the promoter driving the gene of interest is a strong promoter, e.g., ubiquitin, CMV, EF-1α and SR alpha promoters, to increase expression and promote correct splicing of the product of interest.

In one embodiment, the vector of the invention includes a CMV promoter to drive expression of the gene of interest. Use of the CMV promoter is described in U.S. Pat. Nos. 5,385,839 and 5,849,522, incorporated by reference herein. In one embodiment, the CMV promoter used in the vector of the invention is operably linked to the gene of interest and nucleotides 1 to 608 of SEQ ID NO: 1. Also included in the scope of the invention are CMV promoter sequences that are 80%, 85%, 90%, 95%, 96%, 97%, 98%, or 99% identical to nucleotides 1 to 608 of SEQ ID NO: 1.

Another promoter that may be used in the vector of the invention is a promoter from elongation-factor-1a (EF-1α), e.g., human EF-1α. The sequence for the human EF-1α promoter can be found at GenBank Accession No. NM_001402 (gi:83367078). In one embodiment, the vector of the invention comprises nucleotides 76 to 1267 of SEQ ID NO: 2. Also included in the scope of the invention are EF-1α promoter sequences that are 80%, 85%, 90%, 95%, 96%, 97%, 98%, or 99% identical to nucleotides 1 to 608 of SEQ ID NO: 1.

In one embodiment, the vector comprises a SwaI restriction site for cloning purposes.

Typically, genes (e.g., selectable markers and GOIs) are sandwiched between a promoter and a polyadenylation site. The poly A sequence used can be from the gene of interest (i.e., the native poly A sequence can be used) or a heterologous poly A sequence can be used (i.e., from a gene different from the GOI), e.g., BGH polyA and SV40 polyA. An mRNA is transcribed from the promoters and stabilized by the polyadenylation signals located 3' to the coding regions. Poly A signals are well-known in the art, and can be selected based on suitability for use with the vectors and host cells employed in the present invention. Examples of poly A signals that can be used include human BGH poly A, SV40 poly A, human beta actin polyA, rabbit beta globin polyA, and immunoglobulin kappa polyA.

The vector of the invention includes a gene of interest, which the vector as a means for expressing in cell culture. The gene of interest may encode a functional nucleic acid molecule (e.g., an RNA, such as an antisense RNA molecule) or, more typically, encodes a peptide, polypeptide or protein for which increased production is desired. Vectors of the invention can have a gene of interest, inserted at an insertion site such that the gene of interest is operably linked to a regulatory nucleic acid sequence that allows expression of the gene of interest. In one embodiment, the vectors of the invention can be used to express essentially any gene of interest, particularly genes encoding recombinant proteins having therapeutically useful activity or other commercially relevant applications.

Non-limiting examples of genes of interest include hormones, chemokines, cytokines, lymphokines, antibodies, receptors, adhesion molecules, and enzymes. A non-exhaustive list of desired products includes, e.g., human growth hormone, bovine growth hormone, parathyroid hormone, thyroid stimulating hormone, follicle stimulating hormone growth, luteinizing hormone; hormone releasing factor; lipoproteins; alpha-1-antitrypsin; insulin A-chain; insulin B-chain; proinsulin; calcitonin; glucagon; molecules such as renin; clotting factors such as factor VIIIC, factor IX, tissue factor, and von Willebrands factor; anti-clotting factors such as Protein C, atrial natriuretic factor, lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A- or B-chain; prorelaxin; mouse gonadotropin-associated peptide; DNase; inhibin; activin; receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), growth factors including vascular endothelial growth factor (VEGF), nerve growth factor such as NGF-.beta.; platelet-derived growth factor (PDGF); fibroblast growth factor such as aFGF, bFGF, FGF-4, FGF-5, FGF-6; epidermal growth factor (EGF); transforming growth factor (TGF) such as TGF-alpha and TGF-beta, including TGF-131, TGF-β2, TGF-β3, TGF-β4, or TGF-β5; insulin-like growth factor-I and -II (IGF-I and IGF-II); des(1-3)-IGF-I (brain IGF-1), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-33; superoxide dismutase; T-cell receptors; surface membrane proteins, e.g., HER2; decay accelerating factor; viral antigen such as, for example, a portion of the AIDS envelope; transport proteins; homing receptors; addressins; receptors for growth factors, cytokines, chemokines, and lymphokines; regulatory proteins; antibodies; chimeric proteins such as immunoadhesins and fragments of any of the above-listed polypeptides. Examples of bacterial polypeptides or proteins include, e.g., alkaline phosphatase and .beta.-lactamase.

In one aspect of the invention, the vector comprises an antibody heavy or light chain region that is operably linked to the insertion site. Examples of vectors comprising two episomal origins of replication and a light or heavy chain constant region of an antibody, can be found in SEQ ID NOs: 3-32.

One embodiment of the invention includes vectors that can be used to express a complete antibody, i.e., a variable region linked to the constant region for either the heavy or light chain. Thus, the gene of interest may encode an antibody heavy chain or light chain variable region, which can be of any antibody type, e.g., murine, chimeric, humanized, and human. A gene of interest encoding a heavy chain or light chain variable region may include the full length variable region, or alternatively, may encode only a fragment of the heavy chain or light chain, e.g., the antigen binding portion region. In one embodiment, the gene of interest encodes a murine or human antibody variable region. In such an instance, the constant region may be matched to the species of the variable region (SEQ ID NOs: 3-8, 27 and 28 encode murine constant regions, while SEQ ID NOs: 9-26 and 29-32 encode human constant regions).

In one embodiment, the vector of the invention includes a nucleic acid sequence encoding an antibody heavy constant region having certain isotype and/or allotype characteristics. The heavy chain constant region may, for example, be a gamma isotype (IgG), such as gamma 1, gamma 2, gamma 3, or gamma 4. In one embodiment, the heavy chain gamma 1 constant region is a certain allotype, including, but not limited to, allotypes z, a and z, non-a. The z, a, allotype is also known as G1m17 and G1m1 allotypes, and corresponds to IGHG1 with Lys at position 214 (within CH1), Asp at 356 (CH3), and Leu at 358 (CH3) (numbering according to the EU number system). The z, non-a allotype, also known as G1m17, and nG1m1 allotypes, corresponds to IGHG1 with Lys at position 214 (within CH1), Glu at 356 (CH3), and Met at 358 (CH3) (numbering according to the EU number system).

In another embodiment, the heavy chain gamma 2 constant region (hcG2) is a certain allotype, including, but not limited to, n− or n+. The n+ allotype of hcG2, also known as G2m (n) or G2m (23), corresponds to IGHG2 with Thr at position 189 in CH1 and Met at position 282 (numbering according to the EU number system). The n− allotype of hcG2, also known as G2m (n−), corresponds to IGHG2 with Pro at position 189 in CH1 and Val at position 282 (numbering according to the EU number system). Additional details of the n+ and n− allotypes are described in Hougs et al. (2001) *Immunogenetics* 52:242 and Brusco et al. (1995) *Immunogenetics* 42:414.

In other embodiments, the heavy chain constant region may be an IgM, IgA (IgA1 or IgA2), IgD, or IgE isotype.

In one embodiment, the heavy chain constant region may have the following human isotype and allotype characteristics: gamma 1, z, a; gamma 1, z, non-a; gamma 2, n+; gamma 2, n−; or gamma 4. In one embodiment, the isotype/allotype gamma 1, z, non-a may include a mutation at position 234 of the heavy chain constant region. In a further embodiment, the isotype/allotype gamma 1, z, non-a may include mutations at position 234 and 235 or 234 and 237 of the heavy chain constant region. Examples of such vectors are provided in FIGS. 8 to 25.

In another example, the light chain constant region encoded in the vector of the invention may comprise a kappa isotype or lambda isotype.

The constant regions encoded by the vector of the invention are not limited to human, but may instead include murine or other species of constant regions. In one embodiment, the expression vector of the invention comprises a nucleic acid encoding a heavy chain constant region that is either a murine gamma 1 isotype or a murine gamma 2a isotype, or a light chain constant region that is a murine kappa isotype.

Two vectors of the invention, pHybC and pHybE, are empty vectors in that these vectors do not contain constant regions, and may be used for cloning genes of interest. Descriptions of pHybC and pHybE are provided below, and maps of these vectors can be found in FIGS. 1 and 2.

pHybC

The pHybC vector (empty) contains two viral origins of replication, such that the vector may be replicated in different cell lines. pHybC contains the following elements: an SV40 origin of replication ("SV40 Ori"), which allows for vector plasmid replication in cells expressing the large T antigen protein of SV40 (e.g., a COS7 cell); a CMV promoter ("pCMV") operably linked to the insertion site for a gene of interest; a Tripartite leader sequence (TPL); a splice donor site (SD); an Adenovirus major late enhancer element (enh MLP); a splice acceptor site (SA); an open reading frame (ORF) region for a gene of interest followed by a poly A signal (pA); a dyad symmetry element (DS); an Epstein Barr virus-derived eukaryotic origin of replication (OriP), which permits replication of the vector plasmid in cells expressing the viral EBNA-1 protein (e.g., HEK-293-6E cells); a repeat region (FR); an ampicillin resistance marker (AmpR); and a bacterial origin of replication (pMB1ori). The pHybC vector utilizes the pCMV promoter, one of the strongest promoter elements available. A vector map of pHybC (empty) is described in FIG. 1. The nucleic acid sequence of the pHybC vector is set forth in SEQ ID NO:1.

pHybE

The pHybE vector (empty) contains two origins of replication, such that the vector may be replicated in different cell lines. pHybE contains the following elements: an SV40 origin of replication ("SV40 Ori"), which allows for vector plasmid replication in cells expressing the large T antigen protein of SV40 (e.g., a COS7 cell); an EF-1α eukaryotic promoter operably linked to the insertion site for a gene of interest; an open reading frame (ORF) region for a gene of interest followed by a poly A signal (pA); a dyad symmetry element (DS); an Epstein Barr virus-derived eukaryotic origin of replication (OriP); a repeat region (FR); an ampicillin resistance marker (AmpR); and a bacterial origin of replication (pMB1ori) A vector map of pHybE (empty) is described in FIG. 2. pHybE is distinguished from pHybC in that it pHybE contains an EF-1α promoter operably linked to the insertion site for the gene or interest, while pHybC contains a CMV promoter. The nucleic acid sequence of the pHybE vector is set forth in SEQ ID NO:2.

The below-mentioned vectors are based on either pHybE or pHybC, and additionally contain immunoglobulin heavy or light chain constant regions. As with pHybE and pHybC, the following vectors have cloning sites that may be used for the insertion of a gene of interest, e.g., a coding sequence of a immunoglobin variable region, or an antigen binding portion thereof. In each instance, the cloning site for the gene of interest is adjacent to the coding sequence of a constant region contained within the vector. Thus, the vectors below may be used to express antibody light or heavy chains containing a particular constant region and a particular variable region. As with pHybC and pHybE, each of the below-mentioned vectors of the invention contain multiple origins of replication, such that the antibody light or heavy chain may be expressed in different cell lines using the same vector. Descriptions of additional vectors of the invention are described below (see also vector maps provided in FIGS. 8 to 25). It should be noted that pHyb vectors described as version 1 (V1) have an additional Swa I site upstream of the Srf I restriction site, whereas pHyb vectors described as version 2 (V2) do not have the additional Swa I site.

Vectors of the Invention Comprising Murine Constant Regions pHybC-mCg2a

Figure 8:
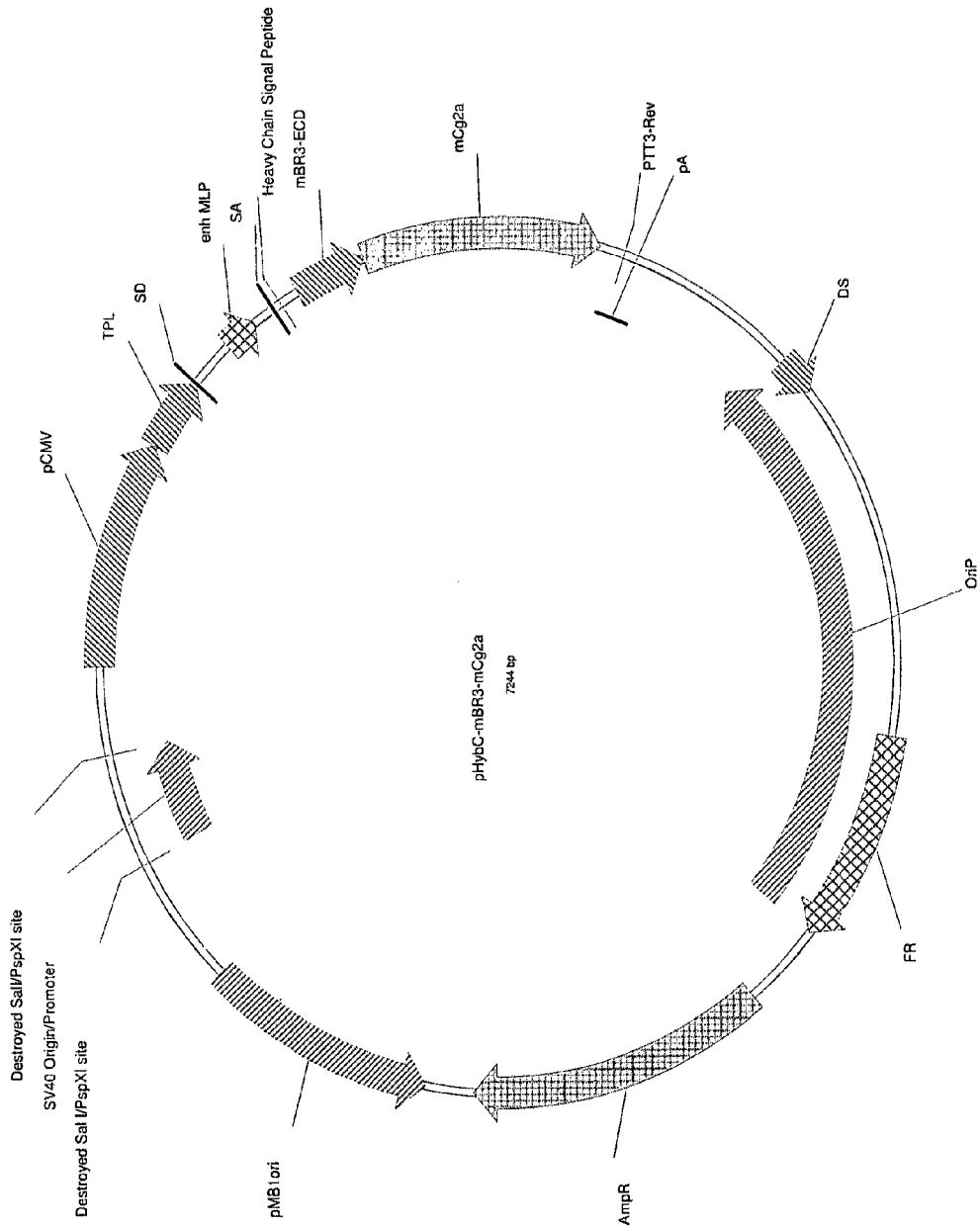
FIG. 8 shows a map of the pHybC-mBR3-mCg2a vector (also referred to as "pHybC-mBR3-Fc").

Vector pHybC-mCg2a is based on the pHybC vector (thus contains all of the elements described above for pHybC). This vector also comprises the murine immunoglobulin coding sequence for the gamma 2a heavy chain constant region. Thus, in one embodiment, the pHybC-mCg2a vector may be used to express an antibody heavy chain comprising an immunoglobulin heavy chain variable region (or portion thereof) and a murine gamma 2 heavy chain constant region. Alternatively, pHybC-mCg2 may be used to express a gene of interest fused to a gamma 2 heavy chain constant region, e.g., an Fc fusion protein. FIG. 8 shows a map of the pHybC-mBR3-mCg2a which comprises the coding sequence for the extracellular domain (ECD) of the murine BR3 protein as the gene of interest. The nucleic acid sequence of pHybC-mBR3-mCg2a is set forth in SEQ ID NO:27.

pHybE-mCk

Figure 9:
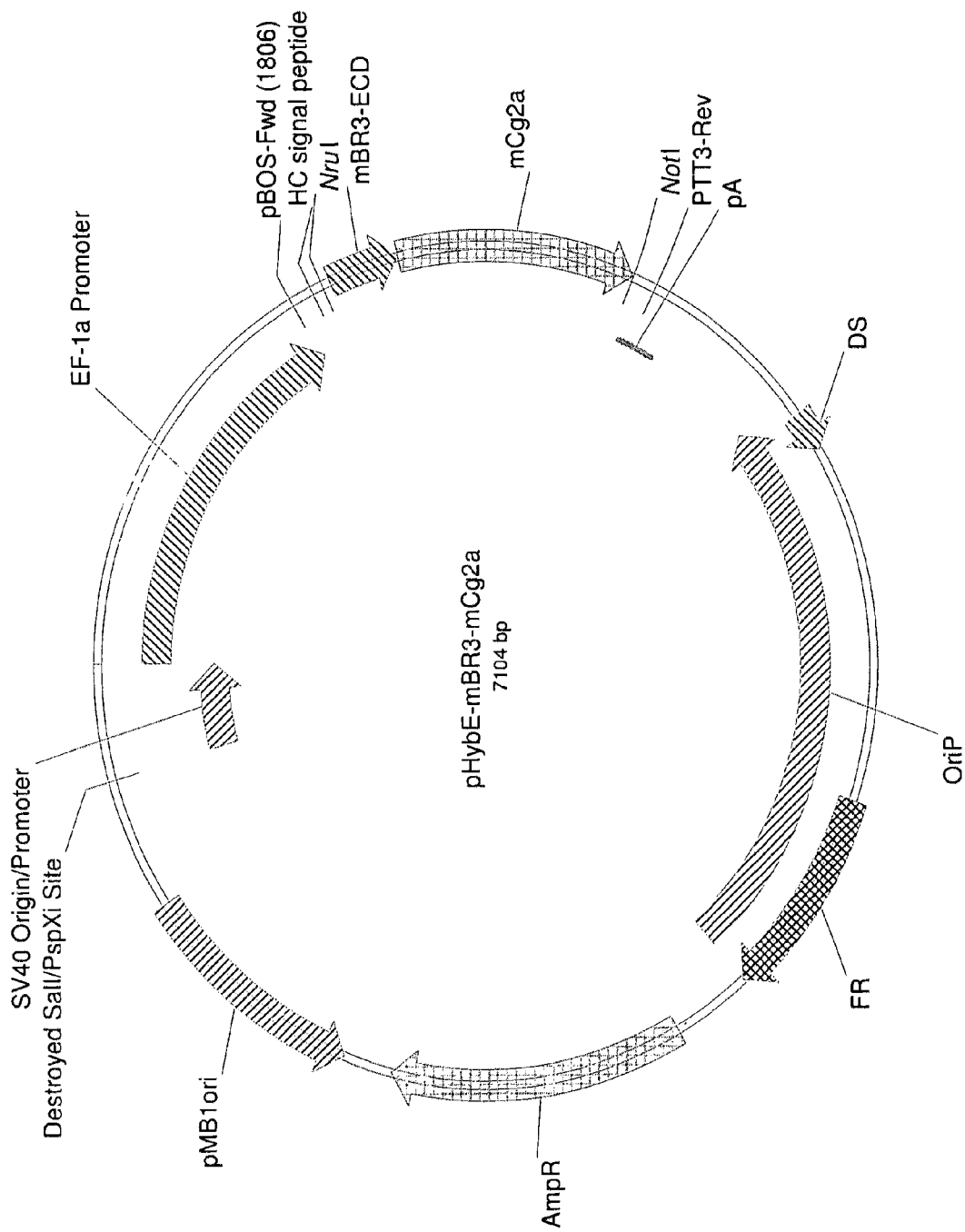
FIG. 9 shows a map of the pHybE-mBR3-mCg2a vector (also referred to as "pHybE-mBR3-Fc").
Figure 10:
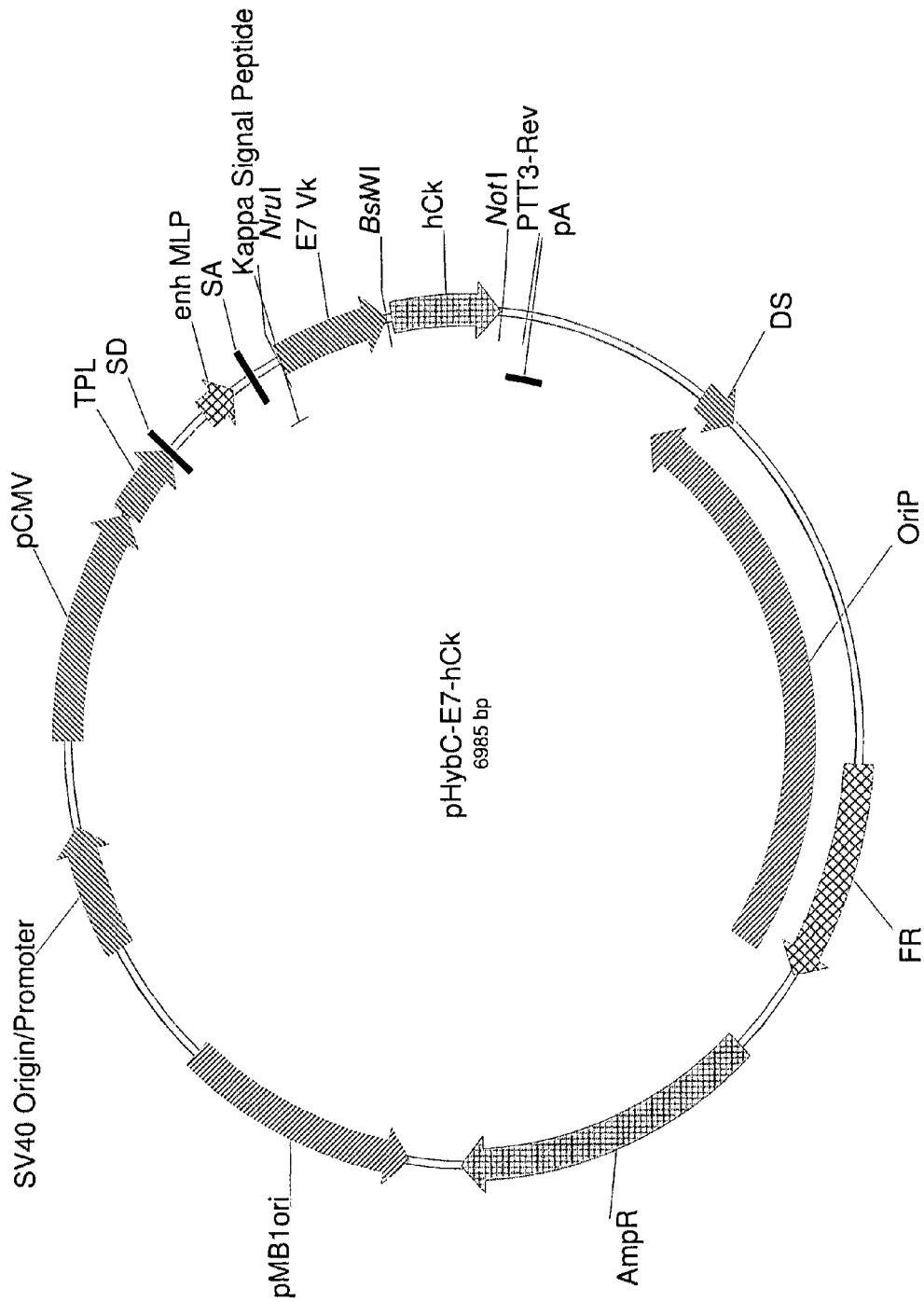
FIG. 10 shows a map of the pHybC-E7-hCk vector (also referred to as "pHybC-E7").
Figure 11:
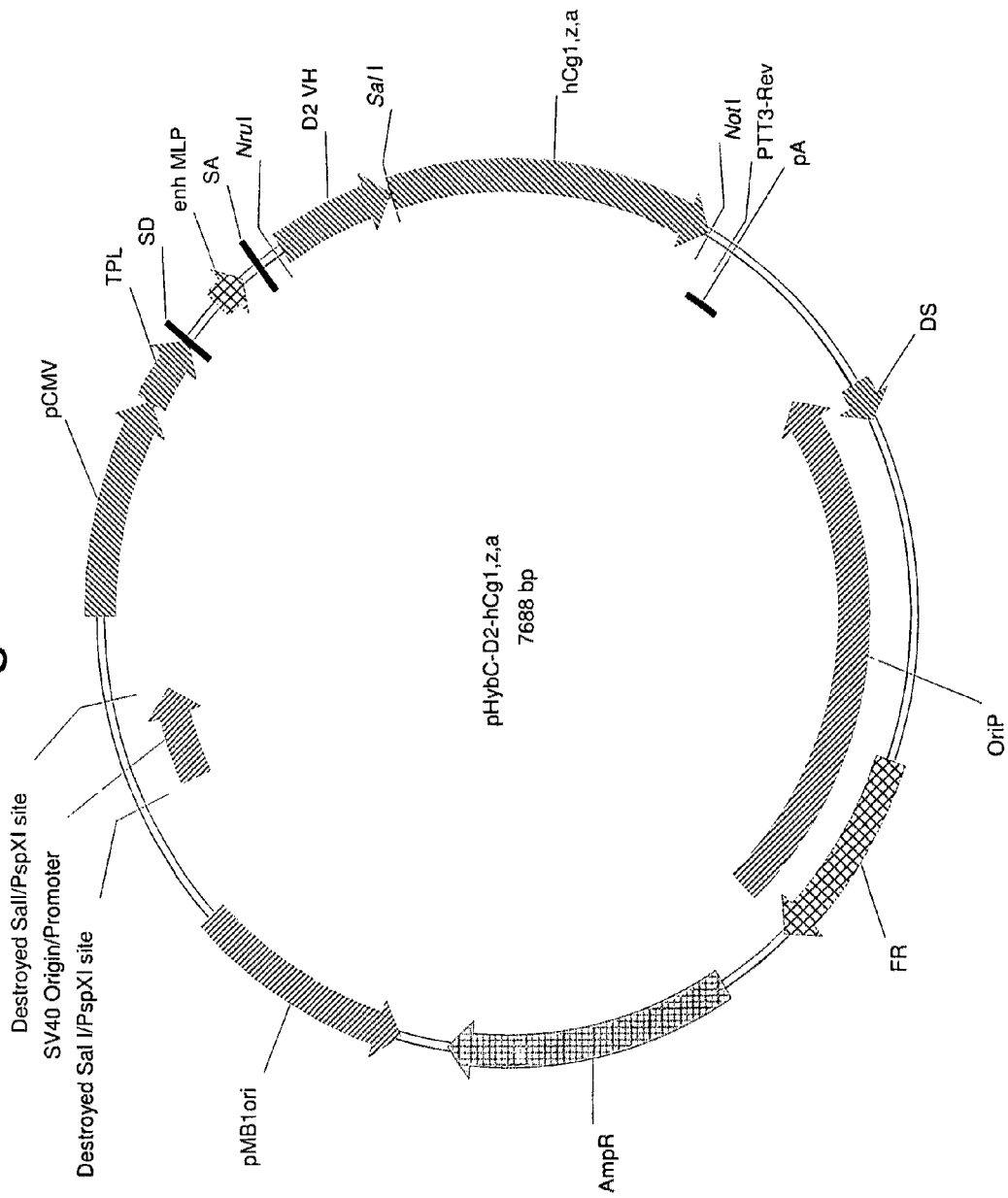
FIG. 11 shows a map of the pHybC-D2-hCg1,z,a vector (also referred to as "pHybC-D2").
Figure 12:
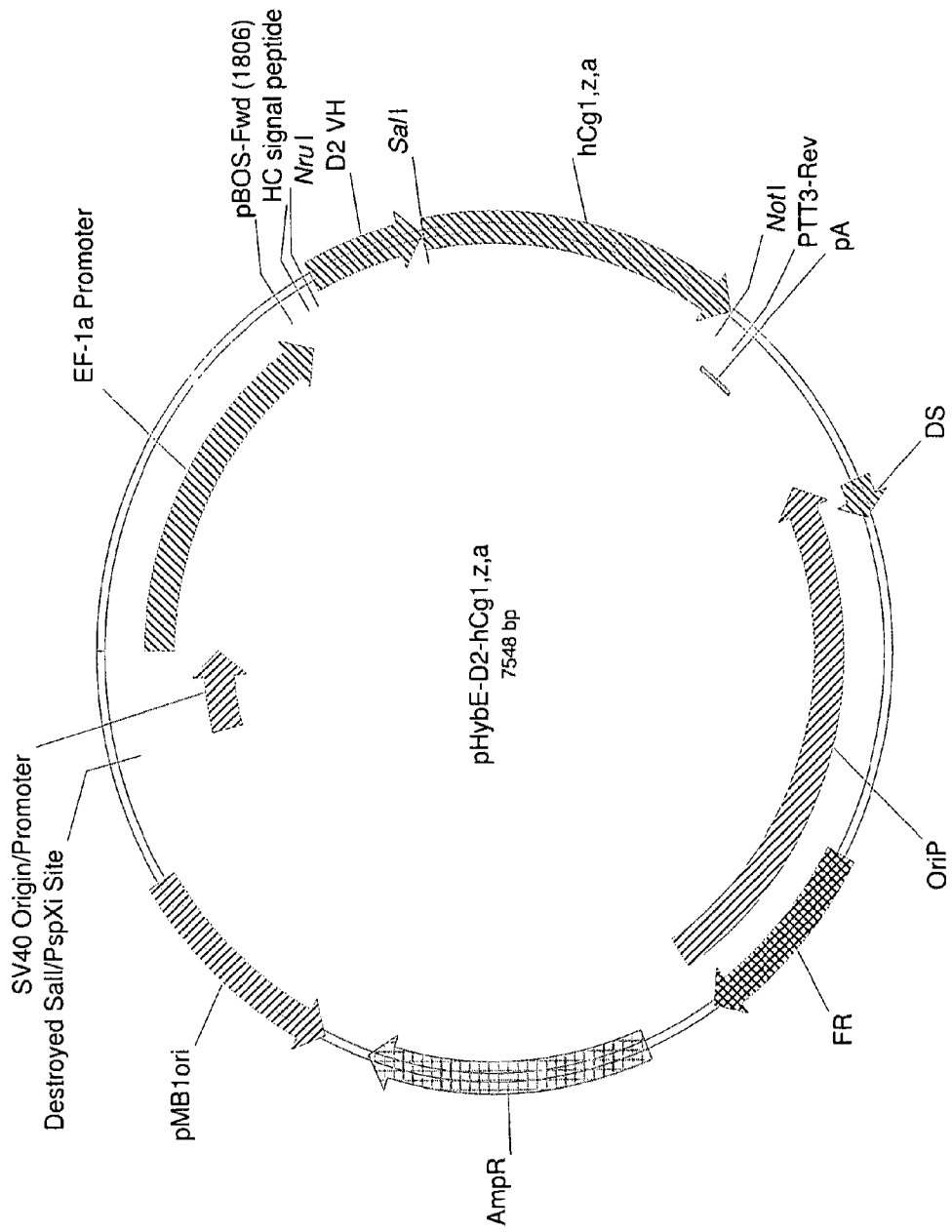
FIG. 12 shows a map of the pHybE-D2-hCg1,z,a vector (also referred to as "pHybE-D2").
Figure 13:
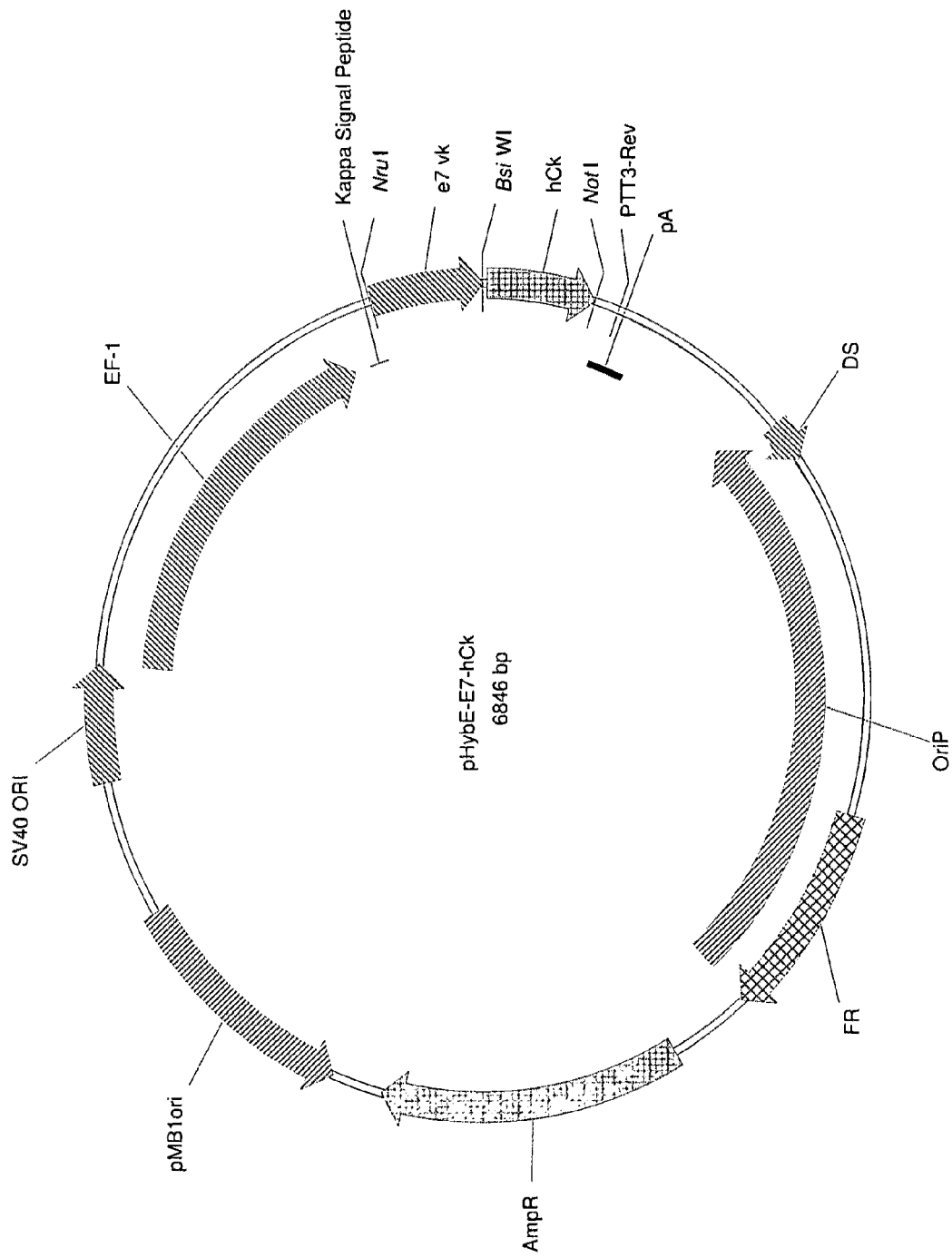
FIG. 13 shows a map of the pHybE-E7-hCk vector (also referred to as "pHybE-E7").
Figure 14:
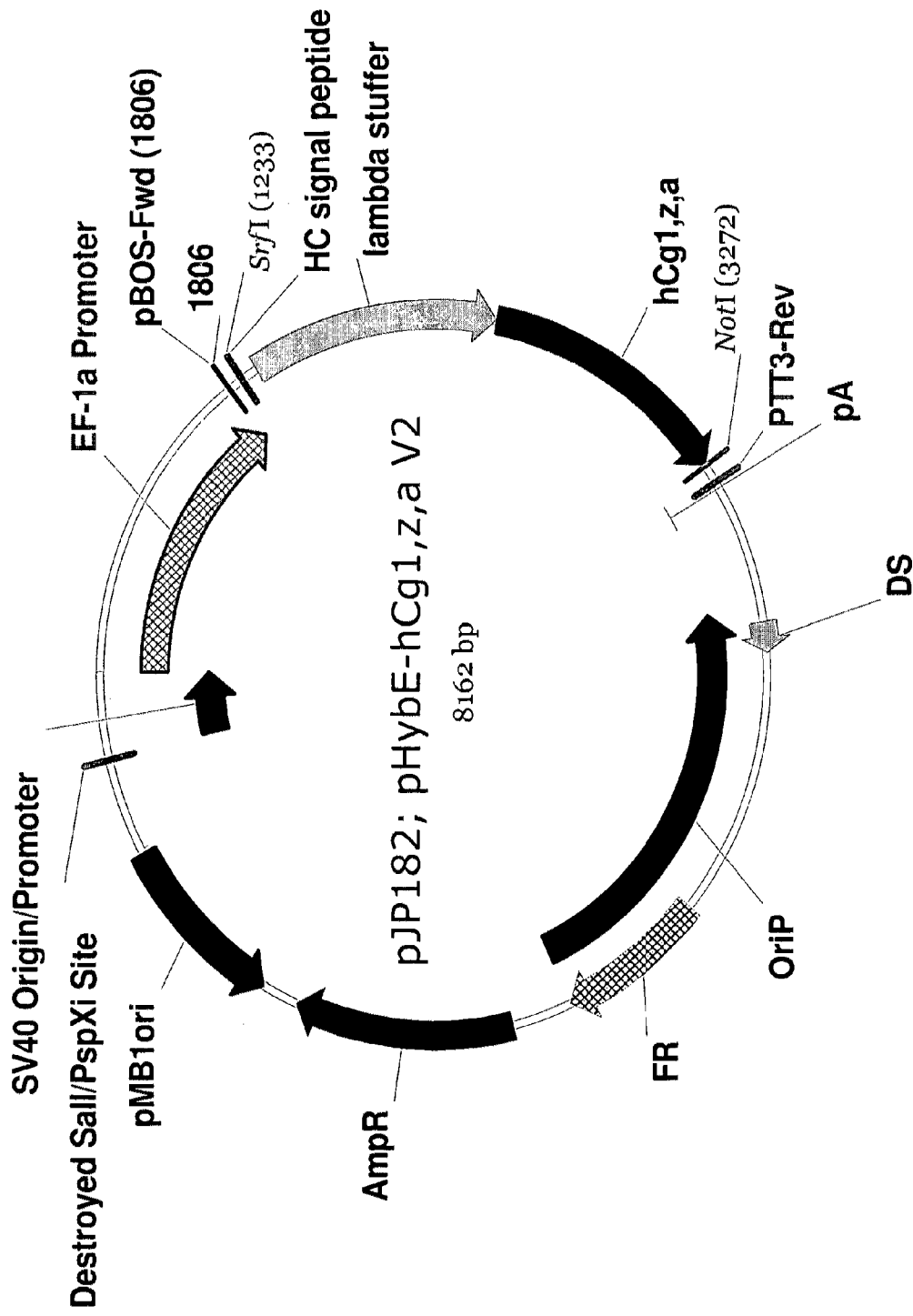
FIG. 14 shows a map of pHybE-hCg1,z,a V2 (also referred to as "pJP182").
Figure 15:
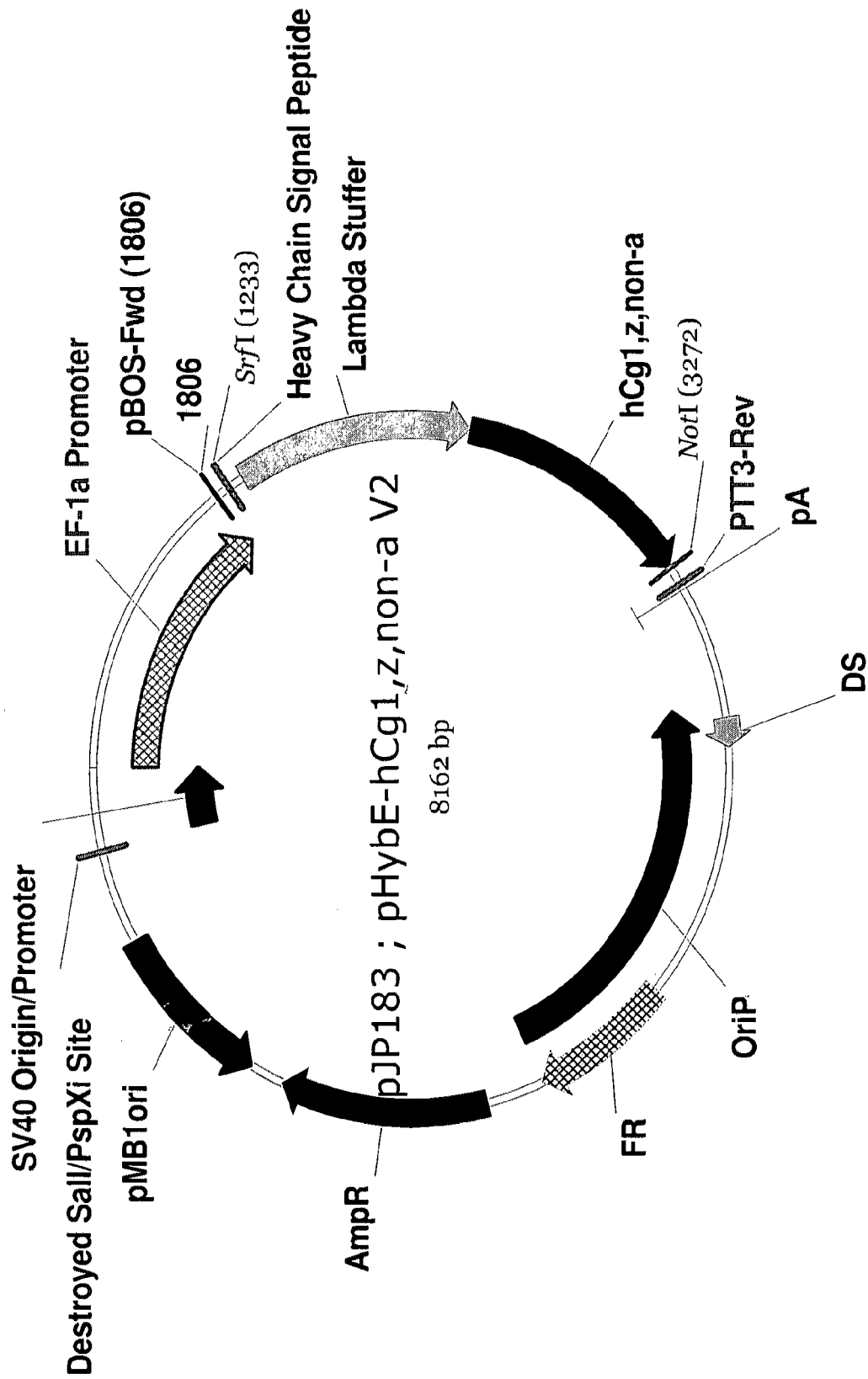
FIG. 15 shows a map of pHybE-hCg1,z,non-a V2 (also referred to as "pJP183").
Figure 16:
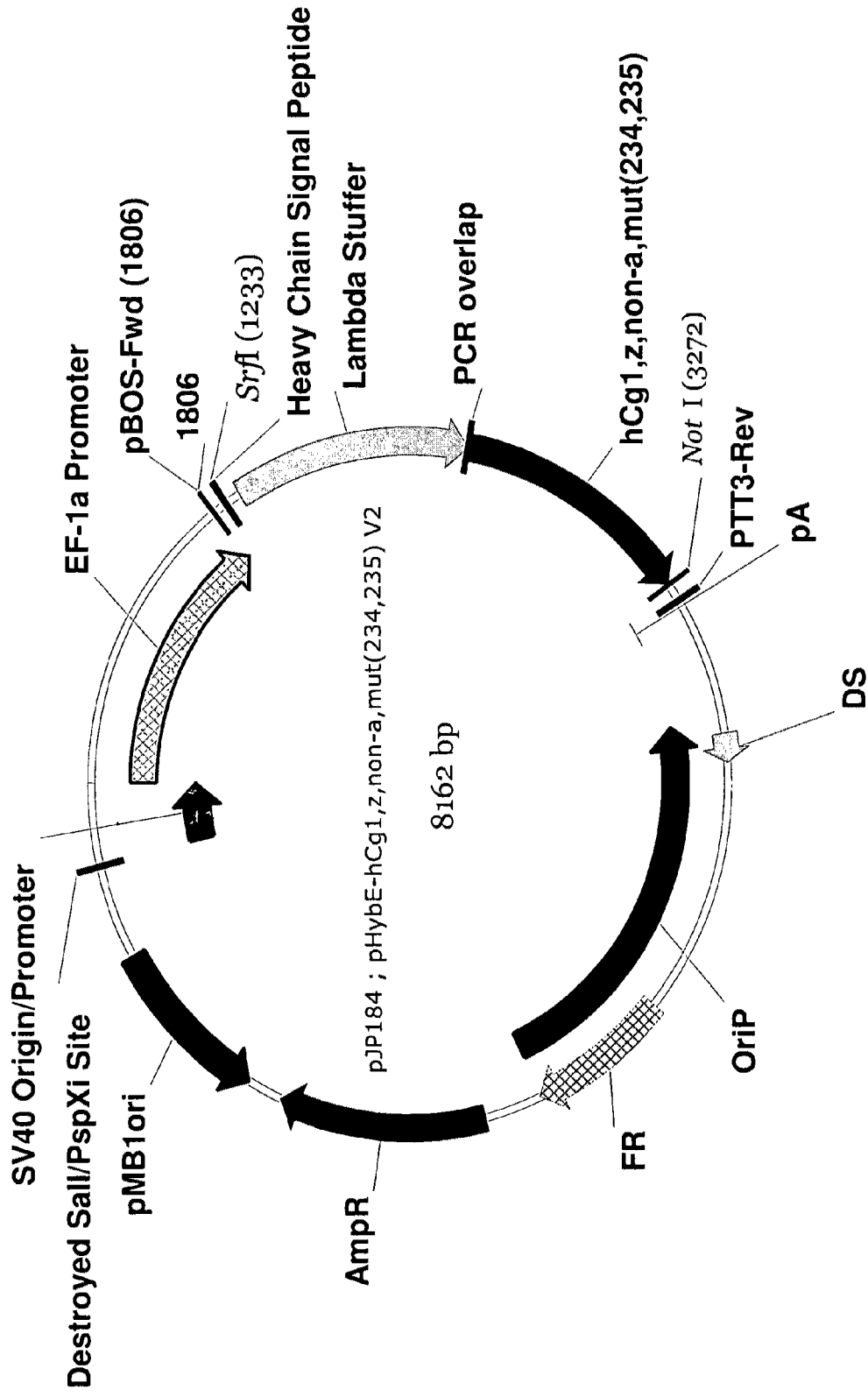
FIG. 16 shows a map of pHybE-hCg1,z,non-a,mut (234, 235) V2 (also referred to as "pJP184").
Figure 17:
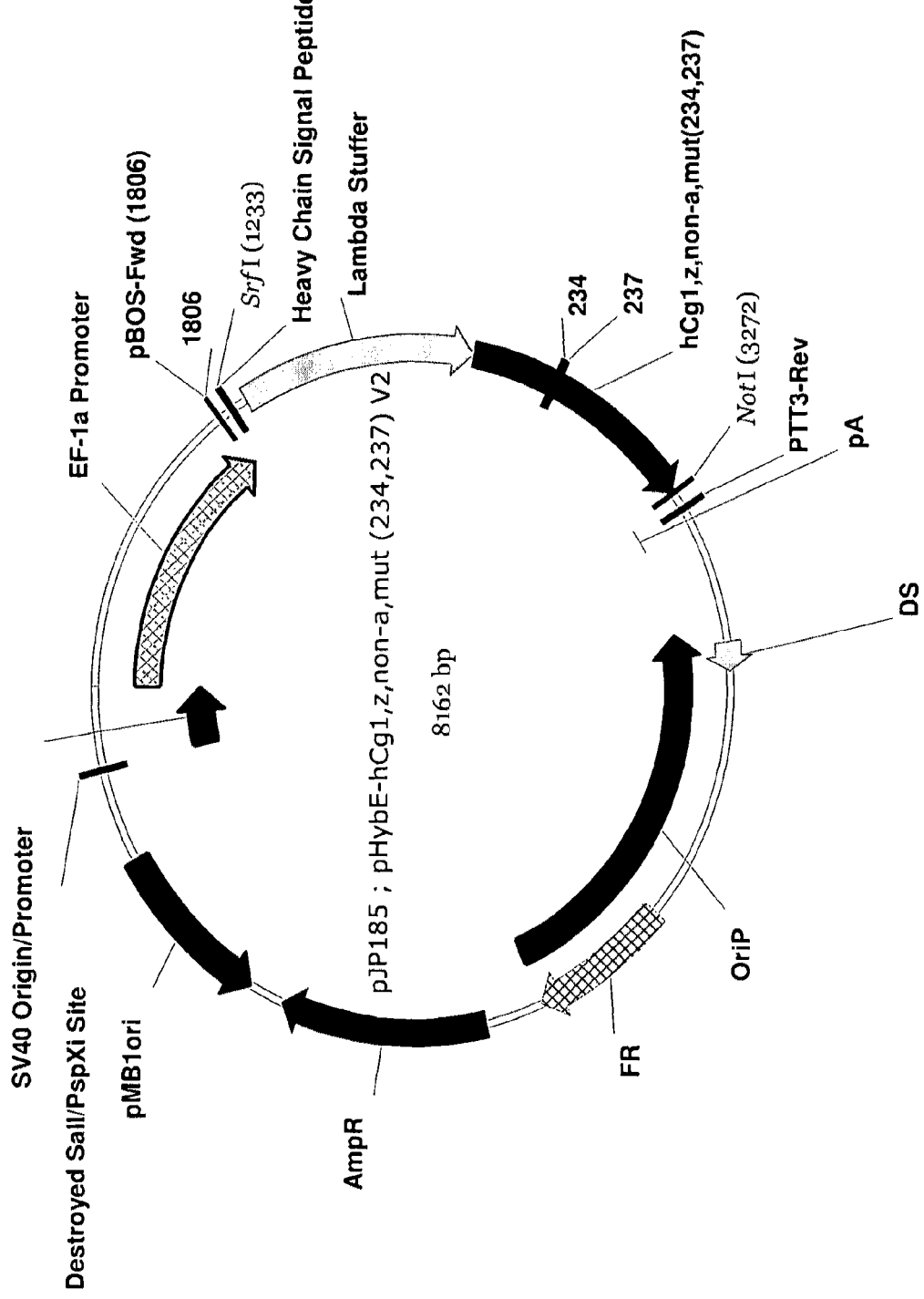
FIG. 17 shows a map of pHybE-hCg1,z,non-a,mut (234, 237) V2 (also referred to as "pJP185").
Figure 18:
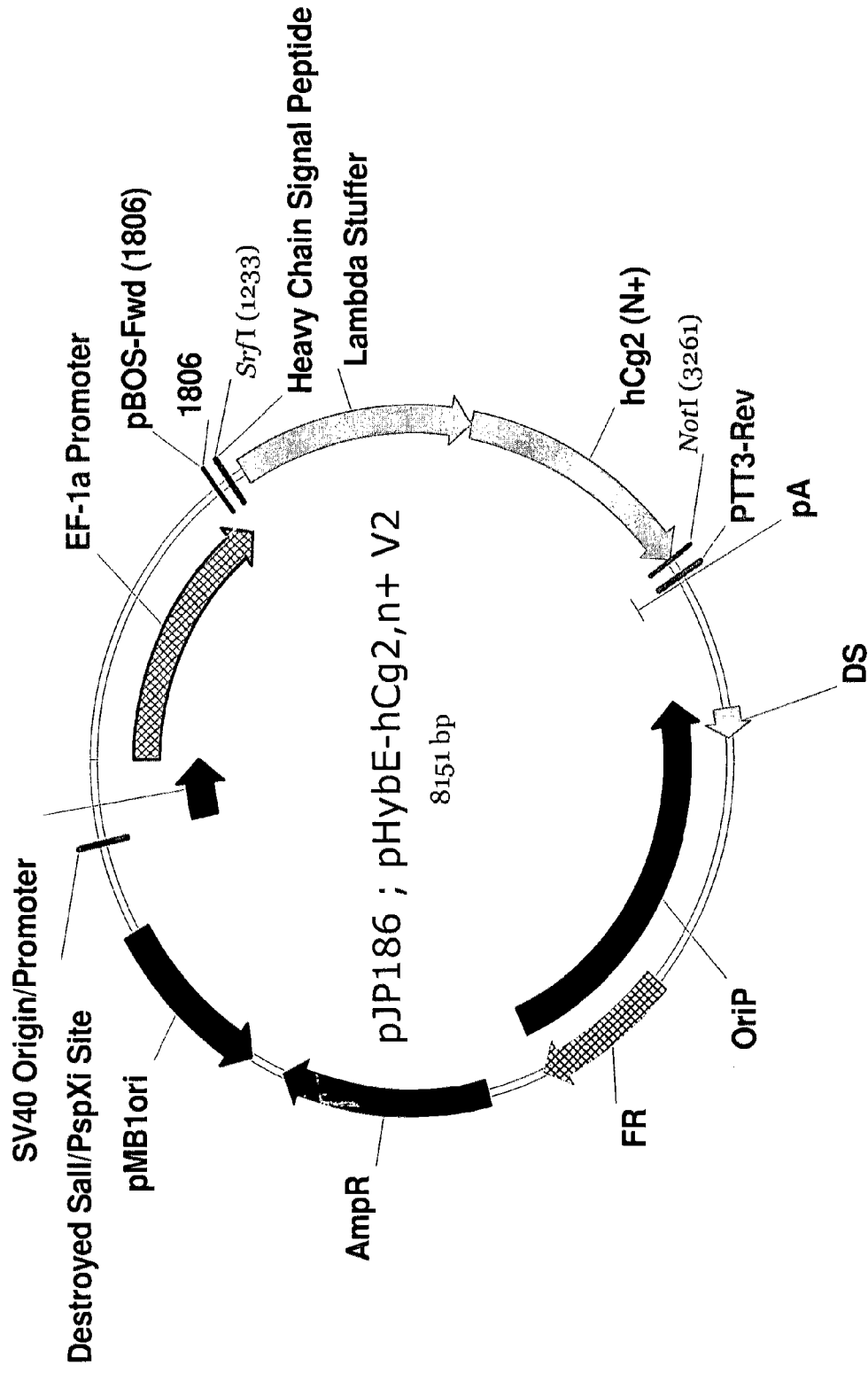
FIG. 18 shows a map of pHybE-hCg2,n+ V2 (also referred to as "pJP186").
Figure 19:
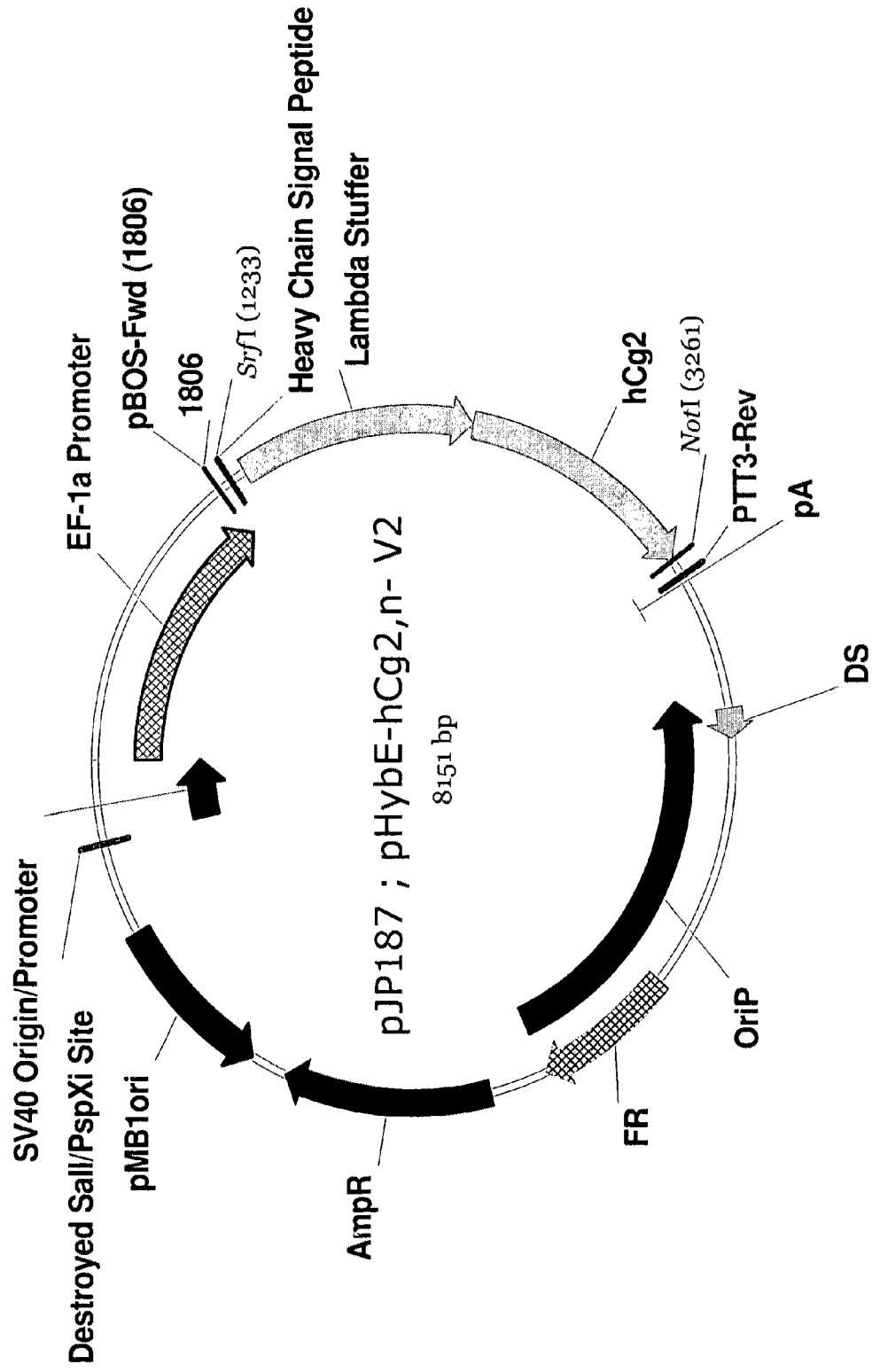
FIG. 19 shows a map of pHybE-hCg2,n− V2 (also referred to as "pJP187").
Figure 20:
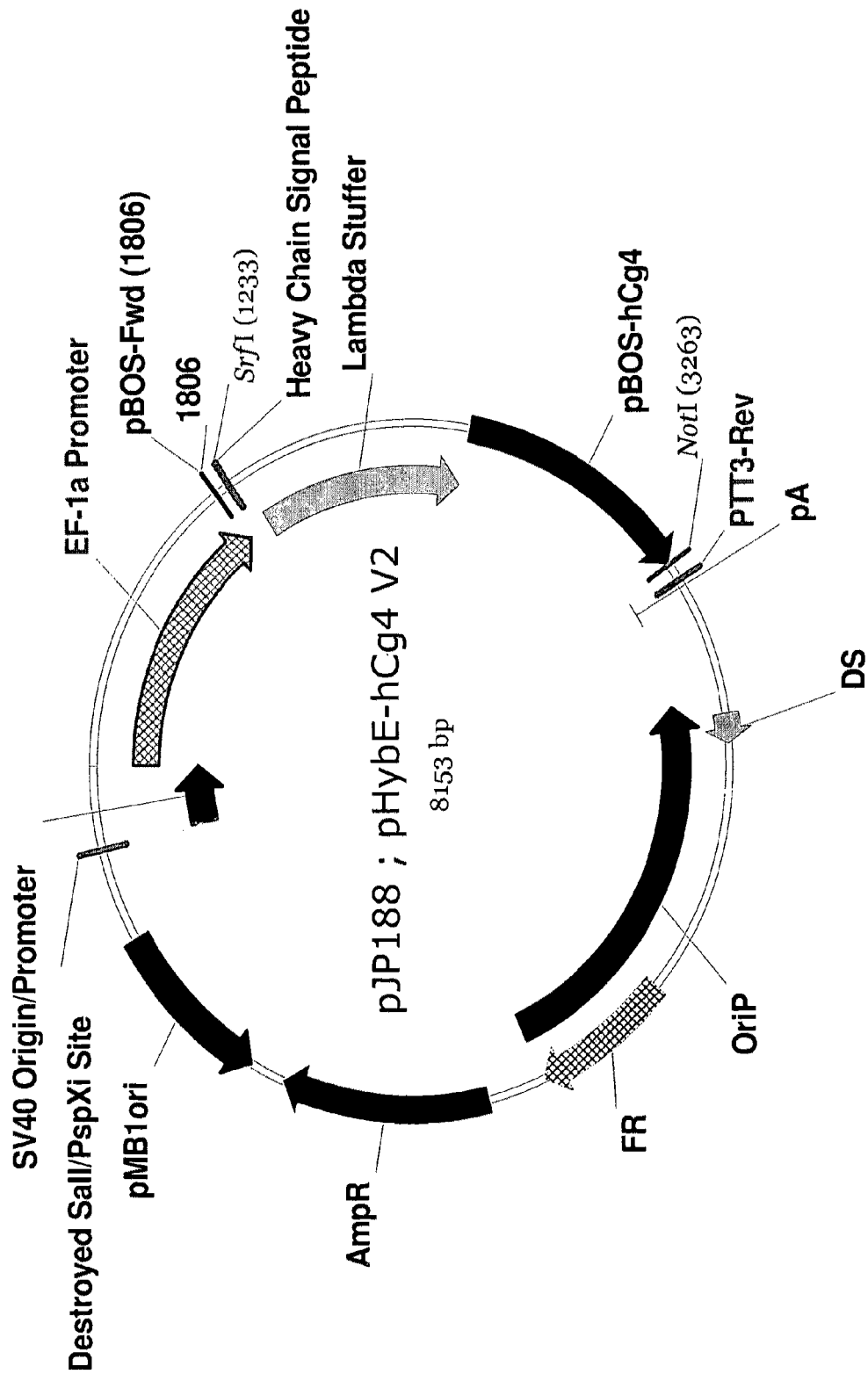
FIG. 20 shows a map of pHybE-hCg4 V2 (also referred to as "pJP188").
Figure 21:
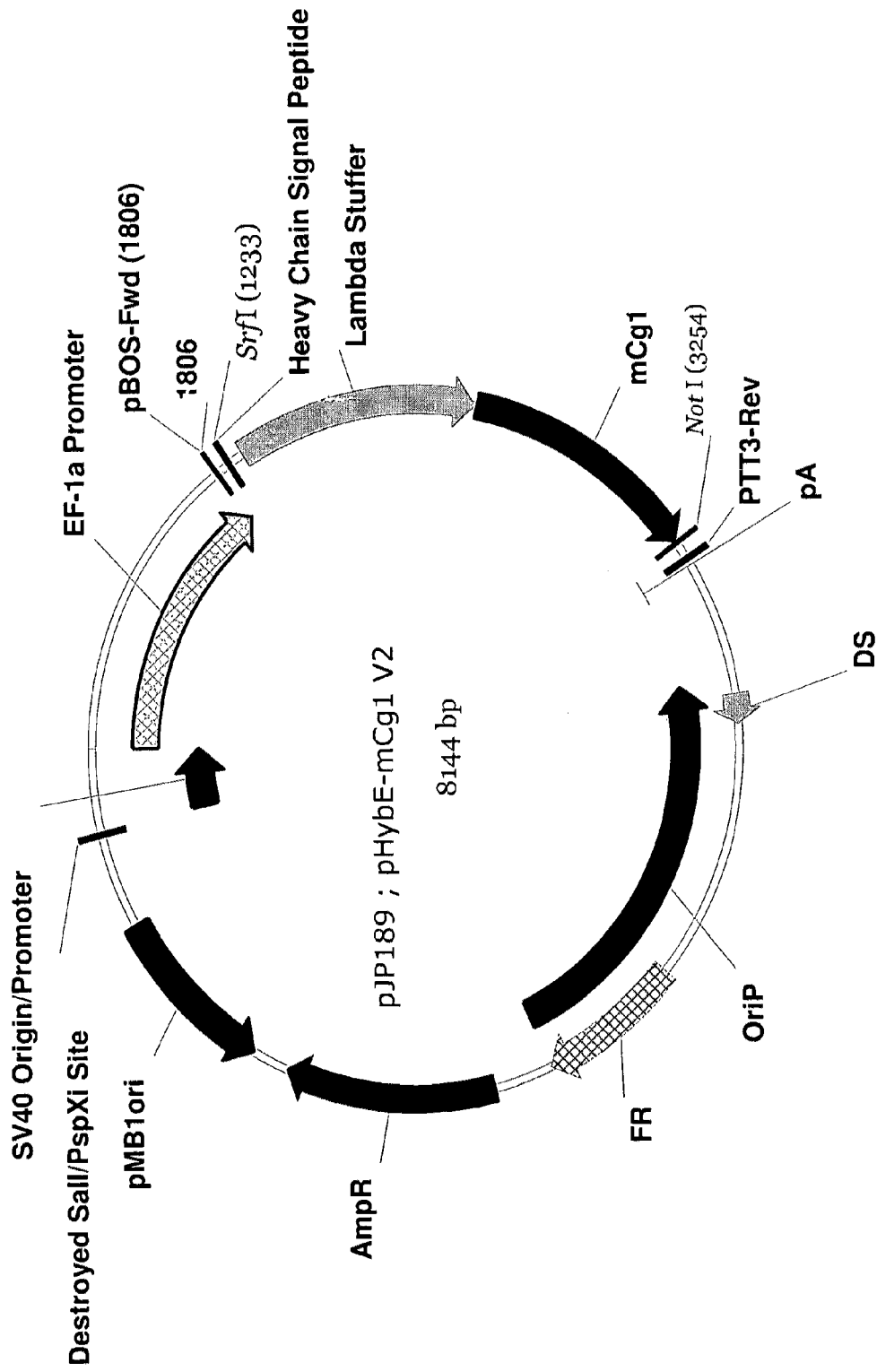
FIG. 21 shows a map of pHybE-mCg1 V2 (also referred to as "pJP189").
Figure 22:
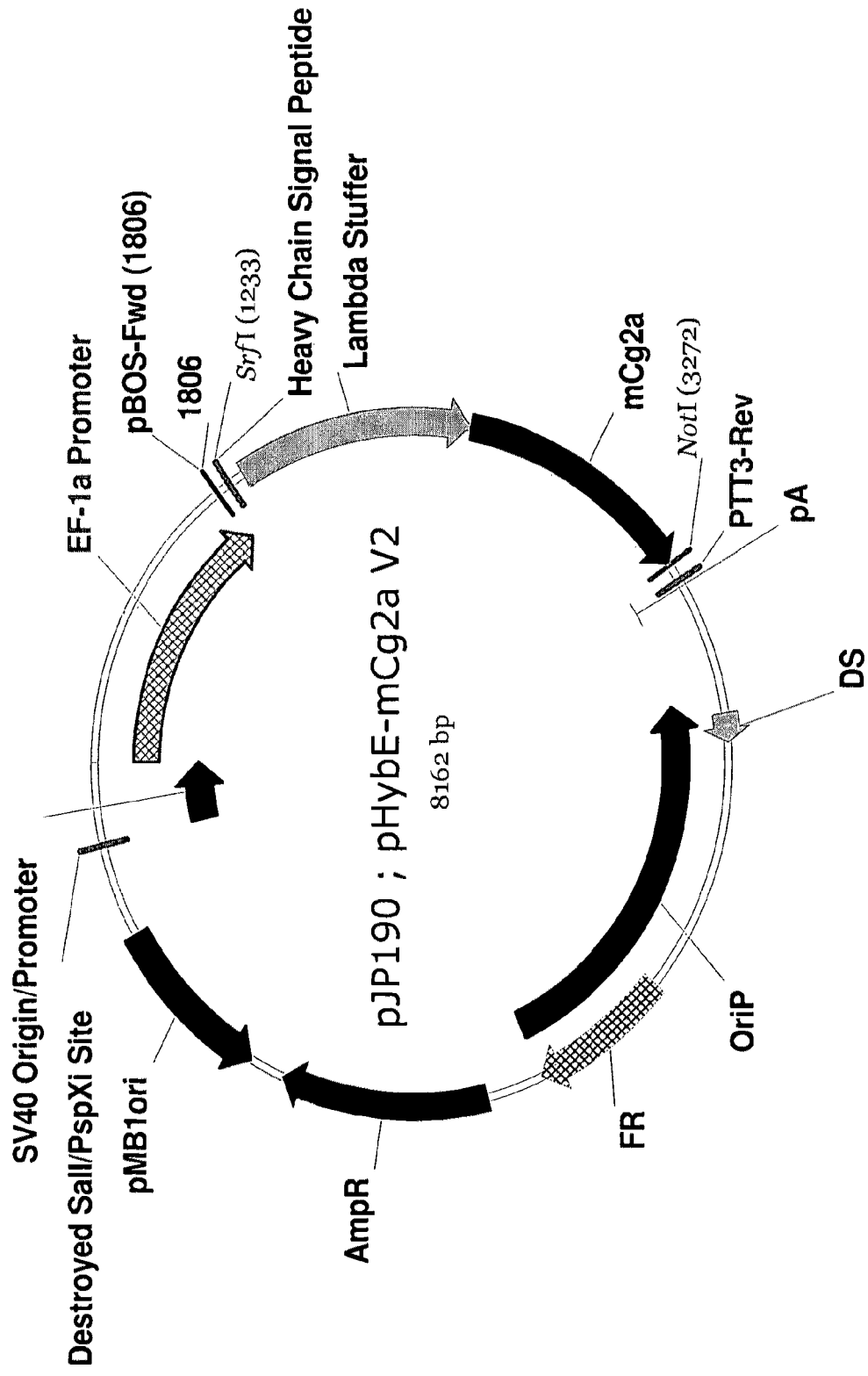
FIG. 22 shows a map of pHybE-mCg2a V2 (also referred to as "pJP190").
Figure 23:
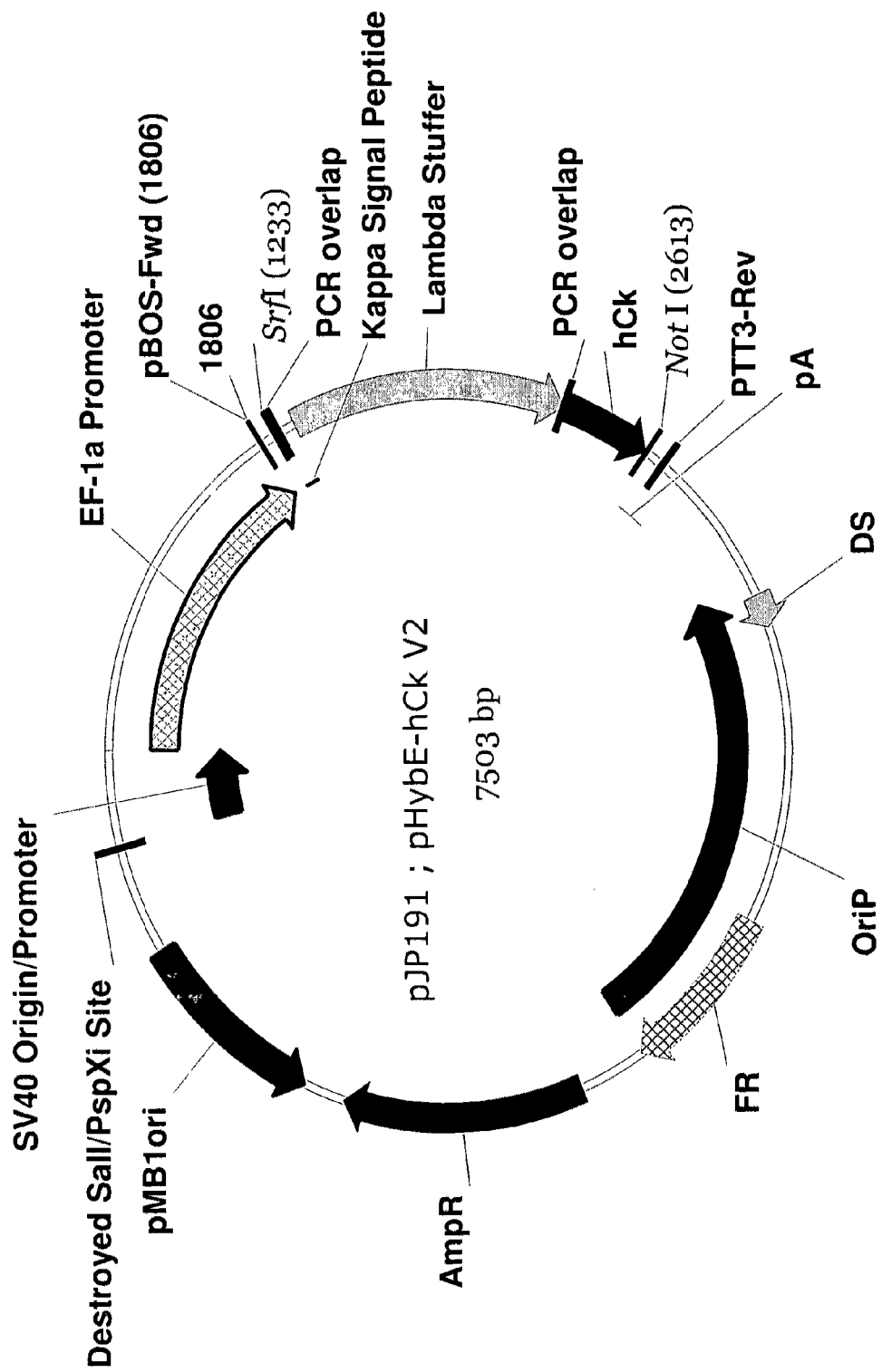
FIG. 23 shows a map of pHybE-hCk V2 (also referred to as "pJP191").
Figure 24:
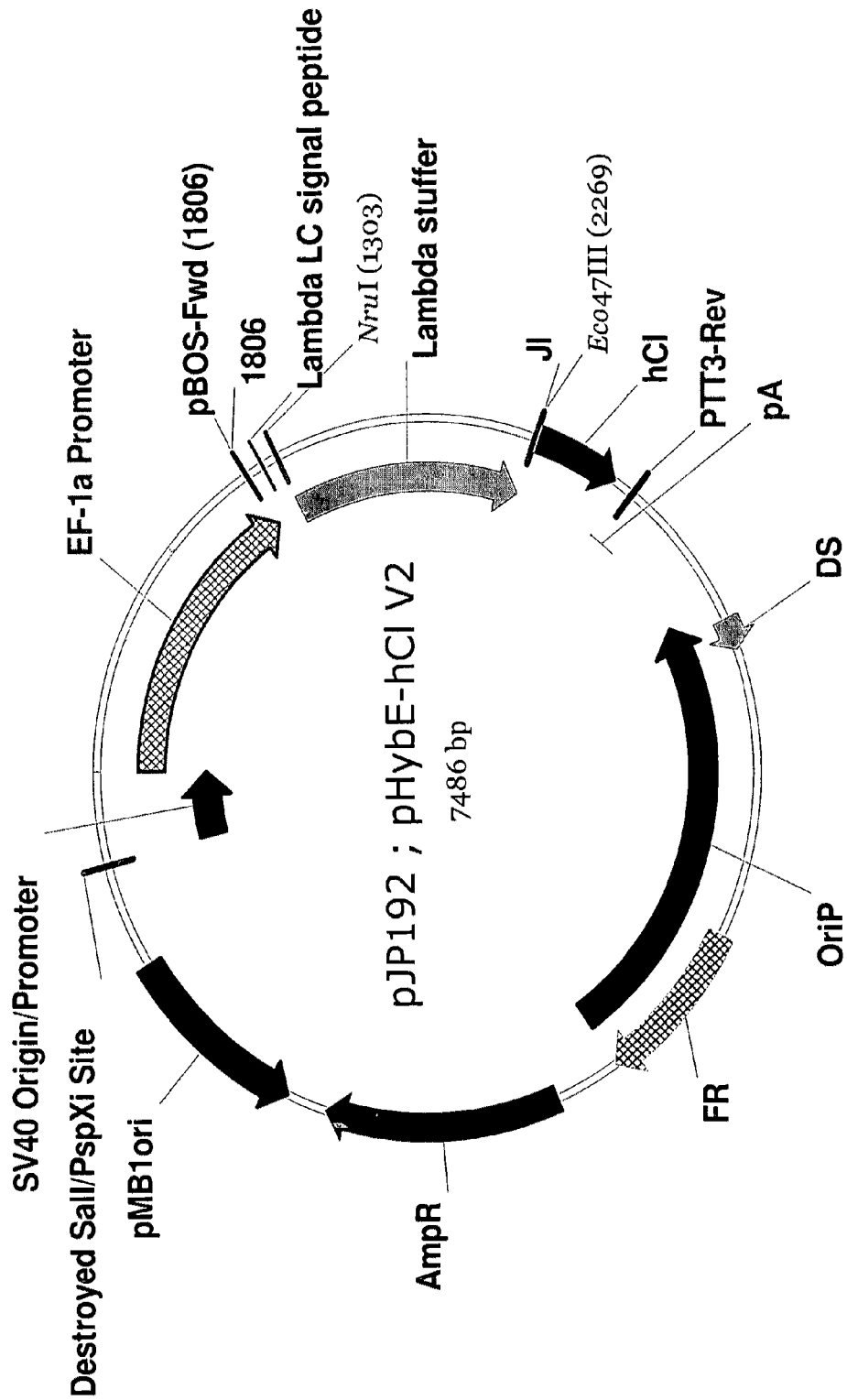
FIG. 24 shows a map of pHybE-hCl V2 (also referred to as "pJP192").
Figure 25:
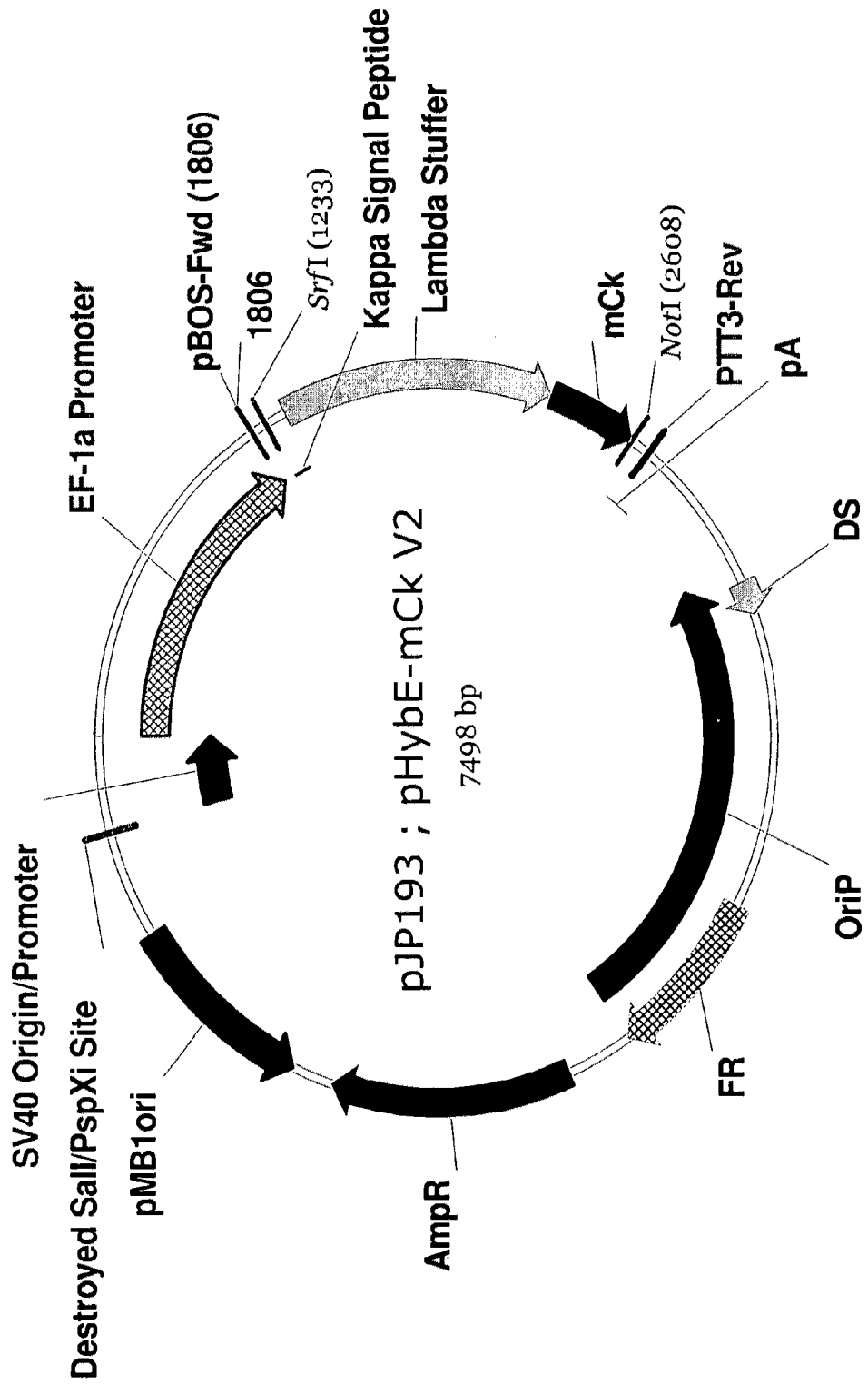
FIG. 25 shows a map of pHybE-mCk V2 (also referred to as "pJP193").

Vector pHybE-mCk is based on the pHybE vector (thus contains all of the elements described above for pHybE). pHybE-mCk also comprises the murine immunoglobulin coding sequence for the kappa light chain constant region. Thus, in one embodiment, the pHybE-mCk vector may be used to express an antibody light chain comprising an immunoglobulin light chain variable region and a murine kappa light chain constant region. Alternatively, pHybE-mCk may be used to express a gene of interest fused to a murine kappa light chain constant region. A vector map of pHybE-mCk V2 is provided in FIG. 25. The nucleic acid sequence of pHybE-mCk V1 is set forth in SEQ ID NO:3 and the nucleic acid sequence of pHybE-mCk V2 is set forth in SEQ ID NO:4.

pHybE-mCg1 pHybE-mCg1 is based on the pHybE vector (thus contains all of the elements described above for pHybE). This vector also comprises the murine immunoglobulin coding sequence for the gamma 1 heavy chain constant region. Thus, in one embodiment, the pHybE-mCg1 vector may be used to express an antibody heavy chain comprising an immunoglobulin heavy chain variable region and a murine gamma 1 heavy chain constant region. Alternatively, pHybE-mCg1 may be used to express a gene of interest fused to a murine gamma 1 heavy chain constant region, e.g, an Fc fusion protein. A vector map of pHybE-mCg1 V2 is provided in FIG. 21. The nucleic acid sequence of pHybE-mCg1 V1 is set forth in SEQ ID NO:5 and the nucleic acid sequence of pHybE-mCg1 V2 is set forth in SEQ ID NO:6.

pHybE-mCg2a pHybE-mCg2a is based on the pHybE vector (thus contains all of the elements described above for pHybE). This vector also comprises the murine immunoglobulin coding sequence for the gamma 2a heavy chain constant region. Thus, in one embodiment, the pHybE-mCg2a vector may be used to express an antibody heavy chain comprising an immunoglobulin heavy chain variable region and a murine gamma 2 heavy chain constant region. Alternatively, pHybE-mCg2a may be used to express a gene of interest fused to a gamma 2 heavy chain constant region, e.g., an Fc fusion protein. A vector map of pHybE-mCg2a V2 is provided in FIG. 22. The nucleic acid sequence of pHybE-mCg2a V1 is set forth as SEQ ID NO:7 and the nucleic acid sequence of pHybE-mCg2a V2 is set forth in SEQ ID NO:8. As an example of one embodiment of how the pHybE-mCg2a may be used, FIG. 9 shows a map of pHybE-mBR3-mCg2a. The vector described in FIG. 9 contains the coding sequence for the extracellular domain (ECD) of the murine BR3 protein. The nucleic acid sequence of pHybE-mBR3-mCg2a is set forth in SEQ ID NO:28.

Vectors of the Invention Comprising Human Constant Regions pHybC-E7-hCk pHybC-E7-hCk is based on the pHybC vector (thus contains all of the elements described above for pHybC). This vector also comprises the human immunoglobulin coding sequence for the kappa light chain constant region. In addition, pHybC-E7-hCk contains the coding sequence of the light chain variable region of adalimumab (also referred to as "E7"). A vector map of pHybC-E7-hCk is provided in FIG. 10, and the nucleic acid sequence of pHybC-E7-hCk is set forth in SEQ ID NO:29.

pHybC-D2-hCg1,z,a pHybC-D2-hCg1,z, a is based on the pHybC vector (thus contains all of the elements described above for pHybC). This vector also comprises the coding sequence for the gamma 1,z,a heavy chain constant region. In addition, pHybC-D2-hCg1,z,a contains the coding sequence of the heavy chain variable region of adalimumab (also referred to as "D2"). A vector map of pHybC-D2-hCg1,z,a is provided in FIG. 11. The nucleic acid sequence of pHybC-D2-hCg1,z,a is set forth in SEQ ID NO:30.

pHybE-hCk pHybE-hCk is based on the pHybE vector (thus contains all of the elements described above for pHybE). This vector also comprises the human immunoglobulin coding sequence for the kappa light chain constant region. Thus, for example, the pHybE-hCk vector may be used to express an antibody light chain comprising an immunoglobulin variable light chain region and a human kappa light chain constant region. Alternatively, pHybE-hCk may be used to express a gene of interest fused to a kappa light chain constant region. A vector map of pHybE-hCk V2 is provided in FIG. 23. The nucleic acid sequence of pHybE-hCk V1 is set forth in SEQ ID NO:9 and the nucleic acid sequence of pHybE-hCk V2 is set forth in SEQ ID NO:10. A vector map of pHybE-E7-hCk is also provided in FIG. 13. In addition to all of the elements of the pHybE-hCk vector described above, pHybE-E7-hCk contains the coding sequence of the light chain variable region of adalimumab (also referred to as "E7"). The nucleic acid sequence of pHybE-E7-hCk is set forth in SEQ ID NO:32.

pHybE-hCl pHybE-hCl is based on the pHybE vector (thus contains all of the elements described above for pHybE). This vector also comprises the human immunoglobulin coding sequence for the lambda light chain constant region. Thus, in one embodiment, the pHybE-hCl vector may be used to express an antibody light chain comprising an immunoglobulin variable light chain region and a human lambda light chain constant region. Alternatively, pHybE-hCl may be used to express a gene of interest fused to a lambda light chain constant region. A vector map of pHybE-hCl V2 is provided in FIG. 24. The nucleic acid sequence of pHybE-hCl V1 is set forth in SEQ ID NO:11 and the nucleic acid sequence of pHybE-hCl V2 is set forth in SEQ ID NO:12.

pHybE-hCg1,z,a pHybE-hCg1,z,a is based on the pHybE vector (thus contains all of the elements described above for pHybE). This vector also comprises human immunoglobulin coding sequence for the gamma 1,z,a heavy chain constant region. Thus, in one embodiment, the pHybE-hCg1,z,a vector may be used to express an antibody heavy chain comprising an immunoglobulin variable heavy chain region and a human gamma 1,z,a heavy chain constant region. Alternatively, pHybE-hCg1,z,a may be used to express a gene of interest fused to a gamma 1,z,a heavy chain constant region, e.g, an Fc fusion protein. A vector map of pHybE-hCg1,z,a is provided in FIG. 14. The nucleic acid sequence of pHybE-hCg1,z,a V1 is set forth in SEQ ID NO:13 and the nucleic acid sequence of pHybE-hCg1,z,a V2 is set forth in SEQ ID NO:14. A vector map for pHybE-D2-hCg1,z,a is provided in FIG. 12. In addition to the elements of pHybE-hCg1,z,a described above, pHybE-D2-hCg1,z,a contains the coding sequence of the heavy chain variable region of adalimumab (also referred to as "D2"). The nucleic acid sequence of pHybE-D2-hCg1,z,a is set forth in SEQ ID NO:31.

pHybE-hCg1,z,non-a pHybE-hCg1,z,non-a is based on the pHybE vector (thus contains all of the elements described above for pHybE). This vector also comprises human immunoglobulin coding sequence for the gamma 1,z,non-a heavy chain constant region. Thus, in one embodiment, the pHybE-hCg1,z,non-a vector may be used to express an antibody heavy chain comprising an immunoglobulin variable heavy chain region and a human gamma 1,z,non-a heavy chain constant region. Alternatively, pHybE-hCg1,z,non-a may be used to express a gene of interest fused to a gamma 1,z,non-a heavy chain constant region, e.g, an Fc fusion protein. A vector map of pHybE-hCg1,z,non-a V2 is provided in FIG. 15. The nucleic acid sequence of pHybE-hCg1,z,non-a V1 is set forth in SEQ ID NO:15 and the nucleic acid sequence of pHybE-hCg1,z, non-a V2 is set forth in SEQ ID NO:16.

pHybE-hCg1,z,non-a,mut (234,235)

pHybE-hCg1,z,non-a,mut (234,235) is based on the pHybE vector (thus contains all of the elements described above for pHybE). This vector also comprises human immunoglobulin coding sequence for the gamma 1,z,non-a,mut (234,235) heavy chain constant region. Thus, in one embodiment, the pHybE-hCg1,z,non-a,mut (234,235) vector may be used to express an antibody heavy chain comprising an immunoglobulin variable heavy chain region and a human gamma 1,z,non-a,mut (234,235) heavy chain constant region. Alternatively, pHybE-hCg1,z,non-a,mut (234,235) may be used to express a gene of interest fused to a gamma 1,z,non-a,mut (234,235) heavy chain constant region, e.g, an Fc fusion protein. A vector map of pHybE-hCg1,z,non-a,mut (234,235) V2 is provided in FIG. 16. The nucleic acid sequence of pHybE-hCg1,z,non-a,mut (234,235) V1 is set forth in SEQ ID NO:17 and the nucleic acid sequence of pHybE-hCg1,z,non-a,mut (234,235) V2 is set forth in SEQ ID NO:18.

pHybE-hCg1,z,non-a,mut (234,237)

pHybE-hCg1,z,non-a,mut (234,237) is based on the pHybE vector (thus contains all of the elements described above for pHybE). This vector also comprises human immunoglobulin coding sequence for the gamma 1,z,non-a,mut (234,237) heavy chain constant region. Thus, in one embodiment, the pHybE-hCg1,z,non-a,mut (234,237) vector may be used to express an antibody heavy chain comprising an immunoglobulin variable heavy chain region and a human gamma 1,z,non-a,mut (234,237) heavy chain constant region. Alternatively, pHybE-hCg1,z,non-a,mut (234,237) may be used to express a gene of interest fused to a gamma 1,z,non-a,mut (234,237) heavy chain constant region, e.g, an Fc fusion protein. A vector map of pHybE-hCg1,z,non-a,mut (234,237) V2 is provided in FIG. 17. The nucleic acid sequence of pHybE-hCg1,z,non-a,mut (234,237) V1 is set forth in SEQ ID NO:19 and the nucleic acid sequence of pHybE-hCg1,z,non-a,mut (234,237) V2 is set forth in SEQ ID NO:20.

pHybE-hCg2,n− pHybE-hCg2,n− is based on the pHybE vector (thus contains all of the elements described above for pHybE). This vector also comprises the human immunoglobulin coding sequence for the gamma 2,n− heavy chain constant region. Thus, in one embodiment, the pHybE-hCg2,n− vector may be used to express an antibody heavy chain comprising an immunoglobulin variable heavy chain region and a human gamma 2,n− heavy chain constant region. Alternatively, pHybE-hCg2,n− may be used to express a gene of interest fused to a gamma 2,n− heavy chain constant region, e.g., an Fc fusion protein. A vector map of pHybE-hCg2,n− V2 is provided in FIG. 19. The nucleic acid sequence of pHybE-hCg2, n− V1 is set forth in SEQ ID NO:21 and the nucleic acid sequence of pHybE-hCg2,n− V2 is set forth in SEQ ID NO:22.

pHybE-hCg2,n+ pHybE-hCg2,n+ is based on the pHybE vector (thus contains all of the elements described above for pHybE). This vector also comprises the human immunoglobulin coding sequence for the gamma 2,n+ heavy chain constant region. Thus, in one embodiment, the pHybE-hCg2,n+ vector may be used to express an antibody heavy chain comprising an immunoglobulin variable heavy chain region and a human gamma 2,n+ heavy chain constant region. Alternatively, pHybE-hCg2,n+ may be used to express a gene of interest fused to a gamma 2,n+ heavy chain constant region, e.g., an Fc fusion protein. A vector map of pHybE-hCg2,n+ is provided in FIG. 18. The nucleic acid sequence of pHybE-hCg2,n+ V1 is set forth in SEQ ID NO:23 and the nucleic acid sequence of pHybE-hCg2,n+ V2 is set forth in SEQ ID NO:24.

pHybE-hCg4 pHybE-hCg4 is based on the pHybE vector (thus contains all of the elements described above for pHybE). This vector also comprises the human immunoglobulin coding sequence for the gamma4 heavy chain constant region. Thus, in one embodiment, the pHybE-hCg4 vector may be used to express an antibody heavy chain comprising an immunoglobulin variable heavy chain region and a human gamma4 heavy chain constant region. Alternatively, pHybE-hCg4 may be used to express a gene of interest fused to a gamma4 heavy chain constant region, e.g., an Fc fusion protein. A vector map of pHybE-hCg4 is provided in FIG. 20. The nucleic acid sequence of pHybE-hCg4 V1 is set forth in SEQ ID NO:25 and the nucleic acid sequence of pHybE-hCg4 V2 is set forth in SEQ ID NO:26.

Sequences of the vectors of the invention are provided in SEQ ID NOs: 1-32. In one embodiment, the vector of the invention comprises a sequence set forth in any one of SEQ ID NOs: 1-32 or sequences that are at least 80%, at least 85%, at least 90%, at least 95%, at least 96%, at least 97%, at least 98% or at least 99% identical thereto.

The invention can be used in the production of human and/or humanized antibodies that immunospecifically recognize specific cellular targets, e.g., any of the aforementioned proteins, the human EGF receptor, the her-2/neu antigen, the CEA antigen, Prostate Specific Membrane Antigen (PSMA), CD5, CD11a, CD18, NGF, CD20, CD45, CD52, Ep-cam, other cancer cell surface molecules, TNF-alpha, TGF-b1, VEGF, other cytokines, alpha 4 beta 7 integrin, IgEs, viral proteins (for example, cytomegalovirus). Examples of antibodies that can be produced using the compositions and methods of the invention include, but are not limited to, an anti-TNFα antibody, an anti-IL-12 antibody, an anti-IL-18 antibody, and an anti-EPO receptor (EPO-R) antibody. In one embodiment, the anti-TNFα antibody is a fully human anti-TNFα antibody, e.g, adalimumab/D2E7 (see U.S. Pat. No. 6,090,382, incorporated by reference herein; Humira®; Abbott Laboratories). In one embodiment, the anti-IL-12 antibody is a fully human, anti-IL-12 antibody, e.g, ABT-874 (Abbott Laboratories; see U.S. Pat. No. 6,914,128, incorporated by reference herein). In one embodiment, the anti-IL-18 antibody is a fully human IL-18 antibody (e.g., ABT-325), e.g. see also antibodies described in US20050147610 A1, incorporated by reference herein. In one embodiment, the anti-EPO/R (also referred to as ABT-007) antibody is a fully human antibody, like that described in US Patent Publication No. US 20060018902 A1, hereby incorporated by reference.

In addition, the constant regions encoded in the vector may also be used to operably link a constant region, e.g., an Fc domain, to a protein to form a fusion protein, e.g., an Fc-fusion protein. Thus, another example of the type of protein that may be produced using the methods and compositions of the invention include fusion proteins. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Another fusion protein is a recombinant TNFR:Fc, also known as entanercept. Entanercept (or Enbrel®; Amgen/Wyeth) is a dimer of two molecules of the extracellular portion of the p75 TNF alpha receptor, each molecule consisting of a 235 amino acid TNFR-derived polypeptide that is fused to a 232 amino acid Fc portion of human IgG1. In fact, any molecule can be expressed as a fusion protein including, but not limited to, the extracellular domain of a cellular receptor molecule, an enzyme, a hormone, a cytokine, a portion of an immunoglobulin molecule, a zipper domain, and an epitope.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waternan algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook et al., 1989, Molecular Cloning: A Laboratory Manual, Cold Spring Harbor Laboratories, New York; or Ausubel et al. (Eds.), Current Protocols In Molecular Biology, John Wiley & Sons, Inc., New York (1997)). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents or detergents in the hybridization solutions (e.g., formamide, dextran sulfate, and polyethylene glycol, and sodium dodecyl sulphate), hybridization reaction temperature and time parameters, as well as, varying wash conditions. The selection of a particular set of hybridization conditions is selected following standard methods in the art (see, for example, see Sambrook, et al., supra or Ausubel et al., supra). A first polynucleotide is "derived from" second polynucleotide if it has the same or substantially the same base pair sequence as a region of the second polynucleotide, its cDNA, complements thereof, or if it displays sequence identity as described above. A first polypeptide is "derived from" a second polypeptide if it is (i) encoded by a first polynucleotide derived from a second polynucleotide, or (ii) displays sequence identity to the second polypeptides as described above.

The invention also provides a kit containing one or more vectors of the invention in a suitable vessel such as a vial. The expression vectors can contain at least one cloning site for insertion of a selected sequence of interest, or can have a specific gene of interest already present in the vector. The vector an be provided in a dehydrated or lyophilized form, or in an aqueous solution. The kit can include a buffer for reconstituting the dehydrated polynucleotide. Other reagents can be included in the kit, e.g., reaction buffers, positive and negative control vectors for comparison. Generally, the kit will also include instructions for use of the reagents therein.

III. Uses of Vectors of Invention

The invention includes methods of expressing proteins using the vectors described herein. Thus, the invention includes a method of producing a recombinant protein comprising introducing the expression vector of the invention into a mammalian host cell, culturing the mammalian host cell under suitable conditions so as to express the protein, and recovering the protein. An advantage of the vector of the invention is that it provides high protein production using mammalian cell culture systems.

Any cell type capable of gene expression via a nucleic acid or expression vector of the present invention can be used in the present invention as a host cell. The term "host cells" refers to cells that have been transformed with a vector constructed using recombinant DNA techniques.

Those having ordinary skill in the art can select a particular host cell line that is best suited for expressing the GOI and selectable marker gene via a vector of the present invention. Cells that can be employed in this invention include mammalian cells and cell lines and cell cultures derived therefrom. Mammalian cells, e.g., germ cells or somatic cells, can be derived from mammals, such as mice, rats, or other rodents, or from primates, such as humans or monkeys. It shall be understood that primary cell cultures or immortalized cells can be employed in carrying out the techniques of this invention.

In particular embodiments, the cell type is mammalian in origin including, but not limited to Chinese hamster ovary (CHO) (e.g., DG44 and DUXB11; Urlaub et al., Som. Cell Molec. Genet. 12:555, 1986; Haynes et al., Nuc. Acid. Res. 11:687-706, 1983; Lau et al., Mol. Cell. Biol. 4:1469-1475, 1984; Methods in Enzymology, 1991, vol. 185, pp 537-566. Academic Press, Inc., San Diego, Calif.), Chinese hamster fibroblast (e.g., R1610), human cervical carcinoma (e.g., HELA), monkey kidney line (e.g., CVI and COS), murine fibroblast (e.g., BALBc/3T3), murine myeloma (P3.times.63–Ag3.653; NS0; SP2/O), hamster kidney line (e.g., HAK), murine L cell (e.g., L-929), human lymphocyte (e.g., RAJI), human kidney (e.g., 293 and 293T). Host cell lines are typically commercially available (e.g., from BD Biosciences, Lexington, Ky.; Promega, Madison, Wis.; Life Technologies, Gaithersburg, Md.) or from the American Type Culture Collection (ATCC, Manassas, Va.).

In a preferred embodiment, the host cell used in the invention provides in trans the replication initiation factor corresponding to at least one origin of replication included in the vector of the invention. For example, if the vector comprises two origins of replication corresponding the SV40 origin and the OriP origin, any cell line, preferably mammalian, that expresses either the large T-antigen or the EBNA protein can be used. In one embodiment, the vector is transformed into a COS cell or a human embryonic kidney (HEK) cell. For example, COS7 cells are derived from CV-1 simian cells transformed by an origin-defective mutant of SV40 (Sigma-Aldrich). EBNA may be provided, for example, by using the HEK-293-6E cell.

Cell lines that have stably integrated replication initiation factors within the genome have the advantage of stable long-term expression of the replication initiation factor and durable support of replication and maintenance of the origin of replication containing plasmids. Examples of commercially available cell lines expressing EBNA-1 are ATCC: 293HEK-EBNA1 and CV1-EBNA1. Specific cell lines over expressing at least one replication initiation factor, preferably the EBNA1 protein or the SV40 large T-antigen, can be generated by transfection and selection of stable cell clones.

Nucleic acids and expression vectors can be introduced or transformed into an appropriate host cell by various techniques well known in the art (see, e.g., Ridgway, 1973, Vectors: Mammalian Expression Vectors, Chapter 24.2, pp. 470-472, Rodriguez and Denhardt eds., Butterworths, Boston, Mass.; Graham et al., 1973, Virology 52:456; Sambrook et al., 1989, Molecular Cloning: A Laboratory Manual, Cold Spring Harbor Laboratories, New York; Davis et al., 1986, Basic Methods in Molecular Biology, Elsevier; and Chu et al., 1981, Gene 13:197). The terms "transformation" and "transfection", and their grammatical variations, are used interchangeably herein and refer to the uptake of foreign DNA by a cell by any means practicable. A cell has been "transformed" when an exogenous nucleic acid has been introduced inside the cell membrane. The uptake of the nucleic acid results in a stable transfectant, regardless of the means by which the uptake is accomplished, which may include transfection (including electroporation), protoplast fusion, calcium phosphate precipitation, cell fusion with enveloped DNA, microinjection, and infection with intact virus. Even transient expression at higher than normal levels is useful for functional studies or for the production and recovery of proteins of interest. Transformed cells are grown under conditions appropriate for the production of the protein of interest (e.g., antibody heavy and/or light chains in one embodiment), and assays are performed to identify the encoded polypeptide of interest. Exemplary assay techniques for identifying and quantifying gene products include enzyme-linked immunosorbent assay (ELISA), radioimmunoassay (RIA), or fluorescence-activated cell sorter analysis (FACS), immunohistochemistry, and the like.

Cells used in the present invention can be cultured according to standard cell culture techniques, e.g., they can be fixed to a solid surface or grown in suspension in appropriate nutrient media.

Also encompassed by the invention is a mammalian host cell comprising the vectors described herein.

The practice of the present invention will employ, unless otherwise indicated, conventional techniques of molecular biology and the like, which are within the skill of the art. Such techniques are explained fully in the literature. See, e.g., Molecular Cloning: A Laboratory Manual, (J. Sambrook et al., Cold Spring Harbor Laboratory, Cold Spring Harbor, N.Y., 1989); Current Protocols in Molecular Biology (F. Ausubel et al., eds., 1987 updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology (R. Wu et al. eds., Academic Press 1989); PCR: A Practical Approach (M. McPherson et al., IRL Press at Oxford University Press 1991); Oligonucleotide Synthesis (M. Gait ed., 1984); Cell Culture for Biochemists (R. Adams ed., Elsevier Science Publishers 1990); Gene Transfer Vectors for Mammalian Cells (J. Miller & M. Calos eds., 1987); Mammalian Cell Biotechnology (M. Butler ed., 1991); Animal Cell Culture (J. Pollard et al. eds., Humana Press 1990); Culture of Animal Cells, 2.sup.nd Ed. (R. Freshney et al. eds., Alan R. Liss 1987); Flow Cytometry and Sorting (M. Melamed et al. eds., Wiley-Liss 1990); the series Methods in Enzymology (Academic Press, Inc.); and Animal Cell Culture (R. Freshney ed., IRL Press 1987); and Wirth M. and Hauser H. (1993) Genetic Engineering of Animal Cells, In: Biotechnology Vol. 2 Puhler A (ed.) VCH, Weinhcim 663-744.

EXEMPLIFICATION

The following examples illustrate an innovative solution to eliminate the need to construct separate vectors for different mammalian host cells, e.g., COS7 and HEK-293-6E cells. The following examples also provide vectors containing nucleic acids encoding constant regions of antibodies, for use in the expression of complete light or heavy chains of an antibody or in the expression of Fc fusion proteins.

Two new vector backbones, termed pHyb-C and pHyb-E, were constructed by combining selected features from various other vectors, i.e., the pBOS and pTT3 vectors (see U.S. Provisional Appln. No. 60/878,165, International Appln. No. PCT/US2007/26482, filed on Dec. 28, 2007 entitled "DUAL-SPECIFIC IL-1A/IL-1b ANTIBODIES" and U.S. Ser. No. 12/006,068, all of which are hereby incorporated by reference herein). Control vector pBOS contains the EF-1α promoter operably linked to the insertion site for the gene of interest, and carries the SV40 replication origin. Control vector pTT3 contains the CMV promoter operably linked to the insertion site for the gene of interest, and an EBNA replication origin (OriP).

The vectors of the invention were tested by evaluating protein expression of both a mouse BR3-Fc fusion and a human antibody (adalimumab) in both COS7 and HEK-293-6E cells. The successful protein expression in COS7 and HEK-293-6E cells demonstrates a unifying vector system for recombinant expression in both cell types.

Example 1

Construction of Vectors pHybC and pHybE

FIGS. 1 and 2 provide maps of the new vectors, which each contain two origins of replication. FIGS. 1 and 2 represent "empty" versions of the vectors, i.e., do not contain the nucleic acid of the gene of interest or the antibody constant regions (described in more detail below in Example 4).

pHybC contains the CMV promoter operably linked to the insertion site for the gene of interest, while pHybE contains the EF-1α promoter.

For pHybC-mBR3-Fc construction ("mBR3" refers to the murine version of the third BLyS receptor, and as used herein refers specifically to the coding sequence for the extracellular domain (ECD) portion of the mBR3 protein), the SV40 origin of replication region from the pEF-BOS vector was PCR amplified with primers that introduced PspX I restriction sites at both 5' and 3' ends of the amplified DNA fragment. This insertion fragment was then digested by PspX I. A pTT3-mBR3-Fc construct, having a Sal I restriction site upstream of the CMV promoter, was digested with Sal I. Then the Psp X I-digested insertion fragment was ligated into the Sal I site of pTT3-mBR3-Fc to create the pHybC-mBR3-Fc vector.

The pHybE-mBR3-Fc construct was created by first amplifying by PCR a 5'-end PspX I modified DNA fragmented containing the SV40 origin of replication region through the mBR3 extracellular domain. This product was then digested at 5' by PspX I and 3' by Bsp68 I, which has a site in the leader sequence upstream of the mBR3 extracellular domain sequence. This digested fragment was subsequently subcloned into a Sal I and Bsp68 I-digested pTT3-mBR3-Fc construct to produce the pHybE-mBR3-Fc construct.

Maps of pHybC-mBR3-Fc and pHybE-mBR3-Fc, which each express the receptor-Fc fusion protein mBR3-Fc, can be found in FIGS. 8 and 9.

The pHybC-E7 vector expressing the light chain protein of D2E7 antibody (adalimumab) was similarly constructed as the pHybC-mBR3-Fc, i.e. by ligating the same PspX I digested SV40 Ori region that was isolated and digested during the creation of pHybC-mBR3-Fc (described above) into a previously constructed pTT3-E7 vector predigested by Sal I.

For pHybE-E7 vector construction, an insert fragment was generated by digestion of a pre-existing pBOS-E7 vector with Hind III and BsiW I restriction enzymes. This insert fragment was then ligated into a pHybC-E7 vector predigested with the same enzymes to generate pHybE-E7 for the expression of the D2E7 light chain protein.

For pHybC-D2 and pHybE-D2 vector construction, an insert fragment consisting of the heavy chain variable and constant coding regions of the D2E7 antibody (Adalimumab) (i.e. the D2 heavy chain coding sequence) was generated by digesting a pre-existing pTT3-D2 vector with Bsp68 I and Not I restriction enzymes. This insert fragment was ligated into pHybC-mBR3-Fc and pHybE-mBR3-Fc vectors predigested with the same enzymes to generate pHybC-D2 and pHybE-D2, respectively, for the expression of the heavy chain protein of D2E7 antibody (Adalimumab).

Example 2

Comparison of Protein Yield

To determine whether the increase in vector size with the addition of two origins of replication impacted protein production by the vectors, the pHyb-E and pHyb-C vectors described above were compared to control vectors pBOS and pTT3, which each only contained one origin of replication. To compare expression from pBOS, pTT3, pHyb-C and pHyb-E, a mouse BAFF receptor-human Fc fusion protein construct (mBR3-Fc) was subcloned into the four vector backbones and prepared in parallel by endo-free DNA prep kit.

The four vectors containing the mBR3-Fc sequence were electroporated into COS cells or transfected into HEK-293-6E cells (protocols described below). The cells were incubated for a period of five or seven days. Media samples were taken and the concentration of the mBR3-Fc secreted protein in the media was measured. Titers were determined by IgG ELISA and adjusted by difference in molecular weight between IgG protein standard and the mBR3-Fc protein from the conditioned media after 5 days for COST cells and 7 days for HEK-293-6E cells. The titer adjustment is required to prevent overestimation of mBR3-Fc protein titer due to the use of a much larger human IgG protein as standards in the ELISA.

293 Transfection

The 293 transient transfection procedure used in the experiment was a modification of the methods published in Durocher et al. (2002); Nucleic Acids Research 30(2):E9 and Pham et al. (2005); Biotechnology Bioengineering 90(3): 332-44. Reagents that were used in the transfection included:

- HEK 293-6E cells (human embryonic kidney cell line stably expressing EBNA1; obtained from National Research Council Canada) cultured in disposable Erlenmeyer flasks in a humidified incubator set at 130 rpm, 37° C. and 5% $CO_2$.
- Culture medium: FreeStyle 293 Expression Medium (Invitrogen 12338-018) plus 25 µg/mL Geneticin (G418) (Invitrogen 10131-027) and 0.1% Pluronic F-68 (Invitrogen 24040-032).
- Transfection medium: FreeStyle 293 Expression Medium plus 10 mM HEPES (Invitrogen 15630-080).
- Polyethylenimine (PEI) stock: 1 mg/mL sterile stock solution, pH 7.0, prepared with linear 25 kDa PEI (Polysciences) and stored at less than −15° C.
- Tryptone Feed Medium: 5% w/v sterile stock of Tryptone N1 (Organotechnie, 19554) in FreeStyle 293 Expression Medium.

Cell preparation for transfection: Approximately 2-4 hours prior to transfection, HEK 293-6E cells were harvested by centrifugation and resuspended in culture medium at a cell density of approximately 1 million viable cells per mL. For each transfection, 40 mL of the cell suspension was transferred into a disposable 250-mL Erlenmeyer flask and incubated for 2-4 hours.

Transfection: The transfection medium and PEI stock were prewarmed to room temperature (RT). For each transfection, 25 µg of plasmid DNA and 50 µg of polyethylenimine (PEI) were combined in 5 mL of transfection medium and incubated for 15-20 minutes at RT to allow the DNA:PEI complexes to form. For the BR3-Ig transfections, 25 µg of BR3-Ig plasmid was used per transfection. Each 5-mL DNA:PEI complex mixture was added to a 40-mL culture prepared previously and returned to the humidified incubator set at 130 rpm, 37° C. and 5% $CO_2$. After 20-28 hours, 5 mL of Tryptone Feed Medium was added to each transfection and the cultures were continued for six days.

COS7 Cell Transfection

Two COS7 150 mm plates per construct were transfected using standard electroporation conditions as follows. For COS7 transfection experiments, COS cells were cultured in DMEM+10% FBS+1× glutamine. Cells from one confluent T-150 flask were used for electroporation. The cells were trypsinized, and spun down in media plus serum to inactivate serum. Cells were then washed in 1×PBS.

For each T-150, the pellet was resuspended in 0.8 mls electroporation buffer. The COS electroporation buffer included 20 mM Hepes (or P3 buffer), 137 mM NaCl, 5 mM KCl, 0.7 mM Na2HPO4, and 6 mM Dextrose. The electroporation buffer was adjusted to a pH of 7.0 and filter sterilized. Sixty micrograms of DNA (30 µg of each heavy and light chain plasmid DNA or 60 µg DNA in the case of an Fc fusion protein) was used for each electroporation. 0.8 mls of cell/ buffer/DNA was mixed to each cuvette. (0.4 cm cuvette—Biorad). In addition, one cuvette was set up with buffer only to use as a blank. Cuvettes were put on ice. Cells were electroporated at 250V and 950 µF for 15 to 25 milliseconds. Cuvettes were then returned to ice. The contents of 2 cuvettes were transferred into one 50 ml conical containing 20 mls Hybridoma SFM. A 10 ml pipette was used to break up clumps and transfer to two 150 mm tissue culture dishes, each containing another 20 ml media. Total media volume in each dish was then 30 ml. The dishes were then incubated at 37° C., 5% $CO_2$ for three days.

The COS cell conditioned media (supernatant) was collected into 50 ml conical tubes and spun down. Following the spin, the supernatant was filtered using 2 micron (um) filter. A sample was removed for ELISA analysis. Supernatants were collected after 5 days and analyzed in a standard IgG ELISA to determine their respective protein yields.

pBOS, pTT3, pHybC and pHybE versions of vectors were tested separately in the mBR3 and adalimumab (D2E7) experiments.

Protein Testing

The mBR3-Fc fusion protein concentrations in culture supernatants were tested 5 days (for COS7 cells) or 7 days post-transfection (for 293-6E cells) using ELISA and/or Poros A.

Results

Figure 3:
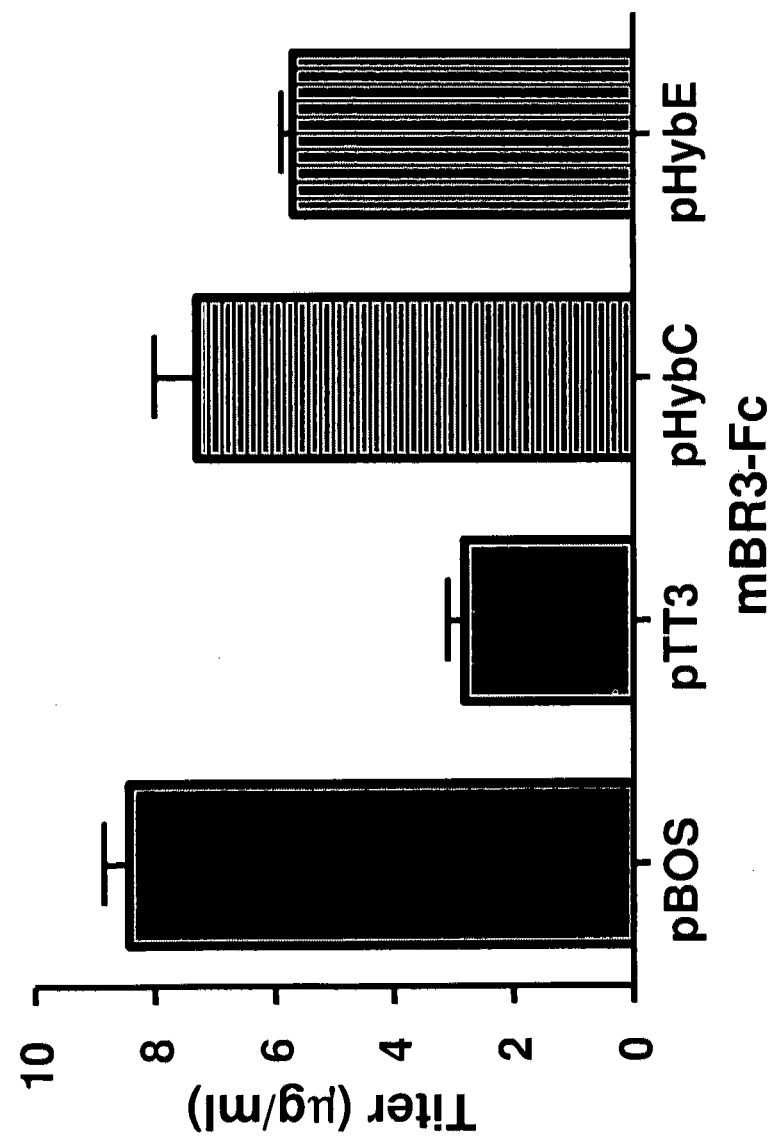
FIG. 3 shows recombinant Fc fusion protein titers produced by COS cells transfected via electroporation with pBOS, pTT3, pHybC and pHybE vectors.
Figure 4:
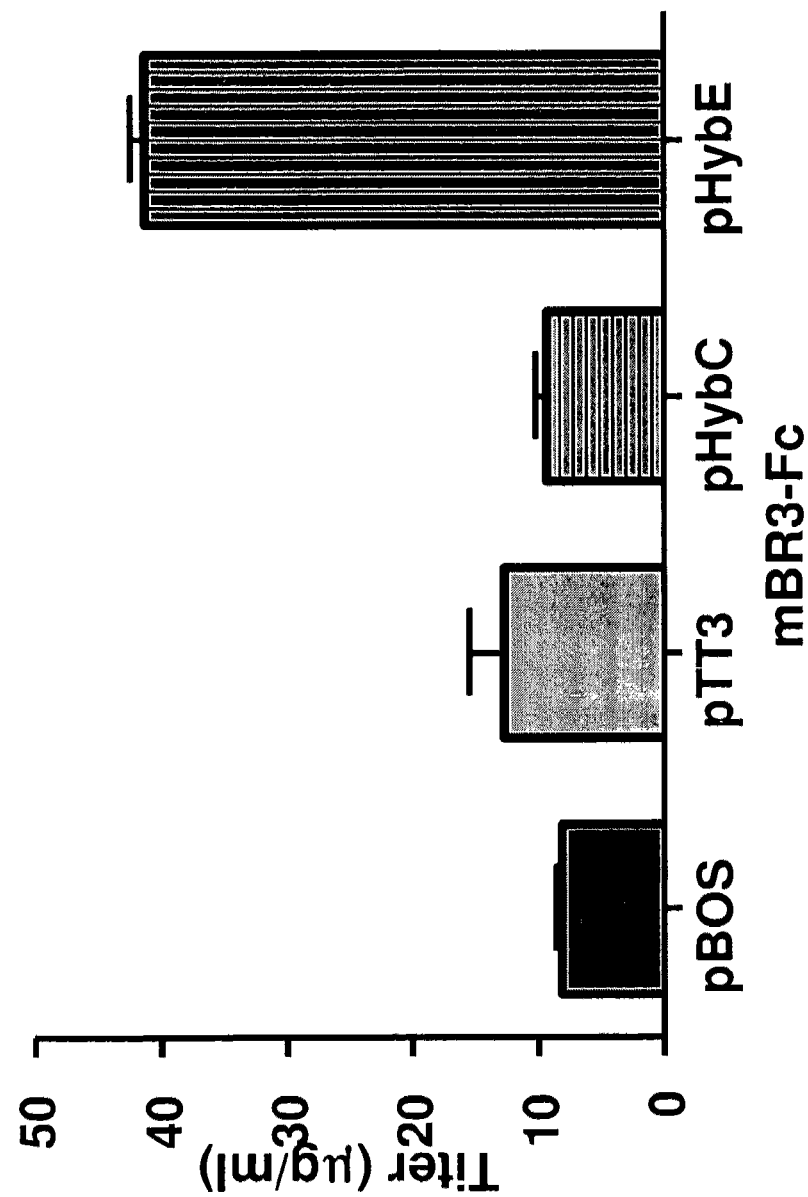
FIG. 4 shows recombinant Fc fusion protein titers produced by HEK-293-6E cells transfected using PEI with pBOS, pTT3, pHybC and pHybE vectors.

Data showing protein expression levels from the control and experimental transfections are shown in FIG. 3 (COS cells) and FIG. 4 (HEK-293 cells). The data in FIG. 3 shows that pHybC and pHybE were both effective at producing the fusion protein in COS cells, where both vectors expressed higher levels than control vector pTT3. The data presented in FIG. 4 shows that the expression levels from HEK cells transfected with the pHyb-E exceeded the expression seen with the other three vectors, while pHyb-C protein production levels were comparable with the controls. Thus, both pHyb-C and pHyb-E were able to express the mBr3-Fc fusion protein as well as, if not better than, control vectors pTT3 and pBOS.

Example 3

Comparison of Protein Yield that Requires Co-Transfection of Two DNA Constructs

A human IgG1/κ monoclonal antibody to TNFα (adalimumab)/D2E7 was subcloned into the four vector backbones and prepared in parallel by endo-free DNA prep kit.

The four vectors containing sequences for expression of adalimumab were electroporated into COS cells; HEK-293-6E cells were transfected using poly(ethylenimine) (PEI).

The 293 transient transfection procedure used was the same as that described in Example 3, except for the adalimumab transfections, in which 10 µg of the D2E7 heavy chain (referred to as "D2") plasmid and 15 µg of the D2E7 light chain (referred to as "E7") plasmid were used per transfection.

The COS7 transfection experiments were performed as described above, except 30 µg of each heavy and light chain vector was used per plate transfection.

The adalimumab antibody concentrations in culture supernatants were tested 7 days post-transfection using ELISA and/or Poros A. Titers were determined by IgG ELISA from the conditioned media after 5 days for COS7 cells and 7 days for HEK-293-6E cells.

Figure 5:
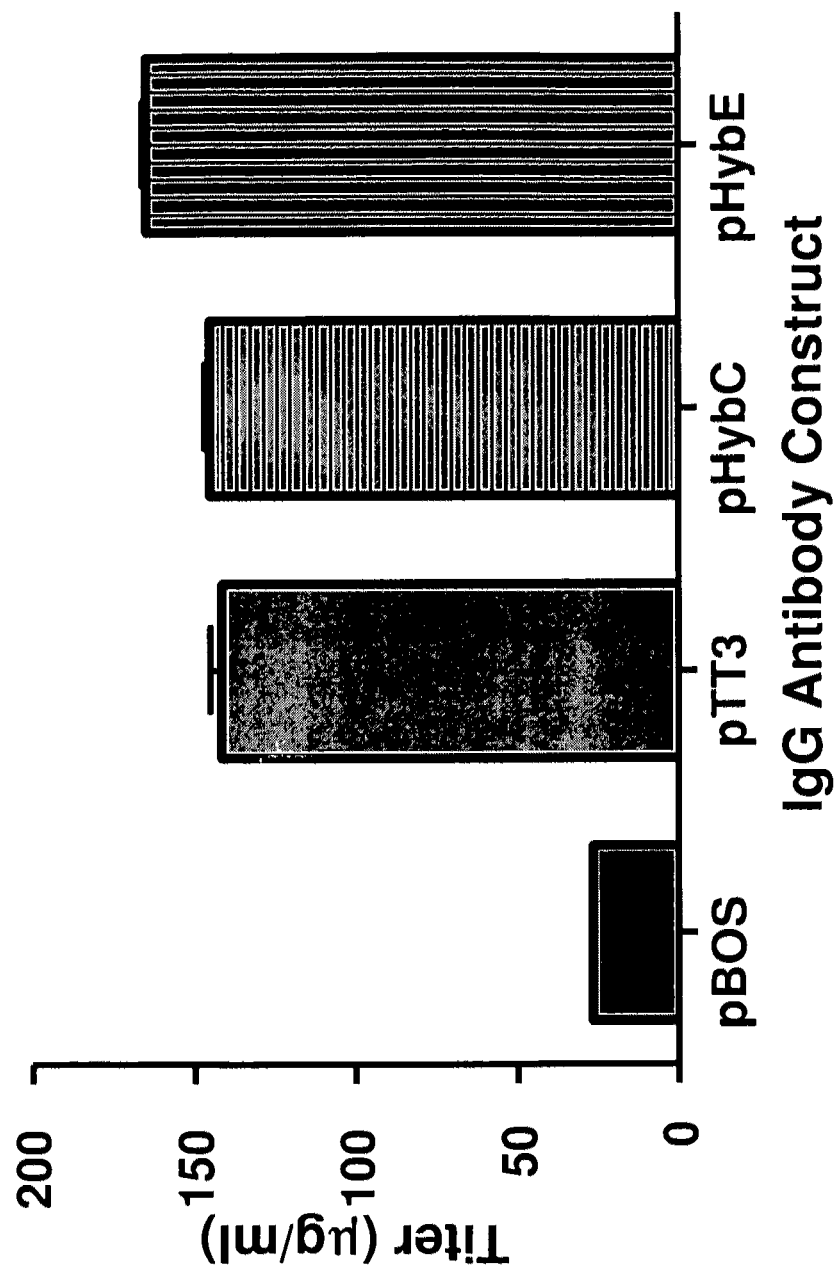
FIG. 5 shows antibody titers produced by HEK-293-6E transfected using PEI with pBOS, pTT3, pHybC and pHybE vectors constructed to express an IgG antibody.
Figure 6:
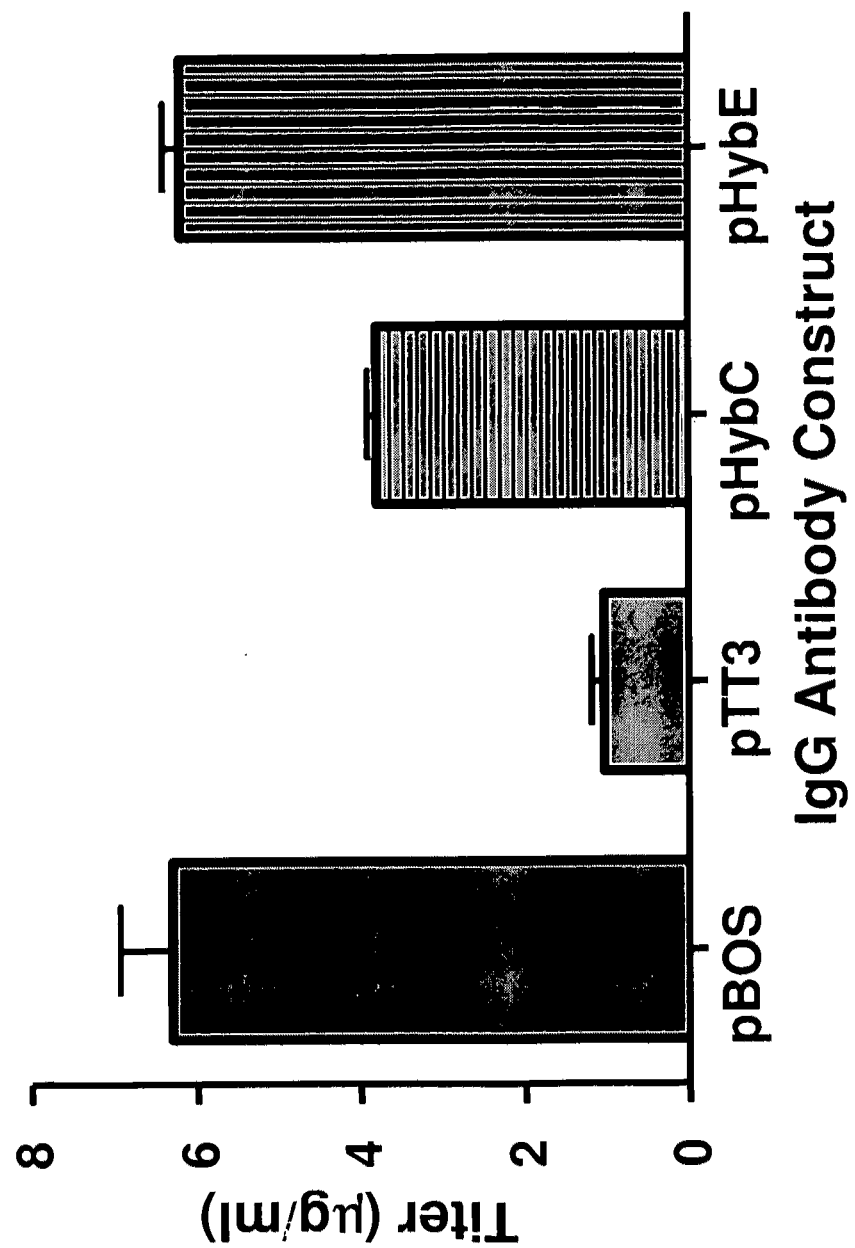
FIG. 6 shows antibody titers produced by COS transfection via electroporation with pBOS, pTT3, pHybC and pHybE vectors constructed to express an IgG antibody.

Data showing protein expression levels from the control and experimental transfections are shown in FIG. 5 (HEK-293 cells) and FIG. 6 (COS cells). Data in FIG. 5 shows that both pHybC and pHybE backbone vectors were able to produce more adalimumab than control vector pBOS, and comparable (pHybC) or greater (pHybE) quantities than control vector pTT3 (Durocher, Y. et al. *Nucleic Acids Res.* 30:E9 (2002)). Similarly, the data in FIG. 6 shows that both pHybC and pHybE backbone vectors were able to produce more protein than control vector pTT3 and comparable levels to control vector pBOS.

Example 4

Construction of the pHyb-E Antibody Constant Region Vector

To facilitate the creation of vectors that could be used for antibody production using the new pHyb-E vector backbone, a panel of twelve different heavy and light chain vectors was generated (overview provided in Tables 2 and 3). Twelve master template pHybE vectors that allow for both human and mouse IgG expression were constructed.

To create the vectors described in FIGS. 14-25, a 6123 bp SrfI/NotI fragment was isolated from pHybE-stuffer-hCg1, z,a (pJP167) and ligated with SrfI/NotI restriction fragments from the pBOS vectors consisting of the signal peptide coding region, lambda stuffer, and constant region coding region. To create the SrfI/NotI restriction fragments, SrfI/NotI restriction digests were performed, in order to generate insertion fragments consisting of the signal peptide coding region, lambda stuffer, and constant region coding region (for constant region sequences, see Table 1). These fragments were derived from pBOS master templates that had been constructed into the pEF-BOS plasmid DNA (see Mizushima, S, and Nagata, S, *Nucleic Acids Res.* 18:5322 (1990); also described in U.S. Provisional Application No. 60/878,165, International Application No. PCT/US2007/026482, filed on Dec. 28, 2007 entitled "DUAL-SPECIFIC IL-1A/IL-1b ANTIBODIES") and U.S. Ser. No. 12/006,068, incorporated by reference herein). The insertion fragment for the pHybE-hCl construct was first modified by overlapping PCR to create an AfeI restriction site at the 3' end of the J region to facilitate cloning into this vector. All inserts were ligated into a previously sequence validated pHyBE construct predigested with SrfI and NotI to generate the following vectors.

The new constant region-containing vectors were then sequence-verified for mouse and human antibody constant regions (see SEQ ID NOs: 3-32).

The vectors described in Tables 2 and 3 all have a ~1-kb 'stuffer' sequence (of λ phage DNA) that can be swapped out by the variable region sequences. These new master vectors also contain a new Swa I restriction site directly upstream of the SrfI site. This novel SwaI site is useful for transferring the antibody open reading frame from pHyb-E to other expression vectors that also utilize a Swa I site for cloning purposes, such as CHO expression vectors. In addition to the flexibility of alternative cloning sites, these vectors are also backward compatible with existing pBOS, pTT3, and CHO vectors.

Figure 7:
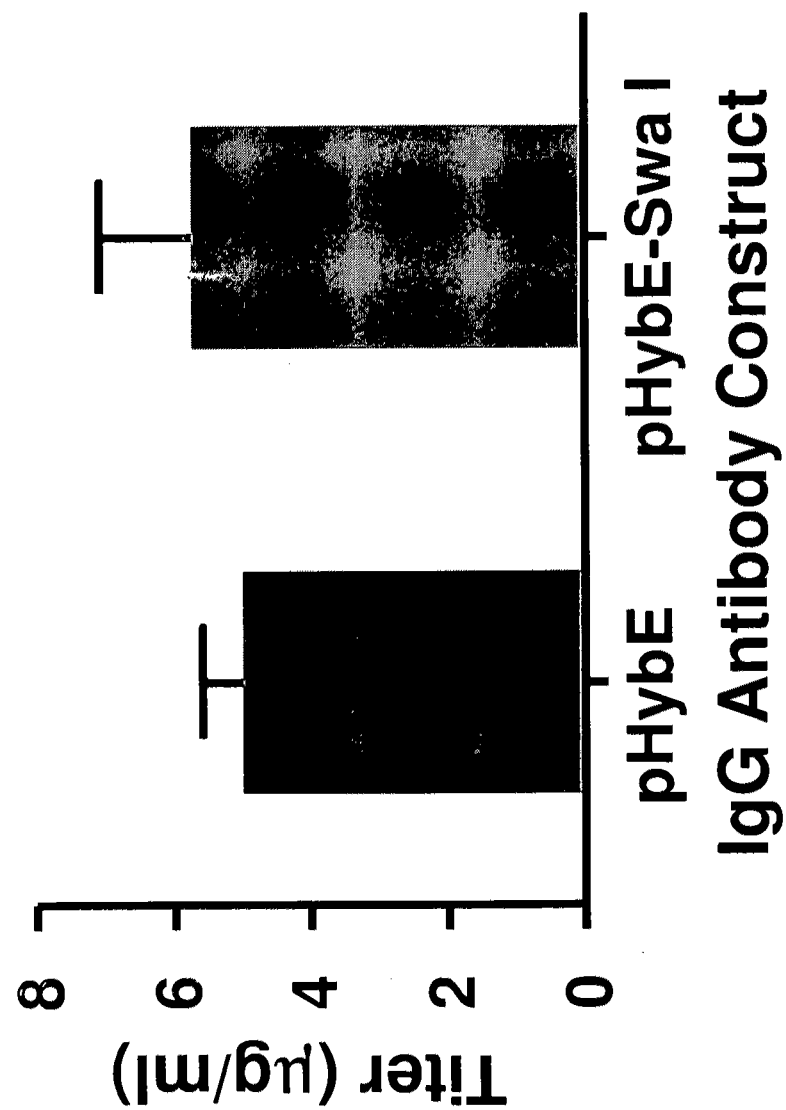
FIG. 7 shows antibody titers produced by COS transfection via electroporation with pHyb-E-Swa I (v1) or pHyb-E (v2) vector constructs expressing an IgG antibody.

As seen in FIG. 7, preliminary transfection data in COST cells showed that this additional Swa I site (v1 vectors) had no significant effect on the levels of adalimumab expression when compared with the constructs without the additional Swa I site (v2 vectors).

TABLE 1

Constant region sequences

| constant region | location of sequence |
| --- | --- |
| mCκ | 2285 to 2605 of SEQ ID NO: 3 |
| mCγ1 | 2277 to 3251 of SEQ ID NO: 5 |
| mCγ2a | 2277 to 3269 of SEQ ID NO: 7 |
| hCκ | 2287 to 2610 of SEQ ID NO: 9 |
| hCλ | 2269 to 2588 of SEQ ID NO: 11 |
| hCγ1, z, a | 2277 to 3269 of SEQ ID NO: 13 |
| hCγ1, z, non-a | 2277 to 3269 of SEQ ID NO: 15 |
| hCγ1, z, non-a, mut(234, 235) | 2277 to 3269 of SEQ ID NO: 17 |
| hCγ1, z, non-a, mut(234, 237) | 2277 to 3269 of SEQ ID NO: 19 |
| hCγ2 (n−) | 2277 to 3257 of SEQ ID NO: 21 |
| hCγ2 (n+) | 2277 to 3257 of SEQ ID NO: 23 |
| hCγ4 | 2277 to 3260 of SEQ ID NO: 25 |

TABLE 2

Exemplary Master Set of pHybE Vectors Made for Human and Mouse IgG Expression

| | Heavy Chain Vectors | Light Chain Vectors |
| --- | --- | --- |
| Human | pHybE-, hCg1, z, a | pHybE-hCk |
| | pHybE-, hCg1, z, non-a | pHybE-hCl |
| | pHybE-, hCg1, z, non-a, (mut 234, 235) | |
| | pHybE-, hCg1, z, non-a, (mut 234, 237) | |
| | pHybE-, hCg2, n+ | |
| | pHybE-, hCg2, n− | |
| | pHybE-, hCg4 | |
| Mouse | pHybE-mCg1 | pHybE-mCk |
| | pHybE-mCg2a | |

Summary:

The preceding experiments described in Examples 1-4 show that the pHyb-C and pHyb-E vectors are functional in more than one cell line while provide ample protein expression that often exceeded the expression levels seen with the original pBOS and pTT3 vectors. This heightened expression was particularly pronounced when the pHyb-E vector was used to express the low yielding mBR3-Fc fusion protein in HEK-293-6E cells. As shown by this data, the pHyb-C and pHyb-E vectors represent a significant advancement in vector technology over previously used vectors.

TABLE 3

Overview of vectors of invention

| SEQ ID NO | DESCRIPTION OF NUCLEIC ACID |
| --- | --- |
| 1 | pHybC-empty |
| 2 | pHybE-empty |
| 3 | pJP180; pHybE-mCk V1 |
| 4 | pJP193; pHybE-mCk V2 |
| 5 | pJP176; pHybE-mCg1 V1 |
| 6 | pJP189; pHybE-mCg1 V2 |
| 7 | pJP177; pHybE-mCg2a V1 |
| 8 | pJP190; pHybE-mCg2a V2 |
| 9 | pJP178; pHybE-hCk V1 |
| 10 | pJP191; pHybE-hCk V2 |
| 11 | pJP179; pHybE-hCl V1 |
| 12 | pJP192; pHybE-hCl V2 |
| 13 | pJP170; pHybE-hCg1, z, a V1 |
| 14 | pJP182; pHybE-hCg1, z, a V2 |
| 15 | pJP171; pHybE-hCg1, z, non-a V1 |
| 16 | pJP183; pHybE-hCg1, z, non-a V2 |
| 17 | pJP172; pHybE-hCg1, z, non-a, mut(234, 235) V1 |
| 18 | pJP184; pHybE-hCg1, z, non-a, mut(234, 235) V2 |
| 19 | pJP173; pHybE-hCg1, z, non-a, mut (234, 237) V1 |
| 20 | pJP185; pHybE-hCg1, z, non-a, mut (234, 237) V2 |
| 21 | pJP174; pHybE-hCg2, n− V1 |
| 22 | pJP187; pHybE-hCg2, n− V2 |
| 23 | pJP181; pHybE-hCg2, n+ V1 |
| 24 | pJP186; pHybE-hCg2, n+ V2 |
| 25 | pJP175; pHybE-hCg4 V1 |
| 26 | pJP188; pHybE-hCg4 V2 |
| 27 | pHybC-mBR3-mCg2a |
| 28 | pHybE-mBR3-mCg2a |
| 29 | pHybC-E7-hCk |
| 30 | pHybC-D2-hCg1, z, a |
| 31 | pHybE-D2-hCg1, z, a |
| 32 | pHybE-E7-hCk | pHyb vectors described as version 1 have an additional Swa I site upstream of the Srf I restriction site.
pHyb vectors described as version 2, do not have additional Swa I site.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The practice of the present invention will employ, unless otherwise indicated, conventional techniques of immunology, molecular biology, cell biology, and drug manufacturing and delivery, which are well known in the art. These techniques include, but are not limited to, techniques described in the following publications:

What is claimed:

1. An expression vector comprising:
   (a) an OriP origin of replication derived from Epstein-Barr virus (EBV);
   (b) an SV40 origin of replication;
   (c) an insertion site for inserting a gene of interest;
   (d) a promoter operably linked to the insertion site, wherein the promoter is a cytomegalovirus (CMV) promoter comprising nucleotides 1 to 608 of SEQ ID NO: 1; and, optionally,
   (e) a nucleic acid sequence encoding an antibody heavy or light chain constant region, operably linked to the insertion site.

2. The expression vector of claim 1, wherein the gene of interest is an antibody heavy or light chain variable region.

3. The expression vector of claim 2, wherein the antibody heavy or light chain variable region is selected from the group consisting of murine, humanized, chimeric and human.

4. The expression vector of claim 3, wherein the antibody heavy chain variable region is the heavy chain variable region of an antibody selected from the group consisting of an anti-TNFα antibody, an anti-IL-18 antibody, and an anti-IL-12 antibody.

5. The expression vector of claim 3, wherein the antibody light chain variable region is the light chain variable region of an antibody selected from the group consisting of an anti-TNFα antibody, an anti-IL-18 antibody, and an anti-IL-12 antibody.

6. The expression vector of claim 1, wherein the antibody heavy chain constant region is murine or human.

7. The expression vector of claim 1, wherein the antibody heavy chain constant region is selected from the group consisting of gamma 1, z, a; gamma 1, z, non-a; gamma 2, n+; gamma 2, n−; and gamma 4.

8. The expression vector of claim 7, wherein the gamma 1, z, non-a antibody heavy chain constant region further comprises an alanine mutation at position 234 of the heavy chain constant region.

9. The expression vector of claim 8, further comprising an alanine mutation at either position 235 or 237 of the antibody heavy chain constant region.

10. The expression vector of claim 1, wherein the antibody light chain constant region is either a human kappa isotype or a human lambda isotype.

11. The expression vector of claim 1, wherein the antibody heavy chain constant region is either a murine gamma 1 isotype or a murine gamma 2a isotype.

12. The expression vector of claim 1, wherein the antibody light chain constant region is a murine kappa isotype.

13. The expression vector of claim 1, wherein the antibody heavy chain constant region is an Fc domain.

14. The expression vector of claim 2, wherein the heavy or light chain antibody variable region is 5' to the insertion site.

15. The expression vector of claim 1, further comprising a selectable marker.

16. The expression vector of claim 15, wherein the selectable marker is an ampicillin resistance gene.

17. The expression vector of claim 1, wherein the OriP origin of replication comprises nucleotides 1795 to 3545 of SEQ ID NO: 1.

18. The expression vector of claim 1, wherein the SV40 origin of replication comprises nucleotides 5834 to 6140 of SEQ ID NO: 1.

19. The expression vector of claim 1, wherein the expression vector comprises a nucleic acid sequence selected from the group consisting of SEQ ID NO: 1, 27, 29, and 30.

20. The expression vector of claim 1, wherein the expression vector is described in a Figure selected from the group consisting of FIGS. 1, 8, 10, and 11.

21. The expression vector of claim 1, further comprising a nucleic acid sequence encoding a signal peptide.

22. A kit comprising the vector of claim 1.

23. A mammalian host cell comprising the vector of claim 1.

24. The mammalian host cell of claim 23, wherein the cell is a COS cell or a human embryonic kidney (HEK) cell.

25. The mammalian host cell of claim 24, wherein the cell is a COST cell.

26. The mammalian host cell of claim 24, wherein the cell is an HEK-293-6E cell.

27. A method for producing a recombinant protein comprising introducing the expression vector of claim 1 into a mammalian host cell, culturing the mammalian host cell under suitable conditions so as to express the protein, and recovering the protein.

28. An expression vector comprising:
(a) an OriP origin of replication derived from Epstein-Barr virus (EBV);
(b) an SV40 origin of replication;
(c) an insertion site for inserting a gene of interest;
(d) a cytomegalovirus (CMV) promoter operably linked to the insertion site,
wherein the vector comprises the nucleic acid sequence of SEQ ID NO: 1.

29. A kit comprising the vector of claim 28.

30. A mammalian host cell comprising the vector of claim 28.

31. A method for producing a recombinant protein comprising introducing the expression vector of claim 28 into a mammalian host cell, culturing the mammalian host cell under suitable conditions so as to express the protein, and recovering the protein.

* * * * *

SEQUENCE LISTING

```
<160> NUMBER OF SEQ ID NOS: 32

<210> SEQ ID NO 1
<211> LENGTH: 6381
<212> TYPE: DNA
<213> ORGANISM: Artificial Sequence
<220> FEATURE:
<223> OTHER INFORMATION: Synthetic construct: pHybC-empty
```

```
<220> FEATURE:
<221> NAME/KEY: misc_feature
<222> LOCATION: (1143)..(1242)
<223> OTHER INFORMATION: n is a, c, g, or t

<400> SEQUENCE: 1
ttgacattga ttattgacta gttattaata gtaatcaatt acggggtcat tagttcatag      60
cccatatatg gagttccgcg ttacataact tacggtaaat ggcccgcctg gctgaccgcc     120
caacgacccc cgcccattga cgtcaataat gacgtatgtt cccatagtaa cgccaatagg     180
gactttccat tgacgtcaat gggtggagta tttacggtaa actgcccact tggcagtaca     240
tcaagtgtat catatgccaa gtccgccccc tattgacgtc aatgacggta aatggcccgc     300
ctggcattat gcccagtaca tgaccttacg ggactttcct acttggcagt acatctacgt     360
attagtcatc gctattacca tggtgatgcg gttttggcag tacaccaatg ggcgtggata     420
gcggtttgac tcacggggat tccaagtct ccaccccatt gacgtcaatg ggagtttgtt     480
ttggcaccaa aatcaacggg actttccaaa atgtcgtaat aaccccgccc cgttgacgca     540
aatgggcggt aggcgtgtac ggtgggaggt ctatataagc agagctcgtt tagtgaaccg     600
tcagatcctc actctcttcc gcatcgctgt ctgcgagggc cagctgttgg gctcgcggtt     660
gaggacaaac tcttcgcggt ctttccagta ctcttggatc ggaaacccgt cggcctccga     720
acggtactcc gccaccgagg acctgagcg agtccgcatc gaccggatcg gaaaacctct     780
cgagaaaggc gtctaaccag tcacagtcgc aaggtaggct gagcaccgtg gcgggcggca     840
gcgggtggcg gtcggggttg tttctggcgg aggtgctgct gatgatgtaa ttaaagtagg     900
cggtcttgag acggcggatg gtcgaggtga ggtgtggcag gcttgagatc cagctgttgg     960
ggtgagtact ccctctcaaa agcgggcatt acttctgcgc taagattgtc agtttccaaa    1020
aacgaggagg attgatatt cacctggccc gatctggcca tacacttgag tgacaatgac    1080
atccactttg cctttctctc cacaggtgtc cactcccagg tccaagtttg gcgccacca    1140 tgnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nntgagcggc cgctcgaggc    1260
cggcaaggcc ggatcccccg acctcgacct ctggctaata aaggaaattt attttcattg    1320
caatagtgtg ttggaatttt ttgtgtctct cactcggaag gacatatggg agggcaaatc    1380
atttggtcga gatccctcgg agatctctag ctagaggatc gatccccgcc ccggacgaac    1440
taaacctgac tacgacatct ctgccccttc ttcgcggggc agtgcatgta atcccttcag    1500
ttggttggta caacttgcca actgggccct gttccacatg tgacacgggg ggggaccaaa    1560
cacaaagggg ttctctgact gtagttgaca tccttataaa tggatgtgca catttgccaa    1620
cactgagtgg ctttcatcct ggagcagact ttgcagtctg tggactgcaa cacaacattg    1680
cctttatgtg taactcttgg ctgaagtctc tacaccaatg ctgggggaca tgtacctccc    1740
aggggcccag gaagactacg ggaggctaca ccaacgtcaa tcagagggc ctgtgtagct    1800 accgataagc ggaccctcaa gagggcatta gcaatagtgt ttataaggcc cccttgttaa    1860
ccctaaacgg gtagcatatg cttcccgggt agtagtatat actatccaga ctaaccctaa    1920
ttcaatagca tatgttaccc aacgggaagc atatgctatc gaattagggt tagtaaaagg    1980
gtcctaagga acagcgatat ctcccacccc atgagctgtc acgttttat ttacatgggg    2040 tcaggattcc acgagggtag tgaaccattt tagtcacaag ggcagtggct gaagatcaag    2100
gagcgggcag tgaactctcc tgaatcttcg cctgcttctt cattctcctt cgtttagcta    2160
atagaataac tgctgagttg tgaacagtaa ggtgtatgtg aggtgctcga aaacaaggtt    2220
```

```
tcaggtgacg cccccagaat aaaatttgga cgggggttc agtggtggca ttgtgctatg    2280
acaccaatat aaccctcaca aaccccttgg gcaataaata ctagtgtagg aatgaaacat    2340
tctgaatatc tttaacaata gaaatccatg gggtggggac aagccgtaaa gactggatgt    2400
ccatctcaca cgaatttatg gctatgggca acacataatc ctagtgcaat atgatactgg    2460
ggttattaag atgtgtccca ggcagggacc aagacaggtg aaccatgttg ttacactcta    2520
tttgtaacaa ggggaaagag agtggacgcc gacagcagcg gactccactg gttgtctcta    2580 acaccccga aaattaaacg gggctccacg ccaatggggc ccataaacaa agacaagtgg    2640
ccactctttt ttttgaaatt gtggagtggg ggcacgcgtc agcccccaca cgccgccctg    2700
cggttttgga ctgtaaaata agggtgtaat aacttggctg attgtaaccc cgctaaccac    2760
tgcggtcaaa ccacttgccc acaaaaccac taatggcacc ccggggaata cctgcataag    2820
taggtgggcg ggccaagata ggggcgcgat tgctgcgatc tggaggacaa attacacaca    2880
cttgcgcctg agcgccaagc acaggggttgt tggtcctcat attcacgagg tcgctgagag    2940
cacggtgggc taatgttgcc atgggtagca tatactaccc aaatatctgg atagcatatg    3000
ctatcctaat ctatatctgg gtagcatagg ctatcctaat ctatatctgg gtagcatatg    3060
ctatcctaat ctatatctgg gtagtatatg ctatcctaat ttatatctgg gtagcatagg    3120
ctatcctaat ctatatctgg gtagcatatg ctatcctaat ctatatctgg gtagtatatg    3180
ctatcctaat ctgtatccgg gtagcatatg ctatcctaat agagattagg gtagtatatg    3240
ctatcctaat ttatatctgg gtagcatata ctacccaaat atctggatag catatgctat    3300
cctaatctat atctgggtag catatgctat cctaatctat atctgggtag cataggctat    3360
cctaatctat atctgggtag catatgctat cctaatctat atctgggtag tatatgctat    3420
cctaatttat atctgggtag cataggctat cctaatctat atctgggtag catatgctat    3480
cctaatctat atctgggtag tatatgctat cctaatctgt atccgggtag catatgctat    3540
cctcatgata agctgtcaaa catgagaatt tcttgaaga cgaaagggcc tcgtgatacg    3600 cctatttta taggttaatg tcatgataat aatggtttct tagacgtcag gtggcacttt    3660
tcggggaaat gtgcgcggaa cccctatttg tttattttc taaatacatt caaatatgta    3720
tccgctcatg agacaataac cctgataaat gcttcaataa tattgaaaaa ggaagagtat    3780
gagtattcaa catttccgtg tcgcccttat ccctttttt gcggcatttt gccttcctgt    3840
ttttgctcac ccagaaacgc tggtgaaagt aaaagatgct gaagatcagt tgggtgcacg    3900
agtgggttac atcgaactgg atctcaacag cggtaagatc cttgagagtt ttcgccccga    3960
agaacgtttt ccaatgatga gcactttta agttctgcta tgtggcgcgg tattatcccg    4020
tgttgacgcc gggcaagagc aactcggtcg ccgcatacac tattctcaga atgacttggt    4080
tgagtactca ccagtcacag aaaagcatct tacggatggc atgacagtaa gagaattatg    4140
cagtgctgcc ataaccatga gtgataacac tgcggccaac ttacttctga acgatcgg     4200 aggaccgaag gagctaaccg cttttttgca aacatgggg gatcatgtaa ctcgccttga    4260
tcgttgggaa ccggagctga atgaagccat accaaacgac gagcgtgaca ccacgatgcc    4320
tgcagcaatg gcaacaacgt tgcgcaaact attaactggc gaactactta ctctagcttc    4380
ccggcaacaa ttaatagact ggatggaggc ggataaagtt gcaggaccac ttctgcgctc    4440
ggcccttccg gctggctggt ttattgctga taaatctgga gccggtgagc gtgggtctcg    4500
cggtatcatt gcagcactgg ggccagatgg taagccctcc cgtatcgtag ttatctacac    4560
gacggggagt caggcaacta tggatgaacg aaatagacag atcgctgaga taggtgcctc    4620
```

```
actgattaag cattggtaac tgtcagacca agtttactca tatatacttt agattgattt    4680
aaaacttcat ttttaattta aaggatctca ggtgaagatc cttttttgata atctcatgac   4740 caaaatccct taacgtgagt tttcgttcca ctgagcgtca gaccccgtag aaaagatcaa    4800
aggatcttct tgagatcctt tttttctgcg cgtaatctgc tgcttgcaaa caaaaaaacc   4860
accgctacca gcggtggttt gtttgccgga tcaagagcta ccaactcttt ttccgaaggt    4920
aactggcttc agcagagcgc agataccaaa tactgttctt ctagtgtagc cgtagttagg    4980
ccaccacttc aagaactctg tagcaccgcc tacatacctc gctctgctaa tcctgttacc    5040
agtggctgct gccagtggcg ataagtcgtg tcttaccggg ttggactcaa gacgatagtt    5100
accggataag gcgcagcggt cgggctgaac ggggggttcg tgcacacagc ccagcttgga    5160
gcgaacgacc tacaccgaac tgagatacct acagcgtgag ctatgagaaa gcgccacgct    5220
tcccgaaggg agaaaggcgg acaggtatcc ggtaagcggc agggtcggaa caggagagcg    5280
cacgagggag cttccagggg gaaacgcctg gtatctttat agtcctgtcg ggtttcgcca    5340
cctctgactt gagcgtcgat ttttgtgatg ctcgtcaggg gggcggagcc tatggaaaaa    5400
cgccagcaac gcggccttttt tacgttcct ggccttttgc tggccttttg ctcacatgtt    5460
ctttcctgcg ttatccctg attctgtgga taaccgtatt accgcctttg agtgagctga    5520
taccgctcgc cgcagccgaa cgaccgagcg cagcgagtca gtgagcgagg aagcggaaga    5580
gcgcccaata cgcaaaccgc ctctccccgc gcgttggccg attcattaat gcagctggca    5640
cgacaggttt cccgactgga aagcgggcag tgagcgcaac gcaattaatg tgagttagct    5700
cactcattag gcaccccagg ctttacactt tatgcttccg gctcgtatgt tgtgtggaat    5760
tgtgagcgga taacaatttc acacaggaaa cagctatgac catgattacg ccaagctcta    5820
gctagaggtc gagtccctcc ccagcaggca gaagtatgca aagcatgcat ctcaattagt    5880
cagcaaccat agtcccgccc ctaactccgc ccatcccgcc cctaactccg cccagttccg    5940
cccattctcc gccccatggc tgactaattt tttttattta tgcagaggcc gaggccgcct    6000
cggcctctga gctattccag aagtagtgag gaggcttttt tggaggccta ggcttttgca    6060
aaaagctttg caaagatgga taaagttttta aacagagagg aatctttgca gctaatggac    6120
cttctaggtc ttgaaaggag ctcgaccaat tctcatgttt gacagcttat catcgcagat    6180
ccgggcaacg ttgttgccat tgctgcaggc gcagaactgg taggtatgga agatctatac    6240
attgaatcaa tattggcaat tagccatatt agtcattggt tatatagcat aaatcaatat    6300
tggctattgg ccattgcata cgttgtatct atatcataat atgtacattt atattggctc    6360
atgtccaata tgaccgccat g                                              6381
```

<210> SEQ ID NO 2
<211> LENGTH: 6212
<212> TYPE: DNA
<213> ORGANISM: Artificial Sequence
<220> FEATURE:
<223> OTHER INFORMATION: Synthetic construct: pHybE-empty
<220> FEATURE:
<221> NAME/KEY: misc_feature
<222> LOCATION: (1320)..(1391)
<223> OTHER INFORMATION: n is a, c, g, or t

<400> SEQUENCE: 2

```
agctttgcaa agatggataa agttttaaac agagaggaat ctttgcagct aatggacctt      60
ctaggtcttg aaaggagtgg gaattggctc cggtgcccgt cagtgggcag agcgcacatc     120
gcccacagtc cccgagaagt tggggggagg ggtcggcaat tgaaccggtg cctagagaag     180
```

```
gtggcgcggg gtaaactggg aaagtgatgt cgtgtactgg ctccgccttt ttcccgaggg      240
tgggggagaa ccgtatataa gtgcagtagt cgccgtgaac gttctttttc gcaacgggtt      300
tgccgccaga acacaggtaa gtgccgtgtg tggttcccgc gggcctggcc tctttacggg      360
ttatggccct tgcgtgcctt gaattacttc cacctggctg cagtacgtga ttcttgatcc      420
cgagcttcgg gttggaagtg ggtgggagag ttcgaggcct tgcgcttaag gagccccttc      480
gcctcgtgct tgagttgagg cctggcctgg gcgctggggc cgccgcgtgc gaatctggtg      540
gcaccttcgc gcctgtctcg ctgctttcga taagtctcta gccatttaaa attttttgatg     600 acctgctgcg acgcttttt tctggcaaga tagtcttgta aatgcgggcc aagatctgca      660
cactggtatt tcggtttttg gggccgcggg cggcgacggg gcccgtgcgt cccagcgcac      720
atgttcggcg aggcggggcc tgcgagcgcg gccaccgaga atcggacggg ggtagtctca      780
agctggccgg cctgctctgg tgcctggcct cgcgccgccg tgtatcgccc cgccctgggc      840
ggcaaggctg gcccggtcgg caccagttgc gtgagcggaa agatggccgc ttcccggccc      900
tgctgcaggg agctcaaaat ggaggacgcg gcgctcggga gagcgggcgg gtgagtcacc      960
cacacaaagg aaaagggcct ttccgtcctc agccgtcgct tcatgtgact ccacggagta     1020
ccgggcgccg tccaggcacc tcgattagtt ctcgagcttt tggagtacgt cgtctttagg     1080 ttgggggggag gggttttatg cgatggagtt tccccacact gagtgggtgg agactgaagt    1140
taggccagct tggcacttga tgtaattctc cttggaattt gcccttttg  agtttggatc    1200 ttggttcatt ctcaagcctc agacagtggt tcaaagtttt tttcttccat ttcaggtgtc     1260
gtgaggaatt ctctagagat ccctcgacct cgagatccat tgtgcccggg cgcaccatgn    1320
nnnnnnnnnn nnnnnnnnnn nnnnnnnnnn nnnnnnnnnn nnnnnnnnnn nnnnnnnnnn     1380
nnnnnnnnnn ntgagcggcc gctcgaggcc ggcaaggccg gatcccccga cctcgacctc     1440
tggctaataa aggaaattta ttttcattgc aatagtgtgt tggaattttt tgtgtctctc     1500
actcggaagg acatatggga gggcaaatca tttggtcgag atccctcgga gatctctagc    1560
tagaggatcg atccccgccc cggacgaact aaacctgact acgacatctc tgccccttct    1620
tcgcggggca gtgcatgtaa tcccttcagt tggttggtac aacttgccaa ctgggccctg    1680
ttccacatgt gacacggggg gggaccaaac acaaagggt tctctgactg tagttgacat      1740
ccttataaat ggatgtgcac atttgccaac actgagtggc tttcatcctg gagcagactt    1800
tgcagtctgt ggactgcaac acaacattgc ctttatgtgt aactcttggc tgaagctctt    1860
acaccaatgc tggggacat gtacctccca ggggcccagg aagactacgg gaggctacac     1920
caacgtcaat cagaggggcc tgtgtagcta ccgataagcg gaccctcaag agggcattag    1980
caatagtgtt tataaggccc ccttgttaac cctaaacggg tagcatatgc ttcccgggta    2040
gtagtatata ctatccagac taaccctaat tcaatagcat atgttaccca acggaaagca     2100
tatgctatcg aattagggtt agtaaaaggg tcctaaggaa cagcgatatc tcccacccca    2160
tgagctgtca cggttttatt tacatggggt caggattcca cgagggtagt gaaccatttt    2220
agtcacaagg gcagtggctg aagatcaagg agcgggcagt gaactctcct gaatcttcgc    2280
ctgcttcttc attctccttc gtttagctaa tagaataact gctgagttgt gaacagtaag    2340
gtgtatgtga ggtgctcgaa aacaaggttt caggtgacgc cccagaata  aaatttggac    2400 ggggggttca gtggtggcat tgtgctatga caccaatata accctcacaa accccttggg    2460 caataaaatac tagtgtagga atgaaacatt ctgaatatct ttaacaatag aaatccatgg    2520
ggtggggaca agccgtaaag actggatgtc catctcacac gaatttatgg ctatgggcaa    2580
```

```
cacataatcc tagtgcaata tgatactggg gttattaaga tgtgtcccag gcagggacca    2640
agacaggtga accatgttgt tacactctat ttgtaacaag gggaaagaga gtggacgccg    2700
acagcagcgg actccactgg ttgtctctaa caccccgaa aattaaacgg ggctccacgc     2760
caatggggcc cataaacaaa gacaagtggc cactcttttt tttgaaattg tggagtgggg    2820
gcacgcgtca gccccacac gccgccctgc ggttttggac tgtaaaataa gggtgtaata    2880
acttggctga ttgtaacccc gctaaccact gcggtcaaac cacttgccca caaaaccact   2940
aatggcaccc cggggaatac ctgcataagt aggtgggcgg gccaagatag gggcgcgatt    3000
gctgcgatct ggaggacaaa ttacacacac ttgcgcctga gcgccaagca cagggttgtt   3060
ggtcctcata ttcacgaggt cgctgagagc acggtgggct aatgttgcca tgggtagcat    3120
atactaccca aatatctgga tagcatatgc tatcctaatc tatatctggg tagcataggc    3180
tatcctaatc tatatctggg tagcatatgc tatcctaatc tatatctggg tagtatatgc    3240
tatcctaatt tatatctggg tagcataggc tatcctaatc tatatctggg tagcatatgc    3300
tatcctaatc tatatctggg tagtatatgc tatcctaatc tgtatccggg tagcatatgc    3360
tatcctaata gagattaggg tagtatatgc tatcctaatt tatatctggg tagcatatac    3420
tacccaaata tctggatagc atatgctatc ctaatctata tctgggtagc atatgctatc    3480
ctaatctata tctgggtagc ataggctatc ctaatctata tctgggtagc atatgctatc    3540
ctaatctata tctgggtagt atatgctatc ctaatttata tctgggtagc ataggctatc    3600
ctaatctata tctgggtagc atatgctatc ctaatctata tctgggtagt atatgctatc    3660
ctaatctgta tccgggtagc atatgctatc ctcatgataa gctgtcaaac atgagaattt    3720
tcttgaagac gaaagggcct cgtgatacgc ctatttttat aggttaatgt catgataata    3780
atggtttctt agacgtcagg tggcactttt cggggaaatg tgcgcggaac ccctatttgt    3840 ttattttct aaatacattc aaatatgtat ccgctcatga acaataacc ctgataaatg    3900 cttcaataat attgaaaaag gaagagtatg agtattcaac atttccgtgt cgcccttatt    3960 ccctttttg cggcattttg ccttcctgtt tttgctcacc cagaaacgct ggtgaaagta    4020
aaagatgctg aagatcagtt gggtgcacga gtgggttaca tcgaactgga tctcaacagc    4080
ggtaagatcc ttgagagttt tcgccccgaa gaacgttttc caatgatgag cacttttaaa    4140
gttctgctat gtggcgcggt attatcccgt gttgacgccg ggcaagagca actcggtcgc    4200
cgcatacact attctcagaa tgacttggtt gagtactcac cagtcacaga aaagcatctt    4260
acggatggca tgacagtaag agaattatgc agtgctgcca taaccatgag tgataacact    4320
gcggccaact tacttctgac aacgatcgga ggaccgaagg agctaaccgc ttttttgcac    4380
aacatggggg atcatgtaac tcgccttgat cgttgggaac cggagctgaa tgaagccata    4440
ccaaacgacg agcgtgacac cacgatgcct gcagcaatgg caacaacgtt gcgcaaacta    4500
ttaactggcg aactacttac tctagcttcc cggcaacaat taatagactg gatggaggcg    4560
gataaagttg caggaccact tctgcgctcg gcccttccgg ctggctggtt tattgctgat    4620
aaatctggag ccggtgagcg tgggtctcgc ggtatcattg cagcactggg gccagatggt    4680
aagccctccc gtatcgtagt tatctacacg acggggagtc aggcaactat ggatgaacga    4740
aatagacaga tcgctgagat aggtgcctca ctgattaagc attggtaact gtcagaccaa    4800
gtttactcat atatacttta gattgattta aaacttcatt tttaatttaa aaggatctag    4860
gtgaagatcc tttttgataa tctcatgacc aaaatccctt aacgtgagtt ttcgttccac    4920
tgagcgtcag accccgtaga aaagatcaaa ggatcttctt gagatccttt ttttctgcgc    4980
```

```
gtaatctgct gcttgcaaac aaaaaaacca ccgctaccag cggtggtttg tttgccggat    5040
caagagctac caactctttt tccgaaggta actggcttca gcagagcgca gataccaaat    5100
actgttcttc tagtgtagcc gtagttaggc caccacttca agaactctgt agcaccgcct    5160
acatacctcg ctctgctaat cctgttacca gtggctgctg ccagtggcga taagtcgtgt    5220
cttaccgggt tggactcaag acgatagtta ccggataagg cgcagcggtc gggctgaacg    5280
gggggttcgt gcacacagcc cagcttggag cgaacgacct acaccgaact gagataccta    5340
cagcgtgagc tatgagaaag cgccacgctt cccgaaggga gaaaggcgga caggtatccg    5400
gtaagcggca gggtcggaac aggagagcgc acgagggagc ttccagggg  aaacgcctgg    5460 tatctttata gtcctgtcgg gtttcgccac ctctgacttg agcgtcgatt tttgtgatgc    5520
tcgtcagggg gcggagcct  atggaaaaac gccagcaacg cggcctttt  acggttcctg    5580 gccttttgct ggccttttgc tcacatgttc tttcctgcgt tatccctga  ttctgtggat    5640 aaccgtatta ccgcctttga gtgagctgat accgctcgcc gcagccgaac gaccgagcgc    5700
agcgagtcag tgagcgagga agcggaagag cgcccaatac gcaaaccgcc tctccccgcg    5760
cgttggccga ttcattaatg cagctggcac gacaggtttc ccgactggaa agcgggcagt    5820
gagcgcaacg caattaatgt gagttagctc actcattagg caccccaggc tttacacttt    5880
atgcttccgg ctcgtatgtt gtgtggaatt gtgagcggat aacaatttca cacaggaaac    5940
agctatgacc atgattacgc caagctctag ctagaggtcg agtccctccc cagcaggcag    6000
aagtatgcaa agcatgcatc tcaattagtc agcaaccata gtcccgcccc taactccgcc    6060
catcccgccc ctaactccgc ccagttccgc ccattctccg ccccatggct gactaatttt    6120
ttttatttat gcagaggccg aggccgcctc ggcctctgag ctattccaga agtagtgagg    6180 aggcttttt  ggaggcctag gcttttgcaa aa                                  6212

<210> SEQ ID NO 3
<211> LENGTH: 7498
<212> TYPE: DNA
<213> ORGANISM: Artificial Sequence
<220> FEATURE:
<223> OTHER INFORMATION: Synthetic construct: pJP180 ; pHybE-mCk V1

<400> SEQUENCE: 3
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg ccttttttcc gagggtgggg gagaaccgta     180
tataagtgca gtagtcgccg tgaacgttct ttttcgcaac gggtttgccg ccagaacaca     240
ggtaagtgcc gtgtgtggtt cccgcgggcc tggcctcttt acgggttatg gcccttgcgt     300
gccttgaatt acttccacct ggctgcagta cgtgattctt gatcccgagc ttcgggttgg     360
aagtgggtgg gagagttcga ggccttgcgc ttaaggagcc cttcgcctc  gtgcttgagt     420 tgaggcctgg cctgggcgct ggggccgccg cgtgcgaatc tggtggcacc ttcgcgcctg     480
tctcgctgct ttcgataagt ctctagccat ttaaattttt tgatgacctg ctgcgacgct     540
ttttttctgg caagatagtc ttgtaaatgc gggccaagat ctgcacactg gtatttcggt     600
ttttggggcc gcgggcggcg acgggcccg  tgcgtcccag cgcacatgtt cggcgaggcg     660
gggcctgcga gcgcggccac cgagaatcgg acggggtag  tctcaagctg gccggcctgc     720
tctggtgcct ggcctcgcgc cgccgtgtat cgccccgccc tgggcggcaa ggctggcccg     780
gtcggcacca gttgcgtgag cggaaagatg gccgcttccc ggccctgctg cagggagctc     840
```

```
aaaatggagg acgcggcgct cgggagagcg ggcgggtgag tcacccacac aaaggaaaag      900
ggcctttccg tcctcagccg tcgcttcatg tgactccacg gagtaccggg cgccgtccag      960
gcacctcgat tagttctcga gcttttggag tacgtcgtct ttaggttggg gggaggggtt     1020
ttatgcgatg gagtttcccc acactgagtg ggtggagact gaagttaggc cagcttggca     1080
cttgatgtaa ttctccttgg aatttgccct ttttgagttt ggatcttggt tcattctcaa     1140
gcctcagaca gtggttcaaa gttttttttct tccatttcag gtgtcgtgag gaattctcta    1200
gagatccctc gacctcgagc atttaaatgc ccgggcgcac catggacatg cgcgtgcccg     1260
cccagctgct gggcctgctg ctgctgtggt tccccggctc gcgatgcgca tggtatgccg     1320
aaagggatgc tgaaattgag aacgaaaagc tgcgccggga ggttgaagaa ctgcggcagg     1380
ccagcgaggc agatctccag ccaggaacta ttgagtacga acgccatcga cttacgcgtg     1440
cgcaggccga cgcacaggaa ctgaagaatg ccagagactc cgctgaagtg gtggaaaccg     1500
cattctgtac tttcgtgctg tcgcggatcg caggtgaaat tgccagtatt ctcgacgggc     1560
tcccctgtc ggtgcagcgg cgttttccgg aactggaaaa ccgacatgtt gatttcctga     1620
aacgggatat catcaaagcc atgaacaaag cagccgcgct ggatgaactg ataccggggt     1680
tgctgagtga atatatcgaa cagtcaggtt aacaggctgc ggcattttgt ccgcgccggg     1740
cttcgctcac tgttcaggcc ggagccacag accgccgttg aatgggcgga tgctaattac     1800
tatctcccga aagaatccgc ataccaggaa gggcgctggg aaacactgcc ctttcagcgg     1860
gccatcatga atgcgatggg cagcgactac atccgtgagg tgaatgtggt gaagtctgcc     1920
cgtgtcggtt attccaaaat gctgctgggt gtttatgcct actttataga gcataagcag     1980
cgcaacaccc ttatctggtt gccgacggat ggtgatgccg agaactttat gaaaacccac     2040
gttgagccga ctattcgtga tattccgtcg ctgctggcgc tggccccgtg gtatggcaaa     2100
aagcaccggg ataacacgct caccatgaag cgtttcacta atgggcgtgg cttctggtgc     2160
ctgggcggta aagcggcaaa aaactaccgt gaaaagtcgg tggatgtggc gggttatgat     2220
gaacttgctg cttttgatga tgatattgaa caggaaggct ctccgacgtt cctgggtgac     2280
aagcgctgat gctgcaccaa ctgtatccat cttcccacca tccagtgagc agttaacatc     2340
tggaggtgcc tcagtcgtgt gcttcttgaa caacttctac cccaaagaca tcaatgtcaa     2400
gtggaagatt gatggcagtg aacgacaaaa tggcgtcctg aacagttgga ctgatcagga     2460
cagcaaagac agcacctaca gcatgagcag caccctcacg ttgaccaagg acgagtatga     2520
acgacataac agctatacct gtgaggccac tcacaagaca tcaacttcac ccattgtcaa     2580
gagcttcaac aggaatgagt gttaagcggc cgctcgaggc cggcaaggcc ggatcccccg     2640
acctcgacct ctggctaata aaggaaattt attttcattg caatagtgtg ttggaatttt     2700
ttgtgtctct cactcggaag gacatatggg agggcaaatc atttggtcga gatccctcgg     2760
agatctctag ctagaggatc gatccccgcc ccggacgaac taaacctgac tacgacatct     2820
ctgcccccttc ttcgcgggc agtgcatgta atcccttcag ttggttggta caacttgcca     2880
actgggcccct gttccacatg tgacacgggg ggggaccaaa cacaaagggg ttctctgact    2940
gtagttgaca tccttataaa tggatgtgca catttgccaa cactgagtgg ctttcatcct     3000
ggagcagact ttgcagtctg tggactgcaa cacaacattg cctttatgtg taactcttgg     3060
ctgaagctct tacaccaatg ctgggggaca tgtacctccc aggggcccag gaagactacg     3120
ggaggctaca ccaacgtcaa tcagagggc ctgtgtagct accgataagc ggaccctcaa      3180
gagggcatta gcaatagtgt ttataaggcc cccttgttaa ccctaaacgg gtagcatatg     3240
```

```
cttcccgggt agtagtatat actatccaga ctaaccctaa ttcaatagca tatgttaccc   3300
aacgggaagc atatgctatc gaattagggt tagtaaaagg gtcctaagga acagcgatat   3360
ctcccacccc atgagctgtc acggttttat ttacatgggg tcaggattcc acgagggtag   3420
tgaaccattt tagtcacaag ggcagtggct gaagatcaag gagcgggcag tgaactctcc   3480
tgaatcttcg cctgcttctt cattctcctt cgtttagcta atagaataac tgctgagttg   3540
tgaacagtaa ggtgtatgtg aggtgctcga aaacaaggtt tcaggtgacg cccccagaat   3600
aaaatttgga cgggggttc agtggtggca ttgtgctatg acaccaatat aaccctcaca   3660
aaccccttgg gcaataaata ctagtgtagg aatgaaacat tctgaatatc tttaacaata   3720
gaaatccatg gggtggggac aagccgtaaa gactggatgt ccatctcaca cgaatttatg   3780
gctatgggca acacataatc ctagtgcaat atgatactgg ggttattaag atgtgtccca   3840
ggcagggacc aagacaggtg aaccatgttg ttacactcta tttgtaacaa ggggaaagag   3900
agtggacgcc gacagcagcg gactccactg gttgtctcta acaccccga aaattaaacg   3960 gggctccacg ccaatggggc ccataaacaa agacaagtgg ccactctttt ttttgaaatt   4020
gtggagtggg ggcacgcgtc agcccccaca cgccgccctg cggttttgga ctgtaaaata   4080
agggtgtaat aacttggctg attgtaaccc cgctaaccac tgcggtcaaa ccacttgccc   4140
acaaaaccac taatggcacc ccggggaata cctgcataag taggtgggcg ggccaagata   4200
ggggcgcgat tgctgcgatc tggaggacaa attacacaca cttgcgcctg agcgccaagc   4260
acagggttgt tggtcctcat attcacgagg tcgctgagag cacggtgggc taatgttgcc   4320
atgggtagca tatactaccc aaatatctgg atagcatatg ctatcctaat ctatatctgg   4380
gtagcatagg ctatcctaat ctatatctgg gtagcatatg ctatcctaat ctatatctgg   4440
gtagtatatg ctatcctaat ttatatctgg gtagcatagg ctatcctaat ctatatctgg   4500
gtagcatatg ctatcctaat ctatatctgg gtagtatatg ctatcctaat ctgtatccgg   4560
gtagcatatg ctatcctaat agagattagg gtagtatatg ctatcctaat ttatatctgg   4620
gtagcatata ctacccaaat atctggatag catatgctat cctaatctat atctgggtag   4680
catatgctat cctaatctat atctgggtag cataggctat cctaatctat atctgggtag   4740
catatgctat cctaatctat atctgggtag tatatgctat cctaatttat atctgggtag   4800
cataggctat cctaatctat atctgggtag catatgctat cctaatctat atctgggtag   4860
tatatgctat cctaatctgt atccgggtag catatgctat cctcatgata agctgtcaaa   4920
catgagaatt ttcttgaaga cgaaagggcc tcgtgatacg cctattttta taggttaatg   4980
tcatgataat aatggtttct tagacgtcag gtggcacttt tcggggaaat gtgcgcggaa   5040
cccctatttg tttattttc taaatacatt caaatatgta tccgctcatg agacaataac   5100
cctgataaat gcttcaataa tattgaaaaa ggaagagtat gagtattcaa catttccgtg   5160
tcgcccttat tccctttttt gcggcatttt gccttcctgt ttttgctcac ccagaaacgc   5220
tggtgaaagt aaaagatgct gaagatcagt tgggtgcacg agtgggttac atcgaactgg   5280
atctcaacag cggtaagatc cttgagagtt ttcgccccga agaacgtttt ccaatgatga   5340
gcacttttaa agttctgcta tgtggcgcgg tattatcccg tgttgacgcc gggcaagagc   5400
aactcggtcg ccgcatacac tattctcaga atgacttggt tgagtactca ccagtcacag   5460
aaaagcatct tacgdatggc atgacagtaa gagaattatg cagtgctgcc ataaccatga   5520
gtgataacac tgcggccaac ttacttctga caacgatcgg aggaccgaag gagctaaccg   5580
cttttttgca caacatgggg gatcatgtaa ctcgccttga tcgttgggaa ccggagctga   5640
```

```
atgaagccat accaaacgac gagcgtgaca ccacgatgcc tgcagcaatg gcaacaacgt      5700
tgcgcaaact attaactggc gaactactta ctctagcttc ccggcaacaa ttaatagact      5760
ggatggaggc ggataaagtt gcaggaccac ttctgcgctc ggcccttccg gctggctggt      5820
ttattgctga taaatctgga gccggtgagc gtgggtctcg cggtatcatt gcagcactgg      5880
ggccagatgg taagccctcc cgtatcgtag ttatctacac gacggggagt caggcaacta      5940
tggatgaacg aaatagacag atcgctgaga taggtgcctc actgattaag cattggtaac      6000
tgtcagacca gtttactcat atatactttt agattgattt aaaacttcat ttttaattta      6060
aaaggatcta ggtgaagatc cttttttgata atctcatgac caaaatccct taacgtgagt      6120
tttcgttcca ctgagcgtca gaccccgtag aaaagatcaa aggatcttct tgagatcctt      6180 ttttctgcg cgtaatctgc tgcttgcaaa caaaaaaacc accgctacca gcggtggttt      6240
gtttgccgga tcaagagcta ccaactcttt ttccgaaggt aactggcttc agcagagcgc      6300
agataccaaa tactgttctt ctagtgtagc cgtagttagg ccaccacttc aagaactctg      6360
tagcaccgcc tacatacctc gctctgctaa tcctgttacc agtggctgct gccagtggcg      6420
ataagtcgtg tcttaccggg ttggactcaa gacgatagtt accggataag cgcagcggt      6480 cgggctgaac ggggggttcg tgcacacagc ccagcttgga gcgaacgacc tacaccgaac      6540
tgagatacct acagcgtgag ctatgagaaa gcgccacgct tcccgaaggg agaaaggcgg      6600
acaggtatcc ggtaagcggc agggtcggaa caggagagcg cacgagggag cttccagggg      6660
gaaacgcctg gtatctttat agtcctgtcg ggtttcgcca cctctgactt gagcgtcgat      6720
ttttgtgatg ctcgtcaggg gggcggagcc tatggaaaaa cgccagcaac gcggcctttt      6780
tacggttcct ggccttttgc tggccttttg ctcacatgtt ctttcctgcg ttatcccctg      6840
attctgtgga taaccgtatt accgcctttg agtgagctga taccgctcgc cgcagccgaa      6900
cgaccgagcg cagcgagtca gtgagcgagg aagcggaaga gcgcccaata cgcaaaccgc      6960
ctctccccgc gcgttggccg attcattaat gcagctggca cgacaggttt cccgactgga      7020
aagcgggcag tgagcgcaac gcaattaatg tgagttagct cactcattag gcaccccagg      7080
ctttacactt tatgcttccg gctcgtatgt tgtgtggaat tgtgagcgga taacaatttc      7140
acacaggaaa cagctatgac catgattacg ccaagctcta gctagaggtc gagtccctcc      7200
ccagcaggca gaagtatgca aagcatgcat ctcaattagt cagcaaccat agtcccgccc      7260
ctaactccgc ccatcccgcc cctaactccg cccagttccg cccattctcc gccccatggc      7320
tgactaattt ttttatttta tgcagaggcc gaggccgcct cggcctctga gctattccag      7380
aagtagtgag gaggcttttt tggaggccta ggcttttgca aaaagctttg caaagatgga      7440
taaagtttta aacagagagg aatctttgca gctaatggac cttctaggtc ttgaaagg         7498

<210> SEQ ID NO 4
<211> LENGTH: 7498
<212> TYPE: DNA
<213> ORGANISM: Artificial Sequence
<220> FEATURE:
<223> OTHER INFORMATION: Synthetic construct: pJP193 ; pHybE-mCk V2

<400> SEQUENCE: 4
agtgggaatt ggctccggtg cccgtcagtg ggcagagcgc acatcgccca cagtccccga        60
gaagttgggg ggaggggtcg gcaattgaac cggtgcctag agaaggtggc gcggggtaaa       120
ctgggaaagt gatgtcgtgt actggctccg ccttttttccc gagggtgggg gagaaccgta       180
tataagtgca gtagtcgccg tgaacgttct ttttcgcaac gggtttgccg ccagaacaca       240
```

```
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540 tttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggaggggtt   1020
ttatgcgatg gagtttcccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gttttttttct tccatttcag gtgtcgtgag gaattctcta   1200
gagatccctc gacctcgaga tccattgtgc ccgggcgcac catggacatg cgcgtgcccg   1260
cccagctgct gggcctgctg ctgctgtggt tccccggctc gcgatgcgca tggtatgccg   1320
aaagggatgc tgaaattgag aacgaaaagc tgcgccggga ggttgaagaa ctgcggcagg   1380
ccagcgagcg agatctccag ccaggaacta ttgagtacga acgccatcga cttacgcgtg   1440
cgcaggccga cgcacaggaa ctgaagaatg ccagagactc cgctgaagtg gtggaaaccg   1500
cattctgtac tttcgtgctg tcgcggatcg caggtgaaat tgccagtatt ctcgacgggc   1560 tcccccctgtc ggtgcagcgg cgttttccgg aactggaaaa ccgacatgtt gatttcctga   1620
aacgggatat catcaaagcc atgaacaaag cagccgcgct ggatgaactg ataccggggt   1680
tgctgagtga atatatcgaa cagtcaggtt aacaggctgc ggcattttgt ccgcgccggg   1740
cttcgctcac tgttcaggcc ggagccacag accgccgttg aatgggcgga tgctaattac   1800
tatctcccga agaatccgc ataccaggaa gggcgctggg aaacactgcc cttcagcgg   1860 gccatcatga atgcgatggg cagcgactac atccgtgagg tgaatgtggt gaagtctgcc   1920
cgtgtcggtt attccaaaat gctgctgggt gtttatgcct actttataga gcataagcag   1980
cgcaacaccc ttatctggtt gccgacggat ggtgatgccg agaactttat gaaaacccac   2040
gttgagccga ctattcgtga tattccgtcg ctgctggcgc tggccccgtg gtatggcaaa   2100
agcaccgggg ataacacgct caccatgaag cgtttcacta atgggcgtgg cttctggtgc   2160
ctgggcggta aagcggcaaa aaactaccgt gaaaagtcgg tggatgtggc gggttatgat   2220
gaacttgctg cttttgatga tgatattgaa caggaaggct ctccgacgtt cctgggtgac   2280
aagcgctgat gctgcaccaa ctgtatccat cttcccacca tccagtgagc agttaacatc   2340
tggaggtgcc tcagtcgtgt gcttcttgaa caacttctac cccaaagaca tcaatgtcaa   2400
gtggaagatt gatggcagtg aacgacaaaa tggcgtcctg aacagttgga ctgatcagga   2460
cagcaaagac agcacctaca gcatgagcag caccctcacg ttgaccaagg acgagtatga   2520
acgacataac agctatacct gtgaggccac tcacaagaca tcaacttcac ccattgtcaa   2580
gagcttcaac aggaatgagt gttaagcggc cgctcgaggc cggcaaggcc ggatcccccg   2640
```

```
acctcgacct ctggctaata aaggaaattt attttcattg caatagtgtg ttggaatttt    2700
ttgtgtctct cactcggaag gacatatggg agggcaaatc atttggtcga gatccctcgg    2760
agatctctag ctagaggatc gatccccgcc ccggacgaac taaacctgac tacgacatct    2820
ctgccccttc ttcgcggggc agtgcatgta atcccttcag ttggttggta caacttgcca    2880
actgggccct gttccacatg tgacacgggg ggggaccaaa cacaaagggg ttctctgact    2940
gtagttgaca tccttataaa tggatgtgca catttgccaa cactgagtgg ctttcatcct    3000
ggagcagact ttgcagtctg tggactgcaa cacaacattg cctttatgtg taactcttgg    3060
ctgaagctct tacaccaatg ctgggggaca tgtacctccc aggggcccag gaagactacg    3120
ggaggctaca ccaacgtcaa tcagaggggc ctgtgtagct accgataagc ggaccctcaa    3180
gagggcatta gcaatagtgt ttataaggcc cccttgttaa ccctaaacgg gtagcatatg    3240
cttcccgggt agtagtatat actatccaga ctaaccctaa ttcaatagca tatgttaccc    3300
aacgggaagc atatgctatc gaattagggt tagtaaaagg gtcctaagga acagcgatat    3360
ctcccacccc atgagctgtc acggttttat ttacatgggg tcaggattcc acgagggtag    3420
tgaaccattt tagtcacaag ggcagtggct gaagatcaag gagcgggcag tgaactctcc    3480
tgaatcttcg cctgcttctt cattctcctt cgtttagcta atagaataac tgctgagttg    3540
tgaacagtaa ggtgtatgtg aggtgctcga aaacaaggtt tcaggtgacg cccccagaat    3600
aaaatttgga cgggggttc agtggtggca ttgtgctatg acaccaatat aaccctcaca    3660
aaccccttgg gcaataaata ctagtgtagg aatgaaacat tctgaatatc tttaacaata    3720
gaaatccatg gggtggggac aagccgtaaa gactggatgt ccatctcaca cgaatttatg    3780
gctatgggca acacataatc ctagtgcaat atgatactgg ggttattaag atgtgtccca    3840
ggcagggacc aagacaggtg aaccatgttg ttacactcta tttgtaacaa ggggaaagag    3900
agtggacgcc gacagcagcg gactccactg gttgtctcta acaccccga aaattaaacg    3960 gggctccacg ccaatggggc ccataaacaa agacaagtgg ccactctttt ttttgaaatt    4020
gtggagtggg ggcacgcgtc agcccccaca cgccgccctg cggttttgga ctgtaaaata    4080
agggtgtaat aacttggctg attgtaaccc cgctaaccac tgcggtcaaa ccacttgccc    4140
acaaaaccac taatggcacc ccggggaata cctgcataag taggtgggcg ggccaagata    4200
ggggcgcgat tgctgcgatc tggaggacaa attcacacac cttgcgcctg agcgccaagc    4260
acagggttgt tggtcctcat attcacgagg tcgctgagag cacggtgggc taatgttgcc    4320
atgggtagca tatactaccc aaatatctgg atagcatatg ctatcctaat ctatatctgg    4380
gtagcatagg ctatcctaat ctatatctgg gtagcatatg ctatcctaat ctatatctgg    4440
gtagtatatg ctatcctaat ttatatctgg gtagcatagg ctatcctaat ctatatctgg    4500
gtagcatatg ctatcctaat ctatatctgg gtagtatatg ctatcctaat ctgtatccgg    4560
gtagcatatg ctatcctaat agagattagg gtagtatatg ctatcctaat ttatatctgg    4620
gtagcatata ctacccaaat atctggatag catatgctat cctaatctat atctgggtag    4680
catatgctat cctaatctat atctgggtag cataggctat cctaatctat atctgggtag    4740
catatgctat cctaatctat atctgggtag tatatgctat cctaatttat atctgggtag    4800
cataggctat cctaatctat atctgggtag catatgctat cctaatctat atctgggtag    4860
tatatgctat cctaatctgt atccgggtag catatgctat cctcatgata agctgtcaaa    4920
catgagaatt ttccttgaaga cgaaagggcc tcgtgatacg cctatttta taggttaatg    4980 tcatgataat aatggtttct tagacgtcag gtggcacttt tcggggaaat gtgcgcggaa    5040
```

```
cccctatttg tttattttc taaatacatt caaatatgta tccgctcatg agacaataac    5100
cctgataaat gcttcaataa tattgaaaaa ggaagagtat gagtattcaa catttccgtg    5160
tcgcccttat tccctttttt gcggcatttt gccttcctgt ttttgctcac ccagaaacgc    5220
tggtgaaagt aaaagatgct gaagatcagt tgggtgcacg agtgggttac atcgaactgg    5280
atctcaacag cggtaagatc cttgagagtt ttcgccccga agaacgtttt ccaatgatga    5340
gcacttttaa agttctgcta tgtggcgcgg tattatcccg tgttgacgcc gggcaagagc    5400
aactcggtcg ccgcatacac tattctcaga atgacttggt tgagtactca ccagtcacag    5460
aaaagcatct tacggatggc atgacagtaa gagaattatg cagtgctgcc ataaccatga    5520
gtgataacac tgcggccaac ttacttctga caacgatcgg aggaccgaag gagctaaccg    5580
cttttttgca caacatgggg gatcatgtaa ctcgccttga tcgttgggaa ccggagctga    5640
atgaagccat accaaacgac gagcgtgaca ccacgatgcc tgcagcaatg gcaacaacgt    5700
tgcgcaaact attaactggc gaactactta ctctagcttc ccggcaacaa ttaatagact    5760
ggatggaggc ggataaagtt gcaggaccac ttctgcgctc ggcccttccg gctggctggt    5820
ttattgctga taaatctgga gccggtgagc gtgggtctcg cggtatcatt gcagcactgg    5880
ggccagatgg taagccctcc cgtatcgtag ttatctacac gacggggagt caggcaacta    5940
tggatgaacg aaatagacag atcgctgaga taggtgcctc actgattaag cattggtaac    6000
tgtcagacca gtttactcat atatacttt agattgattt aaaacttcat ttttaattta    6060
aaaggatcta ggtgaagatc cttttgata atctcatgac caaaatccct taacgtgagt    6120
tttcgttcca ctgagcgtca gaccccgtag aaaagatcaa aggatcttct tgagatcctt    6180
tttttctgcg cgtaatctgc tgcttgcaaa caaaaaaacc accgctacca gcggtggttt    6240
gtttgccgga tcaagagcta ccaactcttt ttccgaaggt aactggcttc agcagagcgc    6300
agataccaaa tactgttctt ctagtgtagc cgtagttagg ccaccacttc aagaactctg    6360
tagcaccgcc tacatacctc gctctgctaa tcctgttacc agtggctgct gccagtggcg    6420
ataagtcgtg tcttaccggg ttggactcaa gacgatagtt accggataag gcgcagcggt    6480
cgggctgaac ggggggttcg tgcacacagc ccagcttgga gcgaacgacc tacaccgaac    6540
tgagatacct acagcgtgag ctatgagaaa gcgccacgct tcccgaaggg agaaaggcgg    6600
acaggtatcc ggtaagcggc agggtcggaa caggagagcg cacgagggag cttccagggg    6660
gaaacgcctg gtatctttat agtcctgtcg ggtttcgcca cctctgactt gagcgtcgat    6720
ttttgtgatg ctcgtcaggg gggcggagcc tatggaaaaa cgccagcaac gcggcctttt    6780
tacggttcct ggccttttgc tggccttttg ctcacatgtt ctttcctgcg ttatcccctg    6840
attctgtgga taaccgtatt accgcctttg agtgagctga taccgctcgc cgcagccgaa    6900
cgaccgagcg cagcgagtca gtgagcgagg aagcggaaga gcgcccaata cgcaaaccgc    6960
ctctccccgc gcgttggccg attcattaat gcagctggca cgacaggttt cccgactgga    7020
aagcgggcag tgagcgcaac gcaattaatg tgagttagct cactcattag gcaccccagg    7080
ctttacactt tatgcttccg gctcgtatgt tgtgtggaat tgtgagcgga taacaatttc    7140
acacaggaaa cagctatgac catgattacg ccaagctcta gctagaggtc gagtccctcc    7200
ccagcaggca gaagtatgca aagcatgcat ctcaattagt cagcaaccat agtcccgccc    7260
ctaactccgc ccatcccgcc cctaactccg cccagttccg cccattctcc gccccatggc    7320
tgactaattt ttttattta tgcagaggcc gaggccgcct cggcctctga gctattccag    7380
aagtagtgag gaggcttttt tggaggccta ggcttttgca aaaagctttg caaagatgga    7440
```

-continued

```
taaagttttta aacagagagg aatctttgca gctaatggac cttctaggtc ttgaaagg    7498
```

<210> SEQ ID NO 5
<211> LENGTH: 8144
<212> TYPE: DNA
<213> ORGANISM: Artificial Sequence
<220> FEATURE:
<223> OTHER INFORMATION: Synthetic construct: pJP176 ; pHybE-mCg1 V1

<400> SEQUENCE: 5

```
agtgggaatt ggctccggtg cccgtcagtg ggcagagcgc acatcgccca cagtccccga     60
gaagttgggg ggaggggtcg gcaattgaac cggtgcctag agaaggtggc gcggggtaaa    120
ctggaaagt gatgtcgtgt actggctccg cctttttccc gagggtgggg gagaaccgta    180
tataagtgca gtagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtgcacc ttcgcgcctg    480
tctcgctgct ttcgataagt ctctagccat ttaaaatttt tgatgacctg ctgcgacgct    540
tttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggagggggtt   1020
ttatgcgatg gagtttcccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gtttttttct tccatttcag gtgtcgtgag gaattctcta   1200
gagatccctc gacctcgagc atttaaatgc ccgggcgcca ccatggagtt tgggctgagc   1260
tggcttttc ttgtcgcgat tttaaaaggt gtccagtgcg catggtatgc cgaaagggat   1320
gctgaaattg agaacgaaaa gctgcgccgg gaggttgaag aactgcggca ggccagcgag   1380
gcagatctcc agccaggaac tattgagtac gaacgccatc gacttacgcg tgcgcaggcc   1440
gacgcacagg aactgaagaa tgccagagac tccgctgaag tggtggaaac cgcattctgt   1500
actttcgtgc tgtcgcggat cgcaggtgaa attgccagta ttctcgacgg gctcccctg   1560
tcggtgcagc ggcgttttcc ggaactggaa aaccgacatg ttgatttcct gaaacgggat   1620
atcatcaaag ccatgaacaa agcagccgcg ctgatgaac tgataccggg gttgctgagt   1680
gaatatatcg aacagtcagg ttaacaggct gcggcatttt gtccgcgccg gcttcgctc   1740
actgttcagg ccggagccac agaccgccgt tgaatgggcg gatgctaatt actatctccc   1800
gaaagaatcc gcataccagg aagggcgctg gaaacactg ccctttcagc gggccatcat   1860
gaatgcgatg ggcagcgact acatccgtga ggtgaatgtg gtgaagtctg cccgtgtcgg   1920
ttattccaaa atgctgctgg gtgttttatgc ctactttata gagcataagc agcgcaacac   1980
ccttatctgg ttgccgacgg atggtgatgc cgagaacttt atgaaaaccc acgttgagcc   2040
```

```
gactattcgt gatattccgt cgctgctggc gctggcccg tggtatggca aaaagcaccg    2100
ggataacacg ctcaccatga agcgtttcac taatgggcgt ggcttctggt gcctgggcgg    2160
taaagcggca aaaactacc gtgaaaagtc ggtggatgtg gcgggttatg atgaacttgc    2220
tgcttttgat gatgatattg aacaggaagg ctctccgacg ttcctgggtg acaagcgcta    2280
aaacgacacc cccatctgtc tatccactgg cccctggatc tgctgcccaa actaactcca    2340
tggtgaccct gggatgcctg gtcaagggct atttccctga ccagtgaca gtgacctgga    2400 actctggatc cctgtccagc ggtgtgcaca ccttcccagc tgtcctgcag tctgacctct    2460
acactctgag cagctcagtg actgtcccct ccagcacctg gcccagcgag accgtcacct    2520
gcaacgttgc ccacccggcc agcagcacca aggtggacaa gaaaattgtg cccagggatt    2580
gtggttgtaa gccttgcata tgtacagtcc cagaagtatc atctgtcttc atcttccccc    2640
caaagcccaa ggatgtgctc accattactc tgactcctaa ggtcacgtgt gttgtggtag    2700
acatcagcaa ggatgatccc gaggtccagt tcagctggtt tgtagatgat gtggaggtgc    2760
acacagctca gacgcaaccc cgggaggagc agttcaacag cactttccgc tcagtcagtg    2820
aacttcccat catgcaccag gactggctca atggcaagga gttcaaatgc agggtcaaca    2880
gtgcagcttt ccctgccccc atcgagaaaa ccatctccaa aaccaaaggc agaccgaagg    2940
ctccacaggt gtacaccatt ccacctccca aggagcagat ggccaaggat aaagtcagtc    3000
tgacctgcat gataacagac ttcttccctg aagacattac tgtggagtgg cagtggaatg    3060
ggcagccagc ggagaactac aagaacactc agcccatcat ggacacagat ggctcttact    3120
tcgtctacag caagctcaat gtgcagaaga gcaactggga ggcaggaaat actttcacct    3180
gctctgtgtt acatgagggc ctgcacaacc accatactga aagagcctc tcccactctc    3240 ctggtaaata agcggccgct cgaggccggc aaggccggat cccccgacct cgacctctgg    3300
ctaataaagg aaatttattt tcattgcaat agtgtgttgg aattttttgt gtctctcact    3360
cggaaggaca tatgggaggg caaatcattt ggtcgagatc cctcggagat ctctagctag    3420
aggatcgatc cccgccccgg acgaactaaa cctgactacg acatctctgc ccttcttcg    3480 cggggcagtg catgtaatcc cttcagttgg ttggtacaac ttgccaactg gccctgttc    3540 cacatgtgac acgggggggg accaaacaca aaggggttct ctgactgtag ttgacatcct    3600
tataaatgga tgtgcacatt tgccaacact gagtggcttt catcctggag cagactttgc    3660
agtctgtgga ctgcaacaca acattgcctt tatgtgtaac tcttggctga agctcttaca    3720
ccaatgctgg gggacatgta cctcccaggg gcccaggaag actacgggag ctacaccaa    3780 cgtcaatcag aggggcctgt gtagctaccg ataagcggac cctcaagagg gcattagcaa    3840
tagtgtttat aaggccccct tgttaaccct aaacgggtag catatgcttc ccgggtagta    3900
gtatatacta tccagactaa ccctaattca atagcatatg ttacccaacg ggaagcatat    3960
gctatcgaat tagggttagt aaaagggtcc taaggaacag cgatatctcc cacccatga    4020 gctgtcacgg tttatttac atggggtcag gattccacga gggtagtgaa ccattttagt    4080
cacaagggca gtggctgaag atcaaggagc gggcagtgaa ctctcctgaa tcttcgcctg    4140
cttcttcatt ctccttcgtt tagctaatag aataactgct gagttgtgaa cagtaaggtg    4200
tatgtgaggt gctcgaaaac aaggtttcag gtgacgcccc cagaataaaa tttgacgggg    4260
gggttcagtg gtggcattgt gctatgacac caatataacc ctcacaaacc ccttgggcaa    4320
taaatactag tgtaggaatg aaacattctg aatatcttta acaatagaaa tccatggggt    4380
ggggacaagc cgtaaagact ggatgtccat ctcacacgaa tttatggcta tgggcaacac    4440
```

```
ataatcctag tgcaatatga tactggggtt attaagatgt gtcccaggca gggaccaaga    4500
caggtgaacc atgttgttac actctatttg taacaagggg aaagagagtg gacgccgaca    4560
gcagcggact ccactggttg tctctaacac ccccgaaaat taaacggggc tccacgccaa    4620
tggggcccat aaacaaagac aagtggccac tcttttttt gaaattgtgg agtgggggca     4680
cgcgtcagcc cccacacgcc gccctgcggt tttggactgt aaaataaggg tgtaataact    4740
tggctgattg taacccgct aaccactgcg gtcaaaccac ttgcccacaa aaccactaat     4800
ggcaccccgg ggaatacctg cataagtagg tgggcgggcc aagataggg cgcgattgct     4860 gcgatctgga ggacaaatta cacacacttg cgcctgagcg ccaagcacag ggttgttggt    4920
cctcatattc acgaggtcgc tgagagcacg gtgggctaat gttgccatgg gtagcatata    4980
ctacccaaat atctggatag catatgctat cctaatctat atctgggtag cataggctat    5040
cctaatctat atctgggtag catatgctat cctaatctat atctgggtag tatatgctat    5100
cctaatttat atctgggtag cataggctat cctaatctat atctgggtag catatgctat    5160
cctaatctat atctgggtag tatatgctat cctaatctgt atccgggtag catatgctat    5220
cctaatagag attagggtag tatatgctat cctaatttat atctgggtag catatactac    5280
ccaaatatct ggatagcata tgctatccta atctatatct gggtagcata tgctatccta    5340
atctatatct gggtagcata ggctatccta atctatatct gggtagcata tgctatccta    5400
atctatatct gggtagtata tgctatccta atttatatct gggtagcata ggctatccta    5460
atctatatct gggtagcata tgctatccta atctatatct gggtagtata tgctatccta    5520
atctgtatcc gggtagcata tgctatcctc atgataagct gtcaaacatg agaattttct    5580
tgaagacgaa agggcctcgt gatacgccta ttttataggt taatgtcat gataataatg      5640 gtttcttaga cgtcaggtgg cacttttcgg ggaaatgtgc gcggaacccc tatttgttta    5700
tttttctaaa tacattcaaa tatgtatccg ctcatgagac aataaccctg ataaatgctt    5760
caataatatt gaaaaaggaa gagtatgagt attcaacatt tccgtgtcgc ccttattccc    5820
ttttttgcgg cattttgcct tcctgttttt gctcacccag aaacgctggt gaaagtaaaa    5880
gatgctgaag atcagttggg tgcacgagtg ggttacatcg aactggatct caacagcggt    5940
aagatccttg agagttttcg ccccgaagaa cgttttccaa tgatgagcac ttttaaagtt    6000
ctgctatgtg gcgcggtatt atcccgtgtt gacgccgggc aagagcaact cggtcgccgc    6060
atacactatt ctcagaatga cttggttgag tactcaccag tcacagaaaa gcatcttacg    6120
gatggcatga cagtaagaga attatgcagt gctgccataa ccatgagtga taacactgcg    6180
gccaacttac ttctgacaac gatcggagga ccgaaggagc taaccgcttt tttgcacaac    6240
atgggggatc atgtaactcg ccttgatcgt tgggaaccgg agctgaatga agccatacca    6300
aacgacgagc gtgacaccac gatgcctgca gcaatggcaa caacgttgcg caaactatta    6360
actggcgaac tacttactct agcttcccgg caacaattaa tagactggat ggaggcggat    6420
aaagttgcag gaccacttct gcgctcggcc cttccggctg gctggtttat tgctgataaa    6480
tctggagccg gtgagcgtgg gtctcgcggt atcattgcag cactggggcc agatggtaag    6540
ccctcccgta tcgtagttat ctacacgacg gggagtcagg caactatgga tgaacgaaat    6600
agacagatcg ctgagatagg tgcctcactg attaagcatt ggtaactgtc agaccaagtt    6660
tactcatata tactttagat tgatttaaaa cttcattttt aatttaaaag gatctaggtg    6720
aagatccttt ttgataatct catgaccaaa atcccttaac gtgagttttc gttccactga    6780
gcgtcagacc ccgtagaaaa gatcaaagga tcttcttgag atccttttt tctgcgcgta    6840
```

| | |
|---|---|
| atctgctgct tgcaaacaaa aaaccaccg ctaccagcgg tggtttgttt gccggatcaa | 6900 |
| gagctaccaa ctcttttttcc gaaggtaact ggcttcagca gagcgcagat accaaatact | 6960 |
| gttcttctag tgtagccgta gttaggccac cacttcaaga actctgtagc accgcctaca | 7020 |
| tacctcgctc tgctaatcct gttaccagtg gctgctgcca gtggcgataa gtcgtgtctt | 7080 |
| accgggttgg actcaagacg atagttaccg gataaggcgc agcggtcggg ctgaacgggg | 7140 |
| ggttcgtgca cacagcccag cttggagcga acgacctaca ccgaactgag atacctacag | 7200 |
| cgtgagctat gagaaagcgc cacgcttccc gaagggagaa aggcggacag gtatccggta | 7260 |
| agcggcaggg tcggaacagg agagcgcacg agggagcttc caggggaaa cgcctggtat | 7320 |
| ctttatagtc ctgtcgggtt cgccacctc tgacttgagc gtcgattttt gtgatgctcg | 7380 |
| tcagggggc ggagcctatg gaaaaacgcc agcaacgcgg cctttttacg gttcctggcc | 7440 |
| ttttgctggc cttttgctca catgttcttt cctgcgttat cccctgattc tgtggataac | 7500 |
| cgtattaccg cctttgagtg agctgatacc gctcgccgca gccgaacgac cgagcgcagc | 7560 |
| gagtcagtga gcgaggaagc ggaagagcgc ccaatacgca aaccgcctct ccccgcgcgt | 7620 |
| tggccgattc attaatgcag ctggcacgac aggtttcccg actggaaagc gggcagtgag | 7680 |
| cgcaacgcaa ttaatgtgag ttagctcact cattaggcac cccaggcttt acactttatg | 7740 |
| cttccggctc gtatgttgtg tggaattgtg agcggataac aatttcacac aggaaacagc | 7800 |
| tatgaccatg attacgccaa gctctagcta gaggtcgagt ccctccccag caggcagaag | 7860 |
| tatgcaaagc atgcatctca attagtcagc aaccatagtc ccgcccctaa ctccgcccat | 7920 |
| cccgcccta actccgccca gttccgccca ttctccgccc catggctgac taattttttt | 7980 |
| tatttatgca gaggccgagg ccgcctcggc ctctgagcta ttccagaagt agtgaggagg | 8040 |
| cttttttgga ggcctaggct tttgcaaaaa gctttgcaaa gatggataaa gttttaaaca | 8100 |
| gagaggaatc tttgcagcta atggaccttc taggtcttga aagg | 8144 |

<210> SEQ ID NO 6
<211> LENGTH: 8144
<212> TYPE: DNA
<213> ORGANISM: Artificial Sequence
<220> FEATURE:
<223> OTHER INFORMATION: Synthetic construct: pJP189 ; pHybE-mCg1 V2

<400> SEQUENCE: 6

| | |
|---|---|
| agtgggaatt ggctccggtg cccgtcagtg ggcagagcgc acatcgccca cagtccccga | 60 |
| gaagttgggg ggaggggtcg gcaattgaac cggtgcctag agaaggtggc gcggggtaaa | 120 |
| ctggaaagt gatgtcgtgt actggctccg cctttttccc gagggtgggg gagaaccgta | 180 |
| tataagtgca gtagtcgccg tgaacgttct ttttcgcaac gggtttgccg ccagaacaca | 240 |
| ggtaagtgcc gtgtgtggtt cccgcgggcc tggcctcttt acgggttatg gcccttgcgt | 300 |
| gccttgaatt acttccacct ggctgcagta cgtgattctt gatcccgagc ttcgggttgg | 360 |
| aagtgggtgg gagagttcga ggccttgcgc ttaaggagcc ccttcgcctc gtgcttgagt | 420 |
| tgaggcctgg cctgggcgct ggggccgccg cgtgcgaatc tggtggcacc ttcgcgcctg | 480 |
| tctcgctgct ttcgataagt ctctagccat ttaaaatttt tgatgacctg ctgcgacgct | 540 |
| ttttttctgg caagatagtc ttgtaaatgc gggccaagat ctgcacactg gtatttcggt | 600 |
| ttttggggcc gcgggcggcg acggggcccg tgcgtcccag cgcacatgtt cggcgaggcg | 660 |
| gggcctgcga gcgcggccac cgagaatcgg acggggtag tctcaagctg gccggcctgc | 720 |
| tctggtgcct ggcctcgcgc cgccgtgtat cgccccgccc tgggcggcaa ggctggcccg | 780 |

```
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggaggggtt   1020
ttatgcgatg gagtttcccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gttttttttct tccatttcag gtgtcgtgag gaattctcta   1200
gagatccctc gacctcgaga tccattgtgc ccgggcgcca ccatggagtt tgggctgagc   1260 tggcttttc ttgtcgcgat tttaaaaggt gtccagtgcg catggtatgc cgaaagggat   1320
gctgaaattg agaacgaaaa gctgcgccgg gaggttgaag aactgcggca ggccagcgag   1380
gcagatctcc agccaggaac tattgagtac gaacgccatc gacttacgcg tgcgcaggcc   1440
gacgcacagg aactgaagaa tgccagagac tccgctgaag tggtggaaac cgcattctgt   1500
actttcgtgc tgtcgcgcgat cgcaggtgaa attgccagta ttctcgacgg gctcccctg   1560 tcggtgcagc ggcgttttcc ggaactggaa aaccgacatg ttgatttcct gaaacgggat   1620
atcatcaaag ccatgaacaa agcagccgcg ctggatgaac tgataccggg gttgctgagt   1680
gaatatatcg aacagtcagg ttaacaggct gcggcatttt gtccgcgccg ggcttcgctc   1740
actgttcagg ccggagccac agaccgccgt tgaatgggcg gatgctaatt actatctccc   1800
gaaagaatcc gcataccagg aagggcgctg ggaaacactg ccctttcagc gggccatcat   1860
gaatgcgatg ggcagcgact acatccgtga ggtgaatgtg gtgaagtctg cccgtgtcgg   1920
ttattccaaa atgctgctgg gtgtttatgc ctactttata gagcataagc agcgcaacac   1980
ccttatctgg ttgccgacgg atggtgatgc cgagaacttt atgaaaaccc acgttgagcc   2040
gactattcgt gatattccgt cgctgctggc gctggcccg tggtatggca aaaagcaccg   2100
ggataacacg ctcaccatga agcgtttcac taatgggcgt ggcttctggt gcctgggcgg   2160
taaagcggca aaaactacc gtgaaaagtc ggtggatgtg gcgggttatg atgaacttgc   2220
tgcttttgat gatgatattg aacaggaagg ctctccgacg ttcctgggtg acaagcgcta   2280
aaacgacacc cccatctgtc tatccactgg cccctggatc tgctgcccaa actaactcca   2340
tggtgaccct gggatgcctg gtcaagggct atttccctga gccagtgaca gtgacctgga   2400
actctggatc cctgtccagc ggtgtgcaca ccttcccagc tgtcctgcag tctgacctct   2460
acactctgag cagctcagtg actgtcccct ccagcacctg gcccagcgag accgtcacct   2520
gcaacgttgc ccaccggcc agcagcacca aggtggacaa gaaaattgtg cccagggatt   2580
gtggttgtaa gccttgcata tgtacagtcc agaagtatc atctgtcttc atcttccccc   2640
caaagcccaa ggatgtgctc accattactc tgactcctaa ggtcacgtgt gttgtggtag   2700
acatcagcaa ggatgatccc gaggtccagt tcagctggtt tgtagatgat gtggaggtgc   2760
acacagctca gacgcaaccc cgggaggagc agttcaacag cactttccgc tcagtcagtg   2820
aacttcccat catgcaccag gactggctca atggcaagga gttcaaatgc agggtcaaca   2880
gtgcagcttt ccctgccccc atcgagaaaa ccatctccaa aaccaaaggc agaccgaagg   2940
ctccacaggt gtacaccatt ccacctccca aggagcagat ggccaaggat aaagtcagtc   3000
tgacctgcat gataacagac ttcttccctg aagacattac tgtggagtgg cagtggaatg   3060
ggcagccagc ggagaactac aagaacactc agcccatcat ggacagagat ggctcttact   3120
tcgtctacag caagctcaat gtgcagaaga gcaactggga ggcaggaaat actttcacct   3180
```

```
gctctgtgtt acatgagggc ctgcacaacc accatactga aaagagcctc tcccactctc    3240
ctggtaaata agcggccgct cgaggccggc aaggccggat ccccgacct cgacctctgg     3300
ctaataaagg aaatttattt tcattgcaat agtgtgttgg aattttttgt gtctctcact    3360
cggaaggaca tatgggaggg caaatcattt ggtcgagatc cctcggagat ctctagctag    3420
aggatcgatc cccgcccgg acgaactaaa cctgactacg acatctctgc cccttcttcg     3480
cggggcagtg catgtaatcc cttcagttgg ttggtacaac ttgccaactg ggccctgttc    3540
cacatgtgac acggggggg accaaaacaca aagggttct ctgactgtag ttgacatcct     3600
tataaatgga tgtgcacatt tgccaacact gagtggcttt catcctggag cagactttgc    3660
agtctgtgga ctgcaacaca acattgcctt tatgtgtaac tcttggctga agctcttaca    3720
ccaatgctgg gggacatgta cctcccaggg gcccaggaag actacgggag ctacaccaa     3780
cgtcaatcag aggggcctgt gtagctaccg ataagcggac cctcaagagg gcattagcaa    3840
tagtgtttat aaggcccct tgttaaccct aaacgggtag catatgcttc ccgggtagta     3900
gtatatacta tccagactaa ccctaattca atagcatatg ttacccaacg ggaagcatat    3960
gctatcgaat taagggttagt aaaagggtcc taaggaacag cgatatctcc caccccatga   4020
gctgtcacgg ttttatttac atggggtcag gattccacga gggtagtgaa ccatttagt     4080
cacaagggca gtggctgaag atcaaggagc gggcagtgaa ctctcctgaa tcttcgcctg    4140
cttcttcatt ctccttcgtt tagctaatag aataactgct gagttgtgaa cagtaaggtg    4200
tatgtgaggt gctcgaaaac aaggtttcag gtgacgcccc cagaataaaa tttggacggg    4260
gggttcagtg gtggcattgt gctatgacac caatataacc ctcacaaacc ccttgggcaa    4320
taaatactag tgtaggaatg aaacattctg aatatcttta acaatagaaa tccatggggt    4380
ggggacaagc cgtaaagact ggatgtccat ctcacacgaa tttatggcta tgggcaacac    4440
ataatcctag tgcaatatga tactgggggtt attaagatgt gtcccaggca gggaccaaga   4500
caggtgaacc atgttgttac actctatttg taacaagggg aaagagagtg gacgccgaca    4560
gcagcggact ccactggttg tctctaacac ccccgaaaat taaacggggc tccacgccaa    4620
tggggcccat aaacaaagac aagtggccac tcttttttttt gaaattgtgg agtgggggca   4680
cgcgtcagcc cccacacgcc gccctgcggt tttggactgt aaaataaggg tgtaataact    4740
tggctgattg taacccgct aaccactgcg gtcaaaccac ttgcccacaa aaccactaat     4800
ggcaccccgg ggaataccctg cataagtagg tgggcgggcc aagataggggg cgcgattgct  4860
gcgatctgga ggacaaatta cacacacttg cgcctgagcg ccaagcacag ggttgttggt    4920
cctcatattc acgaggtcgc tgagagcacg gtgggctaat gttgccatgg gtagcatata    4980
ctacccaaat atctggatag catatgctat cctaatctat atctgggtag cataggctat    5040
cctaatctat atctgggtag catatgctat cctaatctat atctgggtag tatatgctat    5100
cctaatttat atctgggtag cataggctat cctaatctat atctgggtag catatgctat    5160
cctaatctat atctgggtag tatatgctat cctaatctgt atccgggtag catatgctat    5220
cctaatagag attagggtag tatatgctat cctaatttat atctgggtag catatactac    5280
ccaaatatct ggatagcata tgctatccta atctatatct gggtagcata tgctatccta    5340
atctatatct gggtagcata ggctatccta atctatatct gggtagcata tgctatccta    5400
atctatatct gggtagtata tgctatccta atttatatct gggtagcata ggctatccta    5460
atctatatct gggtagcata tgctatccta atctatatct gggtagtata tgctatccta    5520
atctgtatcc gggtagcata tgctatcctc atgataagct gtcaaacatg agaattttct    5580
```

```
tgaagacgaa agggcctcgt gatacgccta ttttttatagg ttaatgtcat gataataatg   5640
gtttcttaga cgtcaggtgg cacttttcgg ggaaatgtgc gcggaacccc tatttgttta   5700
tttttctaaa tacattcaaa tatgtatccg ctcatgagac aataaccctg ataaatgctt   5760
caataatatt gaaaaaggaa gagtatgagt attcaacatt tccgtgtcgc ccttattccc   5820
ttttttgcgg cattttgcct tcctgttttt gctcacccag aaacgctggt gaaagtaaaa   5880
gatgctgaag atcagttggg tgcacgagtg ggttacatcg aactggatct caacagcggt   5940
aagatccttg agagttttcg ccccgaagaa cgttttccaa tgatgagcac ttttaaagtt   6000
ctgctatgtg gcgcggtatt atcccgtgtt gacgccgggc aagagcaact cggtcgccgc   6060
atacactatt ctcagaatga cttggttgag tactcaccag tcacagaaaa gcatcttacg   6120
gatggcatga cagtaagaga attatgcagt gctgccataa ccatgagtga taacactgcg   6180
gccaacttac ttctgacaac gatcggagga ccgaaggagc taaccgcttt tttgcacaac   6240 atggggatc atgtaactcg ccttgatcgt tgggaaccgg agctgaatga agccatacca   6300
aacgacgagc gtgacaccac gatgcctgca gcaatggcaa caacgttgcg caaactatta   6360
actggcgaac tacttactct agcttcccgg caacaattaa tagactggat ggaggcggat   6420
aaagttgcag gaccacttct gcgctcggcc cttccggctg gctggtttat tgctgataaa   6480
tctggagccg gtgagcgtgg gtctcgcggt atcattgcag cactgggcc agatggtaag   6540 ccctcccgta tcgtagttat ctacacgacg gggagtcagg caactatgga tgaacgaaat   6600
agacagatcg ctgagatagg tgcctcactg attaagcatt ggtaactgtc agaccaagtt   6660
tactcatata ctttagat tgatttaaaa cttcattttt aatttaaaag gatctaggtg   6720
aagatccttt ttgataatct catgaccaaa atcccttaac gtgagttttc gttccactga   6780
gcgtcagacc ccgtagaaaa gatcaaagga tcttcttgag atcctttttt tctgcgcgta   6840
atctgctgct tgcaaacaaa aaaccaccgc taccagcgg tggtttgttt gccggatcaa   6900
gagctaccaa ctcttttcc gaaggtaact ggcttcagca gagcgcagat accaaatact   6960
gttcttctag tgtagccgta gttaggccac cacttcaaga actctgtagc accgcctaca   7020
tacctcgctc tgctaatcct gttaccagtg gctgctgcca gtggcgataa gtcgtgtctt   7080
accgggttgg actcaagacg atagttaccg gataaggcgc agcggtcggg ctgaacgggg   7140
ggttcgtgca cacagcccag cttggagcga acgacctaca ccgaactgag atacctacag   7200
cgtgagctat gagaaagcgc cacgcttccc gaagggagaa aggcggacag gtatccggta   7260
agcggcaggg tcggaacagg agagcgcacg agggagcttc caggggaa cgcctggtat   7320 ctttatagtc ctgtcgggtt tcgccacctc tgacttgagc gtcgatttt gtgatgctcg   7380 tcaggggggc ggagcctatg gaaaaacgcc agcaacgcgg cctttttacg gttcctggcc   7440
ttttgctggc cttttgctca catgttcttt cctgcgttat cccctgattc tgtggataac   7500
cgtattaccg cctttgagtg agctgatacc gctcgccgca gccgaacgac cgagcgcagc   7560
gagtcagtga gcgaggaagc ggaagagcgc ccaatacgca aaccgcctct ccccgcgcgt   7620
tggccgattc attaatgcag ctggcacgac aggtttcccg actggaaagc gggcagtgag   7680
cgcaacgcaa ttaatgtgag ttagctcact cattaggcac cccaggcttt acactttatg   7740
cttccggctc gtatgttgtg tggaattgtg agcggataac aatttcacac aggaaacagc   7800
tatgaccatg attacgccaa gctctagcta gaggtcgagt ccctccccag caggcagaag   7860
tatgcaaagc atgcatctca attagtcagc aaccatagtc ccgcccctaa ctccgcccat   7920
cccgccccta actccgccca gttccgccca ttctccgccc catggctgac taatttttt   7980
```

```
tatttatgca gaggccgagg ccgcctcggc ctctgagcta ttccagaagt agtgaggagg    8040
cttttttgga ggcctaggct tttgcaaaaa gctttgcaaa gatggataaa gttttaaaca    8100
gagaggaatc tttgcagcta atggaccttc taggtcttga aagg                    8144

<210> SEQ ID NO 7
<211> LENGTH: 8162
<212> TYPE: DNA
<213> ORGANISM: Artificial Sequence
<220> FEATURE:
<223> OTHER INFORMATION: Synthetic construct: pJP177 ; pHybE-mCg2a V1

<400> SEQUENCE: 7
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg ccttttttcc cgagggtgggg gagaaccgta   180 tataagtgca gtagtcgccg tgaacgttct ttttcgcaac gggtttgccg ccagaacaca     240
ggtaagtgcc gtgtgtggtt cccgcgggcc tggcctcttt acgggttatg gcccttgcgt     300
gccttgaatt acttccacct ggctgcagta cgtgattctt gatcccgagc ttcgggttgg     360
aagtgggtgg gagagttcga ggccttgcgc ttaaggagcc ccttcgcctc gtgcttgagt     420
tgaggcctgg cctgggcgct ggggccgccg cgtgcgaatc tggtggcacc ttcgcgcctg     480
tctcgctgct ttcgataagt ctctagccat ttaaattttt gatgacctg ctgcgacgct     540 ttttttctgg caagatagtc ttgtaaatgc gggccaagat ctgcacactg gtatttcggt     600 ttttgggggcc gcgggcggcg acggggcccg tgcgtcccag cgcacatgtt cggcgaggcg     660
gggcctgcga gcgcggccac cgagaatcgg acggggtag tctcaagctg gccggcctgc      720
tctggtgcct ggcctcgcgc cgccgtgtat cgccccgccc tgggcggcaa ggctggcccg     780
gtcggcacca gttgcgtgag cggaaagatg gccgcttccc ggccctgctg cagggagctc     840
aaaatggagg acgcggcgct cgggagagcg ggcgggtgag tcacccacac aaaggaaaag     900
ggcctttccg tcctcagccg tcgcttcatg tgactccacg gagtaccggg cgccgtccag     960
gcacctcgat tagttctcga gcttttggag tacgtcgtct ttaggttggg gggagggggtt   1020 ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gttttttttct tccatttcag gtgtcgtgag gaattctcta    1200
gagatccctc gacctcgagc atttaaatgc ccgggcgcca ccatggagtt tgggctgagc    1260
tggctttttc ttgtcgcgat tttaaaaggt gtccagtgcg catggtatgc cgaaagggat    1320
gctgaaattg agaacgaaaa gctgcgccgg gaggttgaag aactgcggca ggccagcgag    1380
gcagatctcc agccaggaac tattgagtac gaacgccatc gacttacgcg tgcgcaggcc    1440
gacgcacagg aactgaagaa tgccagagac tccgctgaag tggtggaaac cgcattctgt    1500
actttcgtgc tgtcgcggat cgcaggtgaa attgccagta ttctcgacgg gctcccctg    1560 tcggtgcagc ggcgttttcc ggaactggaa aaccgacatg ttgatttcct gaaacggat    1620 atcatcaaag ccatgaacaa agcagccgcg ctggatgaac tgataccggg gttgctgagt    1680
gaatatatcg aacagtcagg ttaacaggct gcggcatttt gtccgcgccg gcttcgctc    1740 actgttcagg ccggagccac agaccgccgt tgaatgggcg gatgctaatt actatctccc    1800
gaaagaatcc gcataccagg aagggcgctg ggaaacactg cccttcagc gggccatcat    1860 gaatgcgatg ggcagcgact acatccgtga ggtgaatgtg gtgaagtctg cccgtgtcgg    1920
```

```
ttattccaaa atgctgctgg gtgtttatgc ctactttata gagcataagc agcgcaacac   1980
ccttatctgg ttgccgacgg atggtgatgc cgagaacttt atgaaaaccc acgttgagcc   2040
gactattcgt gatattccgt cgctgctggc gctggccccg tggtatggca aaaagcaccg   2100
ggataacacg ctcaccatga agcgtttcac taatgggcgt ggcttctggt gcctgggcgg   2160
taaagcggca aaaactaccg tgaaaagtcg gtggatgtg gcgggttatg atgaacttgc   2220
tgcttttgat gatgatattg aacaggaagg ctctccgacg ttcctgggtg acaagcgcta   2280
aaacaacagc cccatcggtc tatccactgg cccctgtgtg tggagataca actggctcct   2340
cggtgactct aggatgcctg gtcaagggtt atttccctga gccagtgacc ttgacctgga   2400
actctggatc cctgtccagt ggtgtgcaca ccttcccagc tgtcctgcag tctgacctct   2460
acaccctcag cagctcagtg actgtaacct cgagcacctg gccagccag tccatcacct    2520
gcaatgtggc ccacccggca agcagcacca aggtggacaa gaaaattgag cccagagggc   2580
ccacaatcaa gccctgtcct ccatgcaaat gcccagcacc taacctcttg ggtggaccat   2640
ccgtcttcat cttccctcca aagatcaagg atgtactcat gatctccctg agccccatag   2700
tcacatgtgt ggtggtggat gtgagcgagg atgacccaga tgtccagatc agctggtttg   2760
tgaacaacgt ggaagtacac acagctcaga cacaaaccca tagagaggat tacaacagta   2820
ctctccgggt ggtcagtgcc ctccccatcc agcaccagga ctggatgagt ggcaaggagt   2880
tcaaatgcaa ggtcaacaac aaagacctcc cagcgcccat cgagagaacc atctcaaaac   2940
ccaaagggtc agtaagagct ccacaggtat atgtcttgcc tccaccagaa gaagagatga   3000
ctaagaaaca ggtcactctg acctgcatgg tcacagactt catgcctgaa gacatttacg   3060
tggagtggac caacaacggg aaaacagagc taaactacaa gaacactgaa ccagtcctgg   3120
actctgatgg ttcttacttc atgtacagca agctgagagt ggaaaagaag aactgggtgg   3180
aaagaaatag ctactcctgt tcagtggtcc acgagggtct gcacaatcac cacacgacta   3240
agagcttctc ccggactccg ggtaaataag cggccgctcg aggccggcaa ggccggatcc   3300
cccgacctcg acctctggct aataaaggaa atttattttc attgcaatag tgtgttggaa   3360
ttttttgtgt ctctcactcg gaaggacata tgggagggca aatcatttgg tcgagatccc   3420
tcggagatct ctagctagag gatcgatccc cgccccggac gaactaaacc tgactacgac   3480
atctctgccc cttcttcgcg gggcagtgca tgtaatccct tcagttggtt ggtacaactt   3540
gccaactggg ccctgttcca catgtgacac gggggggggac caaacacaaa ggggttctct   3600
gactgtagtt gacatcctta taaatggatg tgcacatttg ccaacactga gtggctttca   3660
tcctggagca gactttgcag tctgtggact gcaacacaac attgccttta tgtgtaactc   3720
ttggctgaag ctcttacacc aatgctgggg gacatgtacc tcccaggggc ccaggaagac   3780
tacgggaggc tacaccaacg tcaatcagag gggcctgtgt agctaccgat aagcggaccc   3840
tcaagagggc attagcaata tgtttataa ggccccttg ttaaccctaa acgggtagca    3900
tatgcttccc gggtagtagt atatactatc cagactaacc ctaattcaat agcatatgtt   3960
acccaacggg aagcatatgc tatcgaatta gggttagtaa aagggtccta aggaacagcg   4020
atatctccca ccccatgagc tgtcacggtt ttatttacat ggggtcagga ttccacgagg   4080
gtagtgaacc attttagtca aagggcagt ggctgaagat caaggagcgg gcagtgaact    4140
ctcctgaatc ttcgcctgct tcttcattct ccttcgttta gctaatagaa taactgctga   4200
gttgtgaaca gtaaggtgta tgtgaggtgc tcgaaaacaa ggtttcaggt gacgccccca   4260
gaataaaatt tggacggggg gttcagtggt ggcattgtgc tatgacacca atataaccct   4320
```

```
cacaaacccc ttgggcaata aatactagtg taggaatgaa acattctgaa tatctttaac    4380
aatagaaatc catggggtgg ggacaagccg taaagactgg atgtccatct cacacgaatt    4440
tatggctatg ggcaacacat aatcctagtg caatatgata ctggggttat taagatgtgt    4500
cccaggcagg gaccaagaca ggtgaaccat gttgttacac tctatttgta acaaggggaa    4560
agagagtgga cgccgacagc agcggactcc actggttgtc tctaacaccc ccgaaaatta    4620 aacgggctc cacgccaatg gggcccataa acaaagacaa gtggccactc ttttttttga     4680
aattgtggag tgggggcacg cgtcagcccc cacacgccgc cctgcggttt tggactgtaa    4740 aataaggtg taataacttg gctgattgta accccgctaa ccactgcggt caaaccactt     4800
gcccacaaaa ccactaatgg caccccgggg aatacctgca taagtaggtg ggcgggccaa    4860 gatagggcg cgattgctgc gatctggagg acaaattaca cacacttgcg cctgagcgcc     4920
aagcacaggg ttgttggtcc tcatattcac gaggtcgctg agagcacggt gggctaatgt    4980
tgccatgggt agcatatact acccaaatat ctggatagca tatgctatcc taatctatat    5040
ctgggtagca taggctatcc taatctatat ctgggtagca tatgctatcc taatctatat    5100
ctgggtagta tatgctatcc taatttatat ctgggtagca taggctatcc taatctatat    5160
ctgggtagca tatgctatcc taatctatat ctgggtagta tatgctatcc taatctgtat    5220
ccgggtagca tatgctatcc taatagagat tagggtagta tatgctatcc taatttatat    5280
ctgggtagca tatactaccc aaatatctgg atagcatatg ctatcctaat ctatatctgg    5340
gtagcatatg ctatcctaat ctatatctgg gtagcatagg ctatcctaat ctatatctgg    5400
gtagcatatg ctatcctaat ctatatctgg gtagtatatg ctatcctaat ttatatctgg    5460
gtagcatagg ctatcctaat ctatatctgg gtagcatatg ctatcctaat ctatatctgg    5520
gtagtatatg ctatcctaat ctgtatccgg gtagcatatg ctatcctcat gataagctgt    5580
caaacatgag aattttcttg aagacgaaag ggcctcgtga tacgcctatt tttataggtt    5640
aatgtcatga taataatggt tccttagacg tcaggtggca cttttcgggg aaatgtgcgc    5700 ggaacccta tttgtttatt tttctaaata cattcaaata tgtatccgct catgagacaa      5760
taaccctgat aaatgcttca ataatattga aaaggaaga gtatgagtat tcaacatttc     5820
cgtgtcgccc ttattccctt ttttgcggca ttttgccttc ctgttttgc tcacccagaa     5880 acgctggtga agtaaaaga tgctgaagat cagttgggtg cacgagtggg ttacatcgaa     5940
ctggatctca acagcggtaa gatccttgag agttttcgcc ccgaagaacg ttttccaatg    6000
atgagcactt ttaaagttct gctatgtggc gcggtattat cccgtgttga cgccgggcaa    6060
gagcaactcg gtcgccgcat acactattct cagaatgact tggttgagta ctcaccagtc    6120
acagaaaagc atcttacgga tggcatgaca gtaagagaat tatgcagtgc tgccataacc    6180
atgagtgata acactgcggc caacttactt ctgacaacga tcggaggacc gaaggagcta    6240
accgcttttt tgcacaacat gggggatcat gtaactcgcc ttgatcgttg ggaaccggag    6300
ctgaatgaag ccataccaaa cgacgagcgt gacaccacga tgcctgcagc aatggcaaca    6360
acgttgcgca aactattaac tggcgaacta cttactctag cttcccggca acaattaata    6420
gactggatgg aggcggataa agttgcagga ccacttctgc gctcggccct tccggctggc    6480
tggtttattg ctgataaatc tggagccggt gagcgtgggt ctcgcggtat cattgcagca    6540
ctggggccag atggtaagcc ctcccgtatc gtagttatct acacgacggg gagtcaggca    6600
actatggatg aacgaaatag acagatcgct gagataggtg cctcactgat taagcattgg    6660
taactgtcag accaagttta ctcatatata ctttagattg atttaaaact tcatttttaa    6720
```

```
tttaaaagga tctaggtgaa gatccttttt gataatctca tgaccaaaat cccttaacgt    6780
gagttttcgt tccactgagc gtcagacccc gtagaaaaga tcaaaggatc ttcttgagat    6840
ccttttttt c tgcgcgtaat ctgctgcttg caaacaaaaa aaccaccgct accagcggtg    6900
gtttgtttgc cggatcaaga gctaccaact cttttttccga aggtaactgg cttcagcaga    6960
gcgcagatac caaatactgt tcttctagtg tagccgtagt taggccacca cttcaagaac    7020
tctgtagcac cgcctacata cctcgctctg ctaatcctgt taccagtggc tgctgccagt    7080
ggcgataagt cgtgtcttac cgggttggac tcaagacgat agttaccgga taaggcgcag    7140
cggtcgggct gaacggggggg ttcgtgcaca gcccagct tggagcgaac gacctacacc      7200
gaactgagat acctacagcg tgagctatga gaaagcgcca cgcttcccga agggagaaag    7260
gcggacaggt atccggtaag cggcagggtc ggaacaggag agcgcacgag ggagcttcca    7320
gggggaaacg cctggtatct ttatagtcct gtcgggtttc gccacctctg acttgagcgt    7380
cgatttttgt gatgctcgtc aggggggcgg agcctatgga aaaacgccag caacgcggcc    7440
tttttacggt tcctggcctt ttgctggcct tttgctcaca tgttctttcc tgcgttatcc    7500
cctgattctg tggataaccg tattaccgcc tttgagtgag ctgataccgc tcgccgcagc    7560
cgaacgaccg agcgcagcga gtcagtgagc gaggaagcgg aagagcgccc aatacgcaaa    7620
ccgcctctcc ccgcgcgttg gccgattcat taatgcagct ggcacgacag gtttcccgac    7680
tggaaagcgg gcagtgagcg caacgcaatt aatgtgagtt agctcactca ttaggcaccc    7740
caggctttac actttatgct tccggctcgt atgttgtgtg gaattgtgag cggataacaa    7800
tttcacacag gaaacagcta tgaccatgat tacgccaagc tctagctaga ggtcgagtcc    7860
ctccccagca ggcagaagta tgcaaagcat gcatctcaat tagtcagcaa ccatagtccc    7920
gcccctaact ccgcccatcc cgcccctaac tccgcccagt tccgcccatt ctccgcccca    7980
tggctgacta attttttta tttatgcaga ggccgaggcc gcctcggcct ctgagctatt    8040
ccagaagtag tgaggaggct ttttggagg cctaggcttt tgcaaaaagc tttgcaaaga    8100
tggataaagt tttaaacaga gaggaatctt tgcagctaat ggaccttcta ggtcttgaaa    8160
gg                                                                   8162
```

<210> SEQ ID NO 8
<211> LENGTH: 8162
<212> TYPE: DNA
<213> ORGANISM: Artificial Sequence
<220> FEATURE:
<223> OTHER INFORMATION: Synthetic construct: pJP190 ; pHybE-mCg2a V2

<400> SEQUENCE: 8

```
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg ccttttttccc gagggtgggg gagaaccgta    180
tataagtgca gtagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct tcgataagt ctctagccat ttaaaatttt tgatgacctg ctgcgacgct    540
ttttttctgg caagatagtc ttgtaaatgc gggccaagat ctgcacactg gtatttcggt    600
```

| | | | |
|---|---|---|---|
| ttttggggcc gcgggcggcg acggggcccg tgcgtcccag cgcacatgtt cggcgaggcg | 660 |
| gggcctgcga gcgcggccac cgagaatcgg acggggtag tctcaagctg gccggcctgc | 720 |
| tctggtgcct ggcctcgcgc cgccgtgtat cgcccgccc tgggcggcaa ggctggcccg | 780 |
| gtcggcacca gttgcgtgag cggaaagatg ccgcttccc ggccctgctg cagggagctc | 840 |
| aaaatggagg acgcggcgct cgggagagcg ggcgggtgag tcacccacac aaaggaaaag | 900 |
| ggcctttccg tcctcagccg tcgcttcatg tgactccacg gagtaccggg cgccgtccag | 960 |
| gcacctcgat tagttctcga gcttttggag tacgtcgtct ttaggttggg gggaggggtt | 1020 |
| ttatgcgatg gagtttcccc acactgagtg ggtggagact gaagttaggc cagcttggca | 1080 |
| cttgatgtaa ttctccttgg aatttgccct ttttgagttt ggatcttggt tcattctcaa | 1140 |
| gcctcagaca gtggttcaaa gttttttttct tccatttcag gtgtcgtgag gaattctcta | 1200 |
| gagatccctc gacctcgaga tccattgtgc ccgggcgcca ccatggagtt tgggctgagc | 1260 |
| tggcttttttc ttgtcgcgat tttaaaaggt gtccagtgcg catggtatgc cgaaagggat | 1320 |
| gctgaaattg agaacgaaaa gctgcgccgg gaggttgaag aactgcggca ggccagcgag | 1380 |
| gcagatctcc agccaggaac tattgagtac gaacgccatc gacttacgcg tgcgcaggcc | 1440 |
| gacgcacagg aactgaagaa tgccagagac tccgctgaag tggtggaaac cgcattctgt | 1500 |
| actttcgtgc tgtcgcggat cgcaggtgaa attgccagta ttctcgacgg gctcccctg | 1560 |
| tcggtgcagc ggcgttttcc ggaactggaa aaccgacatg ttgatttcct gaaacgggat | 1620 |
| atcatcaaag ccatgaacaa agcagccgcg ctggatgaac tgataccggg gttgctgagt | 1680 |
| gaatatatcg aacagtcagg ttaacaggct gcggcatttt gtccgcgccg ggcttcgctc | 1740 |
| actgttcagg ccggagccac agaccgccgt tgaatgggcg gatgctaatt actatctccc | 1800 |
| gaaagaatcc gcataccagg aagggcgctg ggaaacactg cccttcagc gggccatcat | 1860 |
| gaatgcgatg ggcagcgact acatccgtga ggtgaatgtg gtgaagtctg cccgtgtcgg | 1920 |
| ttattccaaa atgctgctgg gtgtttatgc ctactttata gagcataagc agcgcaacac | 1980 |
| ccttatctgg ttgccgacgg atggtgatgc cgagaacttt atgaaaaccc acgttgagcc | 2040 |
| gactattcgt gatattccgt cgctgctggc gctggccccg tggtatggca aaaagcaccg | 2100 |
| ggataacacg ctcaccatga agcgtttcac taatgggcgt ggcttctggt gcctgggcgg | 2160 |
| taaagcggca aaaaactacc gtgaaaagtc ggtggatgtg gcgggttatg atgaacttgc | 2220 |
| tgcttttgat gatgatattg aacaggaagg ctctccgacg ttcctgggtg acaagcgcta | 2280 |
| aaacaacagc cccatcggtc tatccactgg cccctgtgtg tggagataca actggctcct | 2340 |
| cggtgactct aggatgcctg gtcaagggtt atttccctga ccagtgacc ttgacctgga | 2400 |
| actctggatc cctgtccagt ggtgtgcaca ccttcccagc tgtcctgcag tctgacctct | 2460 |
| acaccctcag cagctcagtg actgtaacct cgagcacctg gcccagccag tccatcacct | 2520 |
| gcaatgtggc ccaccggca agcagcacca aggtggacaa gaaaattgag cccagagggc | 2580 |
| ccacaatcaa gccctgtcct ccatgcaaat gcccagcacc taacctcttg ggtggaccat | 2640 |
| ccgtcttcat cttccctcca agatcaagg atgtactcat gatctccctg agccccatag | 2700 |
| tcacatgtgt ggtggtggat gtgagcgagg atgacccaga tgtccagatc agctggtttg | 2760 |
| tgaacaacgt ggaagtacac acagctcaga cacaaaccca tagagaggat tacaacagta | 2820 |
| ctctccgggt ggtcagtgcc ctccccatcc agcaccagga ctggatgagt ggcaaggagt | 2880 |
| tcaaatgcaa ggtcaacaac aaagacctcc cagcgcccat cgagaaacc atctcaaaac | 2940 |
| ccaaagggtc agtaagagct ccacaggtat atgtcttgcc tccaccagaa gaagagatga | 3000 |

```
ctaagaaaca ggtcactctg acctgcatgg tcacagactt catgcctgaa gacatttacg   3060
tggagtggac caacaacggg aaaacagagc taaactacaa gaacactgaa ccagtcctgg   3120
actctgatgg ttcttacttc atgtacagca agctgagagt ggaaaagaag aactgggtgg   3180
aaagaaatag ctactcctgt tcagtggtcc acgagggtct gcacaatcac cacacgacta   3240
agagcttctc ccggactccg ggtaaataag cggccgctcg aggccggcaa ggccggatcc   3300
cccgacctcg acctctggct aataaaggaa atttattttc attgcaatag tgtgttggaa   3360
ttttttgtgt ctctcactcg gaaggacata tgggagggca aatcatttgg tcgagatccc   3420
tcggagatct ctagctagag gatcgatccc cgccccggac gaactaaacc tgactacgac   3480
atctctgccc cttcttcgcg gggcagtgca tgtaatccct tcagttggtt ggtacaactt   3540
gccaactggg ccctgttcca catgtgacac gggggggggac caaacacaaa ggggttctct   3600
gactgtagtt gacatcctta taaatggatg tgcacatttg ccaacactga gtggcttttca   3660 tcctggagca gactttgcag tctgtggact gcaacacaac attgcctta tgtgtaactc   3720 ttggctgaag ctcttacacc aatgctgggg gacatgtacc tcccaggggc ccaggaagac   3780
tacgggaggc tacaccaacg tcaatcagag gggcctgtgt agctaccgat aagcggaccc   3840
tcaagagggc attagcaata gtgtttataa ggccccttg ttaaccctaa acgggtagca   3900
tatgcttccc gggtagtagt atatactatc cagactaacc ctaattcaat agcatatgtt   3960
acccaacggg aagcatatgc tatcgaatta gggttagtaa aagggtccta aggaacagcg   4020
atatctccca ccccatgagc tgtcacggtt ttatttacat ggggtcagga ttccacgagg   4080
gtagtgaacc attttagtca gaggggcagt ggctgaagat caaggagcgg gcagtgaact   4140
ctcctgaatc ttcgcctgct tcttcattct ccttcgttta gctaatagaa taactgctga   4200
gttgtgaaca gtaaggtgta tgtgaggtgc tcgaaaacaa ggtttcaggt gacgccccca   4260
gaataaaatt tggacggggg gttcagtggt ggcattgtgc tatgacacca atataaccct   4320
cacaaacccc ttgggcaata aatactagtg taggaatgaa acattctgaa tatctttaac   4380
aatagaaatc catggggtgg ggacaagccg taaagactgg atgtccatct cacacgaatt   4440
tatggctatg ggcaacacat aatcctagtg caatatgata ctggggttat taagatgtgt   4500
cccaggcagg gaccaagaca ggtgaaccat gttgttacac tctatttgta acaaggggaa   4560
agagagtgga cgccgacagc agcggactcc actggttgtc tctaacaccc ccgaaaatta   4620 aacgggctc cacgccaatg gggcccataa acaaagacaa gtggccactc tttttttga   4680 aattgtggag tgggggcacg cgtcagcccc cacacgccgc cctgcggttt tggactgtaa   4740
aataagggtg taataacttg gctgattgta accccgctaa ccactgcggt caaaccactt   4800
gcccacaaaa ccactaatgg caccccgggg aatacctgca taagtaggtg ggcgggccaa   4860
gataggggcg cgattgctgc gatctggagg acaaattaca cacacttgcg cctgagcgcc   4920
aagcacaggg ttgttggtcc tcatattcac gaggtcgctg agagcacggt gggctaatgt   4980
tgccatgggt agcatatact acccaaatat ctggatagca tatgctatcc taatctatat   5040
ctgggtagca taggctatcc taatctatat ctgggtagca tatgctatcc taatctatat   5100
ctgggtagta tatgctatcc taatttatat ctgggtagca taggctatcc taatctatat   5160
ctgggtagca tatgctatcc taatctatat ctgggtagta tatgctatcc taatctgtat   5220
ccgggtagca tatgctatcc taatagagat tagggtagta tatgctatcc taatttatat   5280
ctgggtagca tatactaccc aaaatctgg atagcatatg ctatcctaat ctatatctgg   5340
gtagcatatg ctatcctaat ctatatctgg gtagcatagg ctatcctaat ctatatctgg   5400
```

```
gtagcatatg ctatcctaat ctatatctgg gtagtatatg ctatcctaat ttatatctgg   5460
gtagcatagg ctatcctaat ctatatctgg gtagcatatg ctatcctaat ctatatctgg   5520
gtagtatatg ctatcctaat ctgtatccgg gtagcatatg ctatcctcat gataagctgt   5580
caaacatgag aattttcttg aagacgaaag ggcctcgtga tacgcctatt tttataggtt   5640
aatgtcatga taataatggt ttcttagacg tcaggtggca cttttcgggg aaatgtgcgc   5700 ggaacccta tttgtttatt tttctaaata cattcaaata tgtatccgct catgagacaa    5760
taaccctgat aaatgcttca ataatattga aaaggaaga gtatgagtat tcaacatttc    5820
cgtgtcgccc ttattccctt ttttgcggca ttttgccttc ctgtttttgc tcacccagaa   5880
acgctggtga agtaaaaga tgctgaagat cagttgggtg cacgagtggg ttacatcgaa    5940
ctggatctca acagcggtaa gatccttgag agttttcgcc ccgaagaacg ttttccaatg   6000
atgagcactt ttaaagttct gctatgtggc gcggtattat cccgtgttga cgccgggcaa   6060
gagcaactcg gtcgccgcat acactattct cagaatgact tggttgagta ctcaccagtc   6120
acagaaaagc atcttacgga tggcatgaca gtaagagaat tatgcagtgc tgccataacc   6180
atgagtgata acactgcggc caacttactt ctgacaacga tcggaggacc gaaggagcta   6240
accgcttttt tgcacaacat gggggatcat gtaactcgcc ttgatcgttg ggaaccggag   6300
ctgaatgaag ccataccaaa cgacgagcgt gacaccacga tgcctgcagc aatggcaaca   6360
acgttgcgca aactattaac tggcgaacta cttactctag cttcccggca acaattaata   6420
gactggatgg aggcggataa agttgcagga ccacttctgc gctcggccct tccggctggc   6480
tggtttattg ctgataaatc tggagccggt gagcgtgggt ctcgcggtat cattgcagca   6540
ctggggccag atggtaagcc ctcccgtatc gtagttatct acacgacggg gagtcaggca   6600
actatggatg aacgaaatag acagatcgct gagataggtg cctcactgat taagcattgg   6660
taactgtcag accaagttta ctcatatata ctttagattg atttaaaact tcatttttaa   6720
tttaaaagga tctaggtgaa gatcctttt gataatctca tgaccaaaat cccttaacgt    6780
gagttttcgt tccactgagc gtcagacccc gtagaaaaga tcaaaggatc ttcttgagat   6840
cctttttttc tgcgcgtaat ctgctgcttg caaacaaaaa aaccaccgct accagcggtg   6900
gtttgtttgc cggatcaaga gctaccaact cttttttccga aggtaactgg cttcagcaga   6960
gcgcagatac caaatactgt tcttctagtg tagccgtagt taggccacca cttcaagaac   7020
tctgtagcac cgcctacata cctcgctctg ctaatcctgt taccagtggc tgctgccagt   7080
ggcgataagt cgtgtcttac cgggttggac tcaagacgat agttaccgga taaggcgcag   7140
cggtcgggct gaacggggg ttcgtgcaca cagcccagct tggagcgaac gacctacacc    7200
gaactgagat acctacagcg tgagctatga gaaagcgcca cgcttcccga agggagaaag   7260
gcggacaggt atccggtaag cggcagggtc ggaacaggag agcgcacgag ggagcttcca   7320
gggggaaacg cctggtatct ttatagtcct gtcgggtttc gccacctctg acttgagcgt   7380
cgatttttgt gatgctcgtc aggggggcgg agcctatgga aaaacgccag caacgcggcc   7440 ttttacggt tcctggcctt ttgctggcct tttgctcaca tgttctttcc tgcgttatcc    7500
cctgattctg tggataaccg tattaccgcc tttgagtgag ctgataccgc tcgccgcagc   7560
cgaacgaccg agcgcagcga gtcagtgagc gaggaagcgg aagagcgccc aatacgcaaa   7620
ccgcctctcc ccgcgcgttg gccgattcat taatgcagct ggcacgacag gtttcccgac   7680
tggaaagcgg gcagtgagcg caacgcaatt aatgtgagtt agctcactca ttaggcaccc   7740
caggctttac actttatgct tccggctcgt atgttgtgtg gaattgtgag cggataacaa   7800
```

| | |
|---|---|
| tttcacacag gaaacagcta tgaccatgat tacgccaagc tctagctaga ggtcgagtcc | 7860 |
| ctccccagca ggcagaagta tgcaaagcat gcatctcaat tagtcagcaa ccatagtccc | 7920 |
| gcccctaact ccgcccatcc cgcccctaac tccgcccagt tccgcccatt ctccgcccca | 7980 |
| tggctgacta atttttttta tttatgcaga ggccgaggcc gcctcggcct ctgagctatt | 8040 |
| ccagaagtag tgaggaggct ttttttggagg cctaggcttt tgcaaaaagc tttgcaaaga | 8100 |
| tggataaagt tttaaacaga gaggaatctt tgcagctaat ggaccttcta ggtcttgaaa | 8160 |
| gg | 8162 |

<210> SEQ ID NO 9
<211> LENGTH: 7503
<212> TYPE: DNA
<213> ORGANISM: Artificial Sequence
<220> FEATURE:
<223> OTHER INFORMATION: Synthetic construct: pJP178 ; pHybE-hCk V1

<400> SEQUENCE: 9

| | |
|---|---|
| agtgggaatt ggctccggtg cccgtcagtg ggcagagcgc acatcgccca cagtccccga | 60 |
| gaagttgggg ggaggggtcg gcaattgaac cggtgcctag agaaggtggc gcggggtaaa | 120 |
| ctgggaaagt gatgtcgtgt actggctccg cctttttccc gagggtgggg gagaaccgta | 180 |
| tataagtgca gtagtcgccg tgaacgttct ttttcgcaac gggtttgccg ccagaacaca | 240 |
| ggtaagtgcc gtgtgtggtt cccgcgggcc tggcctcttt acgggttatg gcccttgcgt | 300 |
| gccttgaatt acttccacct ggctgcagta cgtgattctt gatcccgagc ttcgggttgg | 360 |
| aagtgggtgg gagagttcga ggccttgcgc ttaaggagcc ccttcgcctc gtgcttgagt | 420 |
| tgaggcctgg cctgggcgct ggggccgccg cgtgcgaatc tggtggcacc ttcgcgcctg | 480 |
| tctcgctgct ttcgataagt ctctagccat ttaaattttt gatgacctgc tgcgacgctt | 540 |
| tttttctgg caagatagtc ttgtaaatgc gggccaagat ctgcacactg gtatttcggt | 600 |
| ttttggggcc gcgggcggcg acggggcccg tgcgtcccag cgcacatgtt cggcgaggcg | 660 |
| gggcctgcga gcgcggccac cgagaatcgg acggggtag tctcaagctg gccggcctgc | 720 |
| tctggtgcct ggcctcgcgc cgccgtgtat cgccccgccc tgggcggcaa ggctggcccg | 780 |
| gtcggcacca gttgcgtgag cggaaagatg gccgcttccc ggccctgctg cagggagctc | 840 |
| aaaatggagg acgcggcgct cgggagagcg gcgcggtgag tcacccacac aaaggaaaag | 900 |
| ggcctttccg tcctcagccg tcgcttcatg tgactccacg gagtaccggg cgccgtccag | 960 |
| gcacctcgat tagttctcga gcttttggag tacgtcgtct ttaggttggg gggagggggtt | 1020 |
| ttatgcgatg gagtttcccc acactgagtg ggtggagact gaagttaggc cagcttggca | 1080 |
| cttgatgtaa ttctccttgg aatttgccct ttttgagttt ggatcttggt tcattctcaa | 1140 |
| gcctcagaca gtggttcaaa gtttttttct tccatttcag gtgtcgtgag gaattctcta | 1200 |
| gagatccctc gacctcgagc atttaaatgc ccgggcgcac catggacatg cgcgtgcccg | 1260 |
| cccagctgct gggcctgctg ctgctgtggt tcccggctc gcgatgcgca tggtatgccg | 1320 |
| aaagggatgc tgaaattgag aacgaaaagc tgcgccggga ggttgaagaa ctgcggcagg | 1380 |
| ccagcgaggc agatctccag ccaggaacta ttgagtacga acgccatcga cttacgcgtg | 1440 |
| cgcaggccga cgcacaggaa ctgaagaatg ccagagactc cgctgaagtg gtggaaaccg | 1500 |
| cattctgtac tttcgtgctg tcgcggatcg caggtgaaat tgccagtatt ctcgacgggc | 1560 |
| tcccctgtc ggtgcagcgg cgttttccgg aactggaaaa ccgacatgtt gatttcctga | 1620 |
| aacgggatat catcaaagcc atgaacaaag cagccgcgct ggatgaactg ataccggggt | 1680 |

-continued

```
tgctgagtga atatatcgaa cagtcaggtt aacaggctgc ggcattttgt ccgcgccggg    1740
cttcgctcac tgttcaggcc ggagccacag accgccgttg aatgggcgga tgctaattac    1800
tatctcccga aagaatccgc ataccaggaa gggcgctggg aaacactgcc ctttcagcgg    1860
gccatcatga atgcgatggg cagcgactac atccgtgagg tgaatgtggt gaagtctgcc    1920
cgtgtcggtt attccaaaat gctgctgggt gtttatgcct actttataga gcataagcag    1980
cgcaacaccc ttatctggtt gccgacggat ggtgatgccg agaactttat gaaaacccac    2040
gttgagccga ctattcgtga tattccgtcg ctgctggcgc tggccccgtg gtatggcaaa    2100
aagcaccggg ataacacgct caccatgaag cgtttcacta atgggcgtgg cttctggtgc    2160
ctgggcggta aagcggcaaa aaactaccgt gaaaagtcgg tggatgtggc gggttatgat    2220
gaacttgctg cttttgatga tgatattgaa caggaaggct ctccgacgtt cctgggtgac    2280
aagctacgta cggtggctgc accatctgtc ttcatcttcc cgccatctga tgagcagttg    2340
aaatctggaa ctgcctctgt tgtgtgcctg ctgaataact tctatcccag agaggccaaa    2400
gtacagtgga aggtggataa cgccctccaa tcgggtaact cccaggagag tgtcacagag    2460
caggacagca aggacagcac ctacagcctc agcagcaccc tgacgctgag caaagcagac    2520
tacgagaaac acaaagtcta cgcctgcgaa gtcacccatc agggcctgag ctcgcccgtc    2580
acaaagagct caacagggg agagtgttga gcggccgctc gaggccggca aggccggatc    2640
ccccgacctc gacctctggc taataaagga aatttatttt cattgcaata gtgtgttgga    2700
attttttgtg tctctcactc ggaaggacat atgggagggc aaatcatttg gtcgagatcc    2760
ctcggagatc tctagctaga ggatcgatcc ccgccccgga cgaactaaac ctgactacga    2820
catctctgcc ccttcttcgc ggggcagtgc atgtaatccc ttcagttggt tggtacaact    2880
tgccaactgg gcctgttcc acatgtgaca cgggggggga ccaaacacaa aggggttctc    2940
tgactgtagt tgacatcctt ataaatggat gtgcacattt gccaacactg agtggctttc    3000
atcctggagc agactttgca gtctgtggac tgcaacacaa cattgccttt atgtgtaact    3060
cttggctgaa gctcttacac caatgctggg ggacatgtac ctcccagggg cccaggaaga    3120
ctacgggagg ctacaccaac gtcaatcaga ggggcctgtg tagctaccga taagcggacc    3180
ctcaagaggg cattagcaat agtgtttata aggccccctt gttaacccta aacgggtagc    3240
atatgcttcc cgggtagtag tatatactat ccagactaac cctaattcaa tagcatatgt    3300
tacccaacgg gaagcatatg ctatcgaatt agggttagta aaagggtcct aaggaacagc    3360
gatatctccc accccatgag ctgtcacggt tttatttaca tggggtcagg attccacgag    3420
ggtagtgaac cattttagtc acaagggcag tggctgaaga tcaaggagcg ggcagtgaac    3480
tctcctgaat cttcgcctgc ttcttcattc tccttcgttt agctaataga ataactgctg    3540
agttgtgaac agtaaggtgt atgtgaggtg ctcgaaaaca aggtttcagg tgacgccccc    3600
agaataaaat ttggacgggg ggttcagtgg tggcattgtg ctatgacacc aatataaccc    3660
tcacaaaccc cttgggcaat aaatactagt gtaggaatga acattctga atatctttaa    3720 caatagaaat ccatggggtg gggacaagcc gtaaagactg gatgtccatc tcacacgaat    3780
ttatggctat gggcaacaca taatcctagt gcaatatgat actggggtta ttaagatgtg    3840
tcccaggcag ggaccaagac aggtgaacca tgttgttaca ctctatttgt aacaagggga    3900
aagagagtgg acgccgacag cagcggactc cactggttgt ctctaacacc cccgaaaatt    3960
aaacggggct ccacgccaat ggggcccata aacaaagaca agtggccact ctttttttg    4020 aaattgtgga gtgggggcac gcgtcagccc ccacacgccg ccctgcggtt ttggactgta    4080
```

```
aaataagggt gtaataactt ggctgattgt aaccccgcta accactgcgg tcaaaccact   4140
tgcccacaaa accactaatg gcaccccggg gaatacctgc ataagtaggt gggcgggcca   4200
agataggggc gcgattgctg cgatctggag gacaaattac acacacttgc gcctgagcgc   4260
caagcacagg gttgttggtc ctcatattca cgaggtcgct gagagcacgg tgggctaatg   4320
ttgccatggg tagcatatac tacccaaata tctggatagc atatgctatc ctaatctata   4380
tctgggtagc ataggctatc ctaatctata tctgggtagc atatgctatc ctaatctata   4440
tctgggtagt atatgctatc ctaatttata tctgggtagc ataggctatc ctaatctata   4500
tctgggtagc atatgctatc ctaatctata tctgggtagt atatgctatc ctaatctgta   4560
tccgggtagc atatgctatc ctaatagaga ttagggtagt atatgctatc ctaatttata   4620
tctgggtagc atatactacc caaatatctg gatagcatat gctatcctaa tctatatctg   4680
ggtagcatat gctatcctaa tctatatctg ggtagcatag gctatcctaa tctatatctg   4740
ggtagcatat gctatcctaa tctatatctg ggtagtatat gctatcctaa tttatatctg   4800
ggtagcatag gctatcctaa tctatatctg ggtagcatat gctatcctaa tctatatctg   4860
ggtagtatat gctatcctaa tctgtatccg ggtagcatat gctatcctca tgataagctg   4920
tcaaacatga gaattttctt gaagacgaaa gggcctcgtg atacgcctat ttttataggt   4980
taatgtcatg ataataatgg tttcttagac gtcaggtggc acttttcggg gaaatgtgcg   5040
cggaacccct atttgtttat ttttctaaat acattcaaat atgtatccgc tcatgagaca   5100
ataaccctga taaatgcttc aataatattg aaaaaggaag agtatgagta ttcaacattt   5160
ccgtgtcgcc cttattccct ttttttgcggc attttgcctt cctgttttttg ctcacccaga   5220 aacgctggtg aaagtaaaag atgctgaaga tcagttgggt gcacgagtgg gttacatcga   5280
actggatctc aacagcggta agatccttga gagttttcgc cccgaagaac gttttccaat   5340
gatgagcact tttaaagttc tgctatgtgg cgcggtatta cccgtgttg acgccgggca   5400 agagcaactc ggtcgccgca tacactattc tcagaatgac ttggttgagt actcaccagt   5460
cacagaaaag catcttacgg atggcatgac agtaagagaa ttatgcagtg ctgccataac   5520
catgagtgat aacactgcgg ccaacttact tctgacaacg atcggaggac cgaaggagct   5580
aaccgctttt ttgcacaaca tgggggatca tgtaactcgc cttgatcgtt gggaaccgga   5640
gctgaatgaa gccataccaa acgacgagcg tgacaccacg atgcctgcag caatggcaac   5700
aacgttgcgc aaactattaa ctggcgaact acttactcta gcttcccggc aacaattaat   5760
agactggatg gaggcggata aagttgcagg accacttctg cgctcggccc ttccggctgg   5820
ctggtttatt gctgataaat ctggagccgg tgagcgtggg tctcgcggta tcattgcagc   5880
actggggcca gatggtaagc cctcccgtat cgtagttatc tacacgacgg ggagtcaggc   5940
aactatggat gaacgaaata gacagatcgc tgagataggt gcctcactga ttaagcattg   6000
gtaactgtca gaccaagttt actcatatat actttagatt gatttaaaac ttcattttta   6060
atttaaaagg atctaggtga agatccttt tgataatctc atgaccaaaa tcccttaacg   6120
tgagttttcg ttccactgag cgtcagaccc cgtagaaaag atcaaaggat cttcttgaga   6180
tccttttttt ctgcgcgtaa tctgctgctt gcaaacaaaa aaaccaccgc taccagcggt   6240
ggtttgtttg ccggatcaag agctaccaac tctttttccg aaggtaactg gcttcagcag   6300
agcgcagata ccaaatactg ttcttctagt gtagccgtag ttaggccacc acttcaagaa   6360
ctctgtagca ccgcctacat acctcgctct gctaatcctg ttaccagtgg ctgctgccag   6420
tggcgataag tcgtgtctta ccgggttgga ctcaagacga tagttaccgg ataaggcgca   6480
```

```
gcggtcgggc tgaacggggg gttcgtgcac acagcccagc ttggagcgaa cgacctacac    6540
cgaactgaga tacctacagc gtgagctatg agaaagcgcc acgcttcccg aagggagaaa    6600
ggcggacagg tatccggtaa gcggcagggt cggaacagga gagcgcacga gggagcttcc    6660 aggggggaaac gcctggtatc tttatagtcc tgtcgggttt cgccacctct gacttgagcg    6720
tcgatttttg tgatgctcgt caggggggcg gagcctatgg aaaaacgcca gcaacgcggc    6780 cttttttacgg ttcctggcct tttgctggcc ttttgctcac atgttctttc ctgcgttatc    6840
ccctgattct gtggataacc gtattaccgc ctttgagtga gctgataccg ctcgccgcag    6900
ccgaacgacc gagcgcagcg agtcagtgag cgaggaagcg gaagagcgcc caatacgcaa    6960
accgcctctc cccgcgcgtt ggccgattca ttaatgcagc tggcacgaca ggtttcccga    7020
ctggaaagcg ggcagtgagc gcaacgcaat taatgtgagt tagctcactc attaggcacc    7080
ccaggcttta ctttatgc ttccggctcg tatgttgtgt ggaattgtga gcggataaca    7140
atttcacaca ggaaacagct atgaccatga ttacgccaag ctctagctag aggtcgagtc    7200
cctccccagc aggcagaagt atgcaaagca tgcatctcaa ttagtcagca accatagtcc    7260
cgcccctaac tccgcccatc ccgcccctaa ctccgcccag ttccgcccat tctccgcccc    7320
atggctgact aatttttttt atttatgcag aggccgaggc cgcctcggcc tctgagctat    7380
tccagaagta gtgaggaggc ttttttggag gcctaggctt ttgcaaaaag ctttgcaaag    7440
atggataaag ttttaaacag agaggaatct ttgcagctaa tggaccttct aggtcttgaa    7500
agg                                                                 7503

<210> SEQ ID NO 10
<211> LENGTH: 7503
<212> TYPE: DNA
<213> ORGANISM: Artificial Sequence
<220> FEATURE:
<223> OTHER INFORMATION: Synthetic construct: pJP191 ; pHybE-hCk V2

<400> SEQUENCE: 10
agtgggaatt ggctccggtg cccgtcagtg ggcagagcgc acatcgccca cagtccccga      60
gaagttgggg ggagggggtcg gcaattgaac cggtgcctag agaaggtggc gcggggtaaa     120
ctgggaaagt gatgtcgtgt actggctccg ccttttttccc gagggtgggg gagaaccgta     180
tataagtgca gtagtcgccg tgaacgttct ttttcgcaac gggtttgccg ccagaacaca     240
ggtaagtgcc gtgtgtggtt cccgcgggcc tggcctcttt acgggttatg gcccttgcgt     300
gccttgaatt acttccacct ggctgcagta cgtgattctt gatcccgagc ttcgggttgg     360
aagtgggtgg gagagttcga ggccttgcgc ttaaggagcc ccttcgcctc gtgcttgagt     420
tgaggcctgg cctgggcgct ggggccgccg cgtgcgaatc tggtggcacc ttcgcgcctg     480
tctcgctgct ttcgataagt ctctagccat ttaaaatttt tgatgacctg ctgcgacgct     540 tttttttctgg caagatagtc ttgtaaatgc gggccaagat ctgcacactg gtatttcggt     600
ttttggggcc gcgggcggcg acggggcccg tgcgtcccag cgcacatgtt cggcgaggcg     660
gggcctgcga gcgcggccac cgagaatcgg acggggtag tctcaagctg gccggcctgc     720
tctggtgcct ggcctcgcgc cgccgtgtat cgcccgccc tgggcggcaa ggctggcccg     780
gtcggcacca gttgcgtgag cggaaagatg gccgcttccc ggccctgctg cagggagctc     840
aaaatggagg acgcggcgct cgggagagcg ggcgggtgag tcaccacac aaaggaaaag     900 ggcctttccg tcctcagccg tcgcttcatg tgactccacg gagtaccggg cgccgtccag     960
gcacctcgat tagttctcga gcttttggag tacgtcgtct ttaggttggg gggagggtt    1020
```

```
ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gttttttttct tccatttcag gtgtcgtgag gaattctcta   1200
gagatccctc gacctcgaga tccattgtgc ccgggcgcac catggacatg cgcgtgcccg    1260
cccagctgct gggcctgctg ctgctgtggt tccccggctc gcgatgcgca tggtatgccg    1320
aaagggatgc tgaaattgag aacgaaaagc tgcgccggga ggttgaagaa ctgcggcagg    1380
ccagcgaggc agatctccag ccaggaacta ttgagtacga acgccatcga cttacgcgtg    1440
cgcaggccga cgcacaggaa ctgaagaatg ccagagactc cgctgaagtg gtggaaaccg    1500
cattctgtac tttcgtgctg tcgcggatcg caggtgaaat tgccagtatt ctcgacgggc    1560 tcccccctgtc ggtgcagcgg cgttttccgg aactggaaaa ccgacatgtt gatttcctga   1620
aacgggatat catcaaagcc atgaacaaag cagccgcgct ggatgaactg ataccggggt    1680
tgctgagtga atatatcgaa cagtcaggtt aacaggctgc ggcattttgt ccgcgccggg    1740
cttcgctcac tgttcaggcc ggagccacag accgccgttg aatgggcgga tgctaattac    1800
tatctcccga aagaatccgc ataccaggaa gggcgctggg aaacactgcc ctttcagcgg    1860
gccatcatga atgcgatggg cagcgactac atccgtgagg tgaatgtggt gaagtctgcc    1920
cgtgtcggtt attccaaaat gctgctgggt gtttatgcct actttataga gcataagcag    1980
cgcaacaccc ttatctggtt gccgacggat ggtgatgccg agaactttat gaaaacccac    2040
gttgagccga ctattcgtga tattccgtcg ctgctggcgc tggccccgtg gtatggcaaa    2100
aagcaccggg ataacacgct caccatgaag cgtttcacta atgggcgtgg cttctggtgc    2160
ctgggcggta aagcggcaaa aaactaccgt gaaaagtcgg tggatgtggc gggttatgat    2220
gaacttgctg cttttgatga tgatattgaa caggaaggct ctccgacgtt cctgggtgac    2280
aagctacgta cggtggctgc accatctgtc ttcatcttcc cgccatctga tgagcagttg    2340
aaatctggaa ctgcctctgt tgtgtgcctg ctgaataact tctatcccag agaggccaaa    2400
gtacagtgga aggtggataa cgccctccaa tcgggtaact cccaggagag tgtcacagag    2460
caggacagca aggacagcac ctacagcctc agcagcaccc tgacgctgag caaagcagac    2520
tacgagaaac acaaagtcta cgcctgcgaa gtcacccatc agggcctgag ctcgcccgtc    2580
acaaagagct tcaacagggg agagtgttga gcggccgctc gaggccggca aggccggatc    2640
ccccgacctc gacctctggc taataaagga aatttatttt cattgcaata gtgtgttgga    2700 atttttttgtg tctctcactc ggaaggacat atgggagggc aaatcatttg gtcgagatcc    2760
ctcggagatc tctagctaga ggatcgatcc ccgccccgga cgaactaaac ctgactacga    2820
catctctgcc ccttcttcgc ggggcagtgc atgtaatccc ttcagttggt tggtacaact    2880
tgccaactgg gccctgttcc acatgtgaca cggggggga ccaaacacaa aggggttctc     2940
tgactgtagt tgacatcctt ataaatggat gtgcacattt gccaacactg agtggctttc    3000
atcctggagc agactttgca gtctgtggac tgcaacacaa cattgccttt atgtgtaact    3060
cttggctgaa gctcttacac caatgctggg ggacatgtac ctcccagggg cccaggaaga    3120
ctacgggagg ctacaccaac gtcaatcaga ggggcctgtg tagctaccga taagcggacc    3180
ctcaagaggg cattagcaat agtgtttata aggcccccctt gttaacccta acgggtagc    3240 atatgcttcc cgggtagtag tatatactat ccagactaac cctaattcaa tagcatatgt    3300
tacccaacgg gaagcatatg ctatcgaatt agggttagta aaagggtcct aaggaacagc    3360
gatatctccc accccatgag ctgtcacggt tttatttaca tggggtcagg attccacgag    3420
```

```
ggtagtgaac cattttagtc acaagggcag tggctgaaga tcaaggagcg ggcagtgaac   3480
tctcctgaat cttcgcctgc ttcttcattc tccttcgttt agctaataga ataactgctg   3540
agttgtgaac agtaaggtgt atgtgaggtg ctcgaaaaca aggtttcagg tgacgccccc   3600
agaataaaat ttggacgggg ggttcagtgg tggcattgtg ctatgacacc aatataaccc   3660
tcacaaaccc cttgggcaat aaatactagt gtaggaatga acattctga atatctttaa   3720 caatagaaat ccatggggtg gggacaagcc gtaaagactg gatgtccatc tcacacgaat   3780
ttatggctat gggcaacaca taatcctagt gcaatatgat actggggtta ttaagatgtg   3840
tcccaggcag ggaccaagac aggtgaacca tgttgttaca ctctatttgt aacaagggga   3900
aagagagtgg acgccgacag cagcggactc cactggttgt ctctaacacc cccgaaaatt   3960 aaacgggct ccacgccaat ggggcccata aacaaagaca agtggccact cttttttttg   4020
aaattgtgga gtgggggcac gcgtcagccc ccacacgccg ccctgcggtt ttggactgta   4080
aaataagggt gtaataactt ggctgattgt aaccccgcta accactgcgg tcaaaccact   4140
tgcccacaaa accactaatg gcaccccggg gaatacctgc ataagtaggt gggcgggcca   4200
agataggggc gcgattgctg cgatctggag acaaaattac acacacttgc gcctgagcgc   4260
caagcacagg gttgttggtc ctcatattca cgaggtcgct gagagcacgg tgggctaatg   4320
ttgccatggg tagcatatac tacccaaata tctggatagc atatgctatc ctaatctata   4380
tctgggtagc ataggctatc ctaatctata tctgggtagc atatgctatc ctaatctata   4440
tctgggtagt atatgctatc ctaatttata tctgggtagc ataggctatc ctaatctata   4500
tctgggtagc atatgctatc ctaatctata tctgggtagt atatgctatc ctaatctgta   4560
tccgggtagc atatgctatc ctaatagaga ttagggtagt atatgctatc ctaatttata   4620
tctgggtagc atatactacc caaatatctg gatagcatat gctatcctaa tctatatctg   4680
ggtagcatat gctatcctaa tctatatctg ggtagcatag gctatcctaa tctatatctg   4740
ggtagcatat gctatcctaa tctatatctg ggtagtatat gctatcctaa tttatatctg   4800
ggtagcatag gctatcctaa tctatatctg ggtagcatat gctatcctaa tctatatctg   4860
ggtagtatat gctatcctaa tctgtatccg ggtagcatat gctatcctca tgataagctg   4920
tcaaacatga gaattttctt gaagacgaaa gggcctcgtg atacgcctat ttttataggt   4980
taatgtcatg ataataatgg tttcttagac gtcaggtggc acttttcggg gaaatgtgcg   5040
cggaacccct atttgtttat ttttctaaat acattcaaat atgtatccgc tcatgagaca   5100
ataaccctga taaatgcttc aataatattg aaaaaggaag agtatgagta ttcaacattt   5160
ccgtgtcgcc cttattccct ttttgcggc attttgcctt cctgtttttg ctcacccaga   5220
aacgctggtg aaagtaaaag atgctgaaga tcagttgggt gcacgagtgg gttacatcga   5280
actggatctc aacagcggta agatccttga gagttttcgc cccgaagaac gttttccaat   5340
gatgagcact tttaaagttc tgctatgtgg cgcggtatta tcccgtgttg acgccgggca   5400
agagcaactc ggtcgccgca tacactattc tcagaatgac ttggttgagt actcaccagt   5460
cacagaaaag catcttacgg atggcatgac agtaagagaa ttatgcagtg ctgccataac   5520
catgagtgat aacactgcgg ccaacttact tctgacaacg atcggaggac cgaaggagct   5580
aaccgctttt ttgcacaaca tgggggatca tgtaactcgc cttgatcgtt gggaaccgga   5640
gctgaatgaa gccataccaa acgacgagcg tgacaccacg atgcctgcag caatggcaac   5700
aacgttgcgc aaactattaa ctggcgaact acttactcta gcttcccggc aacaattaat   5760
agactggatg gaggcggata aagttgcagg accacttctg cgctcggccc ttccggctgg   5820
```

```
ctggtttatt gctgataaat ctggagccgg tgagcgtggg tctcgcggta tcattgcagc    5880
actggggcca gatggtaagc cctcccgtat cgtagttatc tacacgacgg ggagtcaggc    5940
aactatggat gaacgaaata cagagatcgc tgagataggt gcctcactga ttaagcattg    6000
gtaactgtca gaccaagttt actcatatat actttagatt gatttaaaac ttcattttta    6060
atttaaaagg atctaggtga agatcctttt tgataatctc atgaccaaaa tcccttaacg    6120
tgagttttcg ttccactgag cgtcagaccc cgtagaaaag atcaaaggat cttcttgaga    6180 tcctttttt ctgcgcgtaa tctgctgctt gcaaacaaaa aaaccaccgc taccagcggt    6240
ggtttgtttg ccggatcaag agctaccaac tcttttccg aaggtaactg gcttcagcag    6300
agcgcagata ccaaatactg ttcttctagt gtagccgtag ttaggccacc acttcaagaa    6360
ctctgtagca ccgcctacat acctcgctct gctaatcctg ttaccagtgg ctgctgccag    6420
tggcgataag tcgtgtctta ccgggttgga ctcaagacga tagttaccgg ataaggcgca    6480
gcggtcgggc tgaacggggg gttcgtgcac acagcccagc ttggagcgaa cgacctacac    6540
cgaactgaga tacctacagc gtgagctatg agaaagcgcc acgcttcccg aagggagaaa    6600
ggcggacagg tatccggtaa gcggcagggt cggaacagga gagcgcacga gggagcttcc    6660
agggggaaac gcctggtatc tttatagtcc tgtcgggttt cgccacctct gacttgagcg    6720
tcgatttttg tgatgctcgt caggggggcg gagcctatgg aaaaacgcca gcaacgcggc    6780 cttttacgg ttcctggcct tttgctggcc ttttgctcac atgttctttc ctgcgttatc    6840
ccctgattct gtggataacc gtattaccgc ctttgagtga gctgataccg ctcgccgcag    6900
ccgaacgacc gagcgcagcg agtcagtgag cgaggaagcg gaagagcgcc caatacgcaa    6960
accgcctctc cccgcgcgtt ggccgattca ttaatgcagc tggcacgaca ggtttcccga    7020
ctggaaagcg ggcagtgagc gcaacgcaat taatgtgagt tagctcactc attaggcacc    7080
ccaggcttta cactttatgc ttccggctcg tatgttgtgt ggaattgtga gcggataaca    7140
atttcacaca ggaaacagct atgaccatga ttacgccaag ctctagctag aggtcgagtc    7200
cctccccagc aggcagaagt atgcaaagca tgcatctcaa ttagtcagca accatagtcc    7260
cgcccctaac tccgcccatc ccgcccctaa ctccgcccag ttccgcccat tctccgcccc    7320
atggctgact aatttttttt atttatgcag aggccgaggc cgcctcggcc tctgagctat    7380
tccagaagta gtgaggaggc ttttttggag gcctaggctt ttgcaaaaag ctttgcaaag    7440
atggataaag ttttaaacag agaggaatct ttgcagctaa tggaccttct aggtcttgaa    7500
agg                                                                  7503

<210> SEQ ID NO 11
<211> LENGTH: 7481
<212> TYPE: DNA
<213> ORGANISM: Artificial Sequence
<220> FEATURE:
<223> OTHER INFORMATION: Synthetic construct: pJP179 ; pHybE-hCl V1

<400> SEQUENCE: 11
agtgggaatt ggctccggtg cccgtcagtg ggcagagcgc acatcgccca cagtccccga     60
gaagttgggg ggaggggtcg gcaattgaac cggtgcctag agaaggtggc gcggggtaaa    120
ctgggaaagt gatgtcgtgt actggctccg cctttttccc gagggtgggg gagaaccgta    180
tataagtgca gtagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
```

```
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540 tttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc     720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggagggggtt   1020 ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gtttttttct tccatttcag gtgtcgtgag gaattctcta    1200
gagatccctc gacctcgagc atttaaatgc ccgggcgcca ccatgacttg gaccccactc    1260
ctcttcctca ccctcctcct ccactgcaca ggaagcttat cgcgaaaggg atgctgaaat    1320
tgagaacgaa aagctgcgcc gggaggttga agaactgcgg caggccagcg aggcagatct    1380
ccagccagga actattgagt acgaacgcca tcgacttacg cgtgcgcagg ccgacgcaca    1440
ggaactgaag aatgccagag actccgctga agtggtggaa accgcattct gtactttcgt    1500
gctgtcgcgg atcgcaggtg aaattgccag tattctcgac gggctccccc tgtcggtgca    1560
gcggcgtttt ccggaactgg aaaaccgaca tgttgatttc ctgaaacggg atatcatcaa    1620
agccatgaac aaagcagccg cgctggatga actgataccg gggttgctga gtgaatatat    1680
cgaacagtca ggttaacagg ctgcggcatt ttgtccgcgc cgggcttcgc tcactgttca    1740
ggccggagcc acagaccgcc gttgaatggg cggatgctaa ttactatctc ccgaaagaat    1800
ccgcatacca ggaagggcgc tgggaaacac tgcccttttca gcgggccatc atgaatgcga    1860
tgggcagcga ctacatccgt gaggtgaatg tggtgaagtc tgcccgtgtc ggttattcca    1920
aaatgctgct gggtgtttat gcctacttta tagagcataa gcagcgcaac cccttatct    1980 ggttgccgac ggatggtgat gccgagaact ttatgaaaac ccacgttgag ccgactattc    2040
gtgatattcc gtcgctgctg gcgctggccc cgtggtatgg caaaaagcac cgggataaca    2100
cgctcaccat gaagcgtttc actaatgggc gtggcttctg gtgcctgggc ggtaaagcgg    2160
caaaaaacta ccgtgaaaag tcggtggatg tggcgggtta tgatgaactt gctgcttttg    2220
atgatgatat tgaacaggaa ggctctccga cgttcctggg tgacaagcgt taacccaagg    2280
ctgccccctc ggtcactctg ttcccgccct cctctgagga gcttcaagcc aacaaggcca    2340
cactggtgtg tctcataagt gacttctacc cgggagccgt gacagtggcc tggaaggcag    2400
atagcagccc cgtcaaggcg ggagtggaga ccaccacacc ctccaaacaa gcaacaaca    2460 agtacgcggc cagcagctac ctgagcctga cgcctgagca gtggaagtcc cacagaagct    2520
acagctgcca ggtcacgcat gaaggagca ccgtggagaa gacagtggcc ctacagaat     2580 gttcatgagc ggccgctcga ggccggcaag gccggatccc ccgacctcga cctctggcta    2640
ataaaggaaa tttattttca ttgcaatagt gtgttggaat ttttttgtgtc tctcactcgg    2700 aaggacatat gggagggcaa atcatttggt cgagatccct cggagatctc tagctagagg    2760
```

```
atcgatcccc gccccggacg aactaaacct gactacgaca tctctgcccc ttcttcgcgg    2820
ggcagtgcat gtaatccctt cagttggttg gtacaacttg ccaactgggc cctgttccac    2880
atgtgacacg ggggggacc aaacacaaag gggttctctg actgtagttg acatccttat     2940
aaatggatgt gcacatttgc caacactgag tggctttcat cctggagcag actttgcagt    3000
ctgtggactg caacacaaca ttgcctttat gtgtaactct tggctgaagc tcttacacca    3060
atgctggggg acatgtacct cccaggggcc caggaagact acgggaggct acaccaacgt    3120
caatcagagg ggcctgtgta gctaccgata agcggaccct caagagggca ttagcaatag    3180
tgtttataag gccccttgt taaccctaaa cgggtagcat atgcttcccg ggtagtagta     3240
tatactatcc agactaaccc taattcaata gcatatgtta cccaacggga agcatatgct    3300
atcgaattag ggttagtaaa agggtcctaa ggaacagcga tatctcccac cccatgagct    3360
gtcacggttt tatttacatg gggtcaggat tccacgaggg tagtgaacca ttttagtcac    3420
aagggcagtg gctgaagatc aaggagcggg cagtgaactc tcctgaatct tcgcctgctt    3480
cttcattctc cttcgtttag ctaatagaat aactgctgag ttgtgaacag taaggtgtat    3540
gtgaggtgct cgaaaacaag gtttcaggtg acgccccag aataaaattt ggacggggggg    3600 ttcagtggtg gcattgtgct atgacaccaa tataaccctc acaaacccct tgggcaataa    3660
atactagtgt aggaatgaaa cattctgaat atctttaaca atagaaatcc atggggtggg    3720
gacaagccgt aaagactgga tgtccatctc acacgaattt atggctatgg caacacata    3780 atcctagtgc aatatgatac tggggttatt aagatgtgtc ccaggcaggg accaagacag    3840
gtgaaccatg ttgttacact ctatttgtaa caaggggaaa gagagtggac gccgacagca    3900
gcggactcca ctggttgtct ctaacacccc cgaaaattaa acggggctcc acgccaatgg    3960
ggcccataaa caaagacaag tggccactct ttttttgaa attgtggagt ggggcacgc      4020 gtcagccccc acacgccgcc ctgcggtttt ggactgtaaa ataagggtgt aataacttgg    4080
ctgattgtaa ccccgctaac cactgcggtc aaaccacttg cccacaaaac cactaatggc    4140
accccgggga atacctgcat aagtaggtgg gcgggccaag ataggggcgc gattgctgcg    4200
atctggagga caaattacac acacttgcgc ctgagcgcca agcacagggt tgttggtcct    4260
catattcacg aggtcgctga gagcacggtg ggctaatgtt gccatgggta gcatatacta    4320
cccaaatatc tggatagcat atgctatcct aatctatatc tgggtagcat aggctatcct    4380
aatctatatc tgggtagcat atgctatcct aatctatatc tgggtagtat atgctatcct    4440
aatttatatc tgggtagcat aggctatcct aatctatatc tgggtagcat atgctatcct    4500
aatctatatc tgggtagtat atgctatcct aatctgtatc cgggtagcat atgctatcct    4560
aatagagatt agggtagtat atgctatcct aatttatatc tgggtagcat atactaccca    4620
aatatctgga tagcatatgc tatcctaatc tatatctggg tagcatatgc tatcctaatc    4680
tatatctggg tagcataggc tatcctaatc tatatctggg tagcatatgc tatcctaatc    4740
tatatctggg tagtatatgc tatcctaatt tatatctggg tagcataggc tatcctaatc    4800
tatatctggg tagcatatgc tatcctaatc tatatctggg tagtatatgc tatcctaatc    4860
tgtatccggg tagcatatgc tatcctcatg ataagctgtc aaacatgaga attttcttga    4920
agacgaaagg gcctcgtgat acgcctattt ttataggtta atgtcatgat aataatggtt    4980
tcttagacgt caggtggcac ttttcgggga aatgtgcgcg gaaccctat tgtttatt      5040 ttctaaatac attcaaatat gtatccgctc atgagacaat aacctgata aatgcttcaa    5100 taatattgaa aaaggaagag tatgagtatt caacatttcc gtgtcgccct tattcccttt    5160
```

```
tttgcggcat tttgccttcc tgttttttgct cacccagaaa cgctggtgaa agtaaaagat    5220
gctgaagatc agttgggtgc acgagtgggt tacatcgaac tggatctcaa cagcggtaag    5280
atccttgaga gttttcgccc cgaagaacgt tttccaatga tgagcacttt taaagttctg    5340
ctatgtggcg cggtattatc ccgtgttgac gccgggcaag agcaactcgg tcgccgcata    5400
cactattctc agaatgactt ggttgagtac tcaccagtca cagaaaagca tcttacggat    5460
ggcatgacag taagagaatt atgcagtgct gccataacca tgagtgataa cactgcggcc    5520
aacttacttc tgacaacgat cggaggaccg aaggagctaa ccgcttttttt gcacaacatg    5580 ggggatcatg taactcgcct tgatcgttgg gaaccggagc tgaatgaagc cataccaaac    5640
gacgagcgtg acaccacgat gcctgcagca atggcaacaa cgttgcgcaa actattaact    5700
ggcgaactac ttactctagc ttcccggcaa caattaatag actggatgga ggcggataaa    5760
gttgcaggac cacttctgcg ctcggccctt ccggctggct ggtttattgc tgataaatct    5820
ggagccggtg agcgtgggtc tcgcggtatc attgcagcac tggggccaga tggtaagccc    5880
tcccgtatcg tagttatcta cacgacgggg agtcaggcaa ctatggatga acgaaataga    5940
cagatcgctg agataggtgc ctcactgatt aagcattggt aactgtcaga ccaagtttac    6000
tcatatatac tttagattga tttaaaactt cattttttaat ttaaaaggat ctaggtgaag    6060
atcctttttg ataatctcat gaccaaaatc ccttaacgtg agttttcgtt ccactgagcg    6120
tcagaccccg tagaaaagat caaaggatct tcttgagatc cttttttttct gcgcgtaatc    6180 tgctgcttgc aaacaaaaaa accaccgcta ccagcggtgg tttgtttgcc ggatcaagag    6240
ctaccaactc tttttccgaa ggtaactggc ttcagcagag cgcagatacc aaatactgtt    6300
cttctagtgt agccgtagtt aggccaccac ttcaagaact ctgtagcacc gcctacatac    6360
ctcgctctgc taatcctgtt accagtggct gctgccagtg gcgataagtc gtgtcttacc    6420
gggttggact caagacgata gttaccggat aaggcgcagc ggtcgggctg aacggggggt    6480
tcgtgcacac agcccagctt ggagcgaacg acctacaccg aactgagata cctacagcgt    6540
gagctatgag aaagcgccac gcttcccgaa gggagaaagg cggacaggta tccggtaagc    6600
ggcagggtcg gaacaggaga gcgcacgagg gagcttccag gggaaacgc ctggtatctt    6660 tatagtcctg tcgggtttcg ccacctctga cttgagcgtc gatttttgtg atgctcgtca    6720
ggggggcgga gcctatggaa aaacgccagc aacgcggcct ttttacggtt cctggccttt    6780
tgctggcctt ttgctcacat gttctttcct gcgttatccc ctgattctgt ggataaccgt    6840
attaccgcct ttgagtgagc tgataccgct cgccgcagcc gaacgaccga gcgcagcgag    6900
tcagtgagcg aggaagcgga agagcgccca atacgcaaac cgcctctccc cgcgcgttgg    6960
ccgattcatt aatgcagctg gcacgacagg tttcccgact ggaaagcggg cagtgagcgc    7020
aacgcaatta atgtgagtta gctcactcat taggcacccc aggctttaca ctttatgctt    7080
ccggctcgta tgttgtgtgg aattgtgagc ggataacaat ttcacacagg aaacagctat    7140
gaccatgatt acgccaagct ctagctagag gtcgagtccc tccccagcag gcagaagtat    7200
gcaaagcatg catctcaatt agtcagcaac catagtcccg cccctaactc cgcccatccc    7260
gcccctaact ccgcccagtt ccgcccattc tccgccccat ggctgactaa ttttttttat    7320
ttatgcagag gccgaggccg cctcggcctc tgagctattc cagaagtagt gaggaggctt    7380
ttttggaggc ctaggctttt gcaaaaagct ttgcaaagat ggataaagtt ttaaacagag    7440
aggaatcttt gcagctaatg gaccttctag gtcttgaaag g                        7481
```

<210> SEQ ID NO 12
<211> LENGTH: 7486
<212> TYPE: DNA
<213> ORGANISM: Artificial Sequence
<220> FEATURE:
<223> OTHER INFORMATION: Synthetic construct: pJP192 ; pHybE-hCl V2

<400> SEQUENCE: 12

```
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctggaaagt gatgtcgtgt actggctccg cctttttccc gagggtgggg gagaaccgta     180
tataagtgca gtagtcgccg tgaacgttct ttttcgcaac gggtttgccg ccagaacaca     240
ggtaagtgcc gtgtgtggtt cccgcgggcc tggcctcttt acgggttatg gcccttgcgt     300
gccttgaatt acttccacct ggctgcagta cgtgattctt gatcccgagc ttcgggttgg     360
aagtgggtgg gagagttcga ggccttgcgc ttaaggagcc ccttcgcctc gtgcttgagt     420
tgaggcctgg cctgggcgct ggggccgccg cgtgcgaatc tggtggcacc ttcgcgcctg     480
tctcgctgct ttcgataagt ctctagccat ttaaaatttt tgatgacctg ctgcgacgct     540
tttttctgg caagatagtc ttgtaaatgc gggccaagat ctgcacactg gtatttcggt     600
ttttggggcc gcgggcggcg acggggcccg tgcgtcccag cgcacatgtt cggcgaggcg     660
gggcctgcga gcgcggccac cgagaatcgg acggggtag tctcaagctg gccggcctgc     720
tctggtgcct ggcctcgcgc cgccgtgtat cgccccgccc tgggcggcaa ggctggcccg     780
gtcggcacca gttgcgtgag cggaaagatg gccgcttccc ggccctgctg cagggagctc     840
aaaatggagg acgcggcgct cgggagagcg ggcgggtgag tcacccacac aaaggaaaag     900
ggccttttccg tcctcagccg tcgcttcatg tgactccacg gagtaccggg cgccgtccag     960
gcacctcgat tagttctcga gcttttggag tacgtcgtct ttaggttggg gggaggggtt    1020
ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gttttttttct tccatttcag gtgtcgtgag gaattctcta    1200
gagatccctc gacctcgaga tccattgtgc ccgggcgcca ccatgacttg accccactc    1260
ctcttcctca ccctcctcct ccactgcaca ggaagcttat cgcgaaaggg atgctgaaat    1320
tgagaacgaa aagctgcgcc gggaggttga agaactgcgg caggccagcg aggcagatct    1380
ccagccagga actattgagt acgaacgcca tcgacttacg cgtgcgcagg ccgacgcaca    1440
ggaactgaag aatgccagag actccgctga agtggtggaa accgcattct gtactttcgt    1500
gctgtcgcgg atcgcaggtg aaattgccag tattctcgac gggctccccc tgtcggtgca    1560
gcggcgtttt ccggaactgg aaaaccgaca tgttgatttc ctgaaacggg atatcatcaa    1620
agccatgaac aaagcagccg cgctggatga actgataccg gggttgctga gtgaatatat    1680
cgaacagtca ggttaacagg ctgcggcatt ttgtccgcgc cgggcttcgc tcactgttca    1740
ggccggagcc acagaccgcc gttgaatggg cggatgctaa ttactatctc ccgaaagaat    1800
ccgcatacca ggaagggcgc tgggaaacac tgcccttttca gcgggccatc atgaatgcga    1860
tgggcagcga ctacatccgt gaggtgaatg tggtgaagtc tgcccgtgtc ggttattcca    1920
aaatgctgct gggtgtttat gcctacttta tagagcataa gcagcgcaac acccttatct    1980
ggttgccgac ggatggtgat gccgagaact ttatgaaaac ccacgttgag ccgactattc    2040
gtgatattcc gtcgctgctg gcgctggccc cgtggtatgg caaaaagcac cgggataaca    2100
cgctcaccat gaagcgtttc actaatgggc gtggcttctg gtgcctgggc ggtaaagcgg    2160
```

| | |
|---|---|
| caaaaaacta ccgtgaaaag tcggtggatg tggcgggtta tgatgaactt gctgcttttg | 2220 |
| atgatgatat tgaacaggaa ggctctccga cgttcctggg tgacaagcgc taggtcaacc | 2280 |
| caaggctgcc ccctcggtca ctctgttccc gccctcctct gaggagcttc aagccaacaa | 2340 |
| ggccacactg gtgtgtctca taagtgactt ctacccggga gccgtgacag tggcctggaa | 2400 |
| ggcagatagc agccccgtca aggcgggagt ggagaccacc acaccctcca aacaaagcaa | 2460 |
| caacaagtac gcggccagca gctacctgag cctgacgcct gagcagtgga gtcccacag | 2520 |
| aagctacagc tgccaggtca cgcatgaagg gagcaccgtg gagaagacag tggcccctac | 2580 |
| agaatgttca tgagcggccg ctcgaggccg gcaaggccgg atcccccgac ctcgacctct | 2640 |
| ggctaataaa ggaaatttat tttcattgca atagtgtgtt ggaattttt gtgtctctca | 2700 |
| ctcggaagga catatgggag ggcaaatcat ttggtcgaga tccctcggag atctctagct | 2760 |
| agaggatcga tccccgcccc ggacgaacta aacctgacta cgacatctct gccccttctt | 2820 |
| cgcggggcag tgcatgtaat cccttcagtt ggttggtaca acttgccaac tgggccctgt | 2880 |
| tccacatgtg acacgggggg ggaccaaaca caaggggtt ctctgactgt agttgacatc | 2940 |
| cttataaatg gatgtgcaca tttgccaaca ctgagtggct ttcatcctgg agcagacttt | 3000 |
| gcagtctgtg gactgcaaca caacattgcc tttatgtgta actcttggct gaagctctta | 3060 |
| caccaatgct gggggacatg tacctcccag ggcccagga agactacggg aggctacacc | 3120 |
| aacgtcaatc agaggggcct gtgtagctac cgataagcgg accctcaaga gggcattagc | 3180 |
| aatagtgttt ataaggcccc cttgttaacc ctaaacgggt agcatatgct tcccgggtag | 3240 |
| tagtatatac tatccagact aaccctaatt caatagcata tgttacccaa cgggaagcat | 3300 |
| atgctatcga attagggtta gtaaaagggt cctaaggaac agcgatatct cccaccccat | 3360 |
| gagctgtcac ggttttattt acatggggtc aggattccac gagggtagtg aaccatttta | 3420 |
| gtcacaaggg cagtggctga agatcaagga gcgggcagtg aactctcctg aatcttcgcc | 3480 |
| tgcttcttca ttctccttcg tttagctaat agaataactg ctgagttgtg aacagtaagg | 3540 |
| tgtatgtgag gtgctcgaaa acaaggtttc aggtgacgcc cccagaataa aatttggacg | 3600 |
| gggggttcag tggtggcatt gtgctatgac accaatataa ccctcacaaa ccccttgggc | 3660 |
| aataaatact agtgtaggaa tgaaacattc tgaatatctt taacaataga aatccatggg | 3720 |
| gtggggacaa gccgtaaaga ctggatgtcc atctcacacg aatttatggc tatgggcaac | 3780 |
| acataatcct agtgcaatat gatactgggg ttattaagat gtgtcccagg cagggaccaa | 3840 |
| gacaggtgaa ccatgttgtt acactctatt tgtaacaagg ggaaagagag tggacgccga | 3900 |
| cagcagcgga ctccactggt tgtctctaac accccgaaa attaaacggg gctccacgcc | 3960 |
| aatgggccc ataaacaaag acaagtggcc actcttttt ttgaaattgt ggagtggggg | 4020 |
| cacgcgtcag cccccacacg ccgccctgcg gttttggact gtaaaataag ggtgtaataa | 4080 |
| cttggctgat tgtaaccccg ctaaccactg cggtcaaacc acttgccac aaaaccacta | 4140 |
| atggcacccc ggggaatacc tgcataagta ggtgggcggg ccaagatagg ggcgcgattg | 4200 |
| ctgcgatctg gaggacaaat tacacacact tgcgcctgag cgccaagcac agggttgttg | 4260 |
| gtcctcatat tcacgaggtc gctgagagca cggtgggcta atgttgccat gggtagcata | 4320 |
| tactacccaa atatctggat agcatatgct atcctaatct atatctgggt agcataggct | 4380 |
| atcctaatct atatctgggt agcatatgct atcctaatct atatctgggt agtatatgct | 4440 |
| atcctaatt atatctgggt agcataggct atcctaatct atatctgggt agcatatgct | 4500 |
| atcctaatct atatctgggt agtatatgct atcctaatct gtatccgggt agcatatgct | 4560 |

```
atcctaatag agattagggt agtatatgct atcctaattt atatctgggt agcatatact   4620
acccaaatat ctggatagca tatgctatcc taatctatat ctgggtagca tatgctatcc   4680
taatctatat ctgggtagca taggctatcc taatctatat ctgggtagca tatgctatcc   4740
taatctatat ctgggtagta tatgctatcc taatttatat ctgggtagca taggctatcc   4800
taatctatat ctgggtagca tatgctatcc taatctatat ctgggtagta tatgctatcc   4860
taatctgtat ccgggtagca tatgctatcc tcatgataag ctgtcaaaca tgagaatttt   4920
cttgaagacg aaagggcctc gtgatacgcc tattttata ggttaatgtc atgataataa    4980
tggtttctta gacgtcaggt ggcactttc ggggaaatgt gcgcggaacc cctatttgtt    5040 tattttcta aatacattca aatatgtatc cgctcatgag acaataaccc tgataaatgc    5100
ttcaataata ttgaaaaagg aagagtatga gtattcaaca tttccgtgtc gcccttattc   5160
ccttttttgc ggcattttgc cttcctgttt ttgctcaccc agaaacgctg gtgaaagtaa   5220
aagatgctga agatcagttg ggtgcacgag tgggttacat cgaactggat ctcaacagcg   5280
gtaagatcct tgagagtttt cgccccgaag aacgttttcc aatgatgagc acttttaaag   5340
ttctgctatg tggcgcggta ttatcccgtg ttgacgccgg gcaagagcaa ctcggtcgcc   5400
gcatacacta ttctcagaat gacttggttg agtactcacc agtcacagaa aagcatctta   5460
cggatggcat gacagtaaga gaattatgca gtgctgccat aaccatgagt gataacactg   5520
cggccaactt acttctgaca acgatcggag gaccgaagga gctaaccgct ttttgcaca    5580 acatggggga tcatgtaact cgccttgatc gttgggaacc ggagctgaat gaagccatac   5640
caaacgacga gcgtgacacc acgatgcctg cagcaatggc aacaacgttg cgcaaactat   5700
taactggcga actacttact ctagcttccc ggcaacaatt aatagactgg atggaggcgg   5760
ataaagttgc aggaccactt ctgcgctcgg cccttccggc tggctggttt attgctgata   5820
aatctggagc cggtgagcgt gggtctcgcg gtatcattgc agcactgggg ccagatggta   5880
agccctcccg tatcgtagtt atctacacga cggggagtca ggcaactatg gatgaacgaa   5940
atagacagat cgctgagata ggtgcctcac tgattaagca ttggtaactg tcagaccaag   6000
tttactcata tatactttag attgatttaa aacttcattt ttaatttaaa aggatctagg   6060
tgaagatcct ttttgataat ctcatgacca aaatccctta acgtgagttt cgttccact    6120 gagcgtcaga ccccgtagaa aagatcaaag gatcttcttg agatcctttt tttctgcgcg   6180
taatctgctg cttgcaaaca aaaaaaccac cgctaccagc ggtggtttgt ttgccggatc   6240
aagagctacc aactcttttt ccgaaggtaa ctggcttcag cagagcgcag ataccaaata   6300
ctgttcttct agtgtagccg tagttaggcc accacttcaa gaactctgta gcaccgccta   6360
catacctcgc tctgctaatc ctgttaccag tggctgctgc cagtggcgat aagtcgtgtc   6420
ttaccgggtt ggactcaaga cgatagttac cggataaggc gcagcggtcg ggctgaacgg   6480
ggggttcgtg cacacagccc agcttggagc gaacgaccta caccgaactg agatacctac   6540
agcgtgagct atgagaaagc gccacgcttc ccgaagggag aaaggcggac aggtatccgg   6600
taagcggcag ggtcggaaca ggagagcgca cgagggagct tccaggggga aacgcctggt   6660
atctttatag tcctgtcggg tttcgccacc tctgacttga gcgtcgattt ttgtgatgct   6720
cgtcaggggg gcggagccta tggaaaaacg ccagcaacgc ggccttttta cggttcctgg   6780
ccttttgctg gccttttgct cacatgttct ttcctgcgtt atcccctgat tctgtggata   6840
accgtattac cgcctttgag tgagctgata ccgctcgccg cagccgaacg accgagcgca   6900
gcgagtcagt gagcgaggaa gcggaagagc gcccaatacg caaaccgcct ctccccgcgc   6960
```

-continued

```
gttggccgat tcattaatgc agctggcacg acaggtttcc cgactggaaa gcgggcagtg    7020
agcgcaacgc aattaatgtg agttagctca ctcattaggc acccaggct ttacacttta     7080 tgcttccggc tcgtatgttg tgtggaattg tgagcggata caatttcac acaggaaaca     7140 gctatgacca tgattacgcc aagctctagc tagaggtcga gtccctcccc agcaggcaga    7200
agtatgcaaa gcatgcatct caattagtca gcaaccatag tccgcccct aactccgccc     7260 atcccgcccc taactccgcc cagttccgcc cattctccgc cccatggctg actaattttt    7320
tttatttatg cagaggccga ggccgcctcg gcctctgagc tattccagaa gtagtgagga    7380
ggcttttttg gaggcctagg cttttgcaaa aagctttgca agatggata aagttttaaa     7440 cagagaggaa tctttgcagc taatggacct tctaggtctt gaaagg                   7486
```

<210> SEQ ID NO 13
<211> LENGTH: 8162
<212> TYPE: DNA
<213> ORGANISM: Artificial Sequence
<220> FEATURE:
<223> OTHER INFORMATION: Synthetic construct: pJP170 ; pHybE-hCg1,z,a V1

<400> SEQUENCE: 13

```
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg ccttttcc gagggtgggg gagaaccgta       180
tataagtgca gtagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc cttcgcctc gtgcttgagt     420 tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540
ttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc     720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg gcggtgag tcacccacac aaaggaaaag      900
ggcctttccg tcctcagccg tcgcttcatg tgactccacg gagtaccggg cgccgtccag    960
gcacctcgat tagttctcga gcttttggag tacgtcgtct ttaggttggg gggaggggtt    1020
ttatgcgatg agtttccccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gtttttttct tccatttcag gtgtcgtgag gaattctcta    1200
gagatccctc gacctcgagc atttaaatgc ccggcgccca ccatggagtt tgggctgagc    1260 tggcttttc ttgtcgcgat tttaaaaggt gtccagtgcg catggtatgc gaaagggat      1320 gctgaaattg agaacgaaaa gctgcgccgg gaggttaag aactgcggca ggccagcgag     1380
gcagatctcc agccaggaac tattgagtac gaacgccatc gacttacgcg tgcgcaggcc    1440
gacgcacagg aactgaagaa tgccagagac tccgctgaag tggtggaaac cgcattctgt    1500
actttcgtgc tgtcgcggat cgcaggtgaa attgccagta ttctcgacgg gctccccctg    1560
```

```
tcggtgcagc ggcgtttcc ggaactggaa aaccgacatg ttgatttcct gaaacgggat    1620
atcatcaaag ccatgaacaa agcagccgcg ctggatgaac tgataccggg gttgctgagt    1680
gaatatatcg aacagtcagg ttaacaggct gcggcatttt gtccgcgccg ggcttcgctc    1740
actgttcagg ccggagccac agaccgccgt tgaatgggcg gatgctaatt actatctccc    1800
gaaagaatcc gcataccagg aagggcgctg gaaacactg ccctttcagc gggccatcat    1860
gaatgcgatg ggcagcgact acatccgtga ggtgaatgtg gtgaagtctg cccgtgtcgg    1920
ttattccaaa atgctgctgg gtgtttatgc ctactttata gagcataagc agcgcaacac    1980
ccttatctgg ttgccgacgg atggtgatgc cgagaacttt atgaaaaccc acgttgagcc    2040
gactattcgt gatattccgt cgctgctggc gctggccccg tggtatggca aaaagcaccg    2100
ggataacacg ctcaccatga agcgtttcac taatgggcgt ggcttctggt gcctgggcgg    2160
taaagcggca aaaaactacc gtgaaaagtc ggtggatgtg gcgggttatg atgaacttgc    2220
tgcttttgat gatgatattg aacaggaagg ctctccgacg ttcctgggtg acaagcgcgt    2280
cgaccaaggg cccatcggtc ttcccctgg cacctcctc caagagcacc tctgggggca    2340
cagcggccct gggctgcctg gtcaaggact acttccccga accggtgacg gtgtcgtgga    2400
actcaggcgc cctgaccagc ggcgtgcaca ccttcccggc tgtcctacag tcctcaggac    2460
tctactccct cagcagcgtg gtgaccgtgc cctccagcag cttgggcacc cagacctaca    2520
tctgcaacgt gaatcacaag cccagcaaca ccaaggtgga caagaaagtt gagcccaaat    2580
cttgtgacaa aactcacaca tgcccaccgt gcccagcacc tgaactcctg ggggaccgt    2640 cagtcttcct cttccccca aaacccaagg acaccctcat gatctcccgg acccctgagg    2700
tcacatgcgt ggtggtggac gtgagccacg aagaccctga ggtcaagttc aactggtacg    2760
tggacggcgt ggaggtgcat aatgccaaga caaagccgcg ggaggagcag tacaacagca    2820
cgtaccgtgt ggtcagcgtc ctcaccgtcc tgcaccagga ctggctgaat ggcaaggagt    2880
acaagtgcaa ggtctccaac aaagccctcc cagcccccat cgagaaaacc atctccaaag    2940
ccaaagggca gccccgagaa ccacaggtgt acaccctgcc cccatcccgg gatgagctga    3000
ccaagaacca ggtcagcctg acctgcctgg tcaaaggctt ctatcccagc gacatcgccg    3060
tggagtggga gagcaatggg cagccggaga caaactacaa gaccacgcct cccgtgctgg    3120
actccgacgg ctccttcttc ctctacagca agctcaccgt ggacaagagc aggtggcagc    3180
aggggaacgt cttctcatgc tccgtgatgc atgaggctct gcacaaccac tacacgcaga    3240
agagcctctc cctgtctccg ggtaaatgag cggccgctcg aggccggcaa ggccggatcc    3300
cccgacctcg acctctggct aataaaggaa atttattttc attgcaatag tgtgttggaa    3360
ttttttgtgt ctctcactcg gaaggacata tgggagggca aatcatttgg tcgagatccc    3420
tcggagatct ctagctagag gatcgatccc cgccccggac gaactaaacc tgactacgac    3480
atctctgccc cttcttcgcg gggcagtgca tgtaatccct tcagttggtt ggtacaactt    3540
gccaactggg ccctgttcca catgtgacac ggggggggac caaacacaaa ggggttctct    3600
gactgtagtt gacatcctta taatggatg tgcacatttg ccaacactga gtggctttca    3660
tcctggagca gactttgcag tctgtggact gcaacacaac attgccttta tgtgtaactc    3720
ttggctgaag ctcttacacc aatgctgggg gacatgtacc tcccaggggc ccaggaagac    3780
tacgggaggc tacaccaacg tcaatcagag gggcctgtgt agctaccgat aagcggaccc    3840
tcaagagggc attagcaata gtgttttataa ggccccttg ttaaccctaa acgggtagca    3900
tatgcttccc gggtagtagt atatactatc cagactaacc ctaattcaat agcatatgtt    3960
```

```
acccaacggg aagcatatgc tatcgaatta gggttagtaa aagggtccta aggaacagcg   4020
atatctccca ccccatgagc tgtcacggtt ttatttacat ggggtcagga ttccacgagg   4080
gtagtgaacc attttagtca caagggcagt ggctgaagat caaggagcgg gcagtgaact   4140
ctcctgaatc ttcgcctgct tcttcattct ccttcgttta gctaatagaa taactgctga   4200
gttgtgaaca gtaaggtgta tgtgaggtgc tcgaaaacaa ggtttcaggt gacgccccca   4260
gaataaaatt tggacggggg gttcagtggt ggcattgtgc tatgacacca atataaccct   4320
cacaaacccc ttgggcaata atactagtg taggaatgaa acattctgaa tatctttaac    4380
aatagaaatc catgggtgg ggacaagccg taaagactgg atgtccatct cacacgaatt    4440
tatggctatg ggcaacacat aatcctagtg caatatgata ctggggttat taagatgtgt   4500
cccaggcagg gaccaagaca ggtgaaccat gttgttacac tctatttgta acaaggggaa   4560
agagagtgga cgccgacagc agcggactcc actggttgtc tctaacaccc ccgaaaatta   4620 aacgggctc cacgccaatg gggcccataa acaaagacaa gtggccactc ttttttttga    4680
aattgtggag tgggggcacg cgtcagcccc cacacgccgc cctgcggttt tggactgtaa   4740
aataagggtg taataacttg gctgattgta accccgctaa ccactgcggt caaaccactt   4800
gcccacaaaa ccactaatgg caccccgggg aatacctgca taagtaggtg ggcgggccaa   4860
gataggggcg cgattgctgc gatctggagg acaaattaca cacacttgcg cctgagcgcc   4920
aagcacaggg ttgttggtcc tcatattcac gaggtcgctg agagcacggt gggctaatgt   4980
tgccatgggt agcatatact acccaaatat ctggatagca tatgctatcc taatctatat   5040
ctgggtagca taggctatcc taatctatat ctgggtagca tatgctatcc taatctatat   5100
ctgggtagta tatgctatcc taatttatat ctgggtagca taggctatcc taatctatat   5160
ctgggtagca tatgctatcc taatctatat ctgggtagta tatgctatcc taatctgtat   5220
ccgggtagca tatgctatcc taatagagat tagggtagta tatgctatcc taatttatat   5280
ctgggtagca tatactaccc aaatatctgg atagcatatg ctatcctaat ctatatctgg   5340
gtagcatatg ctatcctaat ctatatctgg gtagcatagg ctatcctaat ctatatctgg   5400
gtagcatatg ctatcctaat ctatatctgg gtagtatatg ctatcctaat ttatatctgg   5460
gtagcatagg ctatcctaat ctatatctgg gtagcatatg ctatcctaat ctatatctgg   5520
gtagtatatg ctatcctaat ctgtatccgg gtagcatatg ctatcctcat gataagctgt   5580
caaacatgag aattttcttg aagacgaaag ggcctcgtga tacgcctatt tttataggtt   5640
aatgtcatga taataatggt ttcttagacg tcaggtggca cttttcgggg aaatgtgcgc   5700
ggaaccccta tttgtttatt tttctaaata cattcaaata tgtatccgct catgagacaa   5760
taaccctgat aaatgcttca ataatattga aaaggaaga gtatgagtat tcaacatttc    5820
cgtgtcgccc ttattccctt ttttgcggca ttttgccttc ctgttttgc tcacccagaa    5880 acgctggtga agtaaaaga tgctgaagat cagttgggtg cacgagtggg ttacatcgaa    5940
ctggatctca acagcggtaa gatccttgag agttttcgcc ccgaagaacg ttttccaatg   6000
atgagcactt ttaaagttct gctatgtggc gcggtattat cccgtgttga cgccgggcaa   6060
gagcaactcg gtcgccgcat acactattct cagaatgact tggttgagta ctcaccagtc   6120
acagaaaagc atcttacgga tggcatgaca gtaagagaat tatgcagtgc tgccataacc   6180
atgagtgata acactgcggc caacttactt ctgacaacga tcggaggacc gaaggagcta   6240
accgcttttt tgcacaacat ggggatcat gtaactcgcc ttgatcgttg ggaaccggag    6300
ctgaatgaag ccataccaaa cgacgagcgt gacaccacga tgcctgcagc aatggcaaca   6360
```

```
acgttgcgca aactattaac tggcgaacta cttactctag cttcccggca acaattaata      6420
gactggatgg aggcggataa agttgcagga ccacttctgc gctcggccct tccggctggc      6480
tggtttattg ctgataaatc tggagccggt gagcgtgggt ctcgcggtat cattgcagca      6540
ctggggccag atggtaagcc ctcccgtatc gtagttatct acacgacggg gagtcaggca      6600
actatggatg aacgaaatag acagatcgct gagataggtg cctcactgat taagcattgg      6660
taactgtcag accaagttta ctcatatata ctttagattg atttaaaact tcatttttaa      6720
tttaaaagga tctaggtgaa gatcctttt gataatctca tgaccaaaat cccttaacgt       6780
gagttttcgt tccactgagc gtcagacccc gtagaaaaga tcaaaggatc ttcttgagat      6840
cctttttttc tgcgcgtaat ctgctgcttg caaacaaaaa aaccaccgct accagcggtg      6900
gtttgtttgc cggatcaaga gctaccaact cttttttccga aggtaactgg cttcagcaga      6960
gcgcagatac caaatactgt tcttctagtg tagccgtagt taggccacca cttcaagaac      7020
tctgtagcac cgcctacata cctcgctctg ctaatcctgt taccagtggc tgctgccagt     7080
ggcgataagt cgtgtcttac cgggttggac tcaagacgat agttaccgga taaggcgcag      7140
cggtcgggct gaacggggg ttcgtgcaca cagcccagct tggagcgaac gacctacacc       7200
gaactgagat acctacagcg tgagctatga gaaagcgcca cgcttcccga agggagaaag      7260
gcggacaggt atccggtaag cggcagggtc ggaacaggag agcgcacgag ggagcttcca      7320
gggggaaacg cctggtatct ttatagtcct gtcgggttc gccacctctg acttgagcgt       7380
cgatttttgt gatgctcgtc aggggggcgg agcctatgga aaaacgccag caacgcggcc      7440 ttttacggt tcctggcctt ttgctggcct tttgctcaca tgttctttcc tgcgttatcc       7500
cctgattctg tggataaccg tattaccgcc tttgagtgag ctgataccgc tcgccgcagc      7560
cgaacgaccg agcgcagcga gtcagtgagc gaggaagcgg aagagcgccc aatacgcaaa      7620
ccgcctctcc ccgcgcgttg gccgattcat taatgcagct ggcacgacag gtttcccgac      7680
tggaaagcgg gcagtgagcg caacgcaatt aatgtgagtt agctcactca ttaggcaccc      7740
caggctttac actttatgct tccggctcgt atgttgtgtg gaattgtgag cggataacaa     7800
tttcacacag gaaacagcta tgaccatgat tacgccaagc tctagctaga ggtcgagtcc      7860
ctccccagca ggcagaagta tgcaaagcat gcatctcaat tagtcagcaa ccatagtccc      7920
gcccctaact ccgcccatcc cgcccctaac tccgcccagt tccgcccatt ctccgcccca     7980
tggctgacta attttttta tttatgcaga ggccgaggcc gcctcggcct ctgagctatt       8040
ccagaagtag tgaggaggct tttttggagg cctaggcttt tgcaaaaagc tttgcaaaga      8100
tggataaagt tttaaacaga gaggaatctt tgcagctaat ggaccttcta ggtcttgaaa      8160
gg                                                                    8162

<210> SEQ ID NO 14
<211> LENGTH: 8162
<212> TYPE: DNA
<213> ORGANISM: Artificial Sequence
<220> FEATURE:
<223> OTHER INFORMATION: Synthetic construct: pJP182 ; pHybE-hCg1,z,a V2

<400> SEQUENCE: 14
agtgggaatt ggctccggtg cccgtcagtg ggcagagcgc acatcgccca cagtccccga        60
gaagttgggg ggaggggtcg gcaattgaac cggtgcctag agaaggtggc gcggggtaaa       120
ctgggaaagt gatgtcgtgt actggctccg ccttttttccc gagggtgggg gagaaccgta      180
tataagtgca gtagtcgccg tgaacgttct ttttcgcaac gggtttgccg ccagaacaca      240
```

```
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtgcacc  ttcgcgcctg    480
tctcgctgct ttcgataagt ctctagccat ttaaaatttt tgatgacctg ctgcgacgct    540
ttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag  tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggaggggtt   1020
ttatgcgatg gagtttcccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gttttttttct tccatttcag gtgtcgtgag gaattctcta   1200
gagatccctc gacctcgaga tccattgtgc ccgggcgcca ccatggagtt tgggctgagc   1260
tggctttttc ttgtcgcgat tttaaaaggt gtccagtgcg catggtatgc cgaaagggat   1320
gctgaaattg agaacgaaaa gctgcgccgg gaggttgaag aactgcggca ggccagcgag   1380
gcagatctcc agccaggaac tattgagtac gaacgccatc gacttacgcg tgcgcaggcc   1440
gacgcacagg aactgaagaa tgccagagac tccgctgaag tggtggaaac cgcattctgt   1500
actttcgtgt gtcgcggat  cgcaggtgaa attgccagta ttctcgacgg gctcccctg    1560
tcggtgcagc ggcgttttcc ggaactggaa aaccgacatg ttgatttcct gaaacgggat   1620
atcatcaaag ccatgaacaa agcagccgcg ctggatgaac tgataccggg gttgctgagt   1680
gaatatatcg aacagtcagg ttaacaggct gcggcatttt gtccgcgccg ggcttcgctc   1740
actgttcagg ccggagccac agaccgccgt tgaatgggcg gatgctaatt actatctccc   1800
gaaagaatcc gcataccagg aagggcgctg ggaaacactg ccctttcagc gggccatcat   1860
gaatgcgatg ggcagcgact acatccgtga ggtgaatgtg gtgaagtctg cccgtgtcgg   1920
ttattccaaa atgctgctgg gtgtttatgc ctactttata gagcataagc agcgcaacac   1980
ccttatctgg ttgccgacgg atggtgatgc cgagaacttt atgaaaaccc acgttgagcc   2040
gactattcgt gatattccgt cgctgctggc gctggccccg tggtatggca aaaagcaccg   2100
ggataacacg ctcaccatga agcgtttcac taatgggcgt ggcttctggt gcctgggcgg   2160
taaagcggca aaaaactacc gtgaaaagtc ggtggatgtg gcgggttatg atgaacttgc   2220
tgcttttgat gatgatattg aacaggaagg ctcctccgacg ttcctggggtg acaagcgcgt   2280
cgaccaaggg cccatcggtc ttccccctgg caccctcctc caagagcacc tctggggca    2340
cagcggccct gggctgcctg gtcaaggact acttccccga accggtgacg gtgtcgtgga   2400
actcaggcgc cctgaccagc ggcgtgcaca cctttccggc tgtcctacag tcctcaggac   2460
tctactccct cagcagcgtg gtgaccgtgc cctccagcag cttgggcacc cagacctaca   2520
tctgcaacgt gaatcacaag cccagcaaca ccaaggtgga caagaaagtt gagcccaaat   2580
cttgtgacaa aactcacaca tgcccaccgt gcccagcacc tgaactcctg gggggaccgt   2640
```

-continued

```
cagtcttcct cttcccccca aaacccaagg acaccctcat gatctcccgg accccctgagg   2700 tcacatgcgt ggtggtggac gtgagccacg aagaccctga ggtcaagttc aactggtacg   2760
tggacggcgt ggaggtgcat aatgccaaga caaagccgcg ggaggagcag tacaacagca   2820
cgtaccgtgt ggtcagcgtc ctcaccgtcc tgcaccagga ctggctgaat ggcaaggagt   2880
acaagtgcaa ggtctccaac aaagccctcc cagcccccat cgagaaaacc atctccaaag   2940
ccaaagggca gccccgagaa ccacaggtgt acaccctgcc cccatcccgg gatgagctga   3000
ccaagaacca ggtcagcctg acctgcctgg tcaaaggctt ctatcccagc gacatcgccg   3060
tggagtggga gagcaatggg cagccggaga acaactacaa gaccacgcct cccgtgctgg   3120
actccgacgg ctccttcttc ctctacagca agctcaccgt ggacaagagc aggtggcagc   3180
aggggaacgt cttctcatgc tccgtgatgc atgaggctct gcacaaccac tacacgcaga   3240
agagcctctc cctgtctccg ggtaaatgag cggccgctcg aggccggcaa ggccggatcc   3300
cccgacctcg acctctggct aataaaggaa atttattttc attgcaatag tgtgttggaa   3360
ttttttgtgt ctctcactcg gaaggacata tgggagggca aatcatttgg tcgagatccc   3420
tcggagatct ctagctagag gatcgatccc cgccccggac gaactaaacc tgactacgac   3480
atctctgccc cttcttcgcg gggcagtgca tgtaatccct tcagttggtt ggtacaactt   3540
gccaactggg ccctgttcca catgtgacac gggggggac caaacacaaa ggggttctct   3600
gactgtagtt gacatcctta taaatggatg tgcacatttg ccaacactga gtggctttca   3660
tcctggagca gactttgcag tctgtggact gcaacacaac attgccttta tgtgtaactc   3720
ttggctgaag ctcttacacc aatgctgggg gacatgtacc tcccagggc ccaggaagac   3780 tacgggaggc tacaccaacg tcaatcagag gggcctgtgt agctaccgat aagcggaccc   3840
tcaagagggc attagcaata gtgtttataa ggcccccttg ttaaccctaa acgggtagca   3900
tatgcttccc gggtagtagt atatactatc cagactaacc ctaattcaat agcatatgtt   3960
acccaacggg aagcatatgc tatcgaatta gggttagtaa aagggtccta aggaacagcg   4020
atatctccca ccccatgagc tgtcacggtt ttatttacat ggggtcagga ttccacgagg   4080
gtagtgaacc attttagtca aagggcagt ggctgaagat caaggagcgg gcagtgaact   4140
ctcctgaatc ttcgcctgct tcttcattct ccttcgttta gctaatagaa taactgctga   4200
gttgtgaaca gtaaggtgta tgtgaggtgc tcgaaaacaa ggtttcaggt gacgccccca   4260
gaataaaatt tggacggggg gttcagtggt ggcattgtgc tatgacacca atataaccct   4320
cacaaacccc ttgggcaata aatactagtg taggaatgaa acattctgaa tatctttaac   4380
aatagaaatc catggggtgg ggacaagccg taaagactgg atgtccatct cacacgaatt   4440
tatggctatg ggcaacacat aatcctagtg caatatgata ctgggttat taagatgtgt   4500 cccaggcagg gaccaagaca ggtgaaccat gttgttacac tctatttgta acaaggggaa   4560
agagagtgga cgccgacagc agcggactcc actggttgtc tctaacaccc ccgaaaatta   4620 aacgggctc cacgccaatg gggcccataa acaaagacaa gtggccactc ttttttttga   4680
aattgtggag tgggggcacg cgtcagcccc cacacgccgc cctgcggttt tggactgtaa   4740 ataagggtg taataacttg gctgattgta acccgctaa ccactgcggt caaaccactt   4800
gcccacaaaa ccactaatgg caccccgggg aatacctgca taagtaggtg ggcgggccaa   4860
gataggggcg cgattgctgc gatctggagg acaaattaca cacacttgcg cctgagcgcc   4920
aagcacaggt tgttggtcc tcatattcac gaggtcgctg agagcacggt gggctaatgt   4980
tgccatgggt agcatatact acccaaatat ctggatagca tatgctatcc taatctatat   5040
```

```
ctgggtagca taggctatcc taatctatat ctgggtagca tatgctatcc taatctatat   5100
ctgggtagta tatgctatcc taatttatat ctgggtagca taggctatcc taatctatat   5160
ctgggtagca tatgctatcc taatctatat ctgggtagta tatgctatcc taatctgtat   5220
ccgggtagca tatgctatcc taatagagat tagggtagta tatgctatcc taatttatat   5280
ctgggtagca tatactaccc aaatatctgg atagcatatg ctatcctaat ctatatctgg   5340
gtagcatatg ctatcctaat ctatatctgg gtagcatagg ctatcctaat ctatatctgg   5400
gtagcatatg ctatcctaat ctatatctgg gtagtatatg ctatcctaat ttatatctgg   5460
gtagcatagg ctatcctaat ctatatctgg gtagcatatg ctatcctaat ctatatctgg   5520
gtagtatatg ctatcctaat ctgtatccgg gtagcatatg ctatcctcat gataagctgt   5580
caaacatgag aattttcttg aagacgaaag ggcctcgtga tacgcctatt tttataggtt   5640
aatgtcatga taataatggt ttcttagacg tcaggtggca cttttcgggg aaatgtgcgc   5700
ggaaccccta tttgtttatt tttctaaata cattcaaata tgtatccgct catgagacaa   5760
taaccctgat aaatgcttca ataatattga aaaggaaga gtatgagtat tcaacatttc   5820
cgtgtcgccc ttattccctt ttttgcggca ttttgccttc ctgttttgc tcacccagaa   5880
acgctggtga agtaaaaga tgctgaagat cagttgggtg cacgagtggg ttacatcgaa   5940
ctggatctca acagcggtaa gatccttgag agttttcgcc ccgaagaacg ttttccaatg   6000
atgagcactt ttaaagttct gctatgtggc gcggtattat cccgtgttga cgccgggcaa   6060
gagcaactcg gtcgccgcat acactattct cagaatgact tggttgagta ctcaccagtc   6120
acagaaaagc atcttacgga tggcatgaca gtaagagaat tatgcagtgc tgccataacc   6180
atgagtgata acactgcggc caacttactt ctgacaacga tcggaggacc gaaggagcta   6240
accgcttttt tgcacaacat gggggatcat gtaactcgcc ttgatcgttg ggaaccggag   6300
ctgaatgaag ccataccaaa cgacgagcgt gacaccacga tgcctgcagc aatggcaaca   6360
acgttgcgca aactattaac tggcgaacta cttactctag cttcccggca acaattaata   6420
gactggatgg aggcggataa agttgcagga ccacttctgc gctcggccct tccggctggc   6480
tggtttattg ctgataaatc tggagccggt gagcgtgggt ctcgcggtat cattgcagca   6540
ctggggccag atggtaagcc ctcccgtatc gtagttatct acacgacggg gagtcaggca   6600
actatggatg aacgaaatag acagatcgct gagataggtg cctcactgat taagcattgg   6660
taactgtcag accaagttta ctcatatata ctttagattg atttaaaact tcatttttaa   6720
tttaaaagga tctaggtgaa gatcctttt gataatctca tgaccaaaat cccttaacgt   6780
gagttttcgt tccactgagc gtcagacccc gtagaaaaga tcaaaggatc ttcttgagat   6840
cctttttttc tgcgcgtaat ctgctgcttg caaacaaaaa aaccaccgct accagcggtg   6900
gtttgtttgc cggatcaaga gctaccaact cttttccga aggtaactgg cttcagcaga   6960
gcgcagatac caaatactgt tcttctagtg tagccgtagt taggccacca cttcaagaac   7020
tctgtagcac cgcctacata cctcgctctg ctaatcctgt taccagtggc tgctgccagt   7080
ggcgataagt cgtgtcttac cgggttggac tcaagacgat agttaccgga taaggcgcag   7140
cggtcgggct gaacggggg ttcgtgcaca cagcccagct tggagcgaac gacctacacc   7200
gaactgagat acctacagcg tgagctatga gaaagcgcca cgcttcccga agggagaaag   7260
gcggacaggt atccggtaag cggcagggtc ggaacaggag agcgcacgag ggagcttcca   7320
gggggaaacg cctggtatct ttatagtcct gtcgggtttc gccacctctg acttgagcgt   7380
cgatttttgt gatgctcgtc aggggggcgg agcctatgga aaaacgccag caacgcggcc   7440
```

-continued

| | |
|---|---|
| ttttttacggt tcctggcctt ttgctggcct tttgctcaca tgttctttcc tgcgttatcc | 7500 |
| cctgattctg tggataaccg tattaccgcc tttgagtgag ctgataccgc tcgccgcagc | 7560 |
| cgaacgaccg agcgcagcga gtcagtgagc gaggaagcgg aagagcgccc aatacgcaaa | 7620 |
| ccgcctctcc ccgcgcgttg gccgattcat taatgcagct ggcacgacag gtttcccgac | 7680 |
| tggaaagcgg gcagtgagcg caacgcaatt aatgtgagtt agctcactca ttaggcaccc | 7740 |
| caggctttac actttatgct tccggctcgt atgttgtgtg gaattgtgag cggataacaa | 7800 |
| tttcacacag gaaacagcta tgaccatgat tacgccaagc tctagctaga ggtcgagtcc | 7860 |
| ctccccagca ggcagaagta tgcaaagcat gcatctcaat tagtcagcaa ccatagtccc | 7920 |
| gcccctaact ccgcccatcc cgcccctaac tccgcccagt tccgcccatt ctccgcccca | 7980 |
| tggctgacta attttttta tttatgcaga ggccgaggcc gcctcggcct ctgagctatt | 8040 |
| ccagaagtag tgaggaggct ttttggagg cctaggcttt tgcaaaaagc tttgcaaaga | 8100 |
| tggataaagt tttaaacaga gaggaatctt tgcagctaat ggaccttcta ggtcttgaaa | 8160 |
| gg | 8162 |

<210> SEQ ID NO 15
<211> LENGTH: 8162
<212> TYPE: DNA
<213> ORGANISM: Artificial Sequence
<220> FEATURE:
<223> OTHER INFORMATION: Synthetic construct: pJP171 ;
      pHybE-hCg1,z,non-a V1

<400> SEQUENCE: 15

| | |
|---|---|
| agtgggaatt ggctccggtg cccgtcagtg ggcagagcgc acatcgccca cagtccccga | 60 |
| gaagttgggg ggaggggtcg gcaattgaac cggtgcctag agaaggtggc gcggggtaaa | 120 |
| ctggaaagt gatgtcgtgt actggctccg ccttttttccc gagggtgggg gagaaccgta | 180 |
| tataagtgca gtagtcgccg tgaacgttct ttttcgcaac gggtttgccg ccagaacaca | 240 |
| ggtaagtgcc gtgtgtggtt cccgcgggcc tggcctcttt acgggttatg cccttgcgt | 300 |
| gccttgaatt acttccacct ggctgcagta cgtgattctt gatcccgagc ttcgggttgg | 360 |
| aagtgggtgg gagagttcga ggccttgcgc ttaaggagcc ccttcgcctc gtgcttgagt | 420 |
| tgaggcctgg cctgggcgct ggggccgccg cgtgcgaatc tggtggcacc ttcgcgcctg | 480 |
| tctcgctgct ttcgataagt ctctagccat ttaaaatttt tgatgacctg ctgcgacgct | 540 |
| ttttttctgg caagatagtc ttgtaaatgc gggccaagat ctgcacactg gtatttcggt | 600 |
| ttttggggcc gcgggcggcg acggggcccg tgcgtcccag cgcacatgtt cggcgaggcg | 660 |
| gggcctgcga gcgcggccac cgagaatcgg acggggtag tctcaagctg gccggcctgc | 720 |
| tctggtgcct ggcctcgcgc cgccgtgtat cgccccgccc tgggcggcaa ggctggcccg | 780 |
| gtcggcacca gttgcgtgag cggaaagatg gccgcttccc ggccctgctg cagggagctc | 840 |
| aaaatggagg acgcggcgct cgggagagcg ggcgggtgag tcacccacac aaaggaaaag | 900 |
| ggcctttccg tcctcagccg tcgcttcatg tgactccacg gagtaccggg cgccgtccag | 960 |
| gcacctcgat tagttctcga gcttttggag tacgtcgtct ttaggttggg gggagggggtt | 1020 |
| ttatgcgatg gagtttcccc acactgagtg ggtggagact gaagttaggc cagcttggca | 1080 |
| cttgatgtaa ttctccttgg aatttgccct ttttgagttt ggatcttggt tcattctcaa | 1140 |
| gcctcagaca gtggttcaaa gtttttttct tccattttcag gtgtcgtgag gaattctcta | 1200 |
| gagatccctc gacctcgagc atttaaatgc ccgggcgcca ccatggagtt tgggctgagc | 1260 |

```
tggcttttc   ttgtcgcgat   tttaaaaggt   gtccagtgcg   catggtatgc   cgaaagggat    1320
gctgaaattg   agaacgaaaa   gctgcgccgg   gaggttgaag   aactgcggca   ggccagcgag    1380
gcagatctcc   agccaggaac   tattgagtac   gaacgccatc   gacttacgcg   tgcgcaggcc    1440
gacgcacagg   aactgaagaa   tgccagagac   tccgctgaag   tggtggaaac   cgcattctgt    1500
actttcgtgc   tgtcgcggat   cgcaggtgaa   attgccagta   ttctcgacgg   gctcccctg     1560 tcggtgcagc   ggcgttttcc   ggaactggaa   accgacatg    ttgatttcct   gaaacgggat    1620
atcatcaaag   ccatgaacaa   agcagccgcg   ctggatgaac   tgataccggg   gttgctgagt    1680
gaatatatcg   aacagtcagg   ttaacaggct   gcggcatttt   gtccgcgccg   ggcttcgctc    1740
actgttcagg   ccggagccac   agaccgccgt   tgaatgggcg   gatgctaatt   actatctccc    1800
gaaagaatcc   gcataccagg   aagggcgctg   ggaaacactg   ccctttcagc   gggccatcat    1860
gaatgcgatg   ggcagcgact   acatccgtga   ggtgaatgtg   gtgaagtctg   cccgtgtcgg    1920
ttattccaaa   atgctgctgg   gtgtttatgc   ctactttata   gagcataagc   agcgcaacac    1980
ccttatctgg   ttgccgacgg   atggtgatgc   cgagaacttt   atgaaaaccc   acgttgagcc    2040
gactattcgt   gatattccgt   cgctgctggc   gctggccccg   tggtatggca   aaaagcaccg    2100
ggataacacg   ctcaccatga   agcgtttcac   taatgggcgt   ggcttctggt   gcctgggcgg    2160
taaagcggca   aaaactacc    gtgaaaagtc   ggtggatgtg   gcgggttatg   atgaacttgc    2220
tgcttttgat   gatgatattg   aacaggaagg   ctctccgacg   ttcctgggtg   acaagcgcgt    2280
cgaccaaggg   cccatcggtc   ttccccctgg   caccctcctc   caagagcacc   tctgggggca    2340
cagcggccct   gggctgcctg   gtcaaggact   acttccccga   accggtgacg   gtgtcgtgga    2400
actcaggcgc   cctgaccagc   ggcgtgcaca   ccttcccggc   tgtcctacag   tcctcaggac    2460
tctactccct   cagcagcgtg   gtgaccgtgc   cctccagcag   cttgggcacc   cagacctaca    2520
tctgcaacgt   gaatcacaag   cccagcaaca   ccaaggtgga   caagaaagtt   gagcccaaat    2580
cttgtgacaa   aactcacaca   tgcccaccgt   gcccagcacc   tgaactcctg   ggggaccgt     2640 cagtcttcct   cttcccccca   aaacccaagg   acaccctcat   gatctcccgg   acccctgagg    2700
tcacatgcgt   ggtggtggac   gtgagccacg   aagaccctga   ggtcaagttc   aactggtacg    2760
tggacggcgt   ggaggtgcat   aatgccaaga   caaagccgcg   ggaggagcag   tacaacagca    2820
cgtaccgtgt   ggtcagcgtc   ctcaccgtcc   tgcaccagga   ctggctgaat   ggcaaggagt    2880
acaagtgcaa   ggtctccaac   aaagccctcc   cagcccccat   cgagaaaacc   atctccaaag    2940
ccaaagggca   gccccgagaa   ccacaggtgt   acaccctgcc   cccatcccgc   gaggagatga    3000
ccaagaacca   ggtcagcctg   acctgcctgg   tcaaaggctt   ctatcccagc   gacatcgccg    3060
tggagtggga   gagcaatggg   cagccggaga   acaactacaa   gaccacgcct   cccgtgctgg    3120
actccgacgg   ctccttcttc   ctctacagca   agctcaccgt   ggacaagagc   aggtggcagc    3180
aggggaacgt   cttctcatgc   tccgtgatgc   atgaggctct   gcacaaccac   tacacgcaga    3240
agagcctctc   cctgtctccg   ggtaaatgag   cggccgctcg   aggccggcaa   ggccggatcc    3300
cccgacctcg   acctctggct   aataaaggaa   atttattttc   attgcaatag   tgtgttggaa    3360 tttttttgtgt  ctctcactcg   gaaggacata   tgggagggca   aatcatttgg   tcgagatccc    3420
tcggagatct   ctagctagag   gatcgatccc   cgccccggac   gaactaaacc   tgactacgac    3480
atctctgccc   cttcttcgcg   gggcagtgca   tgtaatccct   tcagttggtt   ggtacaactt    3540
gccaactggg   ccctgttcca   catgtgacac   gggggggggac  caaacacaaa   ggggttctct    3600
gactgtagtt   gacatcctta   taaatggatg   tgcacatttg   ccaacactga   gtggctttca    3660
```

```
tcctggagca gactttgcag tctgtggact gcaacacaac attgccttta tgtgtaactc    3720
ttggctgaag ctcttacacc aatgctgggg gacatgtacc tcccaggggc ccaggaagac    3780
tacgggaggc tacaccaacg tcaatcagag gggcctgtgt agctaccgat aagcggaccc    3840
tcaagagggc attagcaata gtgtttataa ggccccttg ttaaccctaa acgggtagca     3900
tatgcttccc gggtagtagt atatactatc cagactaacc ctaattcaat agcatatgtt    3960
acccaacggg aagcatatgc tatcgaatta gggttagtaa aagggtccta aggaacagcg    4020
atatctccca ccccatgagc tgtcacggtt ttatttacat ggggtcagga ttccacgagg    4080
gtagtgaacc attttagtca caagggcagt ggctgaagat caaggagcgg gcagtgaact    4140
ctcctgaatc ttcgcctgct tcttcattct ccttcgttta gctaatagaa taactgctga    4200
gttgtgaaca gtaaggtgta tgtgaggtgc tcgaaaacaa ggtttcaggt gacgcccca     4260
gaataaaatt tggacggggg gttcagtggt ggcattgtgc tatgacacca atataaccct    4320
cacaaacccc ttgggcaata atactagtg taggaatgaa acattctgaa tatctttaac     4380
aatagaaatc catggggtgg ggacaagccg taaagactgg atgtccatct cacacgaatt    4440
tatggctatg ggcaacacat aatcctagtg caatatgata ctggggttat taagatgtgt    4500
cccaggcagg gaccaagaca ggtgaaccat gttgttacac tctatttgta acaaggggaa    4560
agagagtgga cgccgacagc agcggactcc actggttgtc tctaacaccc ccgaaaatta    4620
aacgggctc cacgccaatg gggcccataa acaaagacaa gtggccactc ttttttttga     4680
aattgtggag tgggggcacg cgtcagcccc cacacgccgc cctgcggttt tggactgtaa    4740
aataaggg tg taataacttg gctgattgta accccgctaa ccactgcggt caaaccactt    4800
gcccacaaaa ccactaatgg cacccctgggg aatacctgca taagtaggtg ggcgggccaa    4860
gataggggcg cgattgctgc gatctggagg acaaattaca cacacttgcg cctgagcgcc    4920
aagcacaggg ttgttggtcc tcatattcac gaggtcgctg agagcacggt gggctaatgt    4980
tgccatgggt agcatatact acccaaatat ctggatagca tatgctatcc taatctatat    5040
ctgggtagca taggctatcc taatctatat ctgggtagca tatgctatcc taatctatat    5100
ctgggtagta tatgctatcc taatttatat ctgggtagca taggctatcc taatctatat    5160
ctgggtagca tatgctatcc taatctatat ctgggtagta tatgctatcc taatctgtat    5220
ccgggtagca tatgctatcc taatagagat tagggtagta tatgctatcc taatttatat    5280
ctgggtagca tatactaccc aaatatctgg atagcatatg ctatcctaat ctatatctgg    5340
gtagcatatg ctatcctaat ctatatctgg gtagcatagg ctatcctaat ctatatctgg    5400
gtagcatatg ctatcctaat ctatatctgg gtagtatatg ctatcctaat ttatatctgg    5460
gtagcatagg ctatcctaat ctatatctgg gtagcatatg ctatcctaat ctatatctgg    5520
gtagtatatg ctatcctaat ctgtatccgg gtagcatatg ctatcctcat gataagctgt    5580
caaacatgag aattttcttg aagacgaaag ggcctcgtga tacgcctatt tttataggtt    5640
aatgtcatga taataatggt tcttagacg tcaggtggca cttttcgggg aaatgtgcgc     5700
ggaacccta tttgtttatt tttctaaata cattcaaata tgtatccgct catgagacaa     5760
taaccctgat aaatgcttca ataatattga aaaggaaga gtatgagtat caacatttc      5820
cgtgtcgccc ttattccctt ttttgcggca ttttgccttc ctgttttgc tcacccagaa     5880
acgctggtga aagtaaaaga tgctgaagat cagttgggtg cacgagtggg ttacatcgaa    5940
ctggatctca acagcggtaa gatccttgag agttttcgcc ccgaagaacg ttttccaatg    6000
atgagcactt ttaaagttct gctatgtggc gcggtattat cccgtgttga cgccgggcaa    6060
```

```
gagcaactcg gtcgccgcat acactattct cagaatgact tggttgagta ctcaccagtc    6120
acagaaaagc atcttacgga tggcatgaca gtaagagaat tatgcagtgc tgccataacc    6180
atgagtgata acactgcggc caacttactt ctgacaacga tcggaggacc gaaggagcta    6240
accgcttttt tgcacaacat gggggatcat gtaactcgcc ttgatcgttg ggaaccggag    6300
ctgaatgaag ccataccaaa cgacgagcgt gacaccacga tgcctgcagc aatggcaaca    6360
acgttgcgca aactattaac tggcgaacta cttactctag cttcccggca caattaata    6420 gactggatgg aggcggataa agttgcagga ccacttctgc gctcggccct tccggctggc    6480
tggtttattg ctgataaatc tggagccggt gagcgtgggt ctcgcggtat cattgcagca    6540
ctggggccag atggtaagcc ctcccgtatc gtagttatct acacgacggg gagtcaggca    6600
actatggatg aacgaaatag acagatcgct gagataggtg cctcactgat taagcattgg    6660
taactgtcag accaagttta ctcatatata ctttagattg atttaaaact tcatttttaa    6720
tttaaaagga tctaggtgaa gatcctttt gataatctca tgaccaaaat cccttaacgt    6780
gagttttcgt tccactgagc gtcagacccc gtagaaaaga tcaaaggatc ttcttgagat    6840 ccttttttc tgcgcgtaat ctgctgcttg caaacaaaaa aaccaccgct accagcggtg    6900
gtttgtttgc cggatcaaga gctaccaact cttttccga aggtaactgg cttcagcaga    6960
gcgcagatac caaatactgt tcttctagtg tagccgtagt taggccacca cttcaagaac    7020
tctgtagcac cgcctacata cctcgctctg ctaatcctgt taccagtggc tgctgccagt    7080
ggcgataagt cgtgtcttac cgggttggac tcaagacgat agttaccgga taaggcgcag    7140
cggtcgggct gaacggggg ttcgtgcaca cagcccagct tggagcgaac gacctacacc    7200
gaactgagat acctacagcg tgagctatga gaaagcgcca cgcttcccga agggagaaag    7260
gcggacaggt atccggtaag cggcagggtc ggaacaggag agcgcacgag ggagcttcca    7320
gggggaaacg cctggtatct ttatagtcct gtcgggtttc gccacctctg acttgagcgt    7380
cgatttttgt gatgctcgtc agggggggcgg agcctatgga aaaacgccag caacgcggcc    7440 ttttacggt tcctggcctt ttgctggcct tttgctcaca tgttctttcc tgcgttatcc    7500
cctgattctg tggataaccg tattaccgcc tttgagtgag ctgataccgc tcgccgcagc    7560
cgaacgaccg agcgcagcga gtcagtgagc gaggaagcgg aagagcgccc aatacgcaaa    7620
ccgcctctcc ccgcgcgttg gccgattcat taatgcagct ggcacgacag gtttcccgac    7680
tggaaagcgg gcagtgagcg caacgcaatt aatgtgagtt agctcactca ttaggcaccc    7740
caggctttac actttatgct tccggctcgt atgttgtgtg gaattgtgag cggataacaa    7800
tttcacacag gaaacagcta tgaccatgat tacgccaagc tctagctaga ggtcgagtcc    7860
ctccccagca ggcagaagta tgcaaagcat gcatctcaat tagtcagcaa ccatagtccc    7920
gcccctaact ccgcccatcc cgcccctaac tccgcccagt tccgcccatt ctccgcccca    7980
tggctgacta atttttttta tttatgcaga ggccgaggcc gcctcggcct ctgagctatt    8040
ccagaagtag tgaggaggct ttttggagg cctaggcttt tgcaaaaagc tttgcaaaga    8100
tggataaagt tttaaacaga gaggaatctt tgcagctaat ggaccttcta ggtcttgaaa    8160
gg                                                                   8162

<210> SEQ ID NO 16
<211> LENGTH: 8162
<212> TYPE: DNA
<213> ORGANISM: Artificial Sequence
<220> FEATURE:
<223> OTHER INFORMATION: Synthetic construct: pJP183 ;
      pHybE-hCg1,z,non-a V2
```

```
<400> SEQUENCE: 16
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg ccttttttcc gagggtgggg gagaaccgta     180
tataagtgca gtagtcgccg tgaacgttct ttttcgcaac gggtttgccg ccagaacaca     240
ggtaagtgcc gtgtgtggtt cccgcgggcc tggcctcttt acgggttatg gcccttgcgt     300
gccttgaatt acttccacct ggctgcagta cgtgattctt gatcccgagc ttcgggttgg     360
aagtgggtgg gagagttcga ggccttgcgc ttaaggagcc ccttcgcctc gtgcttgagt     420
tgaggcctgg cctgggcgct ggggccgccg cgtgcgaatc tggtggcacc ttcgcgcctg     480
tctcgctgct ttcgataagt ctctagccat ttaaaatttt tgatgacctg ctgcgacgct     540
tttttctgg caagatagtc ttgtaaatgc gggccaagat ctgcacactg gtatttcggt      600
ttttggggcc gcgggcggcg acggggcccg tgcgtcccag cgcacatgtt cggcgaggcg     660
gggcctgcga gcgcggccac cgagaatcgg acggggtag tctcaagctg gccggcctgc      720
tctggtgcct ggcctcgcgc cgccgtgtat cgccccgccc tgggcggcaa ggctggcccg     780
gtcggcacca gttgcgtgag cggaaagatg gccgcttccc ggccctgctg cagggagctc     840
aaaatggagg acgcggcgct cgggagagcg ggcgggtgag tcacccacac aaaggaaaag     900
ggcctttccg tcctcagccg tcgcttcatg tgactccacg gagtaccggg cgccgtccag     960
gcacctcgat tagttctcga cttttggag tacgtcgtct ttaggttggg gggagggggtt    1020
ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gtttttttct tccatttcag gtgtcgtgag gaattctcta    1200
gagatccctc gacctcgaga tccattgtgc ccgggcgcca ccatggagtt tgggctgagc    1260
tggcttttc ttgtcgcgat tttaaaggt gtccagtgcg catggtatgc cgaaagggat       1320
gctgaaattg agaacgaaaa gctgcgccgg gaggttgaag aactgcggca ggccagcgag    1380
gcagatctcc agccaggaac tattgagtac gaacgccatc gacttacgcg tgcgcaggcc    1440
gacgcacagg aactgaagaa tgccagagac tccgctgaag tggtggaaac cgcattctgt    1500
actttcgtgc tgtcgcggat cgcaggtgaa attgccagta ttctcgacgg gctcccctg     1560
tcggtgcagc ggcgtttttcc ggaactggaa aaccgacatg ttgatttcct gaaacgggat    1620
atcatcaaag ccatgaacaa agcagccgcg ctggatgaac tgataccggg gttgctgagt    1680
gaatatatcg aacagtcagg ttaacaggct gcggcatttt gtccgcgccg gcttcgctc     1740
actgttcagg ccggagccac agaccgccgt tgaatgggcg gatgctaatt actatctccc    1800
gaaagaatcc gcataccagg aagggcgctg ggaaacactg ccctttcagc gggccatcat    1860
gaatgcgatg ggcagcgact acatccgtga ggtgaatgtg gtgaagtctg cccgtgtcgg    1920
ttattccaaa atgctgctgg gtgtttatgc ctactttata gagcataagc agcgcaacac    1980
ccttatctgg ttgccgacgg atggtgatgc cgagaacttt atgaaaaccc acgttgagcc    2040
gactattcgt gatattccgt cgctgctggc gctggcccg tggtatggca aaaagcaccg    2100
ggataacacg ctcaccatga agcgtttcac taatgggcgt ggcttctggt gcctgggcgg    2160
taaagcggca aaaaactacc gtgaaaagtc ggtggatgtg gcgggttatg atgaacttgc    2220
tgcttttgat gatgatattg aacaggaagg ctctccgacg ttcctgggtg acaagcgcgt    2280
cgaccaaggg cccatcggtc ttccccctgg caccctcctc caagagcacc tctggggca     2340
```

```
cagcggccct gggctgcctg gtcaaggact acttccccga accggtgacg gtgtcgtgga   2400
actcaggcgc cctgaccagc ggcgtgcaca ccttcccggc tgtcctacag tcctcaggac   2460
tctactccct cagcagcgtg gtgaccgtgc cctccagcag cttgggcacc cagacctaca   2520
tctgcaacgt gaatcacaag cccagcaaca ccaaggtgga caagaaagtt gagcccaaat   2580
cttgtgacaa aactcacaca tgcccaccgt gcccagcacc tgaactcctg ggggaccgt    2640 cagtcttcct cttccccccca aaacccaagg acaccctcat gatctcccgg acccctgagg   2700
tcacatgcgt ggtggtggac gtgagccacg aagaccctga ggtcaagttc aactggtacg   2760
tggacggcgt ggaggtgcat aatgccaaga caaagccgcg ggaggagcag tacaacagca   2820
cgtaccgtgt ggtcagcgtc ctcaccgtcc tgcaccagga ctggctgaat ggcaaggagt   2880
acaagtgcaa ggtctccaac aaagcccctcc cagcccccat cgagaaaacc atctccaaag   2940
ccaaagggca gccccgagaa ccacaggtgt acaccctgcc cccatcccgc gaggagatga   3000
ccaagaacca ggtcagcctg acctgcctgg tcaaaggctt ctatcccagc gacatcgccg   3060
tggagtggga gagcaatggg cagccggaga caactacaa gaccacgcct cccgtgctgg    3120
actccgacgg ctccttcttc ctctacagca agctcaccgt ggacaagagc aggtggcagc   3180
aggggaacgt cttctcatgc tccgtgatgc atgaggctct gcacaaccac tacacgcaga   3240
agagcctctc cctgtctccg ggtaaatgag cggccgctcg aggccggcaa ggccggatcc   3300
cccgacctcg acctctggct aataaaggaa atttattttc attgcaatag tgtgttggaa   3360
ttttttgtgt ctctcactcg gaaggacata tgggagggca aatcatttgg tcagatccc    3420 tcggagatct ctagctagag gatcgatccc cgccccggac gaactaaacc tgactacgac   3480
atctctgccc cttcttcgcg gggcagtgca tgtaatccct tcagttggtt ggtacaactt   3540
gccaactggg ccctgttcca catgtgacac gggggggggac caaacacaaa ggggttctct   3600
gactgtagtt gacatcctta taaatggatg tgcacatttg ccaacactga gtggctttca   3660
tcctggagca gactttgcag tctgtggact gcaacacaac attgcctta tgtgtaactc     3720 ttggctgaag ctcttacacc aatgctgggg gacatgtacc tcccagggc caggaagac      3780 tacgggaggc tacaccaacg tcaatcagag gggcctgtgt agctaccgat aagcggaccc   3840
tcaagagggc attagcaata gtgttttataa ggccccttg ttaaccctaa acgggtagca    3900
tatgcttccc gggtagtagt atatactatc cagactaacc ctaattcaat agcatatgtt   3960
acccaacggg aagcatatgc tatcgaatta gggttagtaa aagggtccta aggaacagcg   4020
atatctccca ccccatgagc tgtcacggtt ttatttacat ggggtcagga ttccacgagg   4080
gtagtgaacc attttagtca caagggcagt ggctgaagat caaggagcgg gcagtgaact   4140
ctcctgaatc ttcgcctgct tcttcattct ccttcgttta gctaatagaa taactgctga   4200
gttgtgaaca gtaaggtgta tgtgaggtgc tcgaaaacaa ggtttcaggt gacgccccca   4260
gaataaaatt tggacggggg gttcagtggt ggcattgtgc tatgacacca atataaccct   4320
cacaaacccc ttgggcaata aatactagtg taggaatgaa acattctgaa tatctttaac   4380
aatagaaatc catggggtgg ggacaagccg taaagactgg atgtccatct cacacgaatt   4440
tatggctatg ggcaacacat aatcctagtg caatatgata ctggggttat taagatgtgt   4500
cccaggcagg gaccaagaca ggtgaaccat gttgttacac tctatttgta acaagggaa     4560 agagagtgga cgccgacagc agcggactcc actggttgtc tctaacaccc ccgaaaatta   4620 aacgggctc cacgccaatg gggcccataa acaaagacaa gtggccactc ttttttttga   4680
aattgtggag tggggcacg cgtcagcccc cacacgccgc cctgcggttt tggactgtaa    4740
```

```
aataagggtg taataacttg gctgattgta accccgctaa ccactgcggt caaaccactt    4800
gcccacaaaa ccactaatgg caccccgggg aatacctgca taagtaggtg ggcgggccaa    4860
gataggggcg cgattgctgc gatctggagg acaaattaca cacacttgcg cctgagcgcc    4920
aagcacaggg ttgttggtcc tcatattcac gaggtcgctg agagcacggt gggctaatgt    4980
tgccatgggt agcatatact acccaaatat ctggatagca tatgctatcc taatctatat    5040
ctgggtagca taggctatcc taatctatat ctgggtagca tatgctatcc taatctatat    5100
ctgggtagta tatgctatcc taatttatat ctgggtagca taggctatcc taatctatat    5160
ctgggtagca tatgctatcc taatctatat ctgggtagta tatgctatcc taatctgtat    5220
ccgggtagca tatgctatcc taatagagat tagggtagta tatgctatcc taatttatat    5280
ctgggtagca tatactaccc aaatatctgg atagcatatg ctatcctaat ctatatctgg    5340
gtagcatatg ctatcctaat ctatatctgg gtagcatagg ctatcctaat ctatatctgg    5400
gtagcatatg ctatcctaat ctatatctgg gtagtatatg ctatcctaat ttatatctgg    5460
gtagcatagg ctatcctaat ctatatctgg gtagcatatg ctatcctaat ctatatctgg    5520
gtagtatatg ctatcctaat ctgtatccgg gtagcatatg ctatcctcat gataagctgt    5580
caaacatgag aattttcttg aagacgaaag ggcctcgtga tacgcctatt tttataggtt    5640
aatgtcatga taataatggt ttcttagacg tcaggtggca cttttcgggg aaatgtgcgc    5700
ggaaccccta tttgtttatt tttctaaata cattcaaata tgtatccgct catgagacaa    5760
taaccctgat aaatgcttca ataatattga aaaaggaaga gtatgagtat tcaacatttc    5820
cgtgtcgccc ttattccctt ttttgcggca ttttgccttc ctgtttttgc tcacccagaa    5880
acgctggtga agtaaaaga tgctgaagat cagttgggtg cacgagtggg ttacatcgaa    5940
ctggatctca acagcggtaa gatccttgag agttttcgcc ccgaagaacg ttttccaatg    6000
atgagcactt ttaaagttct gctatgtggc gcggtattat cccgtgttga cgccgggcaa    6060
gagcaactcg gtcgccgcat acactattct cagaatgact tggttgagta ctcaccagtc    6120
acagaaaagc atcttacgga tggcatgaca gtaagagaat tatgcagtgc tgccataacc    6180
atgagtgata acactgcggc caacttactt ctgacaacga tcggaggacc gaaggagcta    6240
accgcttttt tgcacaacat gggggatcat gtaactcgcc ttgatcgttg ggaaccggag    6300
ctgaatgaag ccataccaaa cgacgagcgt gacaccacga tgcctgcagc aatggcaaca    6360
acgttgcgca aactattaac tggcgaacta cttactctag cttcccggca acaattaata    6420
gactggatgg aggcggataa agttgcagga ccacttctgc gctcggccct tccggctggc    6480
tggtttattg ctgataaatc tggagccggt gagcgtgggt ctcgcggtat cattgcagca    6540
ctggggccag atggtaagcc ctcccgtatc gtagttatct acacgacggg gagtcaggca    6600 actatgatg aacgaaatag acagatcgct gagataggtg cctcactgat taagcattgg    6660
taactgtcag accaagttta ctcatatata ctttagattg atttaaaact tcattttta    6720 tttaaaagga tctaggtgaa gatcctttt gataatctca tgaccaaaat cccttaacgt    6780
gagttttcgt tccactgagc gtcagacccc gtagaaaaga tcaaaggatc ttcttgagat    6840 ccttttttc tgcgcgtaat ctgctgcttg caaacaaaaa aaccaccgct accagcggtg    6900
gtttgtttgc cggatcaaga gctaccaact ctttttccga aggtaactgg cttcagcaga    6960
gcgcagatac caaatactgt tcttctagtg tagccgtagt taggccacca cttcaagaac    7020
tctgtagcac cgcctacata cctcgctctg ctaatcctgt taccagtggc tgctgccagt    7080
ggcgataagt cgtgtcttac cgggttggac tcaagacgat agttaccgga taaggcgcag    7140
```

```
cggtcgggct gaacggggggg ttcgtgcaca cagcccagct tggagcgaac gacctacacc   7200
gaactgagat acctacagcg tgagctatga gaaagcgcca cgcttcccga agggagaaag   7260
gcggacaggt atccggtaag cggcagggtc ggaacaggag agcgcacgag ggagcttcca   7320
gggggaaacg cctggtatct ttatagtcct gtcgggtttc gccacctctg acttgagcgt   7380 cgattttttgt gatgctcgtc aggggggcgg agcctatgga aaaacgccag caacgcggcc   7440 ttttttacggt tcctggcctt tgctggcct tttgctcaca tgttctttcc tgcgttatcc   7500
cctgattctg tggataaccg tattaccgcc tttgagtgag ctgataccgc tcgccgcagc   7560
cgaacgaccg agcgcagcga gtcagtgagc gaggaagcgg aagagcgccc aatacgcaaa   7620
ccgcctctcc ccgcgcgttg gccgattcat taatgcagct ggcacgacag gtttcccgac   7680
tggaaagcgg gcagtgagcg caacgcaatt aatgtgagtt agctcactca ttaggcaccc   7740
caggctttac actttatgct tccggctcgt atgttgtgtg gaattgtgag cggataacaa   7800
tttcacacag gaaacagcta tgaccatgat tacgccaagc tctagctaga ggtcgagtcc   7860
ctccccagca ggcagaagta tgcaaagcat gcatctcaat tagtcagcaa ccatagtccc   7920
gcccctaact ccgcccatcc cgcccctaac tccgcccagt tccgcccatt ctccgcccca   7980
tggctgacta attttttttta tttatgcaga ggccgaggcc gcctcggcct ctgagctatt   8040
ccagaagtag tgaggaggct ttttggagg cctaggcttt tgcaaaaagc tttgcaaaga   8100
tggataaagt tttaaacaga gaggaatctt tgcagctaat ggaccttcta ggtcttgaaa   8160
gg                                                                  8162

<210> SEQ ID NO 17
<211> LENGTH: 8162
<212> TYPE: DNA
<213> ORGANISM: Artificial Sequence
<220> FEATURE:
<223> OTHER INFORMATION: Synthetic construct: pJP172 ;
      pHybE-hCg1,z,non-a,mut(234,235) V1

<400> SEQUENCE: 17
agtgggaatt ggctccggtg cccgtcagtg ggcagagcgc acatcgccca cagtccccga     60
gaagttgggg ggaggggtcg gcaattgaac cggtgcctag agaaggtggc gcggggtaaa    120
ctgggaaagt gatgtcgtgt actggctccg cctttttccc gagggtgggg gagaaccgta    180
tataagtgca gtagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaattttt tgatgacctg ctgcgacgct    540
ttttttctgg caagatagtc ttgtaaatgc gggccaagat ctgcacactg gtatttcggt    600 tttttggggcc gcggcggcg acggggcccg tgcgtcccag cgcacatgtt cggcgaggcg    660
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcaccacac aaaggaaaag    900 ggcctttccg tcctcagccg tcgcttcatg tgactccacg gagtaccggg cgccgtccag    960
```

-continued

```
gcacctcgat tagttctcga gcttttggag tacgtcgtct ttaggttggg gggaggggtt    1020
ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gttttttct tccatttcag gtgtcgtgag gaattctcta    1200
gagatccctc gacctcgagc atttaaatgc ccgggcgcca ccatggagtt tgggctgagc    1260
tggctttttc ttgtcgcgat tttaaaaggt gtccagtgcg catggtatgc cgaaagggat    1320
gctgaaattg agaacgaaaa gctgcgccgg gaggttgaag aactgcggca ggccagcgag    1380
gcagatctcc agccaggaac tattgagtac gaacgccatc gacttacgcg tgcgcaggcc    1440
gacgcacagg aactgaagaa tgccagagac tccgctgaag tggtggaaac cgcattctgt    1500
actttcgtgc tgtcgcggat cgcaggtgaa attgccagta ttctcgacgg gctcccctg    1560 tcggtgcagc ggcgttttcc ggaactggaa aaccgacatg ttgatttcct gaaacgggat    1620
atcatcaaag ccatgaacaa gcagccgcg ctggatgaac tgataccggg gttgctgagt    1680
gaatatatcg aacagtcagg ttaacaggct gcggcatttt gtccgcgccg ggcttcgctc    1740
actgttcagg ccggagccac agaccgccgt tgaatgggcg gatgctaatt actatctccc    1800
gaaagaatcc gcataccagg aagggcgctg ggaaacactg ccctttcagc gggccatcat    1860
gaatgcgatg ggcagcgact acatccgtga ggtgaatgtg gtgaagtctg cccgtgtcgg    1920
ttattccaaa atgctgctgg gtgtttatgc ctactttata gagcataagc agcgcaacac    1980
ccttatctgg ttgccgacgg atggtgatgc cgagaacttt atgaaaaccc acgttgagcc    2040
gactattcgt gatattccgt cgctgctggc gctggccccg tggtatggca aaaagcaccg    2100
ggataacacg ctcaccatga agcgtttcac taatgggcgt ggcttctggt gcctgggcgg    2160
taaagcggca aaaaactacc gtgaaaagtc ggtggatgtg gcgggttatg atgaacttgc    2220
tgcttttgat gatgatattg aacaggaagg ctctccgacg ttcctgggtg acaagcgcgt    2280
cgaccaaggg cccatcggtc ttccccctgg caccctcctc aagagcacc tctgggggca    2340 cagcggccct gggctgcctg gtcaaggact acttccccga accggtgacg gtgtcgtgga    2400
actcaggcgc cctgaccagc ggcgtgcaca ccttcccggc tgtcctacag tcctcaggac    2460
tctactccct cagcagcgtg gtgaccgtgc cctccagcag cttgggcacc cagacctaca    2520
tctgcaacgt gaatcacaag cccagcaaca ccaaggtgga caagaaagtt gagcccaaat    2580
cttgtgacaa aactcacaca tgcccaccgt gcccagcacc tgaagccgcg gggggaccgt    2640
cagtcttcct cttcccccca aaacccaagg acaccctcat gatctcccgg acccctgagg    2700
tcacatgcgt ggtggtggac gtgagccacg aagaccctga ggtcaagttc aactggtacg    2760
tggacggcgt ggaggtgcat aatgccaaga caaagccgcg ggaggagcag tacaacagca    2820
cgtaccgtgt ggtcagcgtc ctcaccgtcc tgcaccagga ctggctgaat ggcaaggagt    2880
acaagtgcaa ggtctccaac aaagccctcc cagcccccat cgagaaaacc atctccaaag    2940
ccaaagggca gccccgagaa ccacaggtgt acaccctgcc cccatcccgc gaggagatga    3000
ccaagaacca ggtcagcctg acctgcctgg tcaaaggctt ctatcccagc gacatcgccg    3060
tggagtggga gagcaatggg cagccggaga caactacaa gaccacgcct cccgtgctgg    3120
actccgacgg ctccttcttc ctctacagca agctcaccgt ggacaagagc aggtggcagc    3180
aggggaacgt cttctcatgc tccgtgatgc atgaggctct gcacaaccac tacacgcaga    3240
agagcctctc cctgtctccg ggtaaatgag cggccgctcg aggccggcaa ggccggatcc    3300
cccgacctcg acctctggct aataaaggaa atttattttc attgcaatag tgtgttggaa    3360
```

```
tttttttgtgt ctctcactcg aaggacata tgggagggca aatcatttgg tcgagatccc    3420
tcggagatct ctagctagag gatcgatccc cgccccggac gaactaaacc tgactacgac    3480
atctctgccc cttcttcgcg gggcagtgca tgtaatccct tcagttggtt ggtacaactt    3540
gccaactggg ccctgttcca catgtgacac ggggggggca caaacacaaa ggggttctct    3600
gactgtagtt gacatcctta taaatggatg tgcacatttg ccaacactga gtggctttca    3660
tcctggagca gactttgcag tctgtggact gcaacacaac attgccttta tgtgtaactc    3720
ttggctgaag ctcttacacc aatgctgggg gacatgtacc tcccagggcc ccaggaagac    3780
tacgggaggc tacaccaacg tcaatcagag gggcctgtgt agctaccgat aagcggaccc    3840
tcaagagggc attagcaata gtgtttataa ggccccttg ttaaccctaa acgggtagca    3900
tatgcttccc gggtagtagt atatactatc cagactaacc ctaattcaat agcatatgtt    3960
acccaacggg aagcatatgc tatcgaatta gggttagtaa aagggtccta aggaacagcg    4020
atatctccca ccccatgagc tgtcacggtt ttatttacat ggggtcagga ttccacgagg    4080
gtagtgaacc atttagtca aagggcagt ggctgaagat caaggagcgg gcagtgaact    4140
ctcctgaatc ttcgcctgct tcttcattct ccttcgttta gctaatagaa taactgctga    4200
gttgtgaaca gtaaggtgta tgtgaggtgc tcgaaaacaa ggtttcaggt gacgccccca    4260
gaataaaatt tggacggggg gttcagtggt ggcattgtgc tatgacacca atataaccct    4320
cacaaacccc ttgggcaata aatactagtg taggaatgaa acattctgaa tatctttaac    4380
aatagaaatc catggggtgg ggacaagccg taaagactgg atgtccatct cacacgaatt    4440
tatggctatg ggcaacacat aatcctagtg caatatgata ctggggttat taagatgtgt    4500
cccaggcagg gaccaagaca ggtgaaccat gttgttacac tctatttgta acaaggggaa    4560
agagagtgga cgccgacagc agcggactcc actggttgtc tctaacaccc ccgaaaatta    4620 aacgggctc cacgccaatg gggcccataa acaaagacaa gtggccactc ttttttttga    4680
aattgtggag tgggggcacg cgtcagcccc cacacgccgc cctgcggttt tggactgtaa    4740
aataagggtg taataacttg gctgattgta accccgctaa ccactgcggt caaaccactt    4800
gcccacaaaa ccactaatgg caccccgggg aatacctgca taagtaggtg ggcgggccaa    4860
gataggggcg cgattgctgc gatctggagg acaaattaca cacacttgcg cctgagcgcc    4920
aagcacaggg ttgttggtcc tcatattcac gaggtcgctg agagcacggt gggctaatgt    4980
tgccatgggt agcatatact acccaaatat ctggatagca tatgctatcc taatctatat    5040
ctgggtagca taggctatcc taatctatat ctgggtagca tatgctatcc taatctatat    5100
ctgggtagta tatgctatcc taatttatat ctgggtagca taggctatcc taatctatat    5160
ctgggtagca tatgctatcc taatctatat ctgggtagta tatgctatcc taatctgtat    5220
ccgggtagca tatgctatcc taatagagat tagggtagta tatgctatcc taatttatat    5280
ctgggtagca tatactaccc aaaatatctgg atagcatatg ctatcctaat ctatatctgg    5340
gtagcatatg ctatcctaat ctatatctgg gtagcatagg ctatcctaat ctatatctgg    5400
gtagcatatg ctatcctaat ctatatctgg gtagtatatg ctatcctaat ttatatctgg    5460
gtagcatagg ctatcctaat ctatatctgg gtagcatatg ctatcctaat ctatatctgg    5520
gtagtatatg ctatcctaat ctgtatccgg gtagcatatg ctatcctcat gataagctgt    5580
caaacatgag aattttcttg aagacgaaag ggcctcgtga tacgcctatt tttataggtt    5640
aatgtcatga taataatggt ttcttagacg tcaggtggca ctttttcgggg aaatgtgcgc    5700 ggaacccta tttgttttatt tttctaaata cattcaaata tgtatccgct catgagacaa    5760
```

```
taaccctgat aaatgcttca ataatattga aaaaggaaga gtatgagtat tcaacatttc    5820
cgtgtcgccc ttattcccct tttttgcggca ttttgccttc ctgttttgc tcacccagaa    5880 acgctggtga agtaaaaga tgctgaagat cagttgggtg cacgagtggg ttacatcgaa    5940
ctggatctca acagcggtaa gatccttgag agttttcgcc ccgaagaacg ttttccaatg    6000
atgagcactt ttaaagttct gctatgtggc gcggtattat cccgtgttga cgccgggcaa    6060
gagcaactcg gtcgccgcat acactattct cagaatgact tggttgagta ctcaccagtc    6120
acagaaaagc atcttacgga tggcatgaca gtaagagaat tatgcagtgc tgccataacc    6180
atgagtgata acactgcggc caacttactt ctgacaacga tcggaggacc gaaggagcta    6240
accgcttttt tgcacaacat gggggatcat gtaactcgcc ttgatcgttg gaaccggag    6300 ctgaatgaag ccataccaaa cgacgagcgt gacaccacga tgcctgcagc aatggcaaca    6360
acgttgcgca aactattaac tggcgaacta cttactctag cttcccggca acaattaata    6420
gactggatgg aggcggataa agttgcagga ccacttctgc gctcggccct tccggctggc    6480
tggtttattg ctgataaatc tggagccggt gagcgtgggt ctcgcggtat cattgcagca    6540
ctggggccag atggtaagcc ctcccgtatc gtagttatct acacgacggg gagtcaggca    6600
actatggatg aacgaaatag acagatcgct gagataggtg cctcactgat taagcattgg    6660
taactgtcag accaagttta ctcatatata ctttagattg atttaaaact tcatttttaa    6720
tttaaaagga tctaggtgaa gatcctttt gataatctca tgaccaaaat cccttaacgt    6780
gagttttcgt tccactgagc gtcagacccc gtagaaaaga tcaaaggatc ttcttgagat    6840 ccttttttc tgcgcgtaat ctgctgcttg caaacaaaaa aaccaccgct accagcggtg    6900
gtttgtttgc cggatcaaga gctaccaact ctttttccga aggtaactgg cttcagcaga    6960
gcgcagatac caaatactgt tcttctagtg tagccgtagt taggccacca cttcaagaac    7020
tctgtagcac cgcctacata cctcgctctg ctaatcctgt taccagtggc tgctgccagt    7080
ggcgataagt cgtgtcttac cgggttggac tcaagacgat agttaccgga taaggcgcag    7140
cggtcgggct gaacggggg ttcgtgcaca cagcccagct tggagcgaac gacctacacc    7200
gaactgagat acctacagcg tgagctatga gaaagcgcca cgcttcccga agggagaaag    7260
gcggacaggt atccggtaag cggcagggtc ggaacaggag agcgcacgag ggagcttcca    7320
gggggaaacg cctggtatct ttatagtcct gtcgggtttc gccacctctg acttgagcgt    7380
cgatttttgt gatgctcgtc aggggggcgg agcctatgga aaaacgccag caacgcggcc    7440 ttttacggt tcctggcctt ttgctggcct tttgctcaca tgttctttcc tgcgttatcc    7500
cctgattctg tggataaccg tattaccgcc tttgagtgag ctgataccgc tcgccgcagc    7560
cgaacgaccg agcgcagcga gtcagtgagc gaggaagcgg aagagcgccc aatacgcaaa    7620
ccgcctctcc ccgcgcgttg gccgattcat taatgcagct ggcacgacag gtttcccgac    7680
tggaaagcgg gcagtgagcg caacgcaatt aatgtgagtt agctcactca ttaggcaccc    7740
caggctttac actttatgct tccggctcgt atgttgtgtg gaattgtgag cggataacaa    7800
tttcacacag gaaacagcta tgaccatgat tacgccaagc tctagctaga ggtcgagtcc    7860
ctccccagca ggcagaagta tgcaaagcat gcatctcaat tagtcagcaa ccatagtccc    7920
gcccctaact ccgcccatcc cgcccctaac tccgcccagt tccgcccatt ctccgcccca    7980
tggctgacta atttttttta tttatgcaga ggccgaggcc gcctcggcct ctgagctatt    8040
ccagaagtag tgaggaggct ttttggagg cctaggcttt tgcaaaaagc tttgcaaaga    8100
tggataaagt tttaaacaga gaggaatctt tgcagctaat ggaccttcta ggtcttgaaa    8160
``` gg 8162

<210> SEQ ID NO 18
<211> LENGTH: 8162
<212> TYPE: DNA
<213> ORGANISM: Artificial Sequence
<220> FEATURE:
<223> OTHER INFORMATION: Synthetic construct: pJP184 ;
      pHybE-hCg1,z,non-a,mut(234,235) V2

<400> SEQUENCE: 18

| | | | | | |
|---|---|---|---|---|---|
| agtgggaatt | ggctccggtg | cccgtcagtg | ggcagagcgc | acatcgccca | cagtccccga | 60 |
| gaagttgggg | ggaggggtcg | gcaattgaac | cggtgcctag | agaaggtggc | gcggggtaaa | 120 |
| ctggaaagt | gatgtcgtgt | actggctccg | ccttttttccc | gagggtgggg | gagaaccgta | 180 |
| tataagtgca | gtagtcgccg | tgaacgttct | ttttcgcaac | gggtttgccg | ccagaacaca | 240 |
| ggtaagtgcc | gtgtgtggtt | cccgcgggcc | tggcctcttt | acgggttatg | gcccttgcgt | 300 |
| gccttgaatt | acttccacct | ggctgcagta | cgtgattctt | gatcccgagc | ttcgggttgg | 360 |
| aagtgggtgg | gagagttcga | ggccttgcgc | ttaaggagcc | ccttcgcctc | gtgcttgagt | 420 |
| tgaggcctgg | cctgggcgct | ggggccgccg | cgtgcgaatc | tggtggcacc | ttcgcgcctg | 480 |
| tctcgctgct | ttcgataagt | ctctagccat | ttaaaatttt | tgatgacctg | ctgcgacgct | 540 |
| ttttttctgg | caagatagtc | ttgtaaatgc | gggccaagat | ctgcacactg | gtatttcggt | 600 |
| ttttggggcc | gcgggcggcg | acggggcccg | tgcgtcccag | cgcacatgtt | cggcgaggcg | 660 |
| gggcctgcga | gcgcggccac | cgagaatcgg | acggggtag | tctcaagctg | gccggcctgc | 720 |
| tctggtgcct | ggcctcgcgc | cgccgtgtat | cgccccgccc | tgggcggcaa | ggctggcccg | 780 |
| gtcggcacca | gttgcgtgag | cggaaagatg | gccgcttccc | ggccctgctg | cagggagctc | 840 |
| aaaatggagg | acgcggcgct | cgggagagcg | ggcgggtgag | tcacccacac | aaaggaaaag | 900 |
| ggcctttccg | tcctcagccg | tcgcttcatg | tgactccacg | gagtaccggg | cgccgtccag | 960 |
| gcacctcgat | tagttctcga | gcttttggag | tacgtcgtct | ttaggttggg | gggagggggtt | 1020 |
| ttatgcgatg | gagtttcccc | acactgagtg | ggtggagact | gaagttaggc | cagcttggca | 1080 |
| cttgatgtaa | ttctccttgg | aatttgccct | ttttgagttt | ggatcttggt | tcattctcaa | 1140 |
| gcctcagaca | gtggttcaaa | gtttttttct | tccatttcag | gtgtcgtgag | gaattctcta | 1200 |
| gagatccctc | gacctcgaga | tccattgtgc | ccgggcgcca | ccatggagtt | tgggctgagc | 1260 |
| tggcttttc | ttgtcgcgat | tttaaaaggt | gtccagtgcg | catggtatgc | cgaaagggat | 1320 |
| gctgaaattg | agaacgaaaa | gctgcgccgg | gaggttgaag | aactgcggca | ggccagcgag | 1380 |
| gcagatctcc | agccaggaac | tattgagtac | gaacgccatc | gacttacgcg | tgcgcaggcc | 1440 |
| gacgcacagg | aactgaagaa | tgccagagac | tccgctgaag | tggtggaaac | cgcattctgt | 1500 |
| actttcgtgc | tgtcgcggat | cgcaggtgaa | attgccagta | ttctcgacgg | gctcccctg | 1560 |
| tcggtgcagc | ggcgttttcc | ggaactggaa | aaccgacatg | ttgatttcct | gaaacgggat | 1620 |
| atcatcaaag | ccatgaacaa | agcagccgcg | ctggatgaac | tgataccggg | gttgctgagt | 1680 |
| gaatatatcg | aacagtcagg | ttaacaggct | gcggcatttt | gtccgcgccg | gcttcgctc | 1740 |
| actgttcagg | ccggagccac | agaccgccgt | tgaatgggcg | gatgctaatt | actatctccc | 1800 |
| gaaagaatcc | gcataccagg | aagggcgctg | gaaacactg | cccttcagc | gggccatcat | 1860 |
| gaatgcgatg | ggcagcgact | acatccgtga | ggtgaatgtg | gtgaagtctg | cccgtgtcgg | 1920 |
| ttattccaaa | atgctgctgg | gtgtttatgc | ctactttata | gagcataagc | agcgcaacac | 1980 |
| ccttatctgg | ttgccgacgg | atggtgatgc | cgagaacttt | atgaaaaccc | acgttgagcc | 2040 |

```
gactattcgt gatattccgt cgctgctggc gctggcccg tggtatggca aaaagcaccg    2100
ggataacacg ctcaccatga agcgtttcac taatgggcgt ggcttctggt gcctgggcgg    2160
taaagcggca aaaactacc gtgaaaagtc ggtggatgtg gcgggttatg atgaacttgc    2220
tgcttttgat gatgatattg aacaggaagg ctctccgacg ttcctgggtg acaagcgcgt    2280
cgaccaaggg cccatcggtc ttcccctgg caccctcctc caagagcacc tctgggggca    2340
cagcggccct gggctgcctg gtcaaggact acttccccga accggtgacg gtgtcgtgga    2400
actcaggcgc cctgaccagc ggcgtgcaca ccttcccggc tgtcctacag tcctcaggac    2460
tctactccct cagcagcgtg gtgaccgtgc cctccagcag cttgggcacc cagacctaca    2520
tctgcaacgt gaatcacaag cccagcaaca ccaaggtgga caagaaagtt gagcccaaat    2580
cttgtgacaa aactcacaca tgcccaccgt gcccagcacc tgaagccgcg ggggaccgt    2640 cagtcttcct cttccccca aacccaagg acaccctcat gatctcccgg acccctgagg    2700
tcacatgcgt ggtggtggac gtgagccacg aagaccctga ggtcaagttc aactggtacg    2760
tggacggcgt ggaggtgcat aatgccaaga caaagccgcg ggaggagcag tacaacagca    2820
cgtaccgtgt ggtcagcgtc ctcaccgtcc tgcaccagga ctggctgaat ggcaaggagt    2880
acaagtgcaa ggtctccaac aaagccctcc cagcccccat cgagaaaacc atctccaaag    2940
ccaaagggca gccccgagaa ccacaggtgt acaccctgcc cccatcccgc gaggagatga    3000
ccaagaacca ggtcagcctg acctgcctgg tcaaaggctt ctatcccagc gacatcgccg    3060
tggagtggga gagcaatggg cagccggaga caactacaa gaccacgcct cccgtgctgg    3120
actccgacgg ctccttcttc ctctacagca agctcaccgt ggacaagagc aggtggcagc    3180
aggggaacgt cttctcatgc tccgtgatgc atgaggctct gcacaaccac tacacgcaga    3240
agagcctctc cctgtctccg ggtaaatgag cggccgctcg aggccggcaa ggccggatcc    3300
cccgacctcg acctctggct aataaaggaa atttattttc attgcaatag tgtgttggaa    3360
ttttttgtgt ctctcactcg gaaggacata tgggagggca aatcatttgg tcgagatccc    3420
tcggagatct ctagctagag gatcgatccc cgccccggac gaactaaacc tgactacgac    3480
atctctgccc cttcttcgcg gggcagtgca tgtaatccct tcagttggtt ggtacaactt    3540
gccaactggg ccctgttcca catgtgacac ggggggggac caaacacaaa ggggttctct    3600
gactgtagtt gacatcctta taatggatg tgcacatttg ccaacactga gtggctttca    3660
tcctggagca gactttgcag tctgtggact gcaacacaac attgccttta tgtgtaactc    3720
ttggctgaag ctcttacacc aatgctgggg gacatgtacc tcccaggggc ccaggaagac    3780
tacgggaggc tacaccaacg tcaatcagag gggcctgtgt agctaccgat aagcggaccc    3840
tcaagagggc attagcaata gtgtttataa ggccccttg ttaaccctaa acgggtagca    3900
tatgcttccc gggtagtagt atatactatc cagactaacc ctaattcaat agcatatgtt    3960
acccaacggg aagcatatgc tatcgaatta gggttagtaa aagggtccta aggaacagcg    4020
atatctccca ccccatgagc tgtcacggtt ttatttacat ggggtcagga ttccacgagg    4080
gtagtgaacc atttagtca aagggcagt ggctgaagat caaggagcgg gcagtgaact    4140
ctcctgaatc ttcgcctgct tcttcattct ccttcgttta gctaatagaa taactgctga    4200
gttgtgaaca gtaaggtgta tgtgaggtgc tcgaaaacaa ggtttcaggt gacgccccca    4260
gaataaaatt tggacggggg gttcagtggt ggcattgtgc tatgacacca atataaccct    4320
cacaaacccc ttgggcaata aatactagtg taggaatgaa acattctgaa tatctttaac    4380
aatagaaatc catggggtgg ggacaagccg taaagactgg atgtccatct cacacgaatt    4440
```

```
tatggctatg ggcaacacat aatcctagtg caatatgata ctggggttat taagatgtgt    4500
cccaggcagg gaccaagaca ggtgaaccat gttgttacac tctatttgta acaaggggaa    4560
agagagtgga cgccgacagc agcggactcc actggttgtc tctaacaccc ccgaaaatta    4620 aacgggctc cacgccaatg gggcccataa acaaagacaa gtggccactc tttttttga     4680 aattgtggag tggggcacg cgtcagcccc cacacgccgc cctgcggttt tggactgtaa     4740
aataagggtg taataacttg gctgattgta accccgctaa ccactgcggt caaaccactt    4800
gcccacaaaa ccactaatgg caccccgggg aatacctgca taagtaggtg ggcgggccaa    4860
gataggggcg cgattgctgc gatctggagg acaaattaca cacacttgcg cctgagcgcc    4920
aagcacaggg ttgttggtcc tcatattcac gaggtcgctg agagcacggt gggctaatgt    4980
tgccatgggt agcatatact acccaaatat ctggatagca tatgctatcc taatctatat    5040
ctgggtagca taggctatcc taatctatat ctgggtagca tatgctatcc taatctatat    5100
ctgggtagta tatgctatcc taatttatat ctgggtagca taggctatcc taatctatat    5160
ctgggtagca tatgctatcc taatctatat ctgggtagta tatgctatcc taatctgtat    5220
ccgggtagca tatgctatcc taatagagat tagggtagta tatgctatcc taatttatat    5280
ctgggtagca tatactaccc aaatatctgg atagcatatg ctatcctaat ctatatctgg    5340
gtagcatatg ctatcctaat ctatatctgg gtagcatagg ctatcctaat ctatatctgg    5400
gtagcatatg ctatcctaat ctatatctgg gtagtatatg ctatcctaat ttatatctgg    5460
gtagcatagg ctatcctaat ctatatctgg gtagcatatg ctatcctaat ctatatctgg    5520
gtagtatatg ctatcctaat ctgtatccgg gtagcatatg ctatcctcat gataagctgt    5580
caaacatgag aattttcttg aagacgaaag ggcctcgtga tacgcctatt tttataggtt    5640
aatgtcatga taataatggt ttcttagacg tcaggtggca cttttcgggg aaatgtgcgc    5700 ggaacccta tttgtttatt tttctaaata cattcaaata tgtatccgct catgagacaa     5760
taaccctgat aaatgcttca ataatattga aaaggaaga gtatgagtat caacatttc     5820 cgtgtcgccc ttattccctt ttttgcggca ttttgccttc ctgttttgc tcacccagaa     5880 acgctggtga agtaaaaga tgctgaagat cagttgggtg cacgagtggg ttacatcgaa    5940
ctggatctca acagcggtaa gatccttgag agttttcgcc ccgaagaacg ttttccaatg    6000
atgagcactt ttaaagttct gctatgtggc gcggtattat cccgtgttga cgccgggcaa    6060
gagcaactcg gtcgccgcat acactattct cagaatgact tggttgagta ctcaccagtc    6120
acagaaaagc atcttacgga tggcatgaca gtaagagaat tatgcagtgc tgccataacc    6180
atgagtgata acactgcggc caacttactt ctgacaacga tcggaggacc gaaggagcta    6240
accgcttttt tgcacaacat gggggatcat gtaactcgcc ttgatcgttg ggaaccggag    6300
ctgaatgaag ccataccaaa cgacgagcgt gacaccacga tgcctgcagc aatggcaaca    6360
acgttgcgca aactattaac tggcgaacta cttactctag cttcccggca acaattaata    6420
gactggatgg aggcggataa agttgcagga ccacttctgc gctcggccct tccggctggc    6480
tggtttattg ctgataaatc tggagccggt gagcgtgggt ctcgcggtat cattgcagca    6540
ctggggccag atggtaagcc ctcccgtatc gtagttatct acacgacggg gagtcaggca    6600
actatggatg aacgaaatag acagatcgct gagataggtg cctcactgat taagcattgg    6660
taactgtcag accaagttta ctcatatata ctttagattg atttaaaact tcatttttaa    6720
tttaaaagga tctaggtgaa gatcctttt gataatctca tgaccaaaat cccttaacgt     6780
gagttttcgt tccactgagc gtcagacccc gtagaaaaga tcaaaggatc ttcttgagat    6840
```

```
cctttttttc tgcgcgtaat ctgctgcttg caaacaaaaa aaccaccgct accagcggtg    6900
gtttgtttgc cggatcaaga gctaccaact cttttccga aggtaactgg cttcagcaga    6960
gcgcagatac caaatactgt tcttctagtg tagccgtagt taggccacca cttcaagaac    7020
tctgtagcac cgcctacata cctcgctctg ctaatcctgt taccagtggc tgctgccagt    7080
ggcgataagt cgtgtcttac cgggttggac tcaagacgat agttaccgga taaggcgcag    7140
cggtcgggct gaacggggggg ttcgtgcaca cagcccagct tggagcgaac gacctacacc    7200
gaactgagat acctacagcg tgagctatga gaaagcgcca cgcttcccga agggagaaag    7260
gcggacaggt atccggtaag cggcagggtc ggaacaggag agcgcacgag ggagcttcca    7320
gggggaaacg cctggtatct ttatagtcct gtcgggtttc gccacctctg acttgagcgt    7380
cgatttttgt gatgctcgtc agggggcgg agcctatgga aaaacgccag caacgcggcc    7440
tttttacggt tcctggcctt tgctggcct tttgctcaca tgttctttcc tgcgttatcc    7500
cctgattctg tggataaccg tattaccgcc tttgagtgag ctgataccgc tcgccgcagc    7560
cgaacgaccg agcgcagcga gtcagtgagc gaggaagcgg aagagcgccc aatacgcaaa    7620
ccgcctctcc ccgcgcgttg gccgattcat taatgcagct ggcacgacag gtttcccgac    7680
tggaaagcgg gcagtgagcg caacgcaatt aatgtgagtt agctcactca ttaggcaccc    7740
caggctttac actttatgct tccggctcgt atgttgtgtg gaattgtgag cggataacaa    7800
tttcacacag gaaacagcta tgaccatgat tacgccaagc tctagctaga ggtcgagtcc    7860
ctccccagca ggcagaagta tgcaaagcat gcatctcaat tagtcagcaa ccatagtccc    7920
gcccctaact ccgcccatcc cgcccctaac tccgcccagt tccgcccatt ctccgcccca    7980
tggctgacta atttttttta tttatgcaga ggccgaggcc gcctcggcct ctgagctatt    8040
ccagaagtag tgaggaggct ttttggagg cctaggcttt tgcaaaaagc tttgcaaaga    8100
tggataaagt tttaaacaga gaggaatctt tgcagctaat ggaccttcta ggtcttgaaa    8160
gg                                                                  8162
```

<210> SEQ ID NO 19
<211> LENGTH: 8162
<212> TYPE: DNA
<213> ORGANISM: Artificial Sequence
<220> FEATURE:
<223> OTHER INFORMATION: Synthetic construct: pJP173 ;
      pHybE-hCg1,z,non-a,mut (234,237) V1

<400> SEQUENCE: 19

```
agtgggaatt ggctccggtg cccgtcagtg ggcagagcgc acatcgccca cagtccccga     60
gaagttgggg ggaggggtcg gcaattgaac cggtgcctag agaaggtggc gcggggtaaa    120
ctgggaaagt gatgtcgtgt actggctccg ccttttccc gagggtgggg gagaaccgta    180
tataagtgca gtagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc cttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540
ttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
```

```
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggaggggtt   1020
ttatgcgatg gagtttcccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gttttttttct tccatttcag gtgtcgtgag gaattctcta   1200
gagatccctc gacctcgagc atttaaatgc ccgggcgcca ccatggagtt tgggctgagc   1260 tggcttttc ttgtcgcgat tttaaaggt gtccagtgcg catggtatgc cgaaagggat   1320
gctgaaattg agaacgaaaa gctgcgccgg gaggttgaag aactgcggca ggccagcgag   1380
gcagatctcc agccaggaac tattgagtac gaacgccatc gacttacgcg tgcgcaggcc   1440
gacgcacagg aactgaagaa tgccagagac tccgctgaag tggtggaaac cgcattctgt   1500
actttcgtgc tgtcgcggat cgcaggtgaa attgccagta ttctcgacgg gctcccctg   1560 tcggtgcagc ggcgttttcc ggaactggaa aaccgacatg ttgatttcct gaaacgggat   1620
atcatcaaag ccatgaacaa agcagccgcg ctggatgaac tgataccggg gttgctgagt   1680
gaatatatcg aacagtcagg ttaacaggct gcggcatttt gtccgcgccg ggcttcgctc   1740
actgttcagg ccggagccac agaccgccgt tgaatgggcg gatgctaatt actatctccc   1800
gaaagaatcc gcataccagg aagggcgctg ggaaacactg cccttcagc gggccatcat   1860 gaatgcgatg ggcagcgact acatccgtga ggtgaatgtg gtgaagtctg cccgtgtcgg   1920
ttattccaaa atgctgctgg gtgtttatgc ctactttata gagcataagc agcgcaacac   1980
ccttatctgg ttgccgacgg atggtgatgc cgagaacttt atgaaaaccc acgttgagcc   2040
gactattcgt gatattccgt cgctgctggc gctggccccg tggtatggca aaaagcaccg   2100
ggataacacg ctcaccatga gcgtttcac taatgggcgt ggcttctggt gcctgggcgg   2160
taaagcggca aaaactacc gtgaaaagtc ggtggatgtg gcgggttatg atgaacttgc   2220
tgcttttgat gatgatattg aacaggaagg ctctccgacg ttcctgggtg acaagcgcgt   2280
cgaccaaggg cccatcggtc ttccccctgg caccctcctc caagagcacc tctgggggca   2340
cagcggccct gggctgcctg tcaaggact acttccccga accggtgacg gtgtcgtgga   2400
actcaggcgc cctgaccagc ggcgtgcaca ccttcccggc tgtcctacag tcctcaggac   2460
tctactccct cagcagcgtg gtgaccgtgc cctccagcag cttgggcacc cagacctaca   2520
tctgcaacgt gaatcacaag cccagcaaca ccaaggtgga caagaaagtt gagcccaaat   2580
cttgtgacaa aactcacaca tgcccaccgt gcccagcacc tgaagccctg ggggcaccgt   2640
cagtcttcct cttccccca aaacccaagg acaccctcat gatctcccgg acccctgagg   2700
tcacatgcgt ggtggtggac gtgagccacg aagaccctga ggtcaagttc aactggtacg   2760
tggacggcgt ggaggtgcat aatgccaaga caaagccgcg ggaggagcag tacaacagca   2820
cgtaccgtgt ggtcagcgtc ctcaccgtcc tgcaccagga ctggctgaat ggcaaggagt   2880
acaagtgcaa ggtctccaac aaagccctcc cagcccccat cgagaaaacc atctccaaag   2940
ccaaagggca gccccgagaa ccacaggtgt acaccctgcc cccatcccgc gaggagatga   3000
ccaagaacca ggtcagcctg acctgcctgg tcaaaggctt ctatcccagc gacatcgccg   3060
```

```
tggagtggga gagcaatggg cagccggaga acaactacaa gaccacgcct cccgtgctgg    3120
actccgacgg ctccttcttc ctctacagca agctcaccgt ggacaagagc aggtggcagc    3180
aggggaacgt cttctcatgc tccgtgatgc atgaggctct gcacaaccac tacacgcaga    3240
agagcctctc cctgtctccg ggtaaatgag cggccgctcg aggccggcaa ggccggatcc    3300
cccgacctcg acctctggct aataaaggaa atttattttc attgcaatag tgtgttggaa    3360
ttttttgtgt ctctcactcg gaaggacata tgggagggca aatcatttgg tcagatccc     3420 tcggagatct ctagctagag gatcgatccc cgccccggac gaactaaacc tgactacgac    3480
atctctgccc cttcttcgcg gggcagtgca tgtaatccct tcagttggtt ggtacaactt    3540
gccaactggg ccctgttcca catgtgacac gggggggggac caaacacaaa ggggttctct    3600
gactgtagtt gacatcctta taaatggatg tgcacatttg ccaacactga gtggctttca    3660
tcctggagca gactttgcag tctgtggact gcaacacaac attgccttta tgtgtaactc    3720
ttggctgaag ctcttacacc aatgctgggg gacatgtacc tcccagggggc ccaggaagac   3780 tacgggaggc tacaccaacg tcaatcagag gggcctgtgt agctaccgat aagcggaccc    3840
tcaagagggc attagcaata gtgtttataa ggcccccttg ttaaccctaa acgggtagca    3900
tatgcttccc gggtagtagt atatactatc cagactaacc ctaattcaat agcatatgtt    3960
acccaacggg aagcatatgc tatcgaatta gggttagtaa aagggtccta aggaacagcg    4020
atatctccca ccccatgagc tgtcacggtt ttatttacat ggggtcagga ttccacgagg    4080
gtagtgaacc attttagtca caagggcagt ggctgaagat caaggagcgg gcagtgaact    4140
ctcctgaatc ttcgcctgct tcttcattct ccttcgttta gctaatagaa taactgctga    4200
gttgtgaaca gtaaggtgta tgtgaggtgc tcgaaaacaa ggtttcaggt gacgccccca    4260
gaataaaatt tggacggggg gttcagtggt ggcattgtgc tatgacacca atataaccct    4320
cacaaacccc ttgggcaata aatactagtg taggaatgaa acattctgaa tatcttaac    4380 aatagaaatc catgggtgg ggacaagccg taaagactgg atgtccatct cacacgaatt    4440
tatggctatg ggcaacacat aatcctagtg caatatgata ctggggttat taagatgtgt    4500
cccaggcagg gaccaagaca ggtgaaccat gttgttacac tctatttgta acaagggaa    4560 agagagtgga cgccgacagc agcggactcc actggttgtc tctaacaccc ccgaaaatta    4620 aacgggctc cacgccaatg gggcccataa acaaagacaa gtggccactc ttttttttga    4680
aattgtggag tggggcacg cgtcagccc cacacgccgc cctgcggttt tggactgtaa     4740
aataagggtg taataacttg gctgattgta accccgctaa ccactgcggt caaaccactt    4800
gcccacaaaa ccactaatgg caccccgggg aataacctgca taagtaggtg ggcgggccaa    4860
gataggggcg cgattgctgc gatctggagg acaaattaca cacacttgcg cctgagcgcc    4920
aagcacaggg ttgttggtcc tcatattcac gaggtcgctg agagcacggt gggctaatgt    4980
tgccatgggt agcatatact acccaaatat ctggatagca tatgctatcc taatctatat    5040
ctgggtagca taggctatcc taatctatat ctgggtagca tatgctatcc taatctatat    5100
ctgggtagta tatgctatcc taatttatat ctgggtagca taggctatcc taatctatat    5160
ctgggtagca tatgctatcc taatctatat ctgggtagta tatgctatcc taatctgtat    5220
ccgggtagca tatgctatcc taatagagat tagggtagta tatgctatcc taatttatat    5280
ctgggtagca tatactaccc aaatatctgg atagcatatg ctatcctaat ctatatctgg    5340
gtagcatatg ctatcctaat ctatatctgg gtagcatagg ctatcctaat ctatatctgg    5400
gtagcatatg ctatcctaat ctatatctgg gtagtatatg ctatcctaat ttatatctgg    5460
```

```
gtagcatagg ctatcctaat ctatatctgg gtagcatatg ctatcctaat ctatatctgg    5520
gtagtatatg ctatcctaat ctgtatccgg gtagcatatg ctatcctcat gataagctgt    5580
caaacatgag aattttcttg aagacgaaag ggcctcgtga tacgcctatt tttataggtt    5640
aatgtcatga taataatggt ttcttagacg tcaggtggca cttttcgggg aaatgtgcgc    5700 ggaacccta tttgtttatt tttctaaata cattcaaata tgtatccgct catgagacaa     5760
taaccctgat aaatgcttca ataatattga aaaggaaga gtatgagtat tcaacatttc     5820
cgtgtcgccc ttattccctt ttttgcggca ttttgccttc ctgtttttgc tcacccagaa    5880
acgctggtga agtaaaaga tgctgaagat cagttgggtg cacgagtggg ttacatcgaa     5940
ctggatctca acagcggtaa gatccttgag agttttcgcc ccgaagaacg ttttccaatg    6000
atgagcactt ttaaagttct gctatgtggc gcggtattat cccgtgttga cgccgggcaa    6060
gagcaactcg gtcgccgcat acactattct cagaatgact tggttgagta ctcaccagtc    6120
acagaaaagc atcttacgga tggcatgaca gtaagagaat tatgcagtgc tgccataacc    6180
atgagtgata acactgcggc caacttactt ctgacaacga tcggaggacc gaaggagcta    6240 accgctttt tgcacaacat gggggatcat gtaactcgcc ttgatcgttg ggaaccggag     6300
ctgaatgaag ccataccaaa cgacgagcgt gacaccacga tgcctgcagc aatggcaaca    6360
acgttgcgca aactattaac tggcgaacta cttactctag cttcccggca acaattaata    6420
gactggatgg aggcggataa agttgcagga ccacttctgc gctcggccct tccggctggc    6480
tggtttattg ctgataaatc tggagccggt gagcgtgggt ctcgcggtat cattgcagca    6540
ctggggccag atggtaagcc ctcccgtatc gtagttatct acacgacggg gagtcaggca    6600
actatggatg aacgaaatag acagatcgct gagataggtg cctcactgat taagcattgg    6660
taactgtcag accaagttta ctcatatata ctttagattg atttaaaact tcatttttaa    6720
tttaaaagga tctaggtgaa gatcctttt gataatctca tgaccaaaat cccttaacgt     6780
gagttttcgt tccactgagc gtcagacccc gtagaaaaga tcaaaggatc ttcttgagat    6840 ccttttttc tgcgcgtaat ctgctgcttg caaacaaaaa aaccaccgct accagcggtg     6900
gtttgtttgc cggatcaaga gctaccaact cttttttccga aggtaactgg cttcagcaga    6960
gcgcagatac caaatactgt tcttctagtg tagccgtagt taggccacca cttcaagaac    7020
tctgtagcac cgcctacata cctcgctctg ctaatcctgt taccagtggc tgctgccagt    7080
ggcgataagt cgtgtcttac cgggttggac tcaagacgat agttaccgga taaggcgcag    7140
cggtcgggct gaacgggggg ttcgtgcaca cagcccagct tggagcgaac gacctacacc    7200
gaactgagat acctacagcg tgagctatga gaaagcgcca cgcttcccga agggagaaag    7260
gcggacaggt atccggtaag cggcagggtc ggaacaggag agcgcacgag ggagcttcca    7320
gggggaaacg cctggtatct ttatagtcct gtcgggtttc gccacctctg acttgagcgt    7380
cgatttttgt gatgctcgtc agggggggcgg agcctatgga aaaacgccag caacgcggcc    7440
tttttacggt tcctggcctt ttgctggcct tttgctcaca tgttctttcc tgcgttatcc    7500
cctgattctg tggataaccg tattaccgcc tttgagtgag ctgataccgc tcgccgcagc    7560
cgaacgaccg agcgcagcga gtcagtgagc gaggaagcgg aagagcgccc aatacgcaaa    7620
ccgcctctcc ccgcgcgttg gccgattcat taatgcagct ggcacgacag gtttcccgac    7680
tggaaagcgg gcagtgagcg caacgcaatt aatgtgagtt agctcactca ttaggcaccc    7740
caggctttac actttatgct tccggctcgt atgttgtgtg gaattgtgag cggataacaa    7800
tttcacacag gaaacagcta tgaccatgat tacgccaagc tctagctaga ggtcgagtcc    7860
```

```
ctccccagca ggcagaagta tgcaaagcat gcatctcaat tagtcagcaa ccatagtccc    7920
gcccctaact ccgcccatcc cgcccctaac tccgcccagt tccgcccatt ctccgcccca    7980
tggctgacta atttttttta tttatgcaga ggccgaggcc gcctcggcct ctgagctatt    8040
ccagaagtag tgaggaggct tttttggagg cctaggcttt tgcaaaaagc tttgcaaaga    8100
tggataaagt tttaaacaga gaggaatctt tgcagctaat ggaccttcta ggtcttgaaa    8160
gg                                                                  8162

<210> SEQ ID NO 20
<211> LENGTH: 8162
<212> TYPE: DNA
<213> ORGANISM: Artificial Sequence
<220> FEATURE:
<223> OTHER INFORMATION: Synthetic construct: pJP185 ;
      pHybE-hCg1,z,non-a,mut (234,237) V2

<400> SEQUENCE: 20
agtgggaatt ggctccggtg cccgtcagtg ggcagagcgc acatcgccca cagtccccga     60
gaagttgggg ggaggggtcg gcaattgaac cggtgcctag agaaggtggc gcggggtaaa    120
ctgggaaagt gatgtcgtgt actggctccg ccttttttccc gagggtgggg gagaaccgta    180
tataagtgca gtagtcgccg tgaacgttct ttttcgcaac gggtttgccg ccagaacaca    240
ggtaagtgcc gtgtgtggtt cccgcgggcc tggcctcttt acgggttatg cccttgcgt    300 gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540
ttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggagggggtt   1020 ttatgcgatg gagtttcccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gttttttttct tccatttcag gtgtcgtgag gaattctcta   1200
gagatccctc gacctcgaga tccattgtgc ccgggcgcca ccatggagtt gggctgagc   1260 tggcttttc ttgtcgcgat tttaaaaggt gtccagtgcg catggtatgc cgaaagggat   1320
gctgaaattg agaacgaaaa gctgcgccgg gaggttgaag aactgcggca ggccagcgag   1380
gcagatctcc agccaggaac tattgagtac gaacgccatc gacttacgcg tgcgcaggcc   1440
gacgcacagg aactgaagaa tgccagagac tccgctgaag tggtggaaac cgcattctgt   1500
actttcgtgc tgtcgcggat cgcaggtgaa attgccagta ttctcgacgg gctcccctg   1560 tcggtgcagc ggcgttttcc ggaactggaa aaccgacatg ttgatttcct gaaacgggat   1620
atcatcaaag ccatgaacaa agcagccgcg ctggatgaac tgataccggg gttgctgagt   1680
gaatatatcg aacagtcagg ttaacaggct gcggcatttt gtccgcgccg ggcttcgctc   1740
```

```
actgttcagg ccggagccac agaccgccgt tgaatgggcg gatgctaatt actatctccc   1800
gaaagaatcc gcataccagg aagggcgctg ggaaacactg ccctttcagc gggccatcat   1860
gaatgcgatg ggcagcgact acatccgtga ggtgaatgtg gtgaagtctg cccgtgtcgg   1920
ttattccaaa atgctgctgg gtgtttatgc ctactttata gagcataagc agcgcaacac   1980
ccttatctgg ttgccgacgg atggtgatgc cgagaacttt atgaaaaccc acgttgagcc   2040
gactattcgt gatattccgt cgctgctggc gctggccccg tggtatggca aaaagcaccg   2100
ggataacacg ctcaccatga agcgtttcac taatgggcgt ggcttctggt gcctgggcgg   2160
taaagcggca aaaactaccg tgaaaagtc ggtggatgtg gcgggttatg atgaacttgc   2220
tgcttttgat gatgatattg aacaggaagg ctctccgacg ttcctgggtg acaagcgcgt   2280
cgaccaaggg cccatcggtc ttccccctgg caccctcctc aagagcacc tctgggggca   2340 cagcggccct gggctgcctg gtcaaggact acttccccga accggtgacg gtgtcgtgga   2400
actcaggcgc cctgaccagc ggcgtgcaca ccttcccggc tgtcctacag tcctcaggac   2460
tctactccct cagcagcgtg gtgaccgtgc cctccagcag cttgggcacc cagacctaca   2520
tctgcaacgt gaatcacaag cccagcaaca ccaaggtgga caagaaagtt gagcccaaat   2580
cttgtgacaa aactcacaca tgcccaccgt gcccagcacc tgaagccctg ggggcaccgt   2640
cagtcttcct cttccccca aaacccaagg acaccctcat gatctcccgg acccctgagg   2700
tcacatgcgt ggtggtggac gtgagccacg aagaccctga ggtcaagttc aactggtacg   2760
tggacggcgt ggaggtgcat aatgccaaga caaagccgcg ggaggagcag tacaacagca   2820
cgtaccgtgt ggtcagcgtc ctcaccgtcc tgcaccagga ctggctgaat ggcaaggagt   2880
acaagtgcaa ggtctccaac aaagccctcc cagcccccat cgagaaaacc atctccaaag   2940
ccaaagggca gccccgagaa ccacaggtgt acaccctgcc cccatcccgc gaggagatga   3000
ccaagaacca ggtcagcctg acctgcctgg tcaaaggctt ctatcccagc gacatcgccg   3060
tggagtggga gagcaatggg cagccggaga acaactacaa gaccacgcct cccgtgctgg   3120
actccgacgg ctccttcttc ctctacagca agctcaccgt ggacaagagc aggtggcagc   3180
aggggaacgt cttctcatgc tccgtgatgc atgaggctct gcacaaccac tacacgcaga   3240
agagcctctc cctgtctccg ggtaaatgag cggccgctcg aggccggcaa ggccggatcc   3300
cccgacctcg acctctggct aataaaggaa atttattttc attgcaatag tgtgttggaa   3360
ttttttgtgt ctctcactcg gaaggacata tgggagggca aatcatttgg tcgagatccc   3420
tcggagatct ctagctagag gatcgatccc cgccccggac gaactaaacc tgactacgac   3480
atctctgccc cttcttcgcg gggcagtgca tgtaatccct tcagttggtt ggtacaactt   3540
gccaactggg ccctgttcca catgtgacac ggggggggac caaacacaaa ggggttctct   3600
gactgtagtt gacatcctta taaatggatg tgcacatttg ccaacactga gtggctttca   3660
tcctggagca gactttgcag tctgtggact gcaacacaac attgccttta tgtgtaactc   3720
ttggctgaag ctcttacacc aatgctgggg gacatgtacc tcccaggggc caggaagac    3780 tacgggaggc tacaccaacg tcaatcagag gggcctgtgt agctaccgat aagcggaccc   3840
tcaagagggc attagcaata gtgtttataa ggccccttg ttaaccctaa acgggtagca    3900
tatgcttccc gggtagtagt atatactatc cagactaacc ctaattcaat agcatatgtt   3960
acccaacggg aagcatatgc tatcgaatta gggttagtaa aagggtccta aggaacagcg   4020
atatctccca ccccatgagc tgtcacggtt ttatttacat ggggtcagga ttccacgagg   4080
gtagtgaacc attttagtca caagggcagt ggctgaagat caaggagcgg gcagtgaact   4140
```

```
ctcctgaatc ttcgcctgct tcttcattct ccttcgttta gctaatagaa taactgctga   4200
gttgtgaaca gtaaggtgta tgtgaggtgc tcgaaaacaa ggtttcaggt gacgccccca   4260
gaataaaatt tggacggggg gttcagtggt ggcattgtgc tatgacacca atataaccct   4320
cacaaacccc ttgggcaata aatactagtg taggaatgaa acattctgaa tatctttaac   4380
aatagaaatc catggggtgg ggacaagccg taaagactgg atgtccatct cacacgaatt   4440
tatggctatg ggcaacacat aatcctagtg caatatgata ctggggttat taagatgtgt   4500
cccaggcagg gaccaagaca ggtgaaccat gttgttacac tctatttgta acaaggggaa   4560
agagagtgga cgccgacagc agcggactcc actggttgtc tctaacaccc ccgaaaatta   4620 aacgggctc cacgccaatg gggcccataa acaaagacaa gtggccactc tttttttga    4680 aattgtggag tggggcacg cgtcagcccc cacacgccgc cctgcggttt tggactgtaa   4740 aataaggtg taataacttg gctgattgta accccgctaa ccactgcggt caaaccactt    4800
gcccacaaaa ccactaatgg caccccgggg aatacctgca taagtaggtg ggcgggccaa   4860 datagggcg cgattgctgc gatctggagg acaaattaca cacacttgcg cctgagcgcc    4920
aagcacaggg ttgttggtcc tcatattcac gaggtcgctg agagcacggt gggctaatgt   4980
tgccatgggt agcatatact acccaaatat ctggatagca tatgctatcc taatctatat   5040
ctgggtagca taggctatcc taatctatat ctgggtagca tatgctatcc taatctatat   5100
ctgggtagta tatgctatcc taatttatat ctgggtagca taggctatcc taatctatat   5160
ctgggtagca tatgctatcc taatctatat ctgggtagta tatgctatcc taatctgtat   5220
ccgggtagca tatgctatcc taatagagat tagggtagta tatgctatcc taatttatat   5280
ctgggtagca tatactaccc aaatatctgg atagcatatg ctatcctaat ctatatctgg   5340
gtagcatatg ctatcctaat ctatatctgg gtagcatagg ctatcctaat ctatatctgg   5400
gtagcatatg ctatcctaat ctatatctgg gtagtatatg ctatcctaat ttatatctgg   5460
gtagcatagg ctatcctaat ctatatctgg gtagcatatg ctatcctaat ctatatctgg   5520
gtagtatatg ctatcctaat ctgtatccgg gtagcatatg ctatcctcat gataagctgt   5580
caaacatgag aattttcttg aagacgaaag ggcctcgtga tacgcctatt tttataggtt   5640
aatgtcatga taataatggt ttcttagacg tcaggtggca cttttcgggg aaatgtgcgc   5700 ggaacccta tttgtttatt tttctaaata cattcaaata tgtatccgct catgagacaa    5760
taaccctgat aaatgcttca ataatattga aaaaggaaga gtatgagtat tcaacatttc   5820
cgtgtcgccc ttattccctt ttttgcggca ttttgccttc ctgttttgc tcacccagaa    5880 acgctggtga agtaaaaga tgctgaagat cagttgggtg cacgagtggg ttacatcgaa    5940
ctggatctca acagcggtaa gatccttgag agttttcgcc ccgaagaacg ttttccaatg   6000
atgagcactt ttaaagttct gctatgtggc gcggtattat cccgtgttga cgccgggcaa   6060
gagcaactcg gtcgccgcat acactattct cagaatgact tggttgagta ctcaccagtc   6120
acagaaaagc atcttacgga tggcatgaca gtaagagaat tatgcagtgc tgccataacc   6180
atgagtgata acactgcggc caacttactt ctgacaacga tcggaggacc gaaggagcta   6240
accgcttttt tgcacaacat ggggggatcat gtaactcgcc ttgatcgttg ggaaccggag   6300
ctgaatgaag ccataccaaa cgacgagcgt gacaccacga tgcctgcagc aatggcaaca   6360
acgttgcgca aactattaac tggcgaacta cttactctag cttcccggca acaattaata   6420
gactggatga aggcggataa agttgcagga ccacttctgc gctcggccct tccggctggc   6480
tggtttattg ctgataaatc tggagccggt gagcgtgggt ctcgcggtat cattgcagca   6540
```

```
ctggggccag atggtaagcc ctcccgtatc gtagttatct acacgacggg gagtcaggca    6600
actatggatg aacgaaatag acagatcgct gagataggtg cctcactgat taagcattgg    6660
taactgtcag accaagttta ctcatatata ctttagattg atttaaaact tcatttttaa    6720
tttaaaagga tctaggtgaa gatcctttt gataatctca tgaccaaaat cccttaacgt    6780
gagttttcgt tccactgagc gtcagacccc gtagaaaaga tcaaaggatc ttcttgagat    6840 ccttttttc tgcgcgtaat ctgctgcttg caaacaaaaa aaccaccgct accagcggtg    6900
gtttgtttgc cggatcaaga gctaccaact cttttccga aggtaactgg cttcagcaga    6960
gcgcagatac caaatactgt tcttctagtg tagccgtagt taggccacca cttcaagaac    7020
tctgtagcac cgcctacata cctcgctctg ctaatcctgt taccagtggc tgctgccagt    7080
ggcgataagt cgtgtcttac cgggttggac tcaagacgat agttaccgga taaggcgcag    7140
cggtcgggct gaacggggg ttcgtgcaca cagcccagct tggagcgaac gacctacacc    7200
gaactgagat acctacagcg tgagctatga gaaagcgcca cgcttcccga agggagaaag    7260
gcggacaggt atccggtaag cggcagggtc ggaacaggag agcgcacgag ggagcttcca    7320
gggggaaacg cctggtatct ttatagtcct gtcgggtttc gccacctctg acttgagcgt    7380
cgatttttgt gatgctcgtc agggggggcgg agcctatgga aaaacgccag caacgcggcc    7440 ttttttacggt tcctggcctt tgctggcct tttgctcaca tgttctttcc tgcgttatcc    7500
cctgattctg tggataaccg tattaccgcc tttgagtgag ctgataccgc tcgccgcagc    7560
cgaacgaccg agcgcagcga gtcagtgagc gaggaagcgg aagagcgccc aatacgcaaa    7620
ccgcctctcc ccgcgcgttg gccgattcat taatgcagct ggcacgacag gtttcccgac    7680
tggaaagcgg gcagtgagcg caacgcaatt aatgtgagtt agctcactca ttaggcaccc    7740
caggctttac actttatgct tccggctcgt atgttgtgtg gaattgtgag cggataacaa    7800
tttcacacag gaaacagcta tgaccatgat tacgccaagc tctagctaga ggtcgagtcc    7860
ctccccagca ggcagaagta tgcaaagcat gcatctcaat tagtcagcaa ccatagtccc    7920
gcccctaact ccgcccatcc cgcccctaac tccgcccagt tccgcccatt ctccgcccca    7980
tggctgacta attttttta tttatgcaga ggccgaggcc gcctcggcct ctgagctatt    8040
ccagaagtag tgaggaggct ttttggagg cctaggcttt tgcaaaaagc tttgcaaaga    8100
tggataaagt tttaaacaga gaggaatctt tgcagctaat ggaccttcta ggtcttgaaa    8160
gg                                                                   8162
```

<210> SEQ ID NO 21
<211> LENGTH: 8151
<212> TYPE: DNA
<213> ORGANISM: Artificial Sequence
<220> FEATURE:
<223> OTHER INFORMATION: Synthetic construct: pJP174 ; pHybE-hCg2,n- V1

<400> SEQUENCE: 21

```
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120 ctggaaagt gatgtcgtgt actggctccg ccttttccc gagggtgggg gagaaccgta      180
tataagtgca gtagtcgccg tgaacgttct ttttcgcaac gggtttgccg ccagaacaca     240
ggtaagtgcc gtgtgtggtt cccgcgggcc tggcctcttt acgggttatg gccttgcgt     300 gccttgaatt acttccacct ggctgcagta cgtgattctt gatcccgagc ttcgggttgg     360
aagtgggtgg gagagttcga ggccttgcgc ttaaggagcc ccttcgcctc gtgcttgagt     420
```

-continued

```
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540
ttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga gcttttggag tacgtcgtct ttaggttggg gggaggggtt   1020
ttatgcgatg gagtttcccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gtttttttct tccatttcag gtgtcgtgag gaattctcta   1200
gagatccctc gacctcgagc atttaaatgc ccgggcgcca ccatggagtt tgggctgagc   1260 tggcttttc ttgtcgcgat tttaaaggt gtccagtgcg catggtatgc cgaaagggat   1320
gctgaaattg agaacgaaaa gctgcgccgg gaggttaaag aactgcggca ggccagcgag   1380
gcagatctcc agccaggaac tattgagtac gaacgccatc gacttacgcg tgcgcaggcc   1440
gacgcacagg aactgaagaa tgccagagac tccgctgaag tggtggaaac cgcattctgt   1500
actttcgtgc tgtcgcggat cgcaggtgaa attgccagta ttctcgacgg gctcccctg   1560 tcggtgcagc ggcgttttcc ggaactggaa accgacatg ttgatttcct gaaacgggat   1620
atcatcaaag ccatgaacaa agcagccgcg ctggatgaac tgataccggg gttgctgagt   1680
gaatatatcg aacagtcagg ttaacaggct gcggcatttt gtccgcgccg ggcttcgctc   1740
actgttcagg ccggagccac agaccgccgt tgaatgggcg gatgctaatt actatctccc   1800
gaaagaatcc gcataccagg aagggcgctg gaaacactg cccttcagc gggccatcat   1860 gaatgcgatg ggcagcgact acatccgtga ggtgaatgtg gtgaagtctg cccgtgtcgg   1920
ttattccaaa atgctgctgg gtgtttatgc ctactttata gagcataagc agcgcaacac   1980
ccttatctgg ttgccgacgg atggtgatgc cgagaacttt atgaaaaccc acgttgagcc   2040
gactattcgt gatattccgt cgctgctggc gctggccccg tggtatggca aaaagcaccg   2100
ggataacacg ctcaccatga agcgtttcac taatgggcgt ggcttctggt gcctgggcgg   2160
taaagcggca aaaactacc gtgaaaagtc ggtggatgtg gcgggttatg atgaacttgc   2220
tgcttttgat gatgatattg aacaggaagg ctctccgacg ttcctgggtg acaagcgcgt   2280
cgaccaaggg cccatcggtc ttccccctgg cgccctgctc tagaagcacc tccgagagca   2340
cagcggccct gggctgcctg gtcaaggact acttccccga accggtgacg gtgtcgtgga   2400
actcaggcgc tctgaccagc ggcgtgcaca ccttcccagc tgtcctgcag tcctcaggac   2460
tctactccct cagcagcgtg gtgaccgtgc cctccagcaa cttcggcacc cagacctaca   2520
catgcaacgt agatcacaag cccagcaaca ccaaggtgga caagacagtt gagcgcaaat   2580
gttgtgtcga gtgcccaccg tgcccagcac cacctgtggc aggaccgtca gtcttcctct   2640
tccccccaaa acccaaggac accctcatga tctcccggac ccctgaggtc acgtgcgtgg   2700
tggtggacgt gagccacgaa gacccgagg tccagttcaa ctggtacgtg acggcgtgg   2760 aggtgcataa tgccaagaca aagccacggg aggagcagtt caacagcacg ttccgtgtgg   2820
```

```
tcagcgtcct caccgttgtg caccaggact ggctgaacgg caaggagtac aagtgcaagg    2880
tctccaacaa aggcctccca gcccccatcg agaaaaccat ctccaaaacc aagggcagc    2940 cccgagaacc acaggtgtac accctgcccc catcccggga ggagatgacc aagaaccagg   3000
tcagcctgac ctgcctggtc aaaggcttct accccagcga catcgccgtg gagtgggaga   3060
gcaatgggca gccggagaac aactacaaga ccacacctcc catgctggac tccgacggct   3120
ccttcttcct ctacagcaag ctcaccgtgg acaagagcag gtggcagcag gggaacgtct   3180
tctcatgctc cgtgatgcat gaggctctgc acaaccacta cacgcagaag agcctctccc   3240
tgtctccggg taaatgacgc ggccgctcga ggccggcaag gccggatccc ccgacctcga   3300
cctctggcta ataaaggaaa tttattttca ttgcaatagt gtgttggaat tttttgtgtc   3360
tctcactcgg aaggacatat gggagggcaa atcatttggt cgagatccct cggagatctc   3420
tagctagagg atcgatcccc gccccggacg aactaaacct gactacgaca tctctgcccc   3480
ttcttcgcgg ggcagtgcat gtaatccctt cagttggttg gtacaacttg ccaactgggc   3540
cctgttccac atgtgacacg gggggggacc aaacacaaag gggttctctg actgtagttg   3600
acatccttat aaatggatgt gcacatttgc caacactgag tggctttcat cctggagcag   3660
actttgcagt ctgtggactg caacacaaca ttgcctttat gtgtaactct tggctgaagc   3720
tcttacacca atgctggggg acatgtacct cccaggggcc caggaagact acgggaggct   3780
acaccaacgt caatcagagg ggcctgtgta gctaccgata gcggaccct caagagggca    3840 ttagcaatag tgtttataag gcccccttgt taacccctaaa cgggtagcat atgcttcccg   3900
ggtagtagta tatactatcc agactaaccc taattcaata gcatatgtta cccaacggga   3960
agcatatgct atcgaattag ggttagtaaa agggtcctaa ggaacagcga tatctcccac   4020
cccatgagct gtcacggttt tatttacatg gggtcaggat tccacgaggg tagtgaacca   4080
ttttagtcac aagggcagtg gctgaagatc aaggagcggg cagtgaactc tcctgaatct   4140
tcgcctgctt cttcattctc cttcgtttag ctaatagaat aactgctgag ttgtgaacag   4200
taaggtgtat gtgaggtgct cgaaaacaag gtttcaggtg acgccccag aataaaattt    4260 ggacgggggg ttcagtggtg gcattgtgct atgacaccaa tataaccctc acaaacccct   4320
tgggcaataa atactagtgt aggaatgaaa cattctgaat atctttaaca atagaaatcc   4380
atggggtggg gacaagccgt aaagactgga tgtccatctc acacgaattt atggctatgg   4440
gcaacacata atcctagtgc aatatgatac tgggtttatt aagatgtgtc ccaggcaggg   4500
accaagacag gtgaaccatg ttgttacact ctatttgtaa caagggaaa gagagtggac    4560 gccgacagca gcggactcca ctggttgtct ctaacacccc cgaaaattaa acggggctcc   4620
acgccaatgg ggcccataaa caaagacaag tggccactct ttttttttgaa attgtggagt   4680 gggggcacgc gtcagccccc acacgccgcc ctgcggtttt ggactgtaaa ataagggtgt   4740
aataacttgg ctgattgtaa ccccgctaac cactgcggtc aaaccacttg cccacaaaac   4800
cactaatggc accccgggga atacctgcat aagtaggtgg gcgggccaag ataggggcgc   4860
gattgctgcg atctggagga caaattacac acacttgcgc ctgagcgcca agcacagggt   4920
tgttggtcct catattcacg aggtcgctga gagcacggtg ggctaatgtt gccatgggta   4980
gcatatacta cccaaatatc tggatagcat atgctatcct aatctatatc tgggtagcat   5040
aggctatcct aatctatatc tgggtagcat atgctatcct aatctatatc tgggtagtat   5100
atgctatcct aatttatatc tgggtagcat aggctatcct aatctatatc tgggtagcat   5160
atgctatcct aatctatatc tgggtagtat atgctatcct aatctgtatc cgggtagcat   5220
```

```
atgctatcct aatagagatt agggtagtat atgctatcct aatttatatc tgggtagcat      5280
atactaccca aatatctgga tagcatatgc tatcctaatc tatatctggg tagcatatgc      5340
tatcctaatc tatatctggg tagcataggc tatcctaatc tatatctggg tagcatatgc      5400
tatcctaatc tatatctggg tagtatatgc tatcctaatt tatatctggg tagcataggc      5460
tatcctaatc tatatctggg tagcatatgc tatcctaatc tatatctggg tagtatatgc      5520
tatcctaatc tgtatccggg tagcatatgc tatcctcatg ataagctgtc aaacatgaga      5580
attttcttga agacgaaagg gcctcgtgat acgcctattt ttataggtta atgtcatgat      5640
aataatggtt tcttagacgt caggtggcac ttttcgggga atgtgcgcg gaaccoctat      5700 ttgtttattt ttctaaatac attcaaatat gtatccgctc atgagacaat aaccctgata      5760
aatgcttcaa taatattgaa aaggaagag tatgagtatt caacatttcc gtgtcgccct       5820
tattcccttt tttgcggcat tttgccttcc tgttttgct cacccagaaa cgctggtgaa       5880
agtaaaagat gctgaagatc agttgggtgc acgagtgggt tacatcgaac tggatctcaa      5940
cagcggtaag atccttgaga gttttcgccc cgaagaacgt tttccaatga tgagcacttt      6000
taaagttctg ctatgtggcg cggtattatc ccgtgttgac gccgggcaag agcaactcgg      6060
tcgccgcata cactattctc agaatgactt ggttgagtac tcaccagtca cagaaaagca      6120
tcttacggat ggcatgacag taagagaatt atgcagtgct gccataacca tgagtgataa      6180
cactgcggcc aacttacttc tgacaacgat cggaggaccg aaggagctaa ccgcttttt       6240 gcacaacatg ggggatcatg taactcgcct tgatcgttgg gaaccggagc tgaatgaagc      6300
cataccaaac gacgagcgtg acaccacgat gcctgcagca atggcaacaa cgttgcgcaa      6360
actattaact ggcgaactac ttactctagc ttcccggcaa caattaatag actggatgga      6420
ggcggataaa gttgcaggac cacttctgcg ctcggccctt ccggctggct ggtttattgc      6480
tgataaatct ggagccggtg agcgtgggtc tcgcggtatc attgcagcac tggggccaga      6540
tggtaagccc tcccgtatcg tagttatcta cacgacgggg agtcaggcaa ctatggatga      6600
acgaaataga cagatcgctg agataggtgc ctcactgatt aagcattggt aactgtcaga      6660
ccaagtttac tcatatatac tttagattga tttaaaactt cattttttaat ttaaaaggat     6720 ctaggtgaag atccttttg ataatctcat gaccaaaatc ccttaacgtg agttttcgtt       6780
ccactgagcg tcagacccog tagaaaagat caaaggatct tcttgagatc cttttttct       6840 gcgcgtaatc tgctgcttgc aaacaaaaaa accaccgcta ccagcggtgg tttgtttgcc      6900
ggatcaagag ctaccaactc tttttccgaa ggtaactggc ttcagcagag cgcagatacc      6960
aaatactgtt cttctagtgt agccgtagtt aggccaccac ttcaagaact ctgtagcacc      7020
gcctacatac ctcgctctgc taatcctgtt accagtggct gctgccagtg gcgataagtc      7080
gtgtcttacc gggttggact caagacgata gttaccggat aaggcgcagc ggtcgggctg      7140
aacggggggt tcgtgcacac agcccagctt ggagcgaacg acctacaccg aactgagata      7200
cctacagcgt gagctatgag aaagcgccac gcttcccgaa gggagaaagg cggacaggta      7260
tccggtaagc ggcagggtcg gaacaggaga gcgcacgagg gagcttccag ggggaaacgc      7320
ctggtatctt tatagtcctg tcgggtttcg ccacctctga cttgagcgtc gatttttgtg      7380
atgctcgtca gggggggcgga gcctatggaa aaacgccagc aacgcggcct ttttacggtt     7440
cctggccttt tgctggcctt ttgctcacat gttctttcct gcgttatccc ctgattctgt      7500
ggataaccgt attaccgcct ttgagtgagc tgataccgct cgccgcagcc gaacgaccga      7560
gcgcagcgag tcagtgagcg aggaagcgga agagcgccca atacgcaaac cgcctctccc      7620
```

```
cgcgcgttgg ccgattcatt aatgcagctg gcacgacagg tttcccgact ggaaagcggg      7680
cagtgagcgc aacgcaatta atgtgagtta gctcactcat taggcacccc aggctttaca      7740
ctttatgctt ccggctcgta tgttgtgtgg aattgtgagc ggataacaat ttcacacagg      7800
aaacagctat gaccatgatt acgccaagct ctagctagag gtcgagtccc tccccagcag      7860
gcagaagtat gcaaagcatg catctcaatt agtcagcaac catagtcccg cccctaactc      7920
cgcccatccc gcccctaact ccgcccagtt ccgcccattc tccgcccat ggctgactaa       7980 tttttttat ttatgcagag gccgaggccg cctcggcctc tgagctattc cagaagtagt       8040
gaggaggctt ttttggaggc ctaggctttt gcaaaaagct ttgcaaagat ggataaagtt      8100
ttaaacagag aggaatcttt gcagctaatg gaccttctag gtcttgaaag g               8151
```

<210> SEQ ID NO 22  
<211> LENGTH: 8151  
<212> TYPE: DNA  
<213> ORGANISM: Artificial Sequence  
<220> FEATURE:  
<223> OTHER INFORMATION: Synthetic construct: pJP187 ; pHybE-hCg2,n- V2

<400> SEQUENCE: 22

```
agtgggaatt ggctccggtg cccgtcagtg ggcagagcgc acatcgccca cagtccccga        60
gaagttgggg ggaggggtcg gcaattgaac cggtgcctag agaaggtggc gcggggtaaa       120
ctgggaaagt gatgtcgtgt actggctccg ccttttttcc gagggtgggg gagaaccgta      180
tataagtgca gtagtcgccg tgaacgttct ttttcgcaac gggtttgccg ccagaacaca      240
ggtaagtgcc gtgtgtggtt cccgcgggcc tggcctcttt acgggttatg gcccttgcgt      300
gccttgaatt acttccacct ggctgcagta cgtgattctt gatcccgagc ttcgggttgg      360
aagtgggtgg gagagttcga ggccttgcgc ttaaggagcc ccttcgcctc gtgcttgagt      420
tgaggcctgg cctgggcgct ggggccgccg cgtgcgaatc tggtggcacc ttcgcgcctg      480
tctcgctgct ttcgataagt ctctagccat ttaaaatttt tgatgacctg ctgcgacgct      540
ttttttctgg caagatagtc ttgtaaatgc gggccaagat ctgcacactg gtatttcggt      600
ttttgggccc gcgggcggcg acggggcccg tgcgtcccag cgcacatgtt cggcgaggcg      660
gggcctgcga gcgcggccac cgagaatcgg acggggggtag tctcaagctg gccggcctgc     720
tctggtgcct ggcctcgcgc cgccgtgtat cgccccgccc tgggcggcaa ggctggcccg      780
gtcggcacca gttgcgtgag cggaaagatg gccgcttccc ggccctgctg cagggagctc      840
aaaatggagg acgcggcgct cgggagagcg ggcgggtgag tcacccacac aaaggaaaag      900
ggcctttccg tcctcagccg tcgcttcatg tgactccacg gagtaccggg cgccgtccag      960
gcacctcgat tagttctcga gcttttggag tacgtcgtct ttaggttggg gggaggggtt     1020
ttatgcgatg gagtttcccc acactgagtg gtggagact gaagttaggc cagcttggca      1080
cttgatgtaa ttctccttgg aatttgccct ttttgagttt ggatcttggt tcattctcaa     1140
gcctcagaca gtggttcaaa gtttttttct tccatttcag gtgtcgtgag gaattctcta     1200
gagatccctc gacctcgaga tccattgtgc ccgggcgcca ccatggagtt tgggctgagc     1260 tggcttttc ttgtcgcgat tttaaaaggt gtccagtgcg catggtatgc gaaagggat       1320 gctgaaattg agaacgaaaa gctgcgccgg gaggttgaag aactgcggca ggccagcgag     1380
gcagatctcc agccaggaac tattgagtac gaacgccatc gacttacgcg tgcgcaggcc     1440
gacgcacagg aactgaagaa tgccagagac tccgctgaag tggtggaaac cgcattctgt     1500
actttcgtgc tgtcgcggat cgcaggtgaa attgccagta ttctcgacgg gctcccctg     1560
```

```
tcggtgcagc ggcgttttcc ggaactggaa aaccgacatg ttgatttcct gaaacgggat    1620
atcatcaaag ccatgaacaa agcagccgcg ctggatgaac tgataccggg gttgctgagt    1680
gaatatatcg aacagtcagg ttaacaggct gcggcatttt gtccgcgccg ggcttcgctc    1740
actgttcagg ccggagccac agaccgccgt tgaatgggcg gatgctaatt actatctccc    1800
gaaagaatcc gcataccagg aagggcgctg gaaacactg  ccctttcagc gggccatcat    1860
gaatgcgatg ggcagcgact acatccgtga ggtgaatgtg gtgaagtctg cccgtgtcgg    1920
ttattccaaa atgctgctgg gtgtttatgc ctactttata gagcataagc agcgcaacac    1980
ccttatctgg ttgccgacgg atggtgatgc cgagaacttt atgaaaaccc acgttgagcc    2040
gactattcgt gatattccgt cgctgctggc gctggccccg tggtatggca aaaagcaccg    2100
ggataacacg ctcaccatga agcgtttcac taatgggcgt ggcttctggt gcctgggcgg    2160
taaagcggca aaaaactacc gtgaaaagtc ggtggatgtg gcgggttatg atgaacttgc    2220
tgcttttgat gatgatattg aacaggaagg ctctccgacg ttcctgggtg acaagcgcgt    2280
cgaccaaggg cccatcggtc ttccccctgg cgccctgctc tagaagcacc tccgagagca    2340
cagcggccct gggctgcctg gtcaaggact acttccccga accggtgacg gtgtcgtgga    2400
actcaggcgc tctgaccagc ggcgtgcaca ccttcccagc tgtcctgcag tcctcaggac    2460
tctactccct cagcagcgtg gtgaccgtgc cctccagcaa cttcggcacc cagacctaca    2520
catgcaacgt agatcacaag cccagcaaca ccaaggtgga caagacagtt gagcgcaaat    2580
gttgtgtcga gtgcccaccg tgcccagcac cacctgtggc aggaccgtca gtcttcctct    2640
tccccccaaa acccaaggac accctcatga tctcccggac ccctgaggtc acgtgcgtgg    2700
tggtggacgt gagccacgaa gaccccgagg tccagttcaa ctggtacgtg gacggcgtgg    2760
aggtgcataa tgccaagaca aagccacggg aggagcagtt caacagcacg ttccgtgtgg    2820
tcagcgtcct caccgttgtg caccaggact ggctgaacgg caaggagtac aagtgcaagg    2880
tctccaacaa aggcctccca gcccccatcg agaaaaccat ctccaaaacc aaagggcagc    2940
cccgagaacc acaggtgtac accctgcccc catcccggga ggagatgacc aagaaccagg    3000
tcagcctgac ctgcctggtc aaaggcttct accccagcga catcgccgtg gagtgggaga    3060
gcaatgggca gccggagaac aactacaaga ccacacctcc catgctggac tccgacggct    3120
ccttcttcct ctacagcaag ctcaccgtgg acaagagcag gtggcagcag gggaacgtct    3180
tctcatgctc cgtgatgcat gaggctctgc acaaccacta cacgcagaag agcctctccc    3240
tgtctccggg taaatgacgc ggccgctcga ggccggcaag gccggatccc ccgacctcga    3300
cctctggcta ataaaggaaa tttattttca ttgcaatagt gtgttggaat tttttgtgtc    3360
tctcactcgg aaggacatat gggagggcaa atcatttggt cgagatccct cggagatctc    3420
tagctagagg atcgatcccc gccccggacg aactaaacct gactacgaca tctctgcccc    3480
ttcttcgcgg ggcagtgcat gtaatccctt cagttggttg gtacaacttg ccaactgggc    3540
cctgttccac atgtgacacg gggggggacc aaacacaaag gggttctctg actgtagttg    3600
acatccttat aaatggatgt gcacatttgc caacactgag tggctttcat cctggagcag    3660
actttgcagt ctgtgactg  caacacaaca ttgcctttat gtgtaactct tggctgaagc    3720
tcttacacca atgctggggg acatgtacct cccaggggcc caggaagact acgggaggct    3780
acaccaacgt caatcagagg ggcctgtgta gctaccgata gcggaccct  caagagggca    3840 ttagcaatag tgtttataag gccccttgt  taaccctaaa cgggtagcat atgcttcccg    3900
ggtagtagta tatactatcc agactaaccc taattcaata gcatatgtta cccaacggga    3960
```

```
agcatatgct atcgaattag ggttagtaaa agggtcctaa ggaacagcga tatctcccac   4020
cccatgagct gtcacggttt tatttacatg gggtcaggat tccacgaggg tagtgaacca   4080
ttttagtcac aagggcagtg gctgaagatc aaggagcggg cagtgaactc tcctgaatct   4140
tcgcctgctt cttcattctc cttcgtttag ctaatagaat aactgctgag ttgtgaacag   4200
taaggtgtat gtgaggtgct cgaaaacaag gtttcaggtg acgccccag aataaaattt    4260 ggacgggggg ttcagtggtg gcattgtgct atgacaccaa tataaccctc acaaacccct   4320
tgggcaataa atactagtgt aggaatgaaa cattctgaat atctttaaca atagaaatcc   4380
atggggtggg gacaagccgt aaagactgga tgtccatctc acacgaattt atggctatgg   4440
gcaacacata atcctagtgc aatatgatac tggggttatt aagatgtgtc ccaggcaggg   4500
accaagacag gtgaaccatg ttgttacact ctatttgtaa caaggggaaa gagagtggac   4560
gccgacagca gcggactcca ctggttgtct ctaacacccc cgaaaattaa acggggctcc   4620
acgccaatgg ggcccataaa caaagacaag tggccactct tttttttgaa attgtggagt   4680
gggggcacgc gtcagccccc acacgccgcc ctgcggtttt ggactgtaaa ataagggtgt   4740
aataacttgg ctgattgtaa ccccgctaac cactgcggtc aaaccacttg cccacaaaac   4800
cactaatggc accccgggga atacctgcat aagtaggtgg gcgggccaag ataggggcgc   4860
gattgctgcg atctggagga caaattacac acacttgcgc ctgagcgcca agcacagggt   4920
tgttggtcct catattcacg aggtcgctga gagcacggtg ggctaatgtt gccatgggta   4980
gcatatacta cccaaatatc tggatagcat atgctatcct aatctatatc tgggtagcat   5040
aggctatcct aatctatatc tgggtagcat atgctatcct aatctatatc tgggtagtat   5100
atgctatcct aatttatatc tgggtagcat aggctatcct aatctatatc tgggtagcat   5160
atgctatcct aatctatatc tgggtagtat atgctatcct aatctgtatc cgggtagcat   5220
atgctatcct aatagagatt agggtagtat atgctatcct aatttatatc tgggtagcat   5280
atactaccca aatatctgga tagcatatgc tatcctaatc tatatctggg tagcatatgc   5340
tatcctaatc tatatctggg tagcataggc tatcctaatc tatatctggg tagcatatgc   5400
tatcctaatc tatatctggg tagtatatgc tatcctaatt tatatctggg tagcataggc   5460
tatcctaatc tatatctggg tagcatatgc tatcctaatc tatatctggg tagtatatgc   5520
tatcctaatc tgtatccggg tagcatatgc tatcctcatg ataagctgtc aaacatgaga   5580
attttcttga agacgaaagg gcctcgtgat acgcctattt ttataggtta atgtcatgat   5640
aataatggtt tcttagacgt caggtggcac ttttcgggga atgtgcgcg gaaccctat    5700 ttgtttattt ttctaaatac attcaaatat gtatccgctc atgagacaat aaccctgata   5760
aatgcttcaa taatattgaa aaaggaagag tatgagtatt caacatttcc gtgtcgccct   5820
tattcccttt tttgcggcat tttgccttcc tgttttgct cacccagaaa cgctggtgaa     5880
agtaaaagat gctgaagatc agttgggtgc acgagtgggt tacatcgaac tggatctcaa   5940
cagcggtaag atccttgaga gttttcgccc cgaagaacgt tttccaatga tgagcacttt   6000
taaagttctg ctatgtggcg cggtattatc ccgtgttgac gccgggcaag agcaactcgg   6060
tcgccgcata cactattctc agaatgactt ggttgagtac tcaccagtca cagaaaagca   6120
tcttacggat ggcatgacag taagagaatt atgcagtgct gccataacca tgagtgataa   6180
cactgcggcc aacttacttc tgacaacgat cggaggaccg aaggagctaa ccgcttttt    6240 gcacaacatg gggatcatg taactcgcct tgatcgttgg gaaccggagc tgaatgaagc    6300
cataccaaac gacgagcgtg acaccacgat gcctgcagca atggcaacaa cgttgcgcaa   6360
```

| | |
|---|---|
| actattaact ggcgaactac ttactctagc ttcccggcaa caattaatag actggatgga | 6420 |
| ggcggataaa gttgcaggac cacttctgcg ctcggcccct tccggctggct ggtttattgc | 6480 |
| tgataaatct ggagccggtg agcgtgggtc tcgcggtatc attgcagcac tggggccaga | 6540 |
| tggtaagccc tcccgtatcg tagttatcta cacgacgggg agtcaggcaa ctatggatga | 6600 |
| acgaaataga cagatcgctg ataggtgc ctcactgatt aagcattggt aactgtcaga | 6660 |
| ccaagtttac tcatatatac tttagattga tttaaaactt cattttaat ttaaaaggat | 6720 |
| ctaggtgaag atccttttg ataatctcat gaccaaaatc ccttaacgtg agttttcgtt | 6780 |
| ccactgagcg tcagaccccg tagaaaagat caaaggatct tcttgagatc ctttttttct | 6840 |
| gcgcgtaatc tgctgcttgc aaacaaaaaa accaccgcta ccagcggtgg tttgtttgcc | 6900 |
| ggatcaagag ctaccaactc tttttccgaa ggtaactggc ttcagcagag cgcagatacc | 6960 |
| aaatactgtt cttctagtgt agccgtagtt aggccaccac ttcaagaact ctgtagcacc | 7020 |
| gcctacatac ctcgctctgc taatcctgtt accagtggct gctgccagtg gcgataagtc | 7080 |
| gtgtcttacc gggttggact caagacgata gttaccggat aaggcgcagc ggtcgggctg | 7140 |
| aacggggggt tcgtgcacac agcccagctt ggagcgaacg acctacaccg aactgagata | 7200 |
| cctacagcgt gagctatgag aaagcgccac gcttcccgaa gggagaaagg cggacaggta | 7260 |
| tccggtaagc ggcagggtcg gaacaggaga gcgcacgagg gagcttccag ggggaaacgc | 7320 |
| ctggtatctt tatagtcctg tcgggtttcg ccacctctga cttgagcgtc gatttttgtg | 7380 |
| atgctcgtca gggggggga gcctatggaa aaacgccagc aacgcggcct ttttacggtt | 7440 |
| cctggccttt tgctggcctt ttgctcacat gttctttcct gcgttatccc ctgattctgt | 7500 |
| ggataaccgt attaccgcct ttgagtgagc tgataccgct cgccgcagcc gaacgaccga | 7560 |
| gcgcagcgag tcagtgagcg aggaagcgga agagcgccca atacgcaaac cgcctctccc | 7620 |
| cgcgcgttgg ccgattcatt aatgcagctg gcacgacagg tttcccgact ggaaagcggg | 7680 |
| cagtgagcgc aacgcaatta atgtgagtta gctcactcat taggcacccc aggctttaca | 7740 |
| ctttatgctt ccggctcgta tgttgtgtgg aattgtgagc ggataacaat ttcacacagg | 7800 |
| aaacagctat gaccatgatt acgccaagct ctagctagag gtcgagtccc tccccagcag | 7860 |
| gcagaagtat gcaaagcatg catctcaatt agtcagcaac catagtcccg cccctaactc | 7920 |
| cgcccatccc gcccctaact ccgcccagtt ccgcccattc tccgccccat ggctgactaa | 7980 |
| ttttttttat ttatgcagag gccgaggccg cctcggcctc tgagctattc cagaagtagt | 8040 |
| gaggaggctt ttttggaggc ctaggctttt gcaaaaagct ttgcaaagat ggataaagtt | 8100 |
| ttaaacagag aggaatcttt gcagctaatg gaccttctag gtcttgaaag g | 8151 |

<210> SEQ ID NO 23
<211> LENGTH: 8151
<212> TYPE: DNA
<213> ORGANISM: Artificial Sequence
<220> FEATURE:
<223> OTHER INFORMATION: Synthetic construct: pJP181 ; pHybE-hCg2,n+ V1

<400> SEQUENCE: 23

| | |
|---|---|
| agtgggaatt ggctccggtg cccgtcagtg ggcagagcgc acatcgccca cagtccccga | 60 |
| gaagttgggg ggaggggtcg gcaattgaac cggtgcctag agaaggtggc gcggggtaaa | 120 |
| ctgggaaagt gatgtcgtgt actggctccg cctttttccc gagggtgggg gagaaccgta | 180 |
| tataagtgca gtagtcgccg tgaacgttct ttttcgcaac gggtttgccg ccagaacaca | 240 |
| ggtaagtgcc gtgtgtggtt cccgcgggcc tggcctcttt acgggttatg gcccttgcgt | 300 |

```
gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540 tttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc      720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcggtgag tcacccacac aaaggaaaag      900
ggcctttccg tcctcagccg tcgcttcatg tgactccacg gagtaccggg cgccgtccag    960
gcacctcgat tagttctcga gcttttggag tacgtcgtct ttaggttggg gggaggggtt    1020
ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gttttttttct tccatttcag gtgtcgtgag gaattctcta    1200
gagatccctc gacctcgagc atttaaatgc ccggcgcca ccatggagtt tgggctgagc      1260 tggcttttc ttgtcgcgat tttaaaggt gtccagtgcg catggtatgc cgaaagggat       1320
gctgaaattg agaacgaaaa gctgcgccgg gaggttgaag aactgcggca ggccagcgag    1380
gcagatctcc agccaggaac tattgagtac gaacgccatc gacttacgcg tgcgcaggcc    1440
gacgcacagg aactgaagaa tgccagagac tccgctgaag tggtggaaac cgcattctgt    1500
actttcgtgc tgtcgcggat cgcaggtgaa attgccagta ttctcgacgg gctcccctg     1560 tcggtgcagc ggcgttttcc ggaactggaa aaccgacatg ttgatttcct gaaacgggat    1620
atcatcaaag ccatgaacaa agcagccgcg ctggatgaac tgataccggg gttgctgagt    1680
gaatatatcg aacagtcagg ttaacaggct gcggcatttt gtccgcgccg gcttcgctc      1740 actgttcagg ccggagccac agaccgccgt tgaatgggcg gatgctaatt actatctccc    1800
gaaagaatcc gcataccagg aagggcgctg ggaaacactg ccctttcagc gggccatcat    1860
gaatgcgatg ggcagcgact acatccgtga ggtgaatgtg gtgaagtctg cccgtgtcgg    1920
ttattccaaa atgctgctgg gtgtttatgc ctactttata gagcataagc agcgcaacac    1980
ccttatctgg ttgccgacgg atggtgatgc cgagaacttt atgaaaaccc acgttgagcc    2040
gactattcgt gatattccgt cgctgctggc gctggcccg tggtatggca aaaagcaccg      2100
ggataacacg ctcaccatga agcgtttcac taatgggcgt ggcttctggt gcctgggcgg    2160
taaagcggca aaaactacc gtgaaaagtc ggtggatgtg gcgggttatg atgaacttgc      2220
tgcttttgat gatgatattg aacaggaagg ctctccgacg ttcctgggtg acaagcgcgt    2280
cgaccaaggg cccatcggtc ttccccctgg cgccctgctc tagaagcacc tccgagagca    2340
cagcggccct gggctgcctg gtcaaggact acttcccga accggtgacg gtgtcgtgga     2400
actcaggcgc tctgaccagc ggcgtgcaca ccttcccagc tgtcctgcag tcctcaggac    2460
tctactccct cagcagcgtg gtgaccgtga cctccagcaa cttcggcacc cagacctaca    2520
catgcaacgt agatcacaag cccagcaaca ccaaggtgga caagacagtt gagcgcaaat    2580
gttgtgtcga gtgcccaccg tgcccagcac cacctgtggc aggaccgtca gtcttcctct    2640
tccccccaaa acccaaggac accctcatga tctcccggac ccctgaggtc acgtgcgtgg    2700
```

```
tggtggacgt gagccacgaa gaccccgagg tccagttcaa ctggtacgtg gacggcatgg    2760
aggtgcataa tgccaagaca agccacgggg aggagcagtt caacagcacg ttccgtgtgg    2820
tcagcgtcct caccgttgtg caccaggact ggctgaacgg caaggagtac aagtgcaagg    2880
tctccaacaa aggcctccca gcccccatcg agaaaaccat ctccaaaacc aaagggcagc    2940
cccgagaacc acaggtgtac accctgcccc catcccggga ggagatgacc aagaaccagg    3000
tcagcctgac ctgcctggtc aaaggcttct accccagcga catcgccgtg gagtgggaga    3060
gcaatgggca gccggagaac aactacaaga ccacacctcc catgctggac tccgacggct    3120
ccttcttcct ctacagcaag ctcaccgtgg acaagagcag gtggcagcag gggaacgtct    3180
tctcatgctc cgtgatgcat gaggctctgc acaaccacta cacgcagaag agcctctccc    3240
tgtctccggg taaatgacgc ggccgctcga ggccggcaag gccggatccc ccgacctcga    3300
cctctggcta ataaggaaa tttattttca ttgcaatagt gtgttggaat ttttgtgtc    3360 tctcactcgg aaggacatat gggagggcaa atcatttggt cgagatccct cggagatctc    3420
tagctagagg atcgatcccc gccccggacg aactaaacct gactacgaca tctctgcccc    3480
ttcttcgcgg ggcagtgcat gtaatccctt cagttggttg gtacaacttg ccaactgggc    3540
cctgttccac atgtgacacg ggggggacc aaacacaaag gggttctctg actgtagttg    3600
acatccttat aaatggatgt gcacatttgc caacactgag tggctttcat cctggagcag    3660
actttgcagt ctgtggactg caacacaaca ttgcctttat gtgtaactct tggctgaagc    3720
tcttacacca atgctggggg acatgtacct cccaggggcc caggaagact acggaggct    3780 acaccaacgt caatcagagg ggcctgtgta gctaccgata agcggaccct caagagggca    3840
ttagcaatag tgtttataag gccccttgt taacctaaa cgggtagcat atgcttcccg    3900
ggtagtagta tatactatcc agactaaccc taattcaata gcatatgtta cccaacggga    3960
agcatatgct atcgaattag ggttagtaaa agggtcctaa ggaacagcga tatctcccac    4020
cccatgagct gtcacggttt tatttacatg gggtcaggat tccacgaggg tagtgaacca    4080
ttttagtcac aagggcagtg gctgaagatc aaggagcggg cagtgaactc tcctgaatct    4140
tcgcctgctt cttcattctc cttcgtttag ctaatagaat aactgctgag ttgtgaacag    4200
taaggtgtat gtgaggtgct cgaaaacaag gtttcaggtg acgccccag aataaaattt    4260 ggacgggggg ttcagtggtg gcattgtgct atgacaccaa tataaccctc acaaaccct    4320 tgggcaataa atactagtgt aggaatgaaa cattctgaat atctttaaca atagaaatcc    4380
atggggtggg gacaagccgt aaagactgga tgtccatctc acacgaattt atggctatgg    4440
gcaacacata atcctagtgc aatatgatac tggggttatt aagatgtgtc ccaggcaggg    4500
accaagacag gtgaaccatg ttgttacact ctatttgtaa caaggggaaa gagagtggac    4560
gccgacagca gcggactcca ctggttgtct ctaacacccc cgaaaattaa acggggctcc    4620
acgccaatgg ggcccataaa caaagacaag tggccactct tttttttgaa attgtggagt    4680 ggggcacgc gtcagccccc acacgccgcc ctgcggtttt ggactgtaaa ataagggtgt    4740
aataacttgg ctgattgtaa ccccgctaac cactgcggtc aaaccacttg cccacaaaac    4800
cactaatggc accccgggga atacctgcat aagtaggtgg gcgggccaag ataggggcgc    4860
gattgctgcg atctggagga caaattacac acacttgcgc ctgagcgcca agcacagggt    4920
tgttggtcct catattcacg aggtcgctga gagcacggtg ggctaatgtt gccatgggta    4980
gcatatacta cccaaaatatc tggatagcat atgctatcct aatctatatc tgggtagcat    5040
aggctatcct aatctatatc tgggtagcat atgctatcct aatctatatc tgggtagtat    5100
```

```
atgctatcct aatttatatc tgggtagcat aggctatcct aatctatatc tgggtagcat   5160
atgctatcct aatctatatc tgggtagtat atgctatcct aatctgtatc cgggtagcat   5220
atgctatcct aatagagatt agggtagtat atgctatcct aatttatatc tgggtagcat   5280
atactaccca aatatctgga tagcatatgc tatcctaatc tatatctggg tagcatatgc   5340
tatcctaatc tatatctggg tagcataggc tatcctaatc tatatctggg tagcatatgc   5400
tatcctaatc tatatctggg tagtatatgc tatcctaatt tatatctggg tagcataggc   5460
tatcctaatc tatatctggg tagcatatgc tatcctaatc tatatctggg tagtatatgc   5520
tatcctaatc tgtatccggg tagcatatgc tatcctcatg ataagctgtc aaacatgaga   5580
attttcttga agacgaaagg gcctcgtgat acgcctattt ttataggtta atgtcatgat   5640
aataatggtt tcttagacgt caggtggcac ttttcgggga atgtgcgcg gaaccsctat    5700 ttgtttattt ttctaaatac attcaaatat gtatccgctc atgagacaat aaccctgata   5760
aatgcttcaa taatattgaa aaggaagag tatgagtatt caacatttcc gtgtcgccct    5820
tattcccttt tttgcggcat tttgccttcc tgttttgct cacccagaaa cgctggtgaa    5880
agtaaaagat gctgaagatc agttgggtgc acgagtgggt tacatcgaac tggatctcaa   5940
cagcggtaag atccttgaga gttttcgccc cgaagaacgt tttccaatga tgagcacttt   6000
taaagttctg ctatgtggcg cggtattatc ccgtgttgac gccgggcaag agcaactcgg   6060
tcgccgcata cactattctc agaatgactt ggttgagtac tcaccagtca cagaaaagca   6120
tcttacggat ggcatgacag taagagaatt atgcagtgct gccataacca tgagtgataa   6180
cactgcggcc aacttacttc tgacaacgat cggaggaccg aaggagctaa ccgctttttt   6240
gcacaacatg ggggatcatg taactcgcct tgatcgttgg gaaccggagc tgaatgaagc   6300
cataccaaac gacgagcgtg acaccacgat gcctgcagca atggcaacaa cgttgcgcaa   6360
actattaact ggcgaactac ttactctagc ttcccggcaa caattaatag actggatgga   6420
ggcggataaa gttgcaggac cacttctgcg ctcggccctt ccggctggct ggtttattgc   6480
tgataaatct ggagccggtg agcgtgggtc tcgcggtatc attgcagcac tggggccaga   6540
tggtaagccc tcccgtatcg tagttatcta cacgacgggg agtcaggcaa ctatggatga   6600
acgaaataga cagatcgctg agataggtgc ctcactgatt aagcattggt aactgtcaga   6660
ccaagtttac tcatatatac tttagattga tttaaaactt cattttttaat ttaaaaggat   6720 ctaggtgaag atcctttttg ataatctcat gaccaaaatc ccttaacgtg agttttcgtt   6780
ccactgagcg tcagaccccg tagaaaagat caaaggatct tcttgagatc ctttttttct   6840
gcgcgtaatc tgctgcttgc aaacaaaaaa accaccgcta ccagcggtgg tttgtttgcc   6900
ggatcaagag ctaccaactc tttttccgaa ggtaactggc ttcagcagag cgcagatacc   6960
aaatactgtt cttctagtgt agccgtagtt aggccaccac ttcaagaact ctgtagcacc   7020
gcctacatac ctcgctctgc taatcctgtt accagtggct gctgccagtg gcgataagtc   7080
gtgtcttacc gggttggact caagacgata gttaccggat aaggcgcagc ggtcgggctg   7140
aacggggggt tcgtgcacac agcccagctt ggagcgaacg acctacaccg aactgagata   7200
cctacagcgt gagctatgag aaagcgccac gcttcccgaa gggagaaagg cggacaggta   7260
tccggtaagc ggcagggtcg gaacaggaga gcgcacgagg gagcttccag ggggaaacgc   7320
ctggtatctt tatagtcctg tcgggtttcg ccacctctga cttgagcgtc gatttttgtg   7380
atgctcgtca ggggggcgga gcctatggaa aaacgccagc aacgcggcct ttttacggtt   7440
cctggccttt tgctggcctt ttgctcacat gttctttcct gcgttatccc ctgattctgt   7500
```

-continued

```
ggataaccgt attaccgcct ttgagtgagc tgataccgct cgccgcagcc gaacgaccga    7560
gcgcagcgag tcagtgagcg aggaagcgga agagcgccca atacgcaaac cgcctctccc    7620
cgcgcgttgg ccgattcatt aatgcagctg cacgacagg tttcccgact ggaaagcggg     7680
cagtgagcgc aacgcaatta atgtgagtta gctcactcat taggcacccc aggctttaca    7740
ctttatgctt ccggctcgta tgttgtgtgg aattgtgagc ggataacaat ttcacacagg    7800
aaacagctat gaccatgatt acgccaagct ctagctagag gtcgagtccc tccccagcag    7860
gcagaagtat gcaaagcatg catctcaatt agtcagcaac catagtcccg ccctaactc     7920 cgcccatccc gcccctaact ccgcccagtt ccgcccattc tccgcccat ggctgactaa     7980 ttttttttat ttatgcagag gccgaggccg cctcggcctc tgagctattc cagaagtagt    8040
gaggaggctt ttttggaggc ctaggctttt gcaaaaagct ttgcaaagat ggataaagtt    8100
ttaaacagag aggaatcttt gcagctaatg gaccttctag gtcttgaaag g             8151
```

<210> SEQ ID NO 24
<211> LENGTH: 8151
<212> TYPE: DNA
<213> ORGANISM: Artificial Sequence
<220> FEATURE:
<223> OTHER INFORMATION: Synthetic construct: pJP186 ; pHybE-hCg2,n+ V2

<400> SEQUENCE: 24

```
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg cctttttccc gagggtgggg gagaaccgta    180
tataagtgca gtagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540 tttttttctgg caagatagtc ttgtaaatgc gggccaagat ctgcacactg gtatttcggt    600 ttttgggcc gcgggcggcg acggggcccg tgcgtcccag cgcacatgtt cggcgaggcg     660
gggcctgcga gcgcggccac cgagaatcgg acggggttag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg gcgggtgag tcacccacac aaaggaaaag    900
ggcctttccg tcctcagccg tcgcttcatg tgactccacg gagtaccggg cgccgtccag    960
gcacctcgat tagttctcga ctttttggag tacgtcgtct ttaggttggg gggaggggtt   1020
ttatgcgatg agtttccccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gttttttttct tccatttcag gtgtcgtgag gaattctcta   1200
gagatccctc gacctcgaga tccattgtgc ccggggccca ccatggagtt gggctgagc    1260 tggcttttttc ttgtcgcgat tttaaaaggt gtccagtgcg catggtatgc cgaaagggat   1320
gctgaaattg agaacgaaaa gctgcgccgg gaggttgaag aactgcggca ggccagcgag   1380
gcagatctcc agccaggaac tattgagtac gaacgccatc gacttacgcg tgcgcaggcc   1440
```

```
gacgcacagg aactgaagaa tgccagagac tccgctgaag tggtggaaac cgcattctgt    1500
actttcgtgc tgtcgcggat cgcaggtgaa attgccagta ttctcgacgg gctcccctg    1560 tcggtgcagc ggcgttttcc ggaactggaa aaccgacatg ttgatttcct gaaacgggat    1620
atcatcaaag ccatgaacaa agcagccgcg ctggatgaac tgataccggg gttgctgagt    1680
gaatatatcg aacagtcagg ttaacaggct gcggcatttt gtccgcgccg ggcttcgctc    1740
actgttcagg ccggagccac agaccgccgt tgaatgggcg gatgctaatt actatctccc    1800
gaaagaatcc gcataccagg aagggcgctg ggaaacactg ccctttcagc gggccatcat    1860
gaatgcgatg ggcagcgact acatccgtga ggtgaatgtg gtgaagtctg cccgtgtcgg    1920
ttattccaaa atgctgctgg gtgtttatgc ctactttata gagcataagc agcgcaacac    1980
ccttatctgg ttgccgacgg atggtgatgc cgagaacttt atgaaaaccc acgttgagcc    2040
gactattcgt gatattccgt cgctgctggc gctggccccg tggtatggca aaaagcaccg    2100
ggataacacg ctcaccatga agcgtttcac taatgggcgt ggcttctggt gcctgggcgg    2160
taaagcggca aaaaactacc gtgaaaagtc ggtggatgtg gcgggttatg atgaacttgc    2220
tgcttttgat gatgatattg aacaggaagg ctctccgacg ttcctgggtg acaagcgcgt    2280
cgaccaaggg cccatcggtc ttccccctgg cgccctgctc tagaagcacc tccgagagca    2340
cagcggccct gggctgcctg gtcaaggact acttccccga accggtgacg gtgtcgtgga    2400
actcaggcgc tctgaccagc ggcgtgcaca ccttcccagc tgtcctacag tcctcaggac    2460
tctactccct cagcagcgtg gtgaccgtaa cctccagcaa cttcggcacc cagacctaca    2520
catgcaacgt agatcacaag cccagcaaca ccaaggtgga caagacagtt gagcgcaaat    2580
gttgtgtcga gtgcccaccg tgcccagcac cacctgtggc aggaccgtca gtcttcctct    2640
tccccccaaa acccaaggac accctcatga tctcccggac ccctgaggtc acgtgcgtgg    2700
tggtggacgt gagccacgaa gaccccgagg tccagttcaa ctggtacgtg gacggcatgg    2760
aggtgcataa tgccaagaca aagccacggg aggagcagtt caacagcacg ttccgtgtgg    2820
tcagcgtcct caccgttgtg caccaggact ggctgaacgg caaggagtac aagtgcaagg    2880
tctccaacaa aggcctccca gcccccatcg agaaaaccat ctccaaaacc aaagggcagc    2940
cccgagaacc acaggtgtac accctgcccc catcccggga ggagatgacc aagaaccagg    3000
tcagcctgac ctgcctggtc aaaggcttct accccagcga catcgccgtg gagtgggaga    3060
gcaatgggca gccggagaac aactacaaga ccacacctcc catgctggac tccgacggct    3120
ccttcttcct ctacagcaag ctcaccgtgg acaagagcag gtggcagcag gggaacgtct    3180
tctcatgctc cgtgatgcat gaggctctgc acaaccacta cacgcagaag agcctctccc    3240
tgtctccggg taaatgacgc ggccgctcga ggccggcaag gccggatccc ccgacctcga    3300
cctctggcta ataaaggaaa tttattttca ttgcaatagt gtgttggaat ttttttgtgtc    3360 tctcactcgg aaggacatat gggagggcaa atcatttggt cgagatccct cggagatctc    3420
tagctagagg atcgatcccc gccccggacg aactaaacct gactacgaca tctctgcccc    3480
ttcttcgcgg ggcagtgcat gtaatccctt cagttggttg gtacaacttg ccaactgggc    3540
cctgttccac atgtgacacg ggggggggacc aaacacaaag gggttctctg actgtagttg    3600
acatccttat aaatggatgt gcacatttgc caacactgag tggctttcat cctggagcag    3660
actttgcagt ctgtggactg caacacaaca ttgcctttat gtgtaactct ggctgaagc    3720 tcttacacca atgctggggg acatgtacct cccaggggcc caggaagact acggggaggct    3780 acaccaacgt caatcagagg ggcctgtgta gctaccgata agcggaccct caagagggca    3840
```

```
ttagcaatag tgtttataag gcccccttgt taaccctaaa cgggtagcat atgcttcccg    3900
ggtagtagta tatactatcc agactaaccc taattcaata gcatatgtta cccaacggga    3960
agcatatgct atcgaattag ggttagtaaa agggtcctaa ggaacagcga tatctcccac    4020
cccatgagct gtcacggttt tatttacatg gggtcaggat tccacgaggg tagtgaacca    4080
ttttagtcac aagggcagtg gctgaagatc aaggagcggg cagtgaactc tcctgaatct    4140
tcgcctgctt cttcattctc cttcgtttag ctaatagaat aactgctgag ttgtgaacag    4200
taaggtgtat gtgaggtgct cgaaaacaag gtttcaggtg acgccccag aataaaattt     4260
ggacgggggg ttcagtggtg gcattgtgct atgacaccaa tataaccctc acaaacccct    4320
tgggcaataa atactagtgt aggaatgaaa cattctgaat atctttaaca atagaaatcc    4380
atggggtggg gacaagccgt aaagactgga tgtccatctc acacgaattt atggctatgg    4440
gcaacacata atcctagtgc aatatgatac tggggttatt aagatgtgtc ccaggcaggg    4500
accaagacag gtgaaccatg ttgttacact ctatttgtaa caaggggaaa gagagtggac    4560
gccgacagca gcggactcca ctggttgtct ctaacacccc cgaaaattaa acggggctcc    4620
acgccaatgg gcccataaa caaagacaag tggccactct tttttttgaa attgtggagt     4680
gggggcacgc gtcagccccc acacgccgcc ctgcggtttt ggactgtaaa ataagggtgt    4740
aataacttgg ctgattgtaa ccccgctaac cactgcggtc aaaccacttg cccacaaaac    4800
cactaatggc accccgggga atacctgcat aagtaggtgg gcgggccaag atagggcgc     4860
gattgctgcg atctggagga caaattacac acacttgcgc ctgagcgcca agcacaggg t   4920
tgttggtcct catattcacg aggtcgctga gagcacggtg ggctaatgtt gccatgggta    4980
gcatatacta cccaaatatc tggatagcat atgctatcct aatctatatc tgggtagcat    5040
aggctatcct aatctatatc tgggtagcat atgctatcct aatctatatc tgggtagtat    5100
atgctatcct aatttatatc tgggtagcat aggctatcct aatctatatc tgggtagcat    5160
atgctatcct aatctatatc tgggtagtat atgctatcct aatctgtatc cgggtagcat    5220
atgctatcct aatagagatt agggtagtat atgctatcct aatttatatc tgggtagcat    5280
atactaccca aatatctgga tagcatatgc tatcctaatc tatatctggg tagcatatgc    5340
tatcctaatc tatatctggg tagcataggc tatcctaatc tatatctggg tagcatatgc    5400
tatcctaatc tatatctggg tagtatatgc tatcctaatt tatatctggg tagcataggc    5460
tatcctaatc tatatctggg tagcatatgc tatcctaatc tatatctggg tagtatatgc    5520
tatcctaatc tgtatccggg tagcatatgc tatcctcatg ataagctgtc aaacatgaga    5580
attttcttga agacgaaagg gcctcgtgat acgcctattt ttataggtta atgtcatgat    5640
aataatggtt tcttagacgt caggtggcac ttttcgggga atgtgcgcg gaaccc ctat    5700
ttgtttattt ttctaaatac attcaaatat gtatccgctc atgagacaat aaccctgata    5760
aatgcttcaa taatattgaa aaaggaagag tatgagtatt caacatttcc gtgtcgccct    5820
tattcccttt tttgcggcat tttgccttcc tgttttt gct cacccagaaa cgctggtgaa    5880
agtaaaagat gctgaagatc agttgggtgc acgagtgggt tacatcgaac tggatctcaa    5940
cagcggtaag atccttgaga gttttcgccc cgaagaacgt tttccaatga tgagcacttt    6000
taaagttctg ctatgtggcg cggtattatc ccgtgttgac gccgggcaag agcaactcgg    6060
tcgccgcata cactattctc agaatgactt ggttgagtac tcaccagtca cagaaaagca    6120
tcttacggat ggcatgacag taagagaatt atgcagtgct gccataacca tgagtgataa    6180
cactgcggcc aacttacttc tgacaacgat cggaggaccg aaggagctaa ccgcttt ttt   6240
```

```
gcacaacatg ggggatcatg taactcgcct tgatcgttgg gaaccggagc tgaatgaagc    6300
cataccaaac gacgagcgtg acaccacgat gcctgcagca atggcaacaa cgttgcgcaa    6360
actattaact ggcgaactac ttactctagc ttcccggcaa caattaatag actggatgga    6420
ggcggataaa gttgcaggac cacttctgcg ctcggccctt ccggctggct ggtttattgc    6480
tgataaatct ggagccggtg agcgtgggtc tcgcggtatc attgcagcac tggggccaga    6540
tggtaagccc tcccgtatcg tagttatcta cacgacgggg agtcaggcaa ctatggatga    6600
acgaaataga cagatcgctg agataggtgc ctcactgatt aagcattggt aactgtcaga    6660
ccaagtttac tcatatatac tttagattga tttaaaactt cattttttaat ttaaaaggat    6720 ctaggtgaag atcctttttg ataatctcat gaccaaaatc ccttaacgtg agttttcgtt    6780
ccactgagcg tcagaccccg tagaaaagat caaaggatct tcttgagatc cttttttttct    6840 gcgcgtaatc tgctgcttgc aaacaaaaaa accaccgcta ccagcggtgg tttgtttgcc    6900
ggatcaagag ctaccaactc tttttccgaa ggtaactggc ttcagcagag cgcagatacc    6960
aaatactgtt cttctagtgt agccgtagtt aggccaccac ttcaagaact ctgtagcacc    7020
gcctacatac ctcgctctgc taatcctgtt accagtggct gctgccagtg gcgataagtc    7080
gtgtcttacc gggttggact caagacgata gttaccggat aaggcgcagc ggtcgggctg    7140
aacggggggt tcgtgcacac agcccagctt ggagcgaacg acctacaccg aactgagata    7200
cctacagcgt gagctatgag aaagcgccac gcttcccgaa gggagaaagg cggacaggta    7260
tccggtaagc ggcagggtcg gaacaggaga gcgcacgagg gagcttccag ggggaaacgc    7320
ctggtatctt tatagtcctg tcgggtttcg ccacctctga cttgagcgtc gatttttgtg    7380
atgctcgtca gggggggcgga gcctatggaa aaacgccagc aacgcggcct ttttacggtt    7440
cctggccttt tgctggcctt ttgctcacat gttctttcct gcgttatccc ctgattctgt    7500
ggataaccgt attaccgcct ttgagtgagc tgataccgct cgccgcagcc gaacgaccga    7560
gcgcagcgag tcagtgagcg aggaagcgga agagcgccca atacgcaaac cgcctctccc    7620
cgcgcgttgg ccgattcatt aatgcagctg gcacgacagg tttcccgact ggaaagcggg    7680
cagtgagcgc aacgcaatta atgtgagtta gctcactcat taggcacccc aggctttaca    7740
ctttatgctt ccggctcgta tgttgtgtgg aattgtgagc ggataacaat ttcacacagg    7800
aaacagctat gaccatgatt acgccaagct ctagctagag gtcgagtccc tccccagcag    7860
gcagaagtat gcaaagcatg catctcaatt agtcagcaac catagtcccg cccctaactc    7920
cgcccatccc gcccctaact ccgcccagtt ccgcccattc tccgccccat ggctgactaa    7980
ttttttttat ttatgcagag gccgaggccg cctcggcctc tgagctattc cagaagtagt    8040
gaggaggctt ttttggaggc ctaggctttt gcaaaaagct ttgcaaagat ggataaagtt    8100
ttaaacagag aggaatcttt gcagctaatg gaccttctag gtcttgaaag g             8151
```

<210> SEQ ID NO 25
<211> LENGTH: 8153
<212> TYPE: DNA
<213> ORGANISM: Artificial Sequence
<220> FEATURE:
<223> OTHER INFORMATION: Synthetic construct: pJP175 ; pHybE-hCg4 V1

<400> SEQUENCE: 25

```
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg cctttttccc gagggtgggg gagaaccgta     180
```

```
tataagtgca gtagtcgccg tgaacgttct ttttcgcaac gggtttgccg ccagaacaca    240
ggtaagtgcc gtgtgtggtt cccgcgggcc tggcctcttt acgggttatg cccttgcgt    300 gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540
ttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
ggcctttccg tcctcagccg tcgcttcatg tgactccacg gagtaccggg cgccgtccag    960
gcacctcgat tagttctcga cttttggag tacgtcgtct ttaggttggg gggaggggtt    1020
ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gtttttttct tccatttcag gtgtcgtgag gaattctcta    1200
gagatccctc gacctcgagc atttaaatgc ccgggcgcca ccatggagtt tgggctgagc    1260
tggctttttc ttgtcgcgat tttaaaggt gtccagtgcg catggtatgc cgaaagggat    1320
gctgaaattg agaacgaaaa gctgcgccgg gaggttgaag aactgcggca ggccagcgag    1380
gcagatctcc agccaggaac tattgagtac gaacgccatc gacttacgcg tgcgcaggcc    1440
gacgcacagg aactgaagaa tgccagagac tccgctgaag tggtggaaac cgcattctgt    1500
actttcgtgc tgtcgcggat cgcaggtgaa attgccagta ttctcgacgg gctcccctg    1560 tcggtgcagc ggcgttttcc ggaactggaa aaccgacatg ttgatttcct gaaacgggat    1620
atcatcaaag ccatgaacaa agcagccgcg ctggatgaac tgataccggg gttgctgagt    1680
gaatatatcg aacagtcagg ttaacaggct gcggcatttt gtccgcgccg ggcttcgctc    1740
actgttcagg ccggagccac agaccgccgt tgaatgggcg gatgctaatt actatctccc    1800
gaaagaatcc gcataccagg aagggcgctg ggaaacactg ccctttcagc gggccatcat    1860
gaatgcgatg ggcagcgact acatccgtga ggtgaatgtg gtgaagtctg cccgtgtcgg    1920
ttattccaaa atgctgctgg gtgtttatgc ctactttata gagcataagc agcgcaacac    1980
ccttatctgg ttgccgacgg atggtgatgc cgagaacttt atgaaaaccc acgttgagcc    2040
gactattcgt gatattccgt cgctgctggc gctggccccg tggtatggca aaaagcaccg    2100
ggataacacg ctcaccatga agcgtttcac taatgggcgt ggcttctggt gcctgggcgg    2160
taaagcggca aaaactaccg tgaaaagtc ggtggatgtg gcgggttatg atgaacttgc    2220
tgcttttgat gatgatattg aacaggaagg ctctccgacg ttcctgggtg acaagcgcgt    2280
cgaccaaggg cccatccgtc ttcccctgg cgccctgctc caggagcacc tccgagagca    2340
cagcggccct gggctgcctg tcaaggact acttccccga accggtgacg gtgtcgtgga    2400
actcaggcgc cctgaccagc ggcgtgcaca ccttcccggc tgtcctacag tcctcaggac    2460
tctactccct cagcagcgtg gtgaccgtgc cctccagcag cttgggcacg aagacctaca    2520
cctgcaatgt agatcacaag cccagcaaca ccaaggtgga caagagagtt gagtccaaat    2580
```

```
acggtccgcc atgcccatca tgcccagcac ctgaattcct gggggggacca tcagtcttcc    2640 tgttccccccc aaaacccaag dacaccctca tgatctcccg daccctgag gtcacgtgcg    2700 tggtggtgga cgtgagccag gaagaccccg aggtccagtt caactggtac gtggatggcg    2760
tggaggtgca taatgccaag acaaagccgc gggaggagca gttcaacagc acgtaccgtg    2820
tggtcagcgt cctcaccgtc ctgcaccagg actggctgaa cggcaaggag tacaagtgca    2880
aggtctccaa caaaggcctc ccgtcctcca tcgagaaaac catctccaaa gccaagggc    2940 agccccgaga gccacaggtg tacaccctgc ccccatccca ggaggagatg accaagaacc    3000
aggtcagcct gacctgcctg gtcaaaggct tctaccccag cgacatcgcc gtggagtggg    3060
agagcaatgg gcagccggag aacaactaca agaccacgcc tcccgtgctg gactccgacg    3120
gctccttctt cctctacagc aggctaaccg tggacaagag caggtggcag aggggaatg    3180 tcttctcatg ctccgtgatg catgaggctc tgcacaacca ctacacgcag aagagcctct    3240
ccctgtctct gggtaaatga gcggccgctc gaggccggca aggccggatc ccccgacctc    3300
gacctctggc taataaagga aatttatttt cattgcaata gtgtgttgga attttttgtg    3360
tctctcactc ggaaggacat atgggagggc aaatcatttg gtcagatcc ctcggagatc    3420 tctagctaga ggatcgatcc ccgccccgga cgaactaaac ctgactacga catctctgcc    3480
ccttcttcgc ggggcagtgc atgtaatccc ttcagttggt tggtacaact tgccaactgg    3540
gccctgttcc acatgtgaca cggggggga ccaaacacaa aggggttctc tgactgtagt    3600
tgacatcctt ataaatggat gtgcacattt gccaacactg agtggctttc atcctggagc    3660
agactttgca gtctgtggac tgcaacacaa cattgccttt atgtgtaact cttggctgaa    3720
gctcttacac caatgctggg ggacatgtac ctcccagggg cccaggaaga ctacgggagg    3780
ctacaccaac gtcaatcaga ggggcctgtg tagctaccga taagcggacc ctcaagaggg    3840
cattagcaat agtgttata aggccccctt gttaaccta aacgggtagc atatgcttcc    3900
cgggtagtag tatatactat ccagactaac cctaattcaa tagcatatgt tacccaacgg    3960
gaagcatatg ctatcgaatt aggggttagta aagggtcct aaggaacagc gatatctccc    4020
accccatgag ctgtcacggt tttatttaca tggggtcagg attccacgag ggtagtgaac    4080
cattttagtc acaagggcag tggctgaaga tcaaggagcg ggcagtgaac tctcctgaat    4140
cttcgcctgc ttcttcattc tccttcgttt agctaataga ataactgctg agttgtgaac    4200
agtaaggtgt atgtgaggtg ctcgaaaaca aggtttcagg tgacgccccc agaataaaat    4260
ttggacgggg ggttcagtgg tggcattgtg ctatgacacc aatataaccc tcacaaaccc    4320
cttgggcaat aaatactagt gtaggaatga acattctga atatctttaa caatagaaat    4380
ccatggggtg gggacaagcc gtaaagactg gatgtccatc tcacacgaat ttatggctat    4440
gggcaacaca taatcctagt gcaatatgat actggggtta ttaagatgtg tcccaggcag    4500
ggaccaagac aggtgaacca tgttgttaca ctctatttgt aacaagggga aagagagtgg    4560
acgccgacag cagcggactc cactggttgt ctctaacacc cccgaaaatt aaacggggct    4620
ccacgccaat ggggcccata acaaagaca agtggccact cttttttttg aaattgtgga    4680 gtggggcac cgtcagccc ccacacgccg ccctgcggtt ttggactgta aataagggt    4740 gtaataactt ggctgattgt aaccccgcta accactgcgg tcaaaccact tgcccacaaa    4800
accactaatg gcaccccggg gaatacctgc ataagtaggt gggcgggcca agatagggc    4860 gcgattgctg cgatctggag gacaaattac acacacttgc gcctgagcgc caagcacagg    4920
gttgttggtc ctcatattca cgaggtcgct gagagcacgg tgggctaatg ttgccatggg    4980
```

```
tagcatatac tacccaaata tctggatagc atatgctatc ctaatctata tctgggtagc   5040
ataggctatc ctaatctata tctgggtagc atatgctatc ctaatctata tctgggtagt   5100
atatgctatc ctaatttata tctgggtagc ataggctatc ctaatctata tctgggtagc   5160
atatgctatc ctaatctata tctgggtagt atatgctatc ctaatctgta tccgggtagc   5220
atatgctatc ctaatagaga ttagggtagt atatgctatc ctaatttata tctgggtagc   5280
atatactacc caaatatctg gatagcatat gctatcctaa tctatatctg ggtagcatat   5340
gctatcctaa tctatatctg ggtagcatag gctatcctaa tctatatctg ggtagcatat   5400
gctatcctaa tctatatctg ggtagtatat gctatcctaa tttatatctg ggtagcatag   5460
gctatcctaa tctatatctg ggtagcatat gctatcctaa tctatatctg ggtagtatat   5520
gctatcctaa tctgtatccg ggtagcatat gctatcctca tgataagctg tcaaacatga   5580
gaattttctt gaagacgaaa gggcctcgtg atacgcctat ttttataggt taatgtcatg   5640
ataataatgg tttcttagac gtcaggtggc acttttcggg gaaatgtgcg cggaacccct   5700
atttgtttat ttttctaaat acattcaaat atgtatccgc tcatgagaca ataaccctga   5760
taaatgcttc aataatattg aaaaaggaag agtatgagta ttcaacattt ccgtgtcgcc   5820
cttattccct tttttgcggc attttgcctt cctgtttttg ctcacccaga aacgctggtg   5880
aaagtaaaag atgctgaaga tcagttgggt gcacgagtgg gttacatcga actggatctc   5940
aacagcggta agatccttga gagttttcgc cccgaagaac gttttccaat gatgagcact   6000
tttaaagttc tgctatgtgg cgcggtatta tcccgtgttg acgccgggca agagcaactc   6060
ggtcgccgca tacactattc tcagaatgac ttggttgagt actcaccagt cacagaaaag   6120
catcttacgg atggcatgac agtaagagaa ttatgcagtg ctgccataac catgagtgat   6180
aacactgcgg ccaacttact tctgacaacg atcggaggac cgaaggagct aaccgctttt   6240
ttgcacaaca tgggggatca tgtaactcgc cttgatcgtt gggaaccgga gctgaatgaa   6300
gccataccaa acgacgagcg tgacaccacg atgcctgcag caatggcaac aacgttgcgc   6360
aaactattaa ctggcgaact acttactcta gcttcccggc aacaattaat agactggatg   6420
gaggcggata aagttgcagg accacttctg cgctcggccc ttccggctgg ctggtttatt   6480
gctgataaat ctggagccgg tgagcgtggg tctcgcggta tcattgcagc actggggcca   6540
gatggtaagc cctcccgtat cgtagttatc tacacgacgg ggagtcaggc aactatggat   6600
gaacgaaata gacagatcgc tgagataggt gcctcactga ttaagcattg gtaactgtca   6660
gaccaagttt actcatatat actttagatt gatttaaaac ttcattttta atttaaaagg   6720
atctaggtga agatcctttt tgataatctc atgaccaaaa tcccttaacg tgagttttcg   6780
ttccactgag cgtcagaccc cgtagaaaag atcaaaggat cttcttgaga tccttttttt   6840
ctgcgcgtaa tctgctgctt gcaaacaaaa aaaccaccgc taccagcggt ggtttgtttg   6900
ccggatcaag agctaccaac tcttttccg aaggtaactg gcttcagcag agcgcagata   6960
ccaaatactg ttcttctagt gtagccgtag ttaggccacc acttcaagaa ctctgtagca   7020
ccgcctacat acctcgctct gctaatcctg ttaccagtgg ctgctgccag tggcgataag   7080
tcgtgtctta ccgggttgga ctcaagacga tagttaccgg ataaggcgca gcggtcgggc   7140
tgaacggggg gttcgtgcac acagcccagc ttggagcgaa cgacctacac cgaactgaga   7200
tacctacagc gtgagctatg agaaagcgcc acgcttcccg aagggagaaa ggcggacagg   7260
tatccggtaa gcggcagggt cggaacagga gagcgcacga gggagcttcc agggggaaac   7320
gcctggtatc tttatagtcc tgtcgggttt cgccacctct gacttgagcg tcgatttttg   7380
```

```
tgatgctcgt caggggggcg gagcctatgg aaaaacgcca gcaacgcggc cttttacgg      7440 ttcctggcct tttgctggcc ttttgctcac atgttctttc ctgcgttatc ccctgattct      7500
gtggataacc gtattaccgc ctttgagtga gctgataccg ctcgccgcag ccgaacgacc      7560
gagcgcagcg agtcagtgag cgaggaagcg gaagagcgcc caatacgcaa accgcctctc      7620
cccgcgcgtt ggccgattca ttaatgcagc tggcacgaca ggtttcccga ctggaaagcg      7680
ggcagtgagc gcaacgcaat taatgtgagt tagctcactc attaggcacc ccaggcttta      7740
cactttatgc ttccggctcg tatgttgtgt ggaattgtga gcggataaca atttcacaca      7800
ggaaacagct atgaccatga ttacgccaag ctctagctag aggtcgagtc cctccccagc      7860
aggcagaagt atgcaaagca tgcatctcaa ttagtcagca accatagtcc cgcccctaac      7920
tccgcccatc ccgcccctaa ctccgcccag ttccgcccat tctccgcccc atggctgact      7980
aatttttttt atttatgcag aggccgaggc cgcctcggcc tctgagctat tccagaagta      8040
gtgaggaggc ttttttggag gcctaggctt ttgcaaaaag ctttgcaaag atggataaag      8100
ttttaaacag agaggaatct tgcagctaa tggaccttct aggtcttgaa agg             8153

<210> SEQ ID NO 26
<211> LENGTH: 8153
<212> TYPE: DNA
<213> ORGANISM: Artificial Sequence
<220> FEATURE:
<223> OTHER INFORMATION: Synthetic construct: pJP188 ; pHybE-hCg4 V2

<400> SEQUENCE: 26
agtgggaatt ggctccggtg cccgtcagtg ggcagagcgc acatcgccca cagtccccga        60
gaagttgggg ggaggggtcg gcaattgaac cggtgcctag agaaggtggc gcggggtaaa       120
ctgggaaagt gatgtcgtgt actggctccg ccttttttccc gagggtgggg gagaaccgta      180
tataagtgca gtagtcgccg tgaacgttct ttttcgcaac gggtttgccg ccagaacaca      240
ggtaagtgcc gtgtgtggtt cccgcgggcc tggcctcttt acgggttatg gcccttgcgt      300
gccttgaatt acttccacct ggctgcagta cgtgattctt gatcccgagc ttcgggttgg      360
aagtgggtgg gagagttcga ggccttgcgc ttaaggagcc cttcgcctc gtgcttgagt       420 tgaggcctgg cctgggcgct ggggccgccg cgtgcgaatc tggtggcacc ttcgcgcctg      480
tctcgctgct ttcgataagt ctctagccat ttaaaatttt tgatgacctg ctgcgacgct      540 tttttttctgg caagatagtc ttgtaaatgc gggccaagat ctgcacactg gtatttcggt      600 ttttgggcc gcgggcggcg acggggcccg tgcgtcccag cgcacatgtt cggcgaggcg       660
gggcctgcga gcgcggccac cgagaatcgg acggggtag tctcaagctg gccggcctgc       720
tctggtgcct ggcctcgcgc cgccgtgtat cgccccgccc tgggcggcaa ggctggcccg      780
gtcggcacca gttgcgtgag cggaaagatg gccgcttccc ggccctgctg cagggagctc      840
aaaatggagg acgcggcgct cgggagagcg ggcgggtgag tcacccacac aaaggaaaag      900
ggcctttccg tcctcagccg tcgcttcatg tgactccacg gagtaccggg cgccgtccag      960
gcacctcgat tagttctcga gcttttggag tacgtcgtct ttaggttggg ggagggggtt     1020
ttatgcgatg gagtttcccc acactgagtg gtggagact gaagttaggc cagcttggca      1080
cttgatgtaa ttctccttgg aatttgccct ttttgagttt ggatcttggt tcattctcaa     1140
gcctcagaca gtggttcaaa gtttttttct tccatttcag gtgtcgtgag gaattctcta     1200
gagatccctc gacctcgaga tccattgtgc cggggcgcca ccatggagtt tgggctgagc     1260
tggctttttc ttgtcgcgat tttaaaaggt gtccagtgcg catggtatgc cgaaagggat      1320
```

```
gctgaaattg agaacgaaaa gctgcgccgg gaggttgaag aactgcggca ggccagcgag    1380
gcagatctcc agccaggaac tattgagtac gaacgccatc gacttacgcg tgcgcaggcc    1440
gacgcacagg aactgaagaa tgccagagac tccgctgaag tggtggaaac cgcattctgt    1500
actttcgtgc tgtcgcggat cgcaggtgaa attgccagta ttctcgacgg ctcccccctg    1560
tcggtgcagc ggcgttttcc ggaactggaa aaccgacatg ttgatttcct gaaacgggat    1620
atcatcaaag ccatgaacaa agcagccgcg ctggatgaac tgataccggg gttgctgagt    1680
gaatatatcg aacagtcagg ttaacaggct gcggcatttt gtccgcgccg ggcttcgctc    1740
actgttcagg ccggagccac agaccgccgt tgaatgggcg gatgctaatt actatctccc    1800
gaaagaatcc gcataccagg aagggcgctg ggaaacactg cccttcagc gggccatcat     1860 gaatgcgatg ggcagcgact acatccgtga ggtgaatgtg gtgaagtctg cccgtgtcgg    1920
ttattccaaa atgctgctgg gtgtttatgc ctactttata gagcataagc agcgcaacac    1980
ccttatctgg ttgccgacgg atggtgatgc cgagaacttt atgaaaaccc acgttgagcc    2040
gactattcgt gatattccgt cgctgctggc gctggccccg tggtatggca aaaagcaccg    2100
ggataacacg ctcaccatga agcgtttcac taatgggcgt ggcttctggt gcctgggcgg    2160
taaagcggca aaaactacc gtgaaaagtc ggtggatgtg gcgggttatg atgaacttgc      2220
tgcttttgat gatgatattg aacaggaagg ctctccgacg ttcctgggtg acaagcgcgt    2280
cgaccaaggg cccatccgtc ttccccctgg cgccctgctc caggagcacc tccgagagca    2340
cagcggccct gggctgcctg gtcaaggact acttccccga accggtgacg tgtcgtgga     2400 actcaggcgc cctgaccagc ggcgtgcaca ccttcccggc tgtcctacag tcctcaggac    2460
tctactccct cagcagcgtg gtgaccgtgc cctccagcag cttgggcacg aagacctaca    2520
cctgcaatgt agatcacaag cccagcaaca ccaaggtgga caagagagtt gagtccaaat    2580
acggtccgcc atgcccatca tgcccagcac ctgaattcct gggggaccca tcagtcttcc    2640
tgttcccccc aaaacccaag gacaccctca tgatctcccg gacccctgag gtcacgtgcg    2700
tggtggtgga cgtgagccag gaagaccccg aggtccagtt caactggtac gtggatggcg    2760
tggaggtgca taatgccaag acaaagccgc gggaggagca gttcaacagc acgtaccgtg    2820
tggtcagcgt cctcaccgtc ctgcaccagg actggctgaa cggcaaggag tacaagtgca    2880
aggtctccaa caaaggcctc ccgtcctcca tcgagaaaac catctccaaa gccaaagggc    2940
agccccgaga gccacaggtg tacaccctgc cccatcccca ggaggagatg accaagaacc    3000
aggtcagcct gacctgcctg gtcaaaggct tctaccccag cgacatcgcc gtggagtggg    3060
agagcaatgg gcagccggag aacaactaca agaccacgcc tcccgtgctg gactccgacg    3120
gctccttctt cctctacagc aggctaaccg tggacaagag caggtggcag gaggggaatg    3180
tcttctcatg ctccgtgatg catgaggctc tgcacaacca ctacacgcag aagagcctct    3240
ccctgtctct gggtaaatga gcggccgctc gaggccggca aggccggatc ccccgacctc    3300
gacctctggc taataaagga aatttatttt cattgcaata gtgtgttgga attttttgtg    3360
tctctcactc ggaaggacat atgggagggc aaatcatttg gtcgagatcc ctcggagatc    3420
tctagctaga ggatcgatcc ccgccccgga cgaactaaac ctgactacga catctctgcc    3480
ccttcttcgc ggggcagtgc atgtaatccc ttcagttggt tggtacaact tgccaactgg    3540
gccctgttcc acatgtgaca cggggggga ccaaacacaa aggggttctc tgactgtagt     3600
tgacatcctt ataaatggat gtgcacattt gccaacactg agtggctttc atcctggagc    3660
agactttgca gtctgtggac tgcaacacaa cattgccttt atgtgtaact cttggctgaa    3720
```

```
gctcttacac caatgctggg ggacatgtac ctcccagggg cccaggaaga ctacgggagg    3780
ctacaccaac gtcaatcaga ggggcctgtg tagctaccga taagcggacc ctcaagaggg    3840
cattagcaat agtgtttata aggccccctt gttaacccta aacgggtagc atatgcttcc    3900
cgggtagtag tatatactat ccagactaac cctaattcaa tagcatatgt tacccaacgg    3960
gaagcatatg ctatcgaatt agggttagta aaagggtcct aaggaacagc gatatctccc    4020
accccatgag ctgtcacggt tttatttaca tggggtcagg attccacgag ggtagtgaac    4080
cattttagtc acaagggcag tggctgaaga tcaaggagcg ggcagtgaac tctcctgaat    4140
cttcgcctgc ttcttcattc tccttcgttt agctaataga ataactgctg agttgtgaac    4200
agtaaggtgt atgtgaggtg ctcgaaaaca aggtttcagg tgacgccccc agaataaaat    4260
ttggacgggg ggttcagtgg tggcattgtg ctatgacacc aatataaccc tcacaaaccc    4320
cttgggcaat aaaatactagt gtaggaatga aacattctga atatctttaa caatagaaat    4380
ccatggggtg gggacaagcc gtaaagactg gatgtccatc tcacacgaat ttatggctat    4440
gggcaacaca taatcctagt gcaatatgat actggggtta ttaagatgtg tcccaggcag    4500
ggaccaagac aggtgaacca tgttgttaca ctctatttgt aacaagggga agagagtgg    4560 acgccgacag cagcggactc cactggttgt ctctaacacc cccgaaaatt aaacggggct    4620
ccacgccaat ggggcccata acaaagaca agtggccact cttttttttg aaattgtgga    4680
gtgggggcac gcgtcagccc ccacacgccg ccctgcggtt ttggactgta aataagggt    4740 gtaataactt ggctgattgt aaccccgcta accactgcgg tcaaaccact tgcccacaaa    4800
accactaatg gcaccccggg gaatacctgc ataagtaggt gggcgggcca agatagggc    4860 gcgattgctg cgatctggag gacaaattac acacacttgc gcctgagcgc caagcacagg    4920
gttgttggtc ctcatattca cgaggtcgct gagagcacgg tgggctaatg ttgccatggg    4980
tagcatatac tacccaaata tctggatagc atatgctatc ctaatctata tctgggtagc    5040
ataggctatc ctaatctata tctgggtagc atatgctatc ctaatctata tctgggtagt    5100
atatgctatc ctaatttata tctgggtagc ataggctatc ctaatctata tctgggtagc    5160
atatgctatc ctaatctata tctgggtagt atatgctatc ctaatctgta tccgggtagc    5220
atatgctatc ctaatagaga ttagggtagt atatgctatc ctaatttata tctgggtagc    5280
atatactacc caaatatctg gatagcatat gctatcctaa tctatatctg gtagcatat    5340 gctatcctaa tctatatctg gtagcatag gctatcctaa tctatatctg gtagcatat    5400 gctatcctaa tctatatctg gtagtatat gctatcctaa tttatatctg gtagcatag    5460 gctatcctaa tctatatctg gtagcatat gctatcctaa tctatatctg gtagtatat    5520 gctatcctaa tctgtatccg gtagcatat gctatcctca tgataagctg tcaaacatga    5580
gaattttctt gaagacgaaa gggcctcgtg tacgcctat ttttataggt taatgtcatg    5640
ataataatgg tttcttagac gtcaggtggc acttttcggg gaaatgtgcg cggaacccct    5700
atttgtttat ttttctaaat acattcaaat atgtatccgc tcatgagaca ataaccctga    5760
taaatgcttc aataatattg aaaaaggaag agtatgagta ttcaacattt ccgtgtcgcc    5820
cttattccct tttttgcggc attttgcctt cctgttttg ctcacccaga aacgctggtg    5880
aaagtaaaag atgctgaaga tcagttgggt gcacgagtgg gttacatcga actggatctc    5940
aacagcggta agatccttga gagttttcgc cccgaagaac gttttccaat gatgagcact    6000
tttaaagttc tgctatgtgg cgcggtatta tcccgtgttg acgccgggca agagcaactc    6060
ggtcgccgca tacactattc tcagaatgac ttggttgagt actcaccagt cacagaaaag    6120
```

| | |
|---|---|
| catcttacgg atggcatgac agtaagagaa ttatgcagtg ctgccataac catgagtgat | 6180 |
| aacactgcgg ccaacttact tctgacaacg atcggaggac cgaaggagct aaccgctttt | 6240 |
| ttgcacaaca tggggatca tgtaactcgc cttgatcgtt gggaaccgga gctgaatgaa | 6300 |
| gccataccaa acgacgagcg tgacaccacg atgcctgcag caatggcaac aacgttgcgc | 6360 |
| aaactattaa ctggcgaact acttactcta gcttcccggc aacaattaat agactggatg | 6420 |
| gaggcggata aagttgcagg accacttctg cgctcggccc ttccggctgg ctggtttatt | 6480 |
| gctgataaat ctggagccgg tgagcgtggg tctcgcggta tcattgcagc actggggcca | 6540 |
| gatggtaagc cctcccgtat cgtagttatc tacacgacgg ggagtcaggc aactatggat | 6600 |
| gaacgaaata acagatcgc tgagataggt gcctcactga ttaagcattg gtaactgtca | 6660 |
| gaccaagttt actcatatat actttagatt gatttaaaac ttcattttta atttaaaagg | 6720 |
| atctaggtga agatccttt tgataatctc atgaccaaaa tcccttaacg tgagttttcg | 6780 |
| ttccactgag cgtcagaccc cgtagaaaag atcaaaggat cttcttgaga tcctttttt | 6840 |
| ctgcgcgtaa tctgctgctt gcaaacaaaa aaaccaccgc taccagcggt ggtttgtttg | 6900 |
| ccggatcaag agctaccaac tcttttccg aaggtaactg gcttcagcag agcgcagata | 6960 |
| ccaaatactg ttcttctagt gtagccgtag ttaggccacc acttcaagaa ctctgtagca | 7020 |
| ccgcctacat acctcgctct gctaatcctg ttaccagtgg ctgctgccag tggcgataag | 7080 |
| tcgtgtctta ccgggttgga ctcaagacga tagttaccgg ataaggcgca gcggtcgggc | 7140 |
| tgaacgggg gttcgtgcac acagcccagc ttggagcgaa cgacctacac cgaactgaga | 7200 |
| tacctacagc gtgagctatg agaaagcgcc acgcttcccg aagggagaaa ggcggacagg | 7260 |
| tatccggtaa gcggcagggt cggaacagga gagcgcacga gggagcttcc agggggaaac | 7320 |
| gcctggtatc tttatagtcc tgtcgggttt cgccacctct gacttgagcg tcgatttttg | 7380 |
| tgatgctcgt caggggggcg gagcctatgg aaaaacgcca gcaacgcggc cttttacgg | 7440 |
| ttcctggcct tttgctggcc ttttgctcac atgttctttc ctgcgttatc ccctgattct | 7500 |
| gtggataacc gtattaccgc ctttgagtga gctgataccg ctcgccgcag ccgaacgacc | 7560 |
| gagcgcagcg agtcagtgag cgaggaagcg gaagagcgcc caatacgcaa accgcctctc | 7620 |
| cccgcgcgtt ggccgattca ttaatgcagc tggcacgaca ggtttcccga ctggaaagcg | 7680 |
| ggcagtgagc gcaacgcaat taatgtgagt tagctcactc attaggcacc ccaggcttta | 7740 |
| cactttatgc ttccggctcg tatgttgtgt ggaattgtga gcggataaca atttcacaca | 7800 |
| ggaaacagct atgaccatga ttacgccaag ctctagctag aggtcgagtc cctccccagc | 7860 |
| aggcagaagt atgcaaagca tgcatctcaa ttagtcagca accatagtcc cgcccctaac | 7920 |
| tccgcccatc ccgcccctaa ctccgcccag ttccgcccat tctccgcccc atggctgact | 7980 |
| aatttttttt attatgcag aggccgaggc cgcctcggcc tctgagctat tccagaagta | 8040 |
| gtgaggaggc ttttttggag gcctaggctt ttgcaaaaag ctttgcaaag atggataaag | 8100 |
| ttttaaacag agaggaatct ttgcagctaa tggaccttct aggtcttgaa agg | 8153 |

<210> SEQ ID NO 27
<211> LENGTH: 7244
<212> TYPE: DNA
<213> ORGANISM: Artificial Sequence
<220> FEATURE:
<223> OTHER INFORMATION: Synthetic construct: pHybC-mBR3-mCg2a

<400> SEQUENCE: 27

| | |
|---|---|
| ttgacattga ttattgacta gttattaata gtaatcaatt acggggtcat tagttcatag | 60 |

-continued

```
cccatatatg gagttccgcg ttacataact tacggtaaat ggcccgcctg gctgaccgcc    120
caacgacccc cgcccattga cgtcaataat gacgtatgtt cccatagtaa cgccaatagg    180
gactttccat tgacgtcaat gggtggagta tttacggtaa actgcccact tggcagtaca    240
tcaagtgtat catatgccaa gtccgccccc tattgacgtc aatgacggta aatggcccgc    300
ctggcattat gcccagtaca tgaccttacg ggactttcct acttggcagt acatctacgt    360
attagtcatc gctattacca tggtgatgcg gttttggcag tacaccaatg ggcgtggata    420
gcggtttgac tcacggggat ttccaagtct ccaccccatt gacgtcaatg ggagtttgtt    480
ttggcaccaa aatcaacggg actttccaaa atgtcgtaat aaccccgccc cgttgacgca    540
aatgggcggt aggcgtgtac ggtgggaggt ctatataagc agagctcgtt tagtgaaccg    600
tcagatcctc actctcttcc gcatcgctgt ctgcgagggc cagctgttgg gctcgcggtt    660
gaggacaaac tcttcgcggt ctttccagta ctcttggatc ggaaacccgt cggcctccga    720
acggtactcc gccaccgagg gacctgagcg agtccgcatc gaccggatcg gaaaacctct    780
cgagaaaggc gtctaaccag tcacagtcgc aaggtaggct gagcaccgtg gcgggcggca    840
gcgggtggcg gtcggggttg tttctggcgg aggtgctgct gatgatgtaa ttaaagtagg    900
cggtcttgag acggcggatg tcgaggtga ggtgtggcag gcttgagatc cagctgttgg    960
ggtgagtact ccctctcaaa agcgggcatt acttctgcgc taagattgtc agtttccaaa   1020
aacgaggagg atttgatatt cacctggccc gatctggcca tacacttgag tgacaatgac   1080
atccactttg cctttctctc cacaggtgtc cactcccagg tccaagtttg gcgccacca    1140
tggagtttgg gctgagctgg cttttcttg tcgcgatttt aaaaggtgtc cagtgcggcg   1200
ccaggagact ccgggtccga agccagagga gccgggacag ctcggtgccc acccagtgca   1260
atcagaccga gtgcttcgac cctctggtga gaaactgcgt gtcctgtgag ctcttccaca   1320
cgccggacac tggacataca agcagcctgg agcctgggac agctctgcag cctcaggagg   1380
gctccgcgct gagacccgac gtggcggagc ccagagggcc cacaatcaag ccctgtcctc   1440
catgcaaatg cccagcacct aacctcttgg gtggaccatc cgtcttcatc ttccctccaa   1500
agatcaagga tgtactcatg atctccctga gcccatagt cacatgtgtg gtggtggatg    1560
tgagcgagga tgacccagat gtccagatca gctggtttgt gaacaacgtg aagtacaca    1620
cagctcagac acaaacccat agagaggatt acaacagtac tctccgggtg gtcagtgccc   1680
tcccccatcca gcaccaggac tggatgagtg gcaaggagtt caaatgcaag gtcaacaaca   1740
aagacctccc agcgcccatc gagagaacca tctcaaaacc caagggtca gtaagagctc   1800
cacaggtata tgtcttgcct ccaccagaag aagagatgac taagaaacag gtcactctga   1860
cctgcatggt cacagacttc atgcctgaag acatttacgt ggagtggacc aacaacggga   1920
aaacagagct aaactacaag aacactgaac cagtcctgga ctctgatggt tcttacttca   1980
tgtacagcaa gctgagagtg gaaaagaaga actgggtgga agaaatagc tactcctgtt    2040
cagtggtcca cgagggtctg cacaatcacc acacgactaa gagcttctcc cggactccgg   2100
gtaaataagc ggccgctcga ggccggcaag gccggatccc ccgacctcga cctctggcta   2160
ataaaggaaa tttatttca ttgcaatagt gtgttggaat ttttttgtgtc tctcactcgg   2220
aaggacatat gggagggcaa atcatttggt cgagatccct cggagatctc tagctagagg   2280
atcgatcccc gccccggacg aactaaacct gactacgaca tctctgcccc ttcttcgcgg   2340
ggcagtgcat gtaatccctt cagttggttg gtacaacttg ccaactgggc cctgttccac   2400
atgtgacacg ggggggggacc aaacacaaag gggttctctg actgtagttg acatccttat   2460
```

```
aaatggatgt gcacatttgc caacactgag tggctttcat cctggagcag actttgcagt    2520
ctgtggactg caacacaaca ttgcctttat gtgtaactct tggctgaagc tcttacacca    2580
atgctggggg acatgtacct cccaggggcc caggaagact acgggaggct acaccaacgt    2640
caatcagagg ggcctgtgta gctaccgata agcggaccct caagagggca ttagcaatag    2700
tgtttataag gcccccttgt taaccctaaa cgggtagcat atgcttcccg ggtagtagta    2760
tatactatcc agactaaccc taattcaata gcatatgtta cccaacggga agcatatgct    2820
atcgaattag ggttagtaaa agggtcctaa ggaacagcga tatctcccac cccatgagct    2880
gtcacggttt tatttacatg gggtcaggat tccacgaggg tagtgaacca ttttagtcac    2940
aagggcagtg gctgaagatc aaggagcggg cagtgaactc tcctgaatct tcgcctgctt    3000
cttcattctc cttcgtttag ctaatagaat aactgctgag ttgtgaacag taaggtgtat    3060
gtgaggtgct cgaaaacaag gtttcaggtg acgcccccag aataaaattt ggacgggggg    3120
ttcagtggtg gcattgtgct atgacaccaa tataaccctc acaaacccct tgggcaataa    3180
atactagtgt aggaatgaaa cattctgaat atctttaaca atagaaatcc atggggtggg    3240
gacaagccgt aaagactgga tgtccatctc acacgaattt atggctatgg gcaacacata    3300
atcctagtgc aatatgatac tggggttatt aagatgtgtc ccaggcaggg accaagacag    3360
gtgaaccatg ttgttacact ctatttgtaa caaggggaaa gagagtggac gccgacagca    3420
gcggactcca ctggttgtct ctaacacccc cgaaaattaa acggggctcc acgccaatgg    3480
ggcccataaa caaagacaag tggccactct ttttttttgaa attgtggagt gggggcacgc    3540
gtcagccccc acacgccgcc ctgcggtttt ggactgtaaa ataagggtgt aataacttgg    3600
ctgattgtaa ccccgctaac cactgcggtc aaaccacttg cccacaaaac cactaatggc    3660
accccgggga atacctgcat aagtaggtgg gcgggccaag ataggggcgc gattgctgcg    3720
atctggagga caaattacac acacttgcgc ctgagcgcca agcacagggt tgttggtcct    3780
catattcacg aggtcgctga gagcacggtg ggctaatgtt gccatgggta gcatatacta    3840
cccaaatatc tggatagcat atgctatcct aatctatatc tgggtagcat aggctatcct    3900
aatctatatc tgggtagcat atgctatcct aatctatatc tgggtagtat atgctatcct    3960
aatttatatc tgggtagcat aggctatcct aatctatatc tgggtagcat atgctatcct    4020
aatctatatc tgggtagtat atgctatcct aatctgtatc cgggtagcat atgctatcct    4080
aatagagatt agggtagtat atgctatcct aatttatatc tgggtagcat atactaccca    4140
aatatctgga tagcatatgc tatcctaatc tatatctggg tagcatatgc tatcctaatc    4200
tatatctggg tagcataggc tatcctaatc tatatctggg tagcatatgc tatcctaatc    4260
tatatctggg tagtatatgc tatccttaatt tatatctggg tagcataggc tatcctaatc    4320
tatatctggg tagcatatgc tatcctaatc tatatctggg tagtatatgc tatcctaatc    4380
tgtatccggg tagcatatgc tatcctcatg ataagctgtc aaacatgaga attttcttga    4440
agacgaaagg gcctcgtgat acgcctattt ttataggtta atgtcatgat aataatggtt    4500
tcttagacgt caggtggcac ttttcgggga aatgtgcgcg gaacccctat tgtttatttt    4560
ttctaaatac attcaaatat gtatccgctc atgagacaat aaccctgata aatgcttcaa    4620
taatattgaa aaaggaagag tatgagtatt caacatttcc gtgtcgccct tattcccttt    4680
tttgcggcat tttgccttcc tgttttttgct cacccagaaa cgctggtgaa agtaaaagat    4740
gctgaagatc agttgggtgc acgagtgggt tacatcgaac tggatctcaa cagcggtaag    4800
atccttgaga gttttcgccc cgaagaacgt tttccaatga tgagcacttt taaagttctg    4860
```

```
ctatgtggcg cggtattatc ccgtgttgac gccgggcaag agcaactcgg tcgccgcata   4920
cactattctc agaatgactt ggttgagtac tcaccagtca cagaaaagca tcttacggat   4980
ggcatgacag taagagaatt atgcagtgct gccataacca tgagtgataa cactgcggcc   5040
aacttacttc tgacaacgat cggaggaccg aaggagctaa ccgcttttt  gcacaacatg   5100 ggggatcatg taactcgcct tgatcgttgg gaaccgagc  tgaatgaagc cataccaaac   5160
gacgagcgtg acaccacgat gcctgcagca atggcaacaa cgttgcgcaa actattaact   5220
ggcgaactac ttactctagc ttcccggcaa caattaatag actggatgga ggcggataaa   5280
gttgcaggac cacttctgcg ctcggccctt ccggctggct ggtttattgc tgataaatct   5340
ggagccggtg agcgtgggtc tcgcggtatc attgcagcac tggggccaga tggtaagccc   5400
tcccgtatcg tagttatcta cacgacgggg agtcaggcaa ctatggatga acgaaataga   5460
cagatcgctg ataggtgc  ctcactgatt aagcattggt aactgtcaga ccaagtttac   5520
tcatatatac tttagattga tttaaaactt cattttaat  ttaaaaggat ctaggtgaag   5580
atcctttttg ataatctcat gaccaaaatc ccttaacgtg agttttcgtt ccactgagcg   5640
tcagaccccg tagaaaagat caaaggatct tcttgagatc ctttttttct gcgcgtaatc   5700
tgctgcttgc aaacaaaaaa accaccgcta ccagcggtgg tttgtttgcc ggatcaagag   5760
ctaccaactc tttttccgaa ggtaactggc ttcagcagag cgcagatacc aaatactgtt   5820
cttctagtgt agccgtagtt aggccaccac ttcaagaact ctgtagcacc gcctacatac   5880
ctcgctctgc taatcctgtt accagtggct gctgccagtg gcgataagtc gtgtcttacc   5940
gggttggact caagacgata gttaccggat aaggcgcagc ggtcgggctg aacggggggt   6000
tcgtgcacac agcccagctt ggagcgaacg acctacaccg aactgagata cctacagcgt   6060
gagctatgag aaagcgccac gcttcccgaa gggagaaagg cggacaggta tccggtaagc   6120
ggcagggtcg aacaggaga  gcgcacgagg gagcttccag ggggaaacgc ctggtatctt   6180
tatagtcctg tcgggtttcg ccacctctga cttgagcgtc gatttttgtg atgctcgtca   6240
ggggggcgga gcctatggaa aaacgccagc aacgcggcct ttttacggtt cctggccttt   6300
tgctggcctt ttgctcacat gttctttcct gcgttatccc ctgattctgt ggataaccgt   6360
attaccgcct ttgagtgagc tgataccgct cgccgcagcc gaacgaccga gcgcagcgag   6420
tcagtgagcg aggaagcgga agagcgccca atacgcaaac cgcctctccc cgcgcgttgg   6480
ccgattcatt aatgcagctg gcacgacagg tttcccgact ggaaagcggg cagtgagcgc   6540
aacgcaatta atgtgagtta gctcactcat taggcacccc aggctttaca ctttatgctt   6600
ccggctcgta tgttgtgtgg aattgtgagc ggataacaat ttcacacagg aaacagctat   6660
gaccatgatt acgccaagct ctagctagag gtcgagtccc tccccagcag gcagaagtat   6720
gcaaagcatg catctcaatt agtcagcaac catagtcccg ccctaactc  gcccatccc    6780 gcccctaact ccgcccagtt ccgcccattc tccgccccat ggctgactaa ttttttttat   6840
ttatgcagag gccgaggccg cctcggcctc tgagctattc cagaagtagt gaggaggctt   6900
ttttggaggc ctaggctttt gcaaaaagct ttgcaaagat ggataaagtt ttaaacagag   6960
aggaatcttt gcagctaatg gaccttctag gtcttgaaag gagctcgacc aattctcatg   7020
tttgacagct tatcatcgca gatccgggca acgttgttgc cattgctgca ggcgcagaac   7080
tggtaggtat ggaagatcta tacattgaat caatattggc aattagccat attagtcatt   7140
ggttatatag cataaatcaa tattggctat tggccattgc atacgttgta tctatatcat   7200
aatatgtaca tttatattgg ctcatgtcca atatgaccgc catg                    7244
```

<210> SEQ ID NO 28
<211> LENGTH: 7104
<212> TYPE: DNA
<213> ORGANISM: Artificial Sequence
<220> FEATURE:
<223> OTHER INFORMATION: Synthetic construct: pHybE-mBR3-mCg2a

<400> SEQUENCE: 28

```
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg ccttttttccc gagggtgggg gagaaccgta    180
tataagtgca gtagtcgccg tgaacgttct ttttcgcaac gggtttgccg ccagaacaca     240
ggtaagtgcc gtgtgtggtt cccgcgggcc tggcctcttt acgggttatg gcccttgcgt     300
gccttgaatt acttccacct ggctgcagta cgtgattctt gatcccgagc ttcgggttgg     360
aagtgggtgg gagagttcga ggccttgcgc ttaaggagcc ccttcgcctc gtgcttgagt     420
tgaggcctgg cctgggcgct ggggccgccg cgtgcgaatc tggtggcacc ttcgcgcctg     480
tctcgctgct ttcgataagt ctctagccat ttaaattttt tgatgacctg ctgcgacgct     540
ttttttctgg caagatagtc ttgtaaatgc gggccaagat ctgcacactg gtatttcggt     600
ttttggggcc gcgggcggcg acggggcccg tgcgtcccag cgcacatgtt cggcgaggcg     660
gggcctgcga gcgcggccac cgagaatcgg acggggtag tctcaagctg gccggcctgc      720
tctggtgcct ggcctcgcgc cgccgtgtat cgccccgccc tgggcggcaa ggctggcccg     780
gtcggcacca gttgcgtgag cggaaagatg gccgcttccc ggccctgctg cagggagctc     840
aaaatggagg acgcggcgct cgggagagcg ggcgggtgag tcacccacac aaaggaaaag     900
ggcctttccg tcctcagccg tcgcttcatg tgactccacg gagtaccggg cgccgtccag     960
gcacctcgat tagttctcga cttttggag tacgtcgtct ttaggttggg gggaggggtt     1020
ttatgcgatg gagtttcccc acactgagtg ggtggagact gaagttaggc cagcttggca    1080
cttgatgtaa ttctccttgg aatttgccct ttttgagttt ggatcttggt tcattctcaa    1140
gcctcagaca gtggttcaaa gtttttttct tccatttcag gtgtcgtgag gaattctcta    1200
gagatccctc gacctcgaga tccattgtgc ccggggcgcca ccatggagtt tgggctgagc   1260
tggctttttc ttgtcgcgat tttaaaaggt gtccagtgcg gcgccaggag actccgggtc    1320
cgaagccaga ggagccggga cagctcggtg cccacccagt gcaatcagac cgagtgcttc    1380
gaccctctgg tgagaaactg cgtgtcctgt gagctcttcc acacgccgga cactggacat   1440
acaagcagcc tggagcctgg acagctctg cagcctcagg agggctccgc gctgagaccc    1500
gacgtggcgg agcccagagg gcccacaatc aagccctgtc ctccatgcaa atgcccagca   1560
cctaacctct gggtggacc atccgtcttc atcttccctc caaagatcaa ggatgtactc    1620
atgatctccc tgagccccat agtcacatgt gtggtggtgg atgtgagcga ggatgaccca   1680
gatgtccaga tcagctggtt tgtgaacaac gtggaagtac acacagctca gacacaaacc   1740
catagagagg attacaacag tactctccgg gtggtcagtg ccctccccat ccagcaccag    1800
gactggatga gtggcaagga gttcaaatgc aaggtcaaca acaaagacct cccagcgccc    1860
atcgagagaa ccatctcaaa acccaaaggg tcagtaagag ctccacaggt atatgtcttg    1920
cctccaccag aagaagagat gactaagaaa caggtcactc tgacctgcat ggtcacagac    1980
ttcatgcctg aagacattta cgtggagtgg accaacaacg gaaaacagag ctaaactac     2040
aagaacactg aaccagtcct ggactctgat ggttcttact tcatgtacag caagctgaga    2100
```

```
gtggaaaaga agaactgggt ggaaagaaat agctactcct gttcagtggt ccacgagggt    2160
ctgcacaatc accacacgac taagagcttc tcccggactc cgggtaaata agcggccgct    2220
cgaggccggc aaggccggat cccccgacct cgacctctgg ctaataaagg aaatttattt    2280
tcattgcaat agtgtgttgg aattttttgt gtctctcact cggaaggaca tatgggaggg    2340
caaatcattt ggtcgagatc cctcggagat ctctagctag aggatcgatc cccgccccgg    2400
acgaactaaa cctgactacg acatctctgc cccttcttcg cggggcagtg catgtaatcc    2460
cttcagttgg ttggtacaac ttgccaactg ggccctgttc cacatgtgac acggggggg     2520 accaaacaca aaggggttct ctgactgtag ttgacatcct tataaatgga tgtgcacatt    2580
tgccaacact gagtggcttt catcctggag cagactttgc agtctgtgga ctgcaacaca    2640
acattgcctt tatgtgtaac tcttggctga agctcttaca ccaatgctgg gggacatgta    2700
cctcccaggg gcccaggaag actacggagg gctacaccaa cgtcaatcag aggggcctgt    2760
gtagctaccg ataagcggac cctcaagagg gcattagcaa tagtgtttat aaggcccccct   2820 tgttacccct aaacgggtag catatgcttc ccgggtagta gtatatacta tccagactaa    2880
ccctaattca atagcatatg ttacccaacg ggaagcatat gctatcgaat tagggttagt    2940
aaaagggtcc taaggaacag cgatatctcc caccccatga gctgtcacgg ttttatttac    3000
atggggtcag gattccacga gggtagtgaa ccattttagt cacaagggca gtggctgaag    3060
atcaaggagc gggcagtgaa ctcctgaa    tcttcgcctg cttcttcatt ctccttcgtt    3120
tagctaatag aataactgct gagttgtgaa cagtaaggtg tatgtgaggt gctcgaaaac    3180
aaggtttcag gtgacgcccc cagaataaaa tttggacggg gggttcagtg gtggcattgt    3240
gctatgacac caatataacc ctcacaaacc ccttgggcaa taaatactag tgtaggaatg    3300
aaacattctg aatatcttta acaatagaaa tccatggggt ggggacaagc cgtaaagact    3360
ggatgtccat ctcacacgaa tttatggcta tgggcaacac ataatcctag tgcaatatga    3420
tactggggtt attaagatgt gtcccaggca gggaccaaga caggtgaacc atgttgttac    3480
actctatttg taacaagggg aaagagagtg gacgccgaca gcagcggact ccactggttg    3540
tctctaacac ccccgaaaat taaacggggc tccacgccaa tggggcccat aaacaaagac    3600
aagtggccac tctttttttt gaaattgtgg agtgggggca cgcgtcagcc cccacacgcc    3660
gccctgcggt tttggactgt aaaataaggg tgtaataact tggctgattg taaccccgct    3720
aaccactgcg gtcaaaccac ttgcccacaa aaccactaat ggcacccgg  gaatacctg     3780 cataagtagg tgggcgggcc aagataggg  cgcgattgct gcgatctgga ggacaaatta    3840
cacacacttg cgcctgagcg ccaagcacag ggttgttggt cctcatattc acgaggtcgc    3900
tgagagcacg gtgggctaat gttgccatgg gtagcatata ctacccaaat atctggatag    3960
catatgctat cctaatctat atctgggtag cataggctat cctaatctat atctgggtag    4020
catatgctat cctaatctat atctgggtag tatatgctat cctaatttat atctgggtag    4080
cataggctat cctaatctat atctgggtag catatgctat cctaatctat atctgggtag    4140
tatatgctat cctaatctgt atccgggtag catatgctat cctaatagag attagggtag    4200
tatatgctat cctaatttat atctgggtag catatactac ccaaatatct ggatagcata    4260
tgctatccta atctatatct gggtagcata tgctatccta atctatatct gggtagcata    4320
ggctatccta atctatatct gggtagcata tgctatccta atctatatct gggtagtata    4380
tgctatccta atttatatct gggtagcata ggctatccta atctatatct gggtagcata    4440
tgctatccta atctatatct gggtagtata tgctatccta atctgtatcc gggtagcata    4500
```

```
tgctatcctc atgataagct gtcaaacatg agaattttct tgaagacgaa agggcctcgt    4560
gatacgccta ttttatagg ttaatgtcat gataataatg gtttcttaga cgtcaggtgg    4620
cacttttcgg ggaaatgtgc gcggaacccc tatttgttta tttttctaaa tacattcaaa    4680
tatgtatccg ctcatgagac aataaccctg ataaatgctt caataatatt gaaaaggaa    4740 gagtatgagt attcaacatt tccgtgtcgc ccttattccc ttttttgcgg cattttgcct    4800
tcctgttttt gctcacccag aaacgctggt gaaagtaaaa gatgctgaag atcagttggg    4860
tgcacgagtg ggttacatcg aactggatct caacagcggt aagatccttg agagttttcg    4920
ccccgaagaa cgttttccaa tgatgagcac ttttaaagtt ctgctatgtg gcgcggtatt    4980
atcccgtgtt gacgccgggc aagagcaact cggtcgccgc atacactatt ctcagaatga    5040
cttggttgag tactcaccag tcacagaaaa gcatcttacg gatggcatga cagtaagaga    5100
attatgcagt gctgccataa ccatgagtga taacactgcg ccaacttac ttctgacaac    5160 gatcggagga ccgaaggagc taaccgcttt tttgcacaac atggggatc atgtaactcg    5220 ccttgatcgt tgggaaccgg agctgaatga agccatacca aacgacgagc gtgacaccac    5280
gatgcctgca gcaatggcaa caacgttgcg caaactatta actggcgaac tacttactct    5340
agcttcccgg caacaattaa tagactggat ggaggcggat aaagttgcag gaccacttct    5400
gcgctcggcc cttccggctg gctggtttat tgctgataaa tctggagccg gtgagcgtgg    5460
gtctcgcggt atcattgcag cactggggcc agatggtaag ccctcccgta tcgtagttat    5520
ctacacgacg gggagtcagg caactatgga tgaacgaaat agacagatcg ctgagatagg    5580
tgcctcactg attaagcatt ggtaactgtc agaccaagtt tactcatata actttagat    5640 tgatttaaaa cttcattttt aatttaaaag gatctaggtg aagatccttt ttgataatct    5700
catgaccaaa atcccttaac gtgagttttc gttccactga gcgtcagacc ccgtagaaaa    5760
gatcaaagga tcttcttgag atcctttttt tctgcgcgta atctgctgct tgcaaacaaa    5820
aaaaccaccg ctaccagcgg tggtttgttt gccggatcaa gagctaccaa ctcttttcc    5880 gaaggtaact ggcttcagca gagcgcagat accaaatact gttcttctag tgtagccgta    5940
gttaggccac cacttcaaga actctgtagc accgcctaca tacctcgctc tgctaatcct    6000
gttaccagtg gctgctgcca gtggcgataa gtcgtgtctt accgggttgg actcaagacg    6060
atagttaccg gataaggcgc agcggtcggg ctgaacgggg ggttcgtgca cacagcccag    6120
cttggagcga acgacctaca ccgaactgag atacctacag cgtgagctat gagaaagcgc    6180
cacgcttccc gaagggagaa aggcggacag gtatccggta agcggcaggg tcggaacagg    6240
agagcgcacg agggagcttc caggggggaaa cgcctggtat ctttatagtc ctgtcgggtt    6300
tcgccacctc tgacttgagc gtcgattttt gtgatgctcg tcaggggggc ggagcctatg    6360
gaaaaacgcc agcaacgcgg ccttttttacg gttcctggcc ttttgctggc cttttgctca    6420
catgttcttt cctgcgttat cccctgattc tgtggataac cgtattaccg cctttgagtg    6480
agctgatacc gctcgccgca gccgaacgac cgagcgcagc gagtcagtga gcgaggaagc    6540
ggaagagcgc ccaatacgca aaccgcctct ccccgcgcgt tggccgattc attaatgcag    6600
ctggcacgac aggtttcccg actggaaagc gggcagtgag cgcaacgcaa ttaatgtgag    6660
ttagctcact cattaggcac cccaggcttt acactttatg cttccggctc gtatgttgtg    6720
tggaattgtg agcggataac aatttcacac aggaaacagc tatgaccatg attacgccaa    6780
gctctagcta gaggtcgagt ccctccccag caggcagaag tatgcaaagc atgcatctca    6840
attagtcagc aaccatagtc cgcccctaa ctccgcccat cccgccccta actccgccca    6900
```

| | |
|---|---|
| gttccgccca ttctccgccc catggctgac taatttttt tatttatgca gaggccgagg | 6960 |
| ccgcctcggc ctctgagcta ttccagaagt agtgaggagg cttttttgga ggcctaggct | 7020 |
| tttgcaaaaa gctttgcaaa gatggataaa gttttaaaca gagaggaatc tttgcagcta | 7080 |
| atggaccttc taggtcttga aagg | 7104 |

<210> SEQ ID NO 29
<211> LENGTH: 6985
<212> TYPE: DNA
<213> ORGANISM: Artificial Sequence
<220> FEATURE:
<223> OTHER INFORMATION: Synthetic construct: pHybC-E7-hCk

<400> SEQUENCE: 29

| | |
|---|---|
| ttgacattga ttattgacta gttattaata gtaatcaatt acggggtcat tagttcatag | 60 |
| cccatatatg gagttccgcg ttacataact tacggtaaat ggcccgcctg gctgaccgcc | 120 |
| caacgacccc cgcccattga cgtcaataat gacgtatgtt cccatagtaa cgccaatagg | 180 |
| gactttccat tgacgtcaat gggtggagta tttacggtaa actgcccact tggcagtaca | 240 |
| tcaagtgtat catatgccaa gtccgccccc tattgacgtc aatgacgta atggcccgc | 300 |
| ctggcattat gcccagtaca tgaccttacg ggactttcct acttggcagt acatctacgt | 360 |
| attagtcatc gctattacca tggtgatgcg gttttggcag tacaccaatg ggcgtggata | 420 |
| gcggtttgac tcacggggat ttccaagtct ccaccccatt gacgtcaatg ggagtttgtt | 480 |
| ttggcaccaa aatcaacggg actttccaaa atgtcgtaat aaccccgccc cgttgacgca | 540 |
| aatgggcggt aggcgtgtac ggtgggaggt ctatataagc agagctcgtt tagtgaaccg | 600 |
| tcagatcctc actctcttcc gcatcgctgt ctgcgagggc cagctgttgg gctcgcggtt | 660 |
| gaggacaaac tcttcgcggt ctttccagta ctcttggatc ggaaacccgt cggcctccga | 720 |
| acggtactcc gccaccgagg gacctgagcg agtccgcatc gaccggatcg aaaaccctct | 780 |
| cgagaaaggc gtctaaccag tcacagtcgc aaggtaggct gagcaccgtg gcgggcggca | 840 |
| gcgggtggcg gtcggggttg tttctggcgg aggtgctgct gatgatgtaa ttaaagtagg | 900 |
| cggtcttgag acggcggatg gtcgaggtga ggtgtggcag gcttgagatc cagctgttgg | 960 |
| ggtgagtact ccctctcaaa agcgggcatt acttctgcgc taagattgtc agtttccaaa | 1020 |
| aacgaggagg atttgatatt cacctggccc gatctggcca tacacttgag tgacaatgac | 1080 |
| atccactttg cctttctctc cacaggtgtc cactcccagg tccaagtttg gcgcaccat | 1140 |
| ggacatgcgc gtgcccgccc agctgctggg cctgctgctg ctgtggttcc ccggctcgcg | 1200 |
| atgcgacatc cagatgaccc agtctccatc ctccctgtct gcatctatag gggacagagt | 1260 |
| caccatcact tgtcgggcaa gtcagggcat cagaaattac ttagcctggt atcagcaaaa | 1320 |
| accagggaaa gcccctaagc tcctgatcta tgctgcatcc actttgcaat caggggtccc | 1380 |
| atctcggttc agtggcagtg gatctgggac agatttcact ctcaccatca gcagcctaca | 1440 |
| gcctgaagat gttgcaactt attactgtca aaggtataac cgtgccccgt acacttttgg | 1500 |
| ccagggggacc aaggtggaaa tcaaacgtac ggtggctgca ccatctgtct tcatcttccc | 1560 |
| gccatctgat gagcagttga aatctggaac tgcctctgtt gtgtgcctgc tgaataactt | 1620 |
| ctatcccaga gaggccaaag tacagtggaa ggtggataac gccctccaat cgggtaactc | 1680 |
| ccaggagagt gtcacagagc aggacagcaa ggacagcacc tacagcctca gcagcaccct | 1740 |
| gacgctgagc aaagcagact acgagaaaca caaagtctac gcctgcgaag tcacccatca | 1800 |
| gggcctgagc tcgcccgtca caaagagctt caacagggga gagtgttgag cggccgctcg | 1860 |

```
aggccggcaa ggccggatcc cccgacctcg acctctggct aataaaggaa atttattttc   1920
attgcaatag tgtgttggaa ttttttgtgt ctctcactcg gaaggacata tgggagggca   1980
aatcatttgg tcgagatccc tcggagatct tagctagag gatcgatccc cgccccggac    2040
gaactaaacc tgactacgac atctctgccc cttcttcgcg gggcagtgca tgtaatccct   2100
tcagttggtt ggtacaactt gccaactggg ccctgttcca catgtgacac ggggggggac   2160
caaacacaaa ggggttctct gactgtagtt gacatcctta taaatggatg tgcacatttg   2220
ccaacactga gtggctttca tcctggagca gactttgcag tctgtggact gcaacacaac   2280
attgccttta tgtgtaactc ttggctgaag ctcttcacac aatgctgggg gacatgtacc   2340
tcccaggggc ccaggaagac tacgggaggc tacaccaacg tcaatcagag gggcctgtgt   2400
agctaccgat aagcggaccc tcaagagggc attagcaata gtgtttataa ggccccttg    2460 ttaaccctaa acgggtagca tatgcttccc gggtagtagt atatactatc cagactaacc   2520
ctaattcaat agcatatgtt acccaacggg aagcatatgc tatcgaatta gggttagtaa   2580
aagggtccta aggaacagcg atatctccca ccccatgagc tgtcacggtt ttatttacat   2640
ggggtcagga ttccacgagg gtagtgaacc attttagtca aagggcagt ggctgaagat    2700 caaggagcgg gcagtgaact ctcctgaatc ttcgcctgct tcttcattct ccttcgttta   2760
gctaatagaa taactgctga gttgtgaaca gtaaggtgta tgtgaggtgc tcgaaaacaa   2820
ggtttcaggt gacgccccca gaataaaatt tggacggggg gttcagtggt ggcattgtgc   2880
tatgacacca atataaccct cacaaacccc ttgggcaata atactagtg taggaatgaa    2940 acattctgaa tatctttaac aatagaaatc catggggtgg ggacaagccg taaagactgg   3000
atgtccatct cacacgaatt tatggctatg ggcaacacat aatcctagtg caatatgata   3060
ctggggttat taagatgtgt cccaggcagg gaccaagaca ggtgaaccat gttgttacac   3120
tctatttgta acaaggggaa agagagtgga cgccgacagc agcggactcc actggttgtc   3180
tctaacaccc ccgaaaatta acggggctc cacgccaatg gggcccataa acaaagacaa    3240
gtggccactc ttttttttga aattgtggag tgggggcacg cgtcagcccc cacacgccgc   3300
cctgcggttt tggactgtaa aataagggtg taataacttg gctgattgta accccgctaa   3360
ccactgcggt caaccactt gcccacaaaa ccactaatgg caccccgggg aatacctgca    3420
taagtaggtg ggcgggccaa gataggggcg cgattgctgc gatctggagg acaaattaca   3480
cacacttgcg cctgagcgcc aagcacaggg ttgttggtcc tcatattcac gaggtcgctg   3540
agagcacggt gggctaatgt tgccatgggt agcatatact acccaaatat ctggatagca   3600
tatgctatcc taatctatat ctgggtagca taggctatcc taatctatat ctgggtagca   3660
tatgctatcc taatctatat ctgggtagta tatgctatcc taatttatat ctgggtagca   3720
taggctatcc taatctatat ctgggtagca tatgctatcc taatctatat ctgggtagta   3780
tatgctatcc taatctgtat ccgggtagca tatgctatcc taatagagat tagggtagta   3840
tatgctatcc taatttatat ctgggtagca tatactaccc aaatatctgg atagcatatg   3900
ctatcctaat ctatatctgg gtagcatatg ctatcctaat ctatatctgg gtagcatagg   3960
ctatcctaat ctatatctgg gtagcatatg ctatcctaat ctatatctgg gtagtatatg   4020
ctatcctaat ttatatctgg gtagcatagg ctatcctaat ctatatctgg gtagcatatg   4080
ctatcctaat ctatatctgg gtagtatatg ctatcctaat ctgtatccgg gtagcatatg   4140
ctatcctcat gataagctgt caaacatgag aattttcttg aagacgaaag ggcctcgtga   4200
tacgcctatt tttataggtt aatgtcatga taataatggt ttcttagacg tcaggtggca   4260
```

```
cttttcgggg aaatgtgcgc ggaacccta tttgtttatt tttctaaata cattcaaata    4320
tgtatccgct catgagacaa taaccctgat aaatgcttca ataatattga aaaggaaga    4380
gtatgagtat tcaacatttc cgtgtcgccc ttattccctt ttttgcggca ttttgccttc    4440
ctgttttgc tcacccagaa acgctggtga agtaaaaga tgctgaagat cagttgggtg     4500
cacgagtggg ttacatcgaa ctggatctca acagcgtaa gatccttgag agttttcgcc    4560
ccgaagaacg ttttccaatg atgagcactt ttaaagttct gctatgtggc gcggtattat   4620
cccgtgttga cgccgggcaa gagcaactcg gtcgccgcat acactattct cagaatgact   4680
tggttgagta ctcaccagtc acagaaaagc atcttacgga tggcatgaca gtaagagaat   4740
tatgcagtgc tgccataacc atgagtgata acactgcggc caacttactt ctgacaacga   4800
tcggaggacc gaaggagcta accgcttttt tgcacaacat ggggatcat gtaactcgcc    4860
ttgatcgttg ggaaccggag ctgaatgaag ccataccaaa cgacgagcgt gacaccacga   4920
tgcctgcagc aatggcaaca acgttgcgca aactattaac tggcgaacta cttactctag   4980
cttcccggca acaattaata gactggatgg aggcggataa agttgcagga ccacttctgc   5040
gctcggccct tccggctggc tggtttattg ctgataaatc tggagccggt gagcgtgggt   5100
ctcgcggtat cattgcagca ctggggccag atggtaagcc ctcccgtatc gtagttatct   5160
acacgacggg gagtcaggca actatggatg aacgaaatag acagatcgct gagataggtg   5220
cctcactgat taagcattgg taactgtcag accaagttta ctcatatata ctttagattg   5280
atttaaaact tcattttaa tttaaaagga tctaggtgaa gatccttttt gataatctca    5340
tgaccaaaat cccttaacgt gagttttcgt tccactgagc gtcagacccc gtagaaaaga   5400
tcaaaggatc ttcttgagat cctttttttc tgcgcgtaat ctgctgcttg caaacaaaaa   5460
aaccaccgct accagcggtg gtttgtttgc cggatcaaga ctaccaact cttttttccga   5520
aggtaactgg cttcagcaga gcgcagatac caaatactgt tcttctagtg tagccgtagt   5580
taggccacca cttcaagaac tctgtagcac cgcctacata cctcgctctg ctaatcctgt   5640
taccagtggc tgctgccagt ggcgataagt cgtgtcttac cgggttggac tcaagacgat   5700
agttaccgga taaggcgcag cggtcgggct gaacggggg ttcgtgcaca cagcccagct    5760
tggagcgaac gacctacacc gaactgagat acctacagcg tgagctatga gaaagcgcca   5820
cgcttcccga agggagaaag gcggacaggt atccggtaag cggcagggtc ggaacaggag   5880
agcgcacgag ggagcttcca gggggaaacg cctggtatct ttatagtcct gtcgggtttc   5940
gccacctctg acttgagcgt cgatttttgt gatgctcgtc aggggggcgg agcctatgga   6000
aaaacgccag caacgcggcc ttttacggt tcctggcctt tgctggcct tttgctcaca     6060
tgttctttcc tgcgttatcc cctgattctg tggataaccg tattaccgcc tttgagtgag   6120
ctgataccgc tcgccgcagc cgaacgaccg agcgcagcga gtcagtgagc gaggaagcgg   6180
aagagcgccc aatacgcaaa ccgcctctcc ccgcgcgttg gccgattcat taatgcagct   6240
ggcacgacag gtttcccgac tggaaagcgg gcagtgagcg caacgcaatt aatgtgagtt   6300
agctcactca ttaggcaccc caggctttac actttatgct tccggctcgt atgttgtgtg   6360
gaattgtgag cggataacaa tttcacacag gaaacagcta tgaccatgat tacgccaagc   6420
tctagctaga ggtcgagtcc ctccccagca ggcagaagta tgcaaagcat gcatctcaat   6480
tagtcagcaa ccatagtccc gcccctaact ccgcccatcc cgcccctaac tccgcccagt   6540
tccgcccatt ctccgcccca tggctgacta attttttta tttatgcaga ggccgaggcc   6600
gcctcggcct ctgagctatt ccagaagtag tgaggaggct ttttggagg cctaggcttt    6660
```

| | |
|---|---|
| tgcaaaaagc tttgcaaaga tggataaagt tttaaacaga gaggaatctt tgcagctaat | 6720 |
| ggaccttcta ggtcttgaaa ggagctcgac caattctcat gtttgacagc ttatcatcgc | 6780 |
| agatccgggc aacgttgttg ccattgctgc aggcgcagaa ctggtaggta tggaagatct | 6840 |
| atacattgaa tcaatattgg caattagcca tattagtcat tggttatata gcataaatca | 6900 |
| atattggcta tttggccattg catacgttgt atctatatca taatatgtac atttatattg | 6960 |
| gctcatgtcc aatatgaccg ccatg | 6985 |

<210> SEQ ID NO 30
<211> LENGTH: 7688
<212> TYPE: DNA
<213> ORGANISM: Artificial Sequence
<220> FEATURE:
<223> OTHER INFORMATION: Synthetic construct: pHybC-D2-hCg1,z,a

<400> SEQUENCE: 30

| | |
|---|---|
| ttgacattga ttattgacta gttattaata gtaatcaatt acggggtcat tagttcatag | 60 |
| cccatatatg gagttccgcg ttacataact tacggtaaat ggcccgcctg gctgaccgcc | 120 |
| caacgacccc cgcccattga cgtcaataat gacgtatgtt cccatagtaa cgccaatagg | 180 |
| gactttccat tgacgtcaat gggtggagta tttacggtaa actgcccact tggcagtaca | 240 |
| tcaagtgtat catatgccaa gtccgccccc tattgacgtc aatgacggta atggcccgc | 300 |
| ctggcattat gcccagtaca tgaccttacg gactttcct acttggcagt acatctacgt | 360 |
| attagtcatc gctattacca tggtgatgcg gttttggcag tacaccaatg ggcgtggata | 420 |
| gcggtttgac tcacggggat ttccaagtct ccaccccatt gacgtcaatg ggagtttgtt | 480 |
| ttggcaccaa aatcaacggg actttccaaa atgtcgtaat aaccccgccc cgttgacgca | 540 |
| aatgggcggt aggcgtgtac ggtgggaggt ctatataagc agagctcgtt tagtgaaccg | 600 |
| tcagatcctc actctcttcc gcatcgctgt ctgcgagggc cagctgttgg gctcgcggtt | 660 |
| gaggacaaac tcttcgcggt cttttccagta ctcttggatc ggaaacccgt cggcctccga | 720 |
| acggtactcc gccaccgagg gacctgagcg agtccgcatc gaccggatcg gaaaacctct | 780 |
| cgagaaaggc gtctaaccag tcacagtcgc aaggtaggct gagcaccgtg gcgggcggca | 840 |
| gcgggtggcg gtcggggttg tttctggcgg aggtgctgct gatgatgtaa ttaaagtagg | 900 |
| cggtcttgag acggcggatg gtcgaggtga ggtgtggcag gcttgagatc cagctgttgg | 960 |
| ggtgagtact ccctctcaaa agcgggcatt acttctgcgc taagattgtc agtttccaaa | 1020 |
| aacgaggagg atttgatatt cacctggccc gatctggcca tacacttgag tgacaatgac | 1080 |
| atccactttg cctttctctc cacaggtgtc cactcccagg tccaagtttg gcgccacca | 1140 |
| tggagtttgg gctgagctgg cttttttcttg tcgcgatttt aaaaggtgtc cagtgtgagg | 1200 |
| tgcagctggt ggagtctggg ggaggcttgg tacagcccgg caggtccctg agactctcct | 1260 |
| gtgcggcctc tggattcacc tttgatgatt atgccatgca ctgggtccgg caagctccag | 1320 |
| ggaagggcct ggaatgggtc tcagctatca cttggaatag tggtcacata gactatgcgg | 1380 |
| actctgtgga gggccgattc accatctcca gagacaacgc caagaactcc ctgtatctgc | 1440 |
| aaatgaacag tctgagagct gaggatacgg ccgtatatta ctgtgcgaaa gtctcgtacc | 1500 |
| ttagcaccgc gtcctccctt gactattggg gccaaggtac cctggtcacc gtctcgagtg | 1560 |
| cgtcgaccaa gggcccatcg gtcttccccc tggcaccctc ctccaagagc acctctgggg | 1620 |
| gcacagcggc cctgggctgc ctggtcaagg actacttccc cgaaccggtg acggtgtcgt | 1680 |
| ggaactcagg cgccctgacc agcggcgtgc acaccttccc ggctgtccta cagtcctcag | 1740 |

```
gactctactc cctcagcagc gtggtgaccg tgccctccag cagcttgggc acccagacct    1800
acatctgcaa cgtgaatcac aagcccagca acaccaaggt ggacaagaaa gttgagccca    1860
aatcttgtga caaaactcac acatgccac cgtgcccagc acctgaactc ctgggggggac    1920 cgtcagtctt cctcttcccc ccaaaaccca aggacaccct catgatctcc cggacccctg    1980
aggtcacatg cgtggtggtg gacgtgagcc acgaagaccc tgaggtcaag ttcaactggt    2040
acgtggacgg cgtggaggtg cataatgcca agacaaagcc gcgggaggag cagtacaaca    2100
gcacgtaccg tgtggtcagc gtcctcaccg tcctgcacca ggactggctg aatggcaagg    2160
agtacaagtg caaggtctcc aacaaagccc tcccagcccc catcgagaaa accatctcca    2220
aagccaaagg gcagccccga gaaccacagg tgtacaccct gcccccatcc cgggatgagc    2280
tgaccaagaa ccaggtcagc ctgacctgcc tggtcaaagg cttctatccc agcgacatcg    2340
ccgtggagtg ggagagcaat gggcagccgg agaacaacta caagaccacg cctcccgtgc    2400
tggactccga cggctccttc ttcctctaca gcaagctcac cgtggacaag agcaggtggc    2460
agcaggggaa cgtcttctca tgctccgtga tgcatgaggc tctgcacaac cactacacgc    2520
agaagagcct ctccctgtct ccgggtaaat gagcggccgc tcgaggccgg caaggccgga    2580
tcccccgacc tcgacctctg gctaataaag gaaatttatt ttcattgcaa tagtgtgttg    2640 gaatttttg tgtctctcac tcggaaggac atatgggagg gcaaatcatt tggtcgagat    2700
ccctcggaga tctctagcta gaggatcgat ccccgccccg gacgaactaa acctgactac    2760
gacatctctg cccttcttc gcggggcagt gcatgtaatc ccttcagttg gttggtacaa    2820
cttgccaact gggccctgtt ccacatgtga cacggggggg gaccaaacac aaagggggttc    2880 tctgactgta gttgacatcc ttataaatgg atgtgcacat ttgccaacac tgagtggctt    2940
tcatcctgga gcagactttg cagtctgtgg actgcaacac aacattgcct ttatgtgtaa    3000
ctcttggctg aagctcttac accaatgctg ggggacatgt acctcccagg ggcccaggaa    3060
gactacggga ggctacacca acgtcaatca gaggggcctg tgtagctacc gataagcgga    3120
ccctcaagag ggcattagca atagtgttta taaggccccc ttgttaaccc taaacgggta    3180
gcatatgctt cccgggtagt agtatatact atccagacta accctaattc aatagcatat    3240
gttacccaac gggaagcata tgctatcgaa ttagggttag taaaagggtc taaggaaca    3300 gcgatatctc ccaccccatg agctgtcacg gtttatttta catggggtca ggattccacg    3360
agggtagtga accattttag tcacaagggc agtggctgaa gatcaaggag cgggcagtga    3420
actctcctga atcttcgcct gcttcttcat tctccttcgt ttagctaata gaataactgc    3480
tgagttgtga acagtaaggt gtatgtgagg tgctcgaaaa caaggtttca ggtgacgccc    3540
ccagaataaa atttggacgg ggggttcagt ggtggcattg tgctatgaca ccaatataac    3600
cctcacaaac cccttgggca ataaatacta gtgtaggaat gaaacattct gaatatcttt    3660
aacaatagaa atccatgggg tggggacaag ccgtaaagac tggatgtcca tctcacacga    3720
atttatggct atgggcaaca cataatccta gtgcaatatg atactggggt tattaagatg    3780
tgtcccaggc agggaccaag acaggtgaac catgttgtta cactctattt gtaacaaggg    3840
gaaagagagt ggacgccgac agcagcggac tccactggtt gtctctaaca ccccgaaaa    3900 ttaaacgggg ctccacgcca atgggcccca taaacaaaga caagtggcca ctcttttttt    3960
tgaaattgtg gagtggggc acgcgtcagc ccccacacgc cgccctgcgg ttttggactg    4020
taaaataagg gtgtaataac ttggctgatt gtaaccccgc taaccactgc ggtcaaacca    4080
cttgcccaca aaaccactaa tggcaccccg gggaatacct gcataagtag gtgggcgggc    4140
```

```
caagatagggg gcgcgattgc tgcgatctgg aggacaaatt acacacactt gcgcctgagc    4200
gccaagcaca gggttgttgg tcctcatatt cacgaggtcg ctgagagcac ggtgggctaa    4260
tgttgccatg ggtagcatat actacccaaa tatctggata gcatatgcta tcctaatcta    4320
tatctgggta gcataggcta tcctaatcta tatctgggta gcatatgcta tcctaatcta    4380
tatctgggta gtatatgcta tcctaattta tatctgggta gcataggcta tcctaatcta    4440
tatctgggta gcatatgcta tcctaatcta tatctgggta gtatatgcta tcctaatctg    4500
tatccgggta gcatatgcta tcctaataga gattagggta gtatatgcta tcctaattta    4560
tatctgggta gcatatacta cccaaatatc tggatagcat atgctatcct aatctatatc    4620
tgggtagcat atgctatcct aatctatatc tgggtagcat aggctatcct aatctatatc    4680
tgggtagcat atgctatcct aatctatatc tgggtagtat atgctatcct aatttatatc    4740
tgggtagcat aggctatcct aatctatatc tgggtagcat atgctatcct aatctatatc    4800
tgggtagtat atgctatcct aatctgtatc cgggtagcat atgctatcct catgataagc    4860
tgtcaaacat gagaattttc ttgaagacga aagggcctcg tgatacgcct attttatag    4920 gttaatgtca tgataataat ggtttcttag acgtcaggtg cacttttcg gggaaatgtg    4980 cgcggaaccc ctatttgttt attttttctaa atacattcaa atatgtatcc gctcatgaga    5040 caataacccct gataaatgct tcaataatat tgaaaaagga gagtatgag tattcaacat    5100 ttccgtgtcg cccttattcc cttttttgcg gcattttgcc ttcctgtttt tgctcaccca    5160
gaaacgctgg tgaaagtaaa agatgctgaa gatcagttgg gtgcacgagt gggttacatc    5220
gaactggatc tcaacagcgg taagatcctt gagagtttc gccccgaaga acgttttcca    5280
atgatgagca cttttaaagt tctgctatgt ggcgcggtat tatcccgtgt tgacgccggg    5340
caagagcaac tcggtcgccg catacactat tctcagaatg acttggttga gtactcacca    5400
gtcacagaaa agcatcttac ggatggcatg acagtaagag aattatgcag tgctgccata    5460
accatgagtg ataacactgc ggccaactta cttctgacaa cgatcggagg accgaaggag    5520
ctaaccgctt ttttgcacaa catgggggat catgtaactc gccttgatcg ttgggaaccg    5580
gagctgaatg aagccatacc aaacgacgag cgtgacacca cgatgcctgc agcaatggca    5640
acaacgttgc gcaaactatt aactggcgaa ctacttactc tagcttcccg gcaacaatta    5700
atagactgga tggaggcgga taaagttgca ggaccacttc tgcgctcggc ccttccggct    5760
ggctggttta ttgctgataa atctggagcc ggtgagcgtg ggtctcgcgg tatcattgca    5820
gcactggggc cagatggtaa gccctcccgt atcgtagtta tctacacgac ggggagtcag    5880
gcaactatgg atgaacgaaa tagacagatc gctgagatag gtgcctcact gattaagcat    5940
tggtaactgt cagaccaagt ttactcatat atactttaga ttgatttaaa acttcatttt    6000
taatttaaaa ggatctaggt gaagatcctt tttgataatc tcatgaccaa aatcccttaa    6060
cgtgagtttt cgttccactg agcgtcagac cccgtagaaa agatcaaagg atcttcttga    6120
gatccttttt ttctgcgcgt aatctgctgc ttgcaaacaa aaaaaccacc gctaccagcg    6180
gtggtttgtt tgccggatca agagctacca actctttttc cgaaggtaac tggcttcagc    6240
agagcgcaga taccaaatac tgttcttcta gtgtagccgt agttaggcca ccacttcaag    6300
aactctgtag caccgcctac atacctcgct ctgctaatcc tgttaccagt ggctgctgcc    6360
agtggcgata gtcgtgtct taccgggttg gactcaagac gatagttacc ggataaggcg    6420
cagcggtcgg gctgaacggg gggttcgtgc acacagccca gcttggagcg aacgacctac    6480
accgaactga gatacctaca gcgtgagcta tgagaaagcg ccacgcttcc cgaagggaga    6540
```

```
aaggcggaca ggtatccggt aagcggcagg gtcggaacag gagagcgcac gagggagctt    6600 ccaggggaa acgcctggta tctttatagt cctgtcgggt ttcgccacct ctgacttgag     6660
cgtcgatttt tgtgatgctc gtcaggggg cggagcctat ggaaaaacgc cagcaacgcg     6720
gcctttttac ggttcctggc cttttgctgg ccttttgctc acatgttctt tcctgcgtta    6780
tcccctgatt ctgtggataa ccgtattacc gcctttgagt gagctgatac cgctcgccgc    6840
agccgaacga ccgagcgcag cgagtcagtg agcgaggaag cggaagagcg cccaatacgc    6900
aaaccgcctc tccccgcgcg ttggccgatt cattaatgca gctggcacga caggtttccc    6960
gactggaaag cgggcagtga gcgcaacgca attaatgtga gttagctcac tcattaggca    7020
ccccaggctt tacactttat gcttccggct cgtatgttgt gtggaattgt gagcggataa    7080
caatttcaca caggaaacag ctatgaccat gattacgcca agctctagct agaggtcgag    7140
tccctcccca gcaggcagaa gtatgcaaag catgcatctc aattagtcag caaccatagt    7200 cccgcccta actccgccca tcccgcccct aactccgccc agttccgccc attctccgcc     7260
ccatggctga ctaattttt ttatttatgc agaggccgag gccgcctcgg cctctgagct    7320
attccagaag tagtgaggag gcttttttgg aggcctaggc ttttgcaaaa agctttgcaa    7380
agatggataa agttttaaac agagaggaat ctttgcagct aatggacctt ctaggtcttg    7440
aaaggagctc gaccaattct catgtttgac agcttatcat cgcagatccg gcaacgttg     7500 ttgccattgc tgcaggcgca gaactggtag gtatggaaga tctatacatt gaatcaatat    7560
tggcaattag ccatattagt cattggttat atagcataaa tcaatattgg ctattggcca    7620
ttgcatacgt tgtatctata tcataatatg tacatttata ttggctcatg tccaatatga    7680
ccgccatg                                                              7688

<210> SEQ ID NO 31
<211> LENGTH: 7548
<212> TYPE: DNA
<213> ORGANISM: Artificial Sequence
<220> FEATURE:
<223> OTHER INFORMATION: Synthetic construct: pHybE-D2-hCg1,z,a

<400> SEQUENCE: 31
agtgggaatt ggctccggtg cccgtcagtg ggcagagcgc acatcgccca cagtccccga      60
gaagttgggg ggaggggtcg gcaattgaac cggtgcctag agaaggtggc gcggggtaaa     120
ctgggaaagt gatgtcgtgt actggctccg ccttttcc gagggtgggg gagaaccgta      180
tataagtgca gtagtcgccg tgaacgttct ttttcgcaac gggtttgccg ccagaacaca    240
ggtaagtgcc gtgtgtggtt cccgcgggcc tggcctcttt acgggttatg gcccttgcgt    300
gccttgaatt acttccacct ggctgcagta cgtgattctt gatcccgagc ttcgggttgg    360
aagtgggtgg gagagttcga ggccttgcgc ttaaggagcc ccttcgcctc gtgcttgagt    420
tgaggcctgg cctgggcgct ggggccgccg cgtgcgaatc tggtggcacc ttcgcgcctg    480
tctcgctgct ttcgataagt ctctagccat ttaaaatttt tgatgacctg ctgcgacgct    540
ttttttctgg caagatagtc ttgtaaatgc gggccaagat ctgcacactg gtatttcggt    600
ttttggggcc gcgggcggcg acggggcccg tgcgtcccag cgcacatgtt cggcgaggcg    660
gggcctgcga gcgcggccac cgagaatcgg acggggtag tctcaagctg gccggcctgc    720
tctggtgcct ggcctcgcgc cgccgtgtat cgccccgccc tgggcggcaa ggctggcccg    780
gtcggcacca gttgcgtgag cggaaagatg gccgcttccc ggccctgctg cagggagctc    840
aaaatggagg acgcggcgct cgggagagcg ggcgggtgag tcacccacac aaaggaaaag    900
```

```
ggcctttccg tcctcagccg tcgcttcatg tgactccacg gagtaccggg cgccgtccag    960
gcacctcgat tagttctcga gcttttggag tacgtcgtct ttaggttggg gggaggggtt   1020
ttatgcgatg gagtttcccc acactgagtg ggtggagact gaagttaggc cagcttggca   1080
cttgatgtaa ttctccttgg aatttgccct ttttgagttt ggatcttggt tcattctcaa   1140
gcctcagaca gtggttcaaa gttttttttct tccatttcag gtgtcgtgag gaattctcta   1200
gagatccctc gacctcgaga tccattgtgc ccgggcgcca ccatggagtt tgggctgagc   1260
tggctttttc ttgtcgcgat tttaaaaggt gtccagtgtg aggtgcagct ggtggagtct   1320
gggggaggct tggtacagcc cggcaggtcc ctgagactct cctgtgcggc ctctggattc   1380
acctttgatg attatgccat gcactgggtc cggcaagctc agggaaaggg cctggaatgg   1440
gtctcagcta tcacttggaa tagtggtcac atagactatg cggactctgt ggagggccga   1500
ttcaccatct ccagagacaa cgccaagaac tccctgtatc tgcaaatgaa cagtctgaga   1560
gctgaggata cggccgtata ttactgtgcg aaagtctcgt accttagcac cgcgtcctcc   1620
cttgactatt ggggccaagg taccctggtc accgtctcga gtgcgtcgac caagggccca   1680
tcggtcttcc ccctggcacc ctcctccaag agcacctctg ggggcacagc ggccctgggc   1740
tgcctggtca aggactactt ccccgaaccg gtgacggtgt cgtggaactc aggcgccctg   1800
accagcggcg tgcacacctt cccggctgtc ctacagtcct caggactcta ctccctcagc   1860
agcgtggtga ccgtgccctc cagcagcttg ggcacccaga cctacatctg caacgtgaat   1920
cacaagccca gcaacaccaa ggtggacaag aaagttgagc ccaaatcttg tgacaaaact   1980
cacacatgcc caccgtgccc agcacctgaa ctcctggggg gaccgtcagt cttcctcttc   2040
cccccaaaac ccaaggacac cctcatgatc tcccggaccc ctgaggtcac atgcgtggtg   2100
gtggacgtga gccacgaaga ccctgaggtc aagttcaact ggtacgtgga cggcgtggag   2160
gtgcataatg ccaagacaaa gccgcgggag gagcagtaca acagcacgta ccgtgtggtc   2220
agcgtcctca ccgtcctgca ccaggactgg ctgaatggca aggagtacaa gtgcaaggtc   2280
tccaacaaag ccctcccagc ccccatcgag aaaaccatct ccaaagccaa agggcagccc   2340
cgagaaccac aggtgtacac cctgccccca tcccgggatg agctgaccaa gaaccaggtc   2400
agcctgacct gcctggtcaa aggcttctat cccagcgaca tcgccgtgga gtgggagagc   2460
aatgggcagc cggagaacaa ctacaagacc acgcctcccg tgctggactc cgacggctcc   2520
ttcttcctct acagcaagct caccgtggac aagagcaggt ggcagcaggg gaacgtcttc   2580
tcatgctccg tgatgcatga ggctctgcac aaccactaca cgcagaagag cctctccctg   2640
tctccgggta aataagcggc cgctcgaggc cggcaaggcc ggatccccg acctcgacct   2700
ctggctaata aggaaatttt attttcattg caatagtgtg ttggaatttt ttgtgtctct   2760
cactcggaag gacatatggg agggcaaatc atttggtcga gatccctcgg agatctctag   2820
ctagaggatc gatccccgcc ccggacgaac taaacctgac tacgacatct ctgccccttc   2880
ttcgcggggc agtgcatgta atcccttcag ttggttggta caacttgcca actgggccct   2940
gttccacatg tgacacgggg ggggaccaaa cacaaagggg ttctctgact gtagttgaca   3000
tccttataaa tggatgtgca catttgccaa cactgagtgg cttcatcct ggagcagact   3060
ttgcagtctg tggactgcaa cacaacattg cctttatgtg taactcttgg ctgaagctct   3120
tacaccaatg ctgggggaca tgtacctccc aggggcccag gaagactacg ggaggctaca   3180
ccaacgtcaa tcagagggc ctgtgtagct accgataagc ggaccctcaa gagggcatta   3240
gcaatagtgt ttataaggcc cccttgttaa ccctaaacgg gtagcatatg cttcccgggt   3300
```

```
agtagtatat actatccaga ctaaccctaa ttcaatagca tatgttaccc aacgggaagc    3360
atatgctatc gaattagggt tagtaaaagg gtcctaagga acagcgatat ctcccacccc    3420
atgagctgtc acggttttat ttacatgggg tcaggattcc acgagggtag tgaaccattt    3480
tagtcacaag ggcagtggct gaagatcaag gagcgggcag tgaactctcc tgaatcttcg    3540
cctgcttctt cattctcctt cgtttagcta atagaataac tgctgagttg tgaacagtaa    3600
ggtgtatgtg aggtgctcga aaacaaggtt tcaggtgacg cccccagaat aaaatttgga    3660 cgggggttc agtggtggca ttgtgctatg acaccaatat aaccctcaca aaccccttgg    3720
gcaataaata ctagtgtagg aatgaaacat tctgaatatc tttaacaata gaaatccatg    3780
gggtggggac aagccgtaaa gactggatgt ccatctcaca cgaatttatg gctatgggca    3840
acacataatc ctagtgcaat atgatactgg ggttattaag atgtgtccca ggcagggacc    3900
aagacaggtg aaccatgttg ttacactcta tttgtaacaa ggggaaagag agtggacgcc    3960
gacagcagcg gactccactg gttgtctcta acacccccga aaattaaacg gggctccacg    4020
ccaatggggc ccataaacaa agacaagtgg ccactctttt ttttgaaatt gtggagtggg    4080
ggcacgcgtc agcccccaca cgccgccctg cggttttgga ctgtaaaata agggtgtaat    4140
aacttggctg attgtaaccc cgctaaccac tgcggtcaaa ccacttgccc acaaaaccac    4200
taatggcacc ccggggaata cctgcataag taggtgggcg ggccaagata ggggcgcgat    4260
tgctgcgatc tggaggacaa attacacaca cttgcgcctg agcgccaagc acagggttgt    4320
tggtcctcat attcacgagg tcgctgagag cacggtgggc taatgttgcc atgggtagca    4380
tatactaccc aaatatctgg atagcatatg ctatcctaat ctatatctgg gtagcatagg    4440
ctatcctaat ctatatctgg gtagcatatg ctatcctaat ctatatctgg gtagtatatg    4500
ctatcctaat ttatatctgg gtagcatagg ctatcctaat ctatatctgg gtagcatatg    4560
ctatcctaat ctatatctgg gtagtatatg ctatcctaat ctgtatccgg gtagcatatg    4620
ctatcctaat agagattagg gtagtatatg ctatcctaat ttatatctgg gtagcatata    4680
ctacccaaat atctggatag catatgctat cctaatctat atctgggtag catatgctat    4740
cctaatctat atctgggtag cataggctat cctaatctat atctgggtag catatgctat    4800
cctaatctat atctgggtag tatatgctat cctaatttat atctgggtag cataggctat    4860
cctaatctat atctgggtag catatgctat cctaatctat atctgggtag tatatgctat    4920
cctaatctgt atccgggtag catatgctat cctcatgata agctgtcaaa catgagaatt    4980
ttcttgaaga cgaaagggcc tcgtgatacg cctattttta taggttaatg tcatgataat    5040
aatggtttct tagacgtcag gtggcacttt tcggggaaat gtgcgcggaa cccctatttg    5100
tttatttttc taaatacatt caaatatgta tccgctcatg agacaataac cctgataaat    5160
gcttcaataa tattgaaaaa ggaagagtat gagtattcaa catttccgtg tcgcccttat    5220
tccctttttt gcggcatttt gccttcctgt ttttgctcac ccagaaacgc tggtgaaagt    5280
aaaagatgct gaagatcagt tgggtgcacg agtgggttac atcgaactgg atctcaacag    5340
cggtaagatc cttgagagtt ttcgccccga agaacgtttt ccaatgatga gcacttttaa    5400
agttctgcta tgtggcgcgg tattatcccg tgttgacgcc gggcaagagc aactcggtcg    5460
ccgcatacac tattctcaga atgacttggt tgagtactca ccagtcacag aaaagcatct    5520
tacggatggc atgacagtaa gagaattatg cagtgctgcc ataaccatga gtgataacac    5580
tgcggccaac ttacttctga caacgatcgg aggaccgaag gagctaaccg cttttttgca    5640
caacatgggg gatcatgtaa ctcgccttga tcgttgggaa ccggagctga atgaagccat    5700
```

| | |
|---|---:|
| accaaacgac gagcgtgaca ccacgatgcc tgcagcaatg caacaacgt tgcgcaaact | 5760 |
| attaactggc gaactactta ctctagcttc ccggcaacaa ttaatagact ggatggaggc | 5820 |
| ggataaagtt gcaggaccac ttctgcgctc ggcccttccg gctggctggt ttattgctga | 5880 |
| taaatctgga gccggtgagc gtgggtctcg cggtatcatt gcagcactgg ggccagatgg | 5940 |
| taagccctcc cgtatcgtag ttatctacac gacggggagt caggcaacta tggatgaacg | 6000 |
| aaatagacag atcgctgaga taggtgcctc actgattaag cattggtaac tgtcagacca | 6060 |
| agtttactca tatatacttt agattgattt aaaacttcat ttttaattta aaaggatcta | 6120 |
| ggtgaagatc cttttgata atctcatgac caaaatccct aacgtgagt tttcgttcca | 6180 |
| ctgagcgtca gaccccgtag aaaagatcaa aggatcttct tgagatcctt ttttctgcg | 6240 |
| cgtaatctgc tgcttgcaaa caaaaaaacc accgctacca gcggtggttt gtttgccgga | 6300 |
| tcaagagcta ccaactcttt ttccgaaggt aactggcttc agcagagcgc agataccaaa | 6360 |
| tactgttctt ctagtgtagc cgtagttagg ccaccacttc aagaactctg tagcaccgcc | 6420 |
| tacatacctc gctctgctaa tcctgttacc agtggctgct gccagtggcg ataagtcgtg | 6480 |
| tcttaccggg ttggactcaa gacgatagtt accggataag gcgcagcggt cgggctgaac | 6540 |
| ggggggttcg tgcacacagc ccagcttgga gcgaacgacc tacaccgaac tgagatacct | 6600 |
| acagcgtgag ctatgagaaa gcgccacgct tcccgaaggg agaaaggcgg acaggtatcc | 6660 |
| ggtaagcggc agggtcggaa caggagagcg cacgagggag cttccagggg gaaacgcctg | 6720 |
| gtatctttat agtcctgtcg ggtttcgcca cctctgactt gagcgtcgat ttttgtgatg | 6780 |
| ctcgtcaggg gggcggagcc tatggaaaaa cgccagcaac gcggcctttt tacggttcct | 6840 |
| ggccttttgc tggccttttg ctcacatgtt ctttcctgcg ttatcccctg attctgtgga | 6900 |
| taaccgtatt accgcctttg agtgagctga taccgctcgc cgcagccgaa cgaccgagcg | 6960 |
| cagcgagtca gtgagcgagg aagcggaaga gcgcccaata cgcaaaccgc ctctccccgc | 7020 |
| gcgttggccg attcattaat gcagctggca cgacaggttt cccgactgga aagcgggcag | 7080 |
| tgagcgcaac gcaattaatg tgagttagct cactcattag gcaccccagg ctttacactt | 7140 |
| tatgcttccg gctcgtatgt tgtgtggaat tgtgagcgga taacaatttc acacaggaaa | 7200 |
| cagctatgac catgattacg ccaagctcta gctagaggtc gagtccctcc ccagcaggca | 7260 |
| gaagtatgca aagcatgcat ctcaattagt cagcaaccat agtcccgccc ctaactccgc | 7320 |
| ccatcccgcc cctaactccg cccagttccg cccattctcc gccccatggc tgactaattt | 7380 |
| ttttatttta tgcagaggcc gaggccgcct cggcctctga gctattccag aagtagtgag | 7440 |
| gaggcttttt tggaggccta ggcttttgca aaaagctttg caaagatgga taagttttta | 7500 |
| aacagagagg aatctttgca gctaatggac cttctaggtc ttgaaagg | 7548 |

<210> SEQ ID NO 32
<211> LENGTH: 6845
<212> TYPE: DNA
<213> ORGANISM: Artificial Sequence
<220> FEATURE:
<223> OTHER INFORMATION: Synthetic construct: pHybE-E7-hCk

<400> SEQUENCE: 32

| | |
|---|---:|
| agctttgcaa agatggataa agttttaaac agagaggaat ctttgcagct aatggacctt | 60 |
| ctaggtcttg aaaggagtgg gaattggctc cggtgcccgt cagtgggcag agcgcacatc | 120 |
| gcccacagtc cccgagaagt tggggggagg ggtcggcaat tgaaccggtg cctagagaag | 180 |
| gtggcgcggg gtaaactggg aaagtgatgt cgtgtactgg ctccgccttt ttcccgaggg | 240 |

```
tgggggagaa ccgtatataa gtgcagtagt cgccgtgaac gttctttttc gcaacgggtt    300
tgccgccaga acacaggtaa gtgccgtgtg tggttcccgc gggcctggcc tctttacggg    360
ttatggccct tgcgtgcctt gaattacttc cacctggctg cagtacgtga ttcttgatcc    420
cgagcttcgg gttggaagtg ggtgggagag ttcgaggcct tgcgcttaag gagcccttc     480 gcctcgtgct tgagttgagg cctggcctgg gcgctgggc cgccgcgtgc gaatctggtg     540
gcaccttcgc gcctgtctcg ctgctttcga taagtctcta gccatttaaa attttttgatg   600 acctgctgcg acgcttttt tctggcaaga tagtcttgta aatgcgggcc aagatctgca    660
cactggtatt tcggttttg gggccgcggg cggcgacggg gcccgtgcgt cccagcgcac    720
atgttcggcg aggcgggcc tgcgagcgcg gccaccgaga tcggacggg ggtagtctca    780 agctggccgg cctgctctgg tgcctggcct cgcgccgccg tgtatcgccc cgccctgggc   840
ggcaaggctg gcccggtcgg caccagttgc gtgagcggaa agatggccgc ttcccggccc   900
tgctgcaggg agctcaaaat ggaggacgcg cgctcggga gagcgggcgg gtgagtcacc    960
cacacaaagg aaaagggcct ttccgtcctc agccgtcgct tcatgtgact ccacggagta   1020
ccgggcgccg tccaggcacc tcgattagtt ctcgagcttt tggagtacgt cgtcttagg    1080 ttgggggag gggttttatg cgatggagtt tccccacact gagtgggtgg agactgaagt   1140
taggccagct tggcacttga tgtaattctc cttggaattt gccctttttg agtttggatc   1200
ttggttcatt ctcaagcctc agacagtggt tcaaagtttt tttcttccat ttcaggtgtc   1260
gtgaggaatt ctctagagat ccctcgacct cgagatccat tgtgcccggg cgcaccatgg   1320
acatgcgcgt gcccgcccag ctgctgggcc tgctgctgct gtggttcccc ggctcgcgat   1380
gcgacatcca gatgacccag tctccatcct ccctgtctgc atctgtaggg gacagagtca   1440
ccatcacttg tcgggcaagt cagggcatca gaaattactt agcctggtat cagcaaaaac   1500
cagggaaagc ccctaagctc ctgatctatg ctgcatccac tttgcaatca ggggtcccat   1560
ctcggttcag tggcagtgga tctgggacag atttcactct caccatcagc agcctacagc   1620
ctgaagatgt tgcaacttat tactgtcaaa ggtataaccg tgcaccgtat acttttggcc   1680
aggggaccaa ggtggaaatc aaacgtacgg tggctgcacc atctgtcttc atcttcccgc   1740
catctgatga gcagttgaaa tctggaactg cctctgttgt gtgcctgctg aataacttct   1800
atcccagaga ggccaaagta cagtggaagg tggataacgc cctccaatcg ggtaactccc   1860
aggagagtgt cacagagcag gacagcaagg acagcaccta cagcctcagc agcaccctga   1920
cgctgagcaa agcagactac gagaaacaca agtctacgc ctgcgaagtc acccatcagg   1980
gcctgagctc gcccgtcaca aagagcttca cagggagag tgttgagcg ccgctcgag     2040 gccggcaagg ccggatcccc cgacctcgac tctggctaa taaggaaat ttattttcat    2100 tgcaatagtg tgttggaatt ttttgtgtct ctcactcgga aggacatatg ggagggcaaa   2160
tcatttggtc gagatccctc ggagatctct agctagagga tcgatcccg ccccggacga   2220 actaaacctg actacgacat ctctgccct tcttcgcggg gcagtgcatg taatcccttc    2280
agttggttgg tacaacttgc caactgggcc ctgttccaca tgtgacacgg ggggggacca   2340
aacacaaagg ggttctctga ctgtagttga catccttata aatggatgtg cacatttgcc   2400
aacactgagt ggctttcatc ctggagcaga cttttgcagtc tgtggactgc aacacaacat   2460 tgccttttatg tgtaactctt ggctgaagct cttacaccaa tgctggggga catgtacctc   2520
ccaggggccc aggaagacta cgggaggcta caccaacgtc aatcagaggg gcctgtgtag   2580
ctaccgataa gcggaccctc aagagggcat tagcaatagt gtttataagg ccccccttgtt  2640
```

```
aaccctaaac gggtagcata tgcttcccgg gtagtagtat atactatcca gactaaccct   2700
aattcaatag catatgttac ccaacgggaa gcatatgcta tcgaattagg gttagtaaaa   2760
gggtcctaag gaacagcgat atctcccacc ccatgagctg tcacggtttt atttacatgg   2820
ggtcaggatt ccacgagggt agtgaaccat tttagtcaca agggcagtgg ctgaagatca   2880
aggagcgggc agtgaactct cctgaatctt cgcctgcttc ttcattctcc ttcgtttagc   2940
taatagaata actgctgagt tgtgaacagt aaggtgtatg tgaggtgctc gaaaacaagg   3000
tttcaggtga cgcccccaga ataaaatttg gacggggggt tcagtggtgg cattgtgcta   3060
tgacaccaat ataaccctca caaaccccctt gggcaataaa tactagtgta ggaatgaaac   3120
attctgaata tctttaacaa tagaaatcca tggggtgggg acaagccgta aagactggat   3180
gtccatctca cacgaattta tggctatggg caacacataa tcctagtgca atatgatact   3240
ggggttatta agatgtgtcc caggcaggga ccaagacagg tgaaccatgt tgttacactc   3300
tatttgtaac aaggggaaag agagtggacg ccgacagcag cggactccac tggttgtctc   3360
taacaccccc gaaaattaaa cggggctcca cgccaatggg gcccataaac aaagacaagt   3420
ggccactctt ttttttgaaa ttgtggagtg ggggcacgcg tcagccccca cacgccgccc   3480
tgcggttttg gactgtaaaa taagggtgta ataacttggc tgattgtaac cccgctaacc   3540
actgcggtca aaccacttgc ccacaaaacc actaatggca ccccggggaa tacctgcata   3600
agtaggtggg cgggccaaga taggggcgcg attgctgcga tctggaggac aaattacaca   3660
cacttgcgcc tgagcgccaa gcacaggstt gttggtcctc atattcacga ggtcgctgag   3720
agcacggtgg gctaatgttg ccatgggtag catatactac ccaaatatct ggatagcata   3780
tgctatccta atctatatct gggtagcata ggctatccta atctatatct gggtagcata   3840
tgctatccta atctatatct gggtagtata tgctatccta atttatatct gggtagcata   3900
ggctatccta atctatatct gggtagcata tgctatccta atctatatct gggtagtata   3960
tgctatccta atctgtatcc gggtagcata tgctatccta atagagatta gggtagtata   4020
tgctatccta atttatatct gggtagcata tactacccaa atatctggat agcatatgct   4080
atcctaatct atatctgggt agcatatgct atcctaatct atatctgggt agcataggct   4140
atcctaatct atatctgggt agcatatgct atcctaatct atatctgggt agtatatgct   4200 atcctaatt t atatctgggt agcataggct atcctaatct atatctgggt agcatatgct   4260
atcctaatct atatctgggt agtatatgct atcctaatct gtatccgggt agcatatgct   4320
atcctcatga taagctgtca aacatgagaa ttttcttgaa gacgaaaggg cctcgtgata   4380
cgcctatttt tataggttaa tgtcatgata taatggtttt cttagacgtc aggtggcact   4440
tttcggggaa atgtgcgcgg aacccctatt tgtttatttt tctaaataca ttcaaatatg   4500
tatccgctca tgagacaata accctgataa atgcttcaat aatattgaaa aaggaagagt   4560
atgagtattc aacatttccg tgtcgccctt attcccttttt tgcggcatt ttgccttcct   4620 gttttttgctc acccagaaac gctggtgaaa gtaaaagatg ctgaagatca gttgggtgca   4680
cgagtgggtt acatcgaact ggatctcaac agcggtaaga tccttgagag ttttcgcccc   4740
gaagaacgtt ttccaatgat gagcactttt aaagttctgc tatgtggcgc ggtattatcc   4800
cgtgttgacg ccgggcaaga gcaactcggt cgccgcatac actattctca gaatgacttg   4860
gttgagtact caccagtcac agaaaagcat cttacggatg gcatgacagt aagagaatta   4920
tgcagtgctg ccataaccat gagtgataac actgcggcca acttacttct gacaacgatc   4980
ggaggaccga aggagctaac cgcttttttg cacaacatgg gggatcatgt aactcgcctt   5040
```

-continued

```
gatcgttggg aaccggagct gaatgaagcc ataccaaacg acgagcgtga caccacgatg    5100
cctgcagcaa tggcaacaac gttgcgcaaa ctattaactg gcgaactact tactctagct    5160
tcccggcaac aattaataga ctggatggag gcggataaag ttgcaggacc acttctgcgc    5220
tcggccttc cggctggctg gtttattgct gataaatctg gagccggtga gcgtgggtct     5280
cgcggtatca ttgcagcact ggggccagat ggtaagccct cccgtatcgt agttatctac    5340
acgacgggga gtcaggcaac tatggatgaa cgaaatagac agatcgctga gataggtgcc    5400
tcactgatta agcattggta actgtcagac caagtttact catatatact ttagattgat    5460
ttaaaacttc attttaatt taaaaggatc taggtgaaga tcctttttga taatctcatg     5520
accaaaatcc cttaacgtga gttttcgttc cactgagcgt cagacccgt agaaaagatc     5580
aaaggatctt cttgagatcc ttttttctg cgcgtaatct gctgcttgca acaaaaaaa      5640
ccaccgctac cagcggtggt ttgtttgccg gatcaagagc taccaactct ttttccgaag    5700
gtaactggct tcagcagagc gcagatacca aatactgttc ttctagtgta gccgtagtta    5760
ggccaccact tcaagaactc tgtagcaccg cctacatacc tcgctctgct aatcctgtta    5820
ccagtggctg ctgccagtgg cgataagtcg tgtcttaccg ggttggactc aagacgatag    5880
ttaccggata aggcgcagcg gtcgggctga cgggggggtt cgtgcacaca gcccagcttg    5940
gagcgaacga cctacaccga actgagatac ctacagcgtg agctatgaga aagcgccacg    6000
cttcccgaag ggagaaaggc ggacaggtat ccggtaagcg gcagggtcgg aacaggagag    6060
cgcacgaggg agcttccagg gggaaacgcc tggtatcttt atagtcctgt cgggtttcgc    6120
cacctctgac ttgagcgtcg atttttgtga tgctcgtcag ggggcggag cctatggaaa     6180
aacgccagca acgcggcctt tttacggttc ctggccttt gctggccttt tgctcacatg     6240
ttctttcctg cgttatcccc tgattctgtg gataaccgta ttaccgcctt tgagtgagct    6300
gataccgctc gccgcagccg aacgaccgag cgcagcgagt cagtgagcga ggaagcggaa    6360
gagcgcccaa tacgcaaacc gcctctcccc gcgcgttggc cgattcatta atgcagctgg    6420
cacgacaggt ttcccgactg gaaagcgggc agtgagcgca acgcaattaa tgtgagttag    6480
ctcactcatt aggcacccca ggctttacac tttatgcttc cggctcgtat gttgtgtgga    6540
attgtgagcg gataacaatt tcacacagga aacagctatg accatgatta cgccaagctc    6600
tagctagagg tcgagtccct ccccagcagg cagaagtatg caaagcatgc atctcaatta    6660
gtcagcaacc atagtcccgc ccctaactcc gcccatcccg cccctaactc cgcccagttc    6720
cgcccattct ccgccccatg gctgactaat ttttttatt tatgcagagg ccgaggccgc      6780
ctcggcctct gagctattcc agaagtagtg aggaggcttt tttggaggcc taggcttttg    6840
caaaa                                                                6845
```